United States Patent [19]

Milner

[11] Patent Number: 4,609,652
[45] Date of Patent: Sep. 2, 1986

[54] METHODS OF USING β-LACTAM ANTIBACTERIAL AGENTS

[75] Inventor: Peter H. Milner, Horsham, England

[73] Assignee: Beecham Group p.l.c., England

[21] Appl. No.: 694,592

[22] Filed: Jan. 24, 1985

Related U.S. Application Data

[62] Division of Ser. No. 401,266, Jul. 23, 1982, Pat. No. 4,539,149.

[30] Foreign Application Priority Data

| Jul. 25, 1981 | [GB] | United Kingdom | 8123033 |
| Jul. 25, 1981 | [GB] | United Kingdom | 8123034 |
| Dec. 7, 1981 | [GB] | United Kingdom | 8136823 |
| Dec. 7, 1981 | [GB] | United Kingdom | 8136824 |
| Mar. 18, 1982 | [GB] | United Kingdom | 8207966 |
| Apr. 3, 1982 | [GB] | United Kingdom | 8209953 |
| Apr. 3, 1982 | [GB] | United Kingdom | 8209954 |
| May 22, 1982 | [GB] | United Kingdom | 8215007 |

[51] Int. Cl.$^4$ .................... A61K 31/43; A61K 31/545
[52] U.S. Cl. .................... 514/194; 514/201; 540/205; 540/221; 540/301; 540/314; 540/327; 540/331; 540/333; 540/334; 540/337; 540/338; 540/339; 540/341
[58] Field of Search .................... 260/239.1, 245.2 R; 514/194, 201; 544/22

[56] References Cited

U.S. PATENT DOCUMENTS 3,974,150  8/1976  Cook et al. .................... 260/239.1
4,281,117  7/1981  Chauvette et al. .................... 514/201

OTHER PUBLICATIONS

P. H. Bentley et al., "Transformations Using Benzyl-6-Isocyanopenicillanate", JCS Perkin I, (1979), pp. 2455–2467.

P. H. Bentley et al., "6α-Substituted Penicillins", JCS Chem. Comm., (1974), pp. 278–279.

Primary Examiner—Natalie Trousof
Assistant Examiner—Vera C. Clarke
Attorney, Agent, or Firm—Jacobs & Jacobs

[57] ABSTRACT

β-Lactam antibiotics having an α-formamido substituent on the carbon atom adjacent to the carbonyl group of the β-lactam ring and in particular bicyclic compounds having the partial structure:

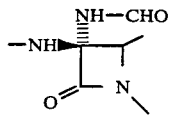

Intermediates and processes for the preparation of the compounds are further disclosed.

32 Claims, No Drawings

METHODS OF USING β-LACTAM ANTIBACTERIAL AGENTS

CROSS REFERENCE

This is a division of Ser. No. 401,266 filed July 23, 1982 now U.S. Pat. No. 4,539,149.

This invention relates to a class of novel β-lactam derivatives, which have antibacterial activity and are of value in the treatment of infections in humans and animals caused by a wide range of organisms, particularly Gram-negative organisms. The invention also relates to a process for the preparation of such compounds, intermediates for use in the preparation of the compounds and to pharmaceutical compositions containing the antibacterially active compounds and methods of treating bacterial infections in humans and animals utilising such compositions.

Accordingly the invention provides a class of β-lactam antibiotic having an α-formamido (formamidyl) substituent on the carbon atom adjacent to the carbonyl group of the β-lactam ring. The term α-formamido denotes the configuration:

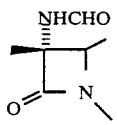

Compounds within the present invention are those having the partial structure:

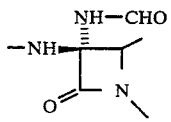

More particularly the present invention comprises a compound of formula (I) or a salt thereof.

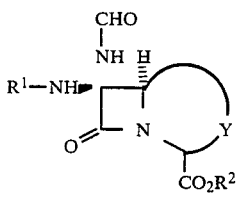

(I)

wherein $R^1$ is hydrogen, an acyl group, in particular those found on antibacterially active penicillins or cephalosporins, or an amino-protecting group; $R^2$ is hydrogen or a readily removable carboxyl protecting group; and Y is:

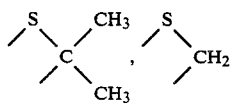

-continued

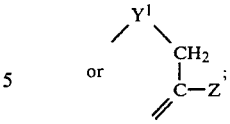

wherein $Y^1$ is oxygen, sulphur or —CH$_2$— and Z represents hydrogen, halogen, or an organic group such as $C_{1-4}$ alkoxy, —CH$_2$Q or —CH=CH—Q wherein Q represents hydrogen, halogen, hydroxy, mercapto, cyano, carboxy, carboxylic ester, $C_{1-4}$ alkyloxy, acyloxy, aryl, a heterocyclyl group bonded via carbon, a heterocyclylthio group or a nitrogen containing heterocyclic group bonded via nitrogen.

When used herein the term "halogen" unless otherwise defined is suitably fluorine, chlorine, bromine, and iodide, preferably chlorine and bromine.

When used herein the term "carboxylic ester" unless otherwise defined suitably includes $C_{1-6}$ alkyl esters.

When used herein the term "acyloxy" unless otherwise defined suitably includes $C_{1-6}$ alkylcarbonyloxy groups.

When used herein the term "aryl" unless otherwise defined suitably includes phenyl and naphthyl, preferably phenyl, optionally substituted with up to five halogen, $C_{1-6}$ alkyl, $C_{1-6}$ alkoxy, halo($C_{1-6}$) alkyl, hydroxy, amino, carboxy, $C_{1-6}$ alkoxycarbonyl, or $C_{1-6}$ alkoxycarbonyl-($C_{1-6}$)akyl groups.

When used herein the term "heterocyclyl" unless otherwise defined suitably includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl($C_{1-6}$) alkyl, aryl or oxo groups.

When used herein the terms lower means the group contains from 1 to 6 carbon atoms.

The compounds of the present invention may contain both an amino group and/or a carboxyl group and may, therefore, exist as the zwitterion or may form salts with suitable acids or bases.

The formamido group can exist in two preferred conformations, those wherein the hydrogen atoms of the —NH—CHO are, cis- or trans-, of which the cis conformation normally predominates.

Suitably Y is —S—C(CH$_3$)$_2$—, —S—CH$_2$—, —S—CH$_2$—C(CH$_2$Q')=; or —O—CH$_2$—C(CH$_2$Q')=, wherein Q' represents hydrogen, halogen, hydroxy, mercapto, cyano, carboxy, carboxylic ester, $C_{1-4}$ alkyloxy, acyloxy or heterocyclylthio group.

Preferred values for Y in the compounds of formula (I) are —S—C(CH$_3$)$_2$— and —S—CH$_2$—C(CH$_2$Q)=, i.e. when the compound of formula (I) is a derivative of a penicillin and cephalosporin.

A particularly preferred value for Y is —S—C(CH$_3$)$_2$13 .

A further preferred value for Y is —S—CH$_2$—CZ=. wherein Z is as hereinbefore defined.

Those compounds of the formula (I) wherein $R^1$ is a hydrogen group, or an amino-protecting group are mainly useful as intermediates in the preparation of compounds of the formula (I) wherein $R^1$ is an acyl group, in particular those found in antibacterially active penicillins or cephalosporins.

Those compounds of the formula (I) wherein $R^2$ is a readily removable carboxyl protecting group or a non-pharmaceutically acceptable, salt are primarily useful as intermediates in the preparation of compounds of the formula (I) wherein $R^2$ is a free carboxyl group or a pharmaceutically acceptable salt thereof. Also included within the readily removable carboxyl protecting groups $R^2$ are pharmaceutically acceptable in vivo hydrolysable ester groups.

Since the β-lactam antibiotic compounds of the present invention are intended for use in pharmaceutical compositions it will readily be understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutial compositions. Although the purity of intermediate compounds of the present invention is less critical it will readily be understood that the substantially pure form is preferred as for the β-lactam antibiotic compounds. Preferably, whenever possible, the compounds of the present invention are obtained in crystalline form.

Suitable amino-protecting groups $R^1$ are those well-known in the art which may be removed under conventional conditions without disruption of the remainder of the molecule.

Examples of amino-protecting groups for $R^1$ include benzyl optionally substituted in the phenyl ring by one or two substituents selected from $C_{1-4}$ alkyl, $C_{1-4}$ alkoxy, trifluoromethyl, halogen or nitro; $C_{1-4}$ alkoxycarbonyl, for example tert-butoxycarbonyl; benzyloxycarbonyl optionally substituted as for benzyl above; allyloxycarbonyl; trityl or trichloroethoxycarbonyl.

Suitable examples of N-protecting groups within $R^1$ include those listed above which are removable under acid conditions optionally in the presence of a group IIb metal.

Examples of suitable pharmaceutically acceptable in vivo hydrolysable ester groups include those which break down readily in the human body to leave the parent acid or its salt. Suitable ester groups of this type include those of part formula (i), (ii) and (iii):

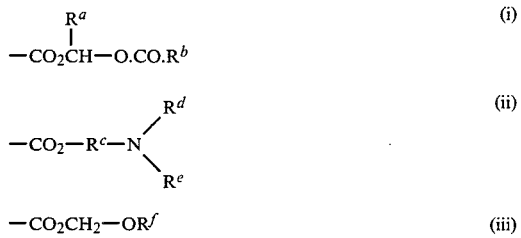

wherin $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups; $R^c$ represents $C_{1-6}$ alkylene optionally substituted with a methyl or ethyl group—$R^d$ and $R^e$ independently represent $C_{1-6}$ alkyl; $R^f$ represents $C_{1-6}$ alkyl. Examples of suitable in vivo hydrolysable ester group include for example acyloxyalkyl groups such as acetoxymethyl, pivaloyloxymethyl, α-acetoxyethyl and βpivaloyloxyethyl groups; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

Suitable readily removable carboxyl protecting groups for the group —$CO_2R^2$ in formula (I) include ester derivatives of the carboxylic acid. The derivative is preferably one which may readily be cleaved.

Suitable ester-forming carboxyl-protecting groups are those which may be removed under conventional conditions. Such groups for $R^2$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR° where R° is aryl or heterocyclic, or an in vivo hydrolysable ester radical such as defined above.

The carboxyl group may be regenerated from any of the above esters by usual methods appropriate to the particular $R^2$ group, for example, acid- and base-catalysed hydrolysis, or by enzymically-catalysed hydrolysis, or by hydrogenolysis.

Suitable pharmaceutically acceptable salts of the carboxy group of the compound of formula (I) include metal salts e.g. aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins.

Such useful salts according to the present invention include the lithium and silver salt.

Some of the compounds of this invention may be crystallised or recrystallised from solvents containing water. In such caes water of hydration may be formed. This invention includes within its scope stoichiometric hydrates as well as compounds containing variable amounts of water that may be produced by processes such as lyophilisation.

Suitable values for Q in the compounds of the formula (I) include the acetoxy, heterocyclylthio group, and nitrogen containing heterocyclic group bonded via nitrogen.

More suitably Q and Q' represent the acetoxy or heterocyclythio group.

The heterocyclylthio group may suitably be represented by the formula:

wherein "Het" is a five or six membered heterocyclic ring containing from 1 to 4 atoms selected from N, O, and S unsubstituted or substituted with one or two groups selected from $C_{1-6}$ alkyl, $C_{1-6}$ alkoxy, hydroxyalkyl, $C_{2-6}$ alkenyl, alkoxyalkyl, carboxyalkyl, sulphonylalkyl, carbamoylalkyl, trifluoromethyl, hydroxy, halogen, oxo, and (subst)aminoalkyl, or two substituents may be linked to form the residue of a heterocyclic or carbocyclic ring.

Examples of the group "Het" include unsubstituted and substituted imidazolyl, triazolyl, tetrazolyl, thiazolyl, thiadiazolyl, thiatriazolyl, oxazolyl, triazinyl and oxadiazolyl.

Suitable groups "Het" include unsubstituted and substituted 1, 2, 3-triazolyl; 1, 2, 4-triazolyl; tetrazolyl; oxazolyl; thiazolyl; 1, 3, 4-oxadiazolyl; 1, 3, 4-thiadiazolyl, or 1, 2, 4-thiadiazolyl. Preferably the heterocyclylthio group is 1-methyl-1H-tetrazol-5-ylthio, 2-methyl-1,3,4-thiadiazol-5-ylthio, 1-carboxymethyl-1H-tetrazol-5-ylthio or 6-hydroxy-2-methyl-5-oxo-2H-1,2,4-triazin-3-ylthio.

The nitrogen containing heterocyclic group bonded via nitrogen is suitably a pyridinium group unsubstituted or substituted with one or two groups selected from $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylmethyl, carbamoyl, trifluoromethyl, hydroxy, halogen, oxo, and aminoalkyl.

From the foregoing it will be realised that preferred antibacterially active compounds of this invention can be represented by the formula (II) or a pharmaceutically acceptable salt or in vivo hydrolysable ester thereof:

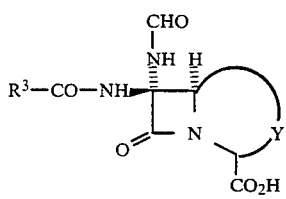   (II)

wherein Y is as defined with respect to formula (I); and $R^3$ is a group such that $R^3$—CO—NH— is an acylamino group, in particular that as found in antibacterially active penicillins or cephalosporins.

Suitable groups $R^3CO$— for inclusion in the compounds of the formula (II) include those of the subformulae (a)–(e):

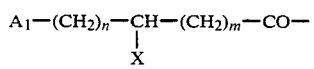   (a)

$A_2$—CO—   (b)

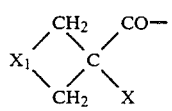   (c)

$A_2$—$X_2$—$(CH_2)_n$—CO—   (d)

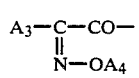   (e)

wherein n is 0, 1 or 2; m is 0, 1 or 2; $A_1$ is $C_{1-6}$ alkyl, substituted $C_{1-6}$ alkyl, $C_{3-6}$ cycloalkyl, cyclohexenyl, cyclohexadienyl, an aromatic group, such as phenyl, substituted phenyl, thienyl, pyridyl, an optionally substituted thiazolyl group, a $C_{1-6}$ alkylthio group or $C_{1-6}$ alkyloxy; X is a hydrogen or halogen atom, a carboxylic acid, carboxylic ester, sulphonic acid, azido, tetrazolyl, hydroxy, acyloxy, amino, ureido, acylamino, heterocylamino, guanidino or acylureido group; $A_2$ is an aromatic group such as a phenyl, a 2,6-dimethoxyphenyl, 2-alkoxy-1-naphthyl, 3-arylisoxazolyl, 3-aryl-5-methylisoxazolyl group, a substituted alkyl group, or a substituted dithietane; $X_1$ is a $CH_2OCH_2$, $CH_2SCH_2$ or $(CH_2)_n$ group; $X_2$ is an oxygen or sulphur atom; $A_3$ is an aryl or heteroaryl group such as phenyl, substituted phenyl or aminothiazolyl; and $A_4$ is hydrogen, $C_{1-6}$ alkyl, $C_{3-6}$ cycloalkyl, arylamino-carbonyl, $C_{1-6}$ alkylaminocarbonyl, $C_{1-6}$ alkanoyl, $C_{1-6}$ alkoxycarbony, $C_{2-6}$ alkenyl, carboxy $C_{1-6}$ alkyl, $C_{1-6}$ alkylsulphonyl and di-$C_{1-6}$ alkylphosphatomethyl.

More suitably $A_1$ is $C_{1-6}$ alkyl, $C_{3-6}$ cycloalkyl, cyclohexenyl, cyclohexadienyl, phenyl, hydroxy-phenyl, thienyl or pyridyl group; and X is a hydrogen or halogen atom, a carboxylic acid, carboxylic ester, azido, tetrazolyl, hydroxy, acyloxy, amino, ureido, guanidino or acylureido group.

Other more suitable groups $A_1$ include dihydroxyphenyl and diacetoxyphenyl.

Favoured groups $R^3$ for inclusion in the compounds of the formula (II) include those of the sub-formula

   (f)

   (g)

wherein $R^4$ is a phenyl, thienyl or phenoxy group; a hydrogen atom or methyl group; $R^6$ is a phenyl, substituted phenyl, substituted thiazolyl, thienyl or cyclohexadienyl group; and $R^7$ is a hydroxyl, carboxylic acid group or lower alkyl or phenyl, tolyl or indanyl ester thereof, amino or a substituted amino group.

Suitably the substituted phenyl group for $R^6$ is a phenyl group substituted with up to three groups selected from $C_{1-6}$ alkyl, phenyl, halogen, $C_{1-6}$ alkoxy, amino, nitro, hydroxy, $C_{1-6}$ alkylamido, $C_{1-6}$ alkylcarbonyloxy, carboxy, $C_{1-6}$ alkoxycarbonyl, halo ($C_{1-6}$) alkyl, oxo ($C_{1-6}$) alkyl, $C_{1-6}$ alkylcarbonyl, aryloxy, aralkyloxy, arylcarbonyl, $C_{1-6}$ alkylamino or di($C_{1-6}$) alkylamino.

Preferably $R^6$ is a phenyl, p-hydroxyphenyl, thienyl or cyclohexadienyl group.

Other preferred groups $R^6$ include 3,4-dihydroxyphenyl and 3,4-diacetoxyphenyl.

Preferably $R^7$ is a substituted amino group.

More preferably the substituted amino group $R^7$ is a ureido, acylamino or acylureido group.

One suitable sub-group within the present invention provides a compound of formula (III) or a pharmaceutically acceptable salt or in vivo hydrolysable ester thereof:

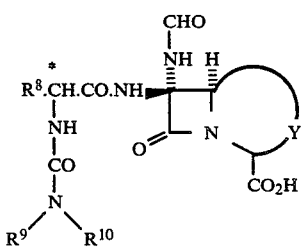   (III)

wherein Y is as defined with respect to formula (I) and $R^8$ is phenyl, substituted phenyl, cyclohexenyl, cyclohexadienyl, or a 5- or 6-membered heterocyclic ring containing up to three hetero-atoms selected from oxygen, sulphur or nitrogen, optionally substituted with hydroxy, amino, halogen, substituted amino or $C_{1-6}$ alkoxy; $R^9$ is hydrogen or a $C_{1-6}$ alkyl group and $R^{10}$ is an optionally substituted 5- or 6- membered heterocyclic group containing one or two nitrogen heteroatoms; or $R^9$ and $R^{10}$ together with the nitrogen atom to which they are attached form an optionally substituted five- or six-membered heterocyclic group containing one or two nitrogen heteroatoms.

Suitably the substituted phenyl group for $R^8$ is a phenyl group substituted with up to three groups selected from $C_{1-6}$ alkyl, phenyl, halogen, $C_{1-6}$ alkoxy, amino, nitro, hydroxy, $C_{1-6}$ alkylamido, $C_{1-6}$ alkylcarbonyloxy, carboxy, $C_{1-6}$ alkoxycarbonyl, halo ($C_{1-6}$) alkyl, oxo ($C_{1-6}$) alkyl, $C_{1-6}$ alkylcarbonyl, aryloxy, aralkyloxy, arylcarbonyl, $C_{1-6}$ alkylamino or di($C_{1-6}$) alkylamino.

In formula (III), the group $R^8$ is preferably phenyl, 4-hydroxyphenyl, 3,4-di($C_{1-6}$alkylcarbonyloxy)phenyl, 3,4-dihydroxyphenyl, 2-thienyl, 3-thienyl or 2-amino-4-thiazolyl.

Particularly preferred groups $R^8$ are 3,4-dihydroxyphenyl and 3,4-diacetoxyphenyl.

Suitably $R^9$ is hydrogen.

Suitable substituents for the 5- or 6- membered heterocyclic group of $R^{10}$ or $R^9$ and $R^{10}$ together include the optionally substituted alkyl, alkenyl, alkynyl, cycloalkyl or cycloalkenyl group; optionally substituted phenyl, oxo; the hydroxy group optionally substituted by alkyl, alkenyl, cycloalkyl, phenyl, pyridyl, pyrimidyl or benzyl; the optionally substituted mercapto group, the alkylsulphonyl group; the substituted imino group; or the amino group optionally substituted by an alkyl, alkenyl, cycloalkyl, phenyl, substituted phenyl or benzyl group. Alternatively two substituents on the ring may form the residue of a further carbocyclic or heterocyclic ring.

Preferred values for Y in the compounds of formula (III) are $-S-C(CH_3)_2-$ and $-S-CH_2-C(CH_2Q)=$, wherein Q is as hereinbefore defined i.e. when the compound of formula (III) are derivatives of a penicillin and cephalosporin.

The carbon atom marked * in formulae herein is asymmetric so that the compounds may exist as two optically active diastereoisomers. In general that prepared from the D-side chain exhibits the highest antibacterial activity and accordingly the D compound or the DL mixtures are preferred, with the D compound being particularly preferred.

Preferred compounds within formula (III) are the penicillin derivatives of formula (IV) or a pharmaceutically acceptable salt or in vivo hydrolysable ester thereof:

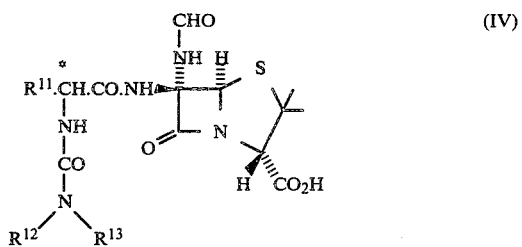

(IV)

wherein $R^{11}$ is phenyl, substituted phenyl, cyclohexenyl, cyclohexadienyl, or a 5- or 6-membered heterocyclic ring containing up to three heteroatoms selected from oxygen, sulphur or nitrogen, optionally substituted with hydroxy, amino, halogen or $C_{1-6}$ alkoxy; $R^{12}$ is hydrogen or $C_{1-6}$ alkyl and $R^{13}$ is an optionally substituted five- or six-membered heterocyclic group containing one or two nitrogen heteroatoms; or $R^{12}$ and $R^{13}$ together with the nitrogen atom to which they are attached form an optionally substituted five- or six-membered heterocyclic group containing one or two nitrogen heteroatoms.

In formula (IV) the group $R^{11}$ is preferably phenyl, 4-hydroxyphenyl, 2-thienyl, 3-thienyl, 2-amino-4-thiazolyl, 3,4-dihydroxyphenyl or 3,4-diacetoxyphenyl.

Particularly preferred groups $R^{11}$ include 3,4-dihydroxyphenyl and 3,4-diacetoxyphenyl.

Suitable substituents for the five- or six-membered heterocyclic group of $R^{13}$ or $R^{12}$ and $R^{13}$ together include the alkyl, alkenyl, alkynyl, cycloalkyl or cycloalkenyl group, optionally substituted phenyl, oxo, the hydroxy group optionally substituted by alkyl, alkenyl, cycloalkyl, phenyl, pyridyl, pyrimidyl or benzyl, the optionally substituted mercapto group, the alkylsulphonyl group, the substituted imino group, or the amino group optionally substituted by an alkyl, alkenyl, cycloalkyl, phenyl, substituted phenyl or benzyl group. Alternatively two substituents on the ring may form the residue of a further carbocyclic or heterocyclic ring.

Preferably $R^{12}$ is hydrogen.

One particularly preferred sub-group within the present invention provides a compound of formula (V) or a pharmaceutically acceptable salt or in vivo hydrolysable ester thereof:

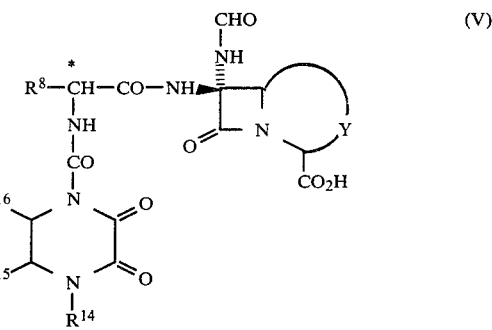

(V)

wherein $R^8$ and Y are as defined with respect to formula (III) and $R^{14}$ represents hydrogen, $C_{1-6}$ alkyl, substituted alkyl, aryl, or aralkyl; $R^{15}$ and $R^{16}$ are the same or different and represent hydrogen, $C_{1-6}$ alkyl, substituted alkyl, halogen, amino, hydroxy or $C_{1-6}$ alkoxy or $R^{15}$ and $R^{16}$ form the residue of 5- or 6-membered carbocyclic or heterocyclic ring.

Suitable values for Y in the compounds of formula (V) are $-S-C(CH_3)_2-$ and $-S-CH_2-C(CH_2Q)=$ wherein Q is as hereinbefore defined.

Preferably Y in the compounds of formula (V) is $-S-C(CH_3)_2-$ or $-S-CH_2-C(CH_2Q')=$ wherein $Q'$ is as hereinbefore defined.

Preferred compounds within formula (V) are the penicillin derivatives of formula (VI) or a pharmaceutically acceptable salt or in vivo hydrolysable ester thereof:

$$\text{(VI)}$$

[Structure VI: R¹¹—CH(NH—CO—N(R¹⁶)(R¹⁵)—N(R¹⁴))—CO—NH—β-lactam-penicillanic acid with CHO-NH group]

wherein $R^{11}$, $R^{14}$, $R^{15}$ and $R^{16}$ are as hereinbefore defined.

Suitable $C_{1-6}$ alkyl groups for the groups $R^{14}$, $R^{15}$ and $R^{16}$ in formula (V) and formula (VI) include methyl, ethyl, n- and iso-propyl, n, sec-, iso- and tert-butyl. Preferably $R^{14}$ is ethyl. Preferably $R^{15}$ and $R^{16}$ are hydrogen.

A further preferred subgroup of compounds within the present invention are the compounds of formula (VII) or a pharmaceutically acceptable salt or in vivo hydrolysable ester thereof:

$$\text{(VII)}$$

[Structure VII: R³.CO.NH—β-lactam with CHO-NH, Y¹, CH₂Q², CO₂H]

wherein $R^3$ is as hereinbefore defined; $Y^1$ is oxygen or sulphur; and $Q^2$ represents acetyloxy, a group -SHet, wherein Het is as hereinbefore defined, or $Q^2$ represents a subgroup of formula (h):

$$\text{(h)}$$

[Structure h: pyridinium ring with R^p and R^q substituents]

wherein $R^q$ and $R^p$ may be the same or different and each represents hydrogen, $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylalkyl, carbamoyl, trifluoromethyl, hydroxy, halogen, and aminoalkyl.

Suitable values of $R^3CO—$ within formula (VII) are those of formulae (a) to (g) as hereinbefore defined with reference to formula (II).

Suitable groups 'Het' within formula (VII) include substituted and unsubstituted 1,2,3-triazolyl; 1,2,4-triazolyl; tetrazolyl; oxazolyl; thiazolyl; 1,3,4-oxadiazolyl; 1,2,4-triazinyl; 1,3,4-thiadiazolyl or 1,2,4-thiadiazolyl. Preferably the groups 'SHet' is 1-methyl-1H-tetrazol-5-ylthio, -methyl-1,3,4-thiadiazol-5-ylthio, 1-carboxymethyl-1H-tetrazol-5-ylthio or 6-hydroxy- 2-methyl-5-oxo-2H-1,2,4-triazin-3-ylthio.

Suitably $\overline{R^q}$ represents hydrogen.

Suitably $R^p$ represents hydrogen, sulphonylalkyl or carbamoyl, preferably the substituent $R^p$ is in the 4-position.

Suitably $Y^1$ is sulphur.

Suitably $Y^1$ is oxygen.

Preferably $R^3$ within formula (VII) is a subgroup of formula (j):

$$\text{(j)}$$

[Structure j: CO—NH—CH(R⁸)— attached to piperazine-2,3-dione ring with N(R¹⁴), R¹⁵, R¹⁶]

wherein $R^8$, $R^{14}$, $R^{15}$ and $R^{16}$ are as hereinbefore defined with reference to formula (V).

Specific compounds within this invention include the following and pharmaceutically acceptable salts and in-vivo hydrolysable esters thereof:

(a)

6α-formamido-6β-[D-2-[(4-ethyl-2,3-dioxopiperazin-1-yl)carbonylamino]-2-phenylacetamido]penicillanic acid;

6α-formamido-6β-phenoxyacetamidopenicillanic acid;

6α-formamido-6β-[2-carboxy-2-(3-thienyl)acetamido]-penicillanic acid;

6α-formamido-6β-(2-carboxy-2-phenylacetamido)-penicillanic acid; and (b)

6β-[D-2-[(4-ethyl-2,3-dioxopiperazin-1-yl)carbonyl amino]-2-(4-hydroxyphenyl)acetamido]-6α-formamidopenicillanic acid;

6β-]L-2-[(4-ethyl-2,3-dioxopiperazin-1-yl)carbonyl amino]-2-(4-hydroxyphenyl)acetamido]-6α-formamidopenicillanic acid;

6α-Formamido-6β-[D-2-[(4-hydroxy-2-phenylaminopyrimidin-5-yl)ureido]-2-phenylacetamido]penicillanic acid;

6β-[D-2-Amino-2-(4-hydroxyphenyl)acetamido]6α-formamidopenicillanic acid;

6β8-[D-2-(3-cinnamoyl-3-methylureido)-2-phenylacetamido]-6α-formamidopenicillanic acid;

6α-Formamido-6β-[D-2-[(2-oxoimidazolidin-1-yl) carbonylamino]-2-phenylacetamido]penicillanic acid;

6α-Formamido-6β-[D-2-](3-methylsulphonyl-2-oxoimidazolidin-1-yl)carbonylamino]-2-phenylacetamido]penicillanic acid;

6α-Formamido-6β-[D-2-[3-methyl-3-(thien-2-ylcarbonyl)ureido]-2-phenylacetamido]penicillanic acid;

6α-Formamido-6β-[D-2-[(7-hydroxy-1,2,4-triazolo [2,3-a]pyrimidin-6-yl)carbonylamino]-2-phenylacetamido]penicillanic acid;

6β-[D-2-[(2-Benzylamino-4-hydroxypyrimidin-5-yl)carbonylamino]carbonylamino]-2-phenylacetamido]-6α-formamidopenicillanic acid;

6α-Formamido-6β-[D-2-(4-hydroxyphenyl)-2-[(2-oxoimidazolidin-1-yl)carbonylamino]acetamido]-penicillanic acid;

6β[D-2-(3-cinnamoyl-3-methylureido)-2-(4-hydroxyphenyl)acetamido]-6α-formamidopenicillanic acid; and (c)

6α-Formamido-6β-[D-2-[(4-ethyl-2,3-dioxopiperazin1-yl)carbonylamino]-2-(3,4-diacetoxyphenyl)acetamido]penicillanic acid;

6α-Formamido-6β-8-[D-2-[(4-ethyl2,3-dioxopiperazin 1-yl)carbonylamino]-2-(3,4-dihydroxyphenyl-)acetamido]penicillanic acid; and (d)

6β-[D-2-[3-[2-(4-Aminosulphonylphenyl)amino-4- hydroxypyrimidin-5-yl]ureido]-2-(4-hydroxyphenyl-)acetamido]-6α-formamidopenicillanic acid;

6α-Formamido-6β-[D-2-[[3-(furan-2-ylmethyleneamino)-2-oxoimidazolidin-1-yl]carbonylamino]-2-(4-hydroxyphenyl)acetamido]penicillanic acid;

6β-[D2-Carbamoylamino-3-phenylpropionamido)2-(4-hydroxyphenyl)acetamido]-6α-formamidopenicillanic acid;

6β-[2-[(Coumarin-3-yl)carbonylamino]-2-(4-hydroxyphenyl)acetamido]-6α-formamidopenicillanic acid;

6α-Formamido-6β-[D-2-(4-hydroxyphenyl)-2-[(3- methylsulphonyl-2-oxoimidazolidin-1-yl)carbonylamino]acetamido]penicillanic acid;

6β-[D-2-[(5-Ethoxycarbonylimadazol-4-yl)carbonylamino]-2-(4-hydroxyphenyl)acetamido]-6α-formamidopenicillanic acid;

6β-[D-2-[(4-Ethyl-2,3-dioxopiperazin-1-yl)carbonylamino]-2-(thien-2-yl)acetamido]-6α-formamido penicillanic acid;

6β-[L-2-[(4-Ethyl-2,3-dioxopiperazin-1-yl)carbonylamino]-2-(thien-2-yl)acetamido]-6α-formamidopenicillanic acid;

6β-[D-2-Amino-2-(thien-2-yl)acetamido]-6α-formamidopenicillanic acid;

6β-[L-2-Amino-2-(thien-2-yl)acetamido]-6α-formamidopenicillanic acid;

6β-[(2R,3S)-3-Benzyloxy-2-[(4-ethyl-2,3-dioxopiperazin-1-yl)carbonylamino]butyramido]-6α-formamidopenicillanic acid;

6α-Formamido-6β-[D-2-(4-hydroxyphenyl)-2-[3-[4- hydroxy-2-(phenylamino)pyrimidin-5-yl]ureido]acetamido]penicillanic acid;

7β-(D-2-Amino-2-phenylacetamido)-7β-formamidocephalosporanic acid; p0 7β-[D-2-[(4-Ethyl-2,3-dioxopiperazin-1-yl)carbonylamino]-2-phenylacetamido]-7α-formamidocephalosporanic acid;

7α-Formamido-7β-[D-2-[[3-(methylsulphonyl)-2- oxoimidazolidin-1-yl]carbonylamino]-2-phenylacetamido]cephalosporanic acid;

7β-[D-2-[(4-Ethyl-2,3-dioxopiperazin-1-yl)carbonylamino]-2-(4-hydroxyphenyl)acetamido]-7β-formamidocephalosporanic acid;

7β-[L-2-(4-Ethyl-2,3-dioxopiperazin-1-yl)carbonylamino]-2-(4-hydroxyphenyl)acetamido]-7α-formamidocephalosporanic acid;

7β-[D-2-[(4-Ethyl-2,3-dioxopiperazin-1-yl)carbonylamino]-2-(3,4-diacetoxyphenyl)acetamido]-7α-formamidocephalosporanic acid;

7α-Formamido-7β-(thien-2-ylacetamido)cephalosporanic acid;

7β-[2-Carboxy-2-(thien-3-yl)acetamido ]-7α-formamidocephalosporanic acid;

7β-[D-2-[(4-Ethyl-2,3-dioxopiperazin-1-yl)carbonylamino]-2-(thien-2-yl)acetamido]-7α-formamidocephalosporanic acid;

7β-[L-2-(4-Ethyl-2,3-dioxopiperazin-1yl)carbonylamino]-2-(thien-2-yl)acetamido]-7β-formamidocephalosporanic acid;

7β-[2-(2-Aminothiazol-4-yl)acetamido]-7α-formamido cephalosporanic acid; and (e)

6β-[D-2-[(Coumarin-3-yl)ureido]-2-(4-hydroxyphenyl-)acetamido]-6α-formamidopenicillanic acid;

6β-[D-2-[3-(4-oxo-4H-1-benzopyran-3-yl)ureido]-2-(4-hydroxyphenyl)acetamido]-6α-formamidopenicillanic acid;

6α-Formamido-6β-[D-2-[(4-hydroxy-7-methyl-1,8-naphthyridin-3-yl)carbonylamino]-2-(4-hydroxyphenyl)acetamido]penicillanic acid;

6β-[D-2-[D-2-amino-3-(N-methylcarbamoyl)propionamido]-2-(4-hydroxyphenyl)acetamido]-6α-formamidopenicillanic acid;

7β-[2-(Cyanomethylthio)acetamido]-7α-formamido cephalosporanic acid;

7β-[2-[(Aminocarbonyl)amino]-2-(thien-2-yl)acetamido]-7α-formamidocephalosporanic acid;

(f)

7α-Formamido-7β-[2-(thien-2-yl)acetamido]-3-[(1-methyl-1H-tetrazol-5-yl)thiomethyl]ceph-3-em-4- carboxylic acid;

7α-Formamido-7β-[2-(thien-2-yl)acetamido]-3-[(2-methyl-1,3,4-thiadiazol-5-yl)thiomethyl]ceph-3-em-4-carboxylic acid; and 7β-[2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]ceph-3-em-4-carboxylic acid;

7β-[2-(3,4-dihydroxyphenyl)-2-[(4-ethyl-2,3dioxopiperazin-1-yl)carbonylamino]-7α-formamido-3-[(1- methyl-1H-tetrazol-5-yl)thiomethyl]ceph-3-em-4-carboxylic acid;

6β-[L-2-[(4-ethyl-2,3-dioxopiperazin-1-yl)carbonylamino]-2-(3,4-dihydroxyphenyl)acetamido]-6α-formamidopenicillanic acid;

7α-formamido-3-(pyridiniummethyl)-7β-(thien-2-yl-acetamido)-ceph-3-em-4-carboxylic acid;

6β-phenoxyacetamido-6α-formamidopenam-3-carboxylic acid;

7β-[D-2-[(4-ethyl-2,3-dioxopiperazin-1-yl)-carbonylamino]-2-phenylacetamido]-7α-formamido 3-methyl-1-oxadethia-ceph-3-em-4-carboxylic acid;

6α-formamido-6β-(R-2-phenyl-2-sulphoacetamido)-penicillanic acid;

6β-[D-2-amino-2-(3,4-diacetoxyphenyl)acetamido]-6α-formamidopenicillanic acid;

7α-formamido-7β-[DL-2-phenoxycarbonyl-2-(thien-3-yl)acetamido]-3-methyl-1-oxadethia-ceph-3-em-4carboxylic acid;

6α-formamido-6β-(phenylacetamido)penicillanic acid;

7β-[(Z)-2-(2-aminothiazol-4-yl)-2-(1-carboxy-1-methylethoxyimino)acetamido]-7β-formamidocephalosporanic acid;

7β-[2-(3,4-diacetoxyphenyl)-2-[(4-ethyl-2,3-dioxopiperazin-1-yl)carbonylamino]acetamido]-7α-formamido-3-[(2-methyl-1,3,4-thiadiazol-5-yl)thiomethyl]ceph-3-em-4-carboxylic acid;

7β-[D-2-[(4-ethyl-2,3-dioxopiperazin-1-yl)carbonylamino]-2-(3,4-dihydroxyphenyl)acetamido]-7α-formamidocephalosporanic acid;

6β-[D-2-(3,4-diacetoxyphenyl)-2-[3-[2-(4-aminosulphonylphenyl)amino-4-hydroxypyrimidin-5-yl]ureido]acetamido-6α-formamidopenicillanic acid;

6β-[D-2-[D-2-amino-3-(N-methylcarbamoyl)propionamido]-2-(3,4-diacetoxyphenyl)acetamido]-6α-formamidopenicillanic acid;

7β-[2-[(4-ethyl-2,3-dioxopiperazin-1-yl)carbonylamino]-2-(4-hydroxyphenyl)acetamido]-7α-formamido-3-[(1-methyl-1H-tetrazol-5-yl)thiomethyl]-ceph-3-em-4-carboxylic acid;

7β-[2-[(4-ethyl-2,3-dioxopiperazin-1-yl)carbonylamino]-2-(3,4-diacetoxyphenyl)acetamido]-7α-formamido-3-[(2-methoxy-1,3,4-thiadiazol-5-yl)thiomethyl]ceph-3-em-4-carboxylic acid.

Of those compounds listed above part preferred compounds are the following and pharmaceutically acceptable salts and in-vivo hydrolysable esters thereof:

6β-Formamido-6β-[D-2-[(4-ethyl-2,3-dioxopiperazin-1-yl)carbonylamino]-2-(3,4-dihydroxyphenyl)acetamido]penicillanic acid; and 7β-[2-(3,4-dihydroxyphenyl)-2-[(4-ethyl-2,3-dioxopiperazin-1-yl)carbonylamino]-7α-formamido-3-[(1-methyl-1H-tetrazol-5-yl)thiomethyl)ceph-3-em-4-carboxylic acid.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a compound of formula (II) above together with a pharmaceutically acceptable carrier or excipient.

The composition may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth,or polyvinylpyrollidone; fillers, for example lactose, sugar, maizestarch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle befbre use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository base, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% to 99.5% by weight active agent, preferably from 10-60% by weight, of the active material, depending on the method of administration. Where the compositions are in unit dosage form, each unit will preferably contain from 50-500 mg of the active ingredient. The dosage as employed for adult human treatment will preferably range from 100 to 10000 mg per day, for instance 1500 mg per day depending on the route and frequency of administration.

The antibiotic compound according to the present invention may be the sole therapeutic agent in the compositions of the invention or is present in combination with other antibiotics and/or β-lactamase inhibitory agents.

Advantageously the compositions also comprise a compound of formula (VIII) or a pharmaceutically acceptable salt or ester thereof:

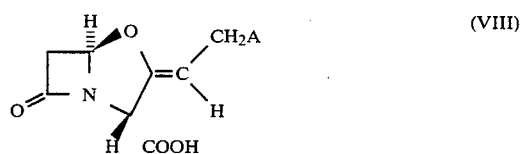

(VIII)

wherein A is hydroxyl, substituted hydroxyl, thiol, substituted thiol, amino, mono- or di-hydrocarbyl substituted amino, or mono- or di-acylamino.

A further advantageous composition comprises an antibacterially effective amount of an antibiotic compound according to the invention together with a β-lactamse inhibitory amount of a β-lactamase inhibitor of formula (IX) or a pharmaceutically acceptable salt or in vivo hydrolysable ester thereof:

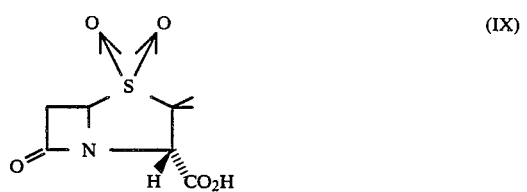

(IX)

and a pharmaceutically acceptable carrier or excipient.

Further suitable β-lactamase inhibitors include 6β-bromopenicillanic acid and salts and in vivo hydrolysable esters and 6β-iodopenicillanic acid and salts and in vivo hydrolysable esters thereof.

Such compositions of this invention which include a β-lactamase inhibitory amount of a β-lactamase inhibitor are formulated in a conventional manner using techniques and procedures per se known in the art.

The present invention also includes a method of treating bacterial infections in humans and animals which comprises the administration of a therapeutically effective amount of an antibiotic compound of this invention.

The antibiotic cmpounds of the present invention are active against a broad range of gram positive and gram negative bacteria, in particular they are useful for treatment of respiratory tract and urinary tract infections in humans and mastitis in cattle. A particular advantage of the antibacterially active compounds of this invention is their stability to β-lactamase enzymes and they are therefore effective against β-lactamase producing organisms.

In another aspect the present invention provides a process for the preparation of a compound of the present invention which process comprises formylating a β-lactam having an α-amino substituent on the carbon atom adjacent to the carbonyl group of the β-lactam ring.

The present invention further provides a process for the preparation of a compound of formula (I) which process comprises formylating a compound of formula (X):

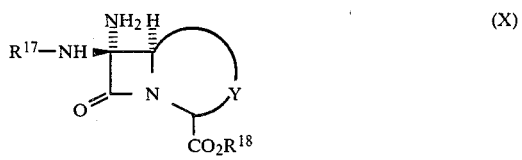

where any reactive groups may be protected; $R^{17}$ is an amino-protecting group or an acyl group as found in antibacterially active penicillins and cephalosporins and wherein any reactive groups may be protected; and $R^{18}$ is a readily removable carboxy protecting group; and thereafter, if necessary, carrying out one or more of the following steps:

(i) converting a group $R^{17}$ to a group $R^1$;
(ii) converting a group $R^{18}$ to a group $R^2$;
(iii) converting one group Z into a different group Z;
(iv) converting the product into a salt.

Suitable formylating agents include mixed anhydrides such as formic acetic anhydride. The reaction may suitably be carried out in a temperature in the range −50° C. to 30° C. in aprotic solvent such as, for example, dichloromethane, chloroform, dimethylformamide, tetrahydrofuran, hexamethylphosphoramide, or dimethylsulphoxide, in the presence of a tertiary base. A preferred tertiary base employed in the reaction is a base of the pyridine type, such as pyridine, lutidine or picoline.

A process for preparing compounds within formula (X) is disclosed in U.S. Pat. No. 3,962,214 and in UK Pat. No. 1348984.

Compounds of the formula (X) may be prepared by the reaction of a corresponding compound of the formula (XI):

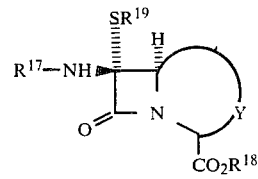

wherein Y, $R^{17}$ and $R^{18}$ are as hereinbefore defined, and $R^{19}$ is $C_{1-6}$ alkyl, aryl or benzyl; with anhydrous ammonia, an ammonium salt or an amine of the formula (XII):

$$R^{20}-NH_2 \quad (XII)$$

wherein $R^{20}$ is a removable protecting group such as benzyl; in the presence of a metal ion such as mercury, silver, thallium, lead or copper and thereafter if necessary removing any protecting group to form the compound of formula (X).

Suitable examples of the alkyl group for $R^{19}$ include $C_{1-6}$ alkyl groups such as methyl, ethyl, n-, or iso-propyl, and n-, sec-; iso-, or tert-butyl groups.

A preferred alkyl group for $R^{19}$ is methyl.

Suitable examples of the aryl group $R^{19}$ include phenyl, optionally substituted with $C_{1-6}$ alkyl, $C_{1-6}$ alkoxy, halogen, or nitro. Preferred aryl groups for $R^{19}$ include phenyl, o-, m- or p-methylphenyl, o-, m- or p-nitrophenyl, in particular p-methylphenyl.

Suitable solvents in which the reaction may be performed include for example, diethylether, tetrahydrofuran, dimethylformamide, methanol and hexamethylphosphoramide. The reactions are generally carried out under an inert atmosphere and at moderate to low temperatures i.e. in the range −100° C. to 30° C. The course of the reaction may be followed by conventional methods such as thin layer chromatography and terminated when an optimum quantity of product is present in the reaction mixture.

The preferred metal ion for use in the above process is the mercuric ion, aptly in the form of mercuric acetate.

Alternatively compounds of the formula (X) may be prepared by the reaction of a corresponding compound of the formula (XIII):

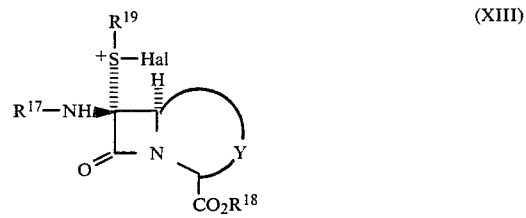

wherein $R^{17}$, $R^{18}$ and $R^{19}$ are as hereinbefore defined; Hal is chloro or bromo, with anhydrous ammonia, an ammonium salt or an amine of formula (XII) as hereinbefore defined and thereafter if necessary removing any protecting group to form the compound of formula (X). The compounds of the formula (XIII) may be prepared by the reaction of a compound of the formula (XI) as hereinbefore defined, with a halogenating agent such as chlorine or bromine in an inert solvent, for example dichloromethane, at a depressed temperature such as −80° C. to −30° C.

A further method of preparation of the compounds of the formula (X) comprises the reaction of a compound of the formula (XIV):

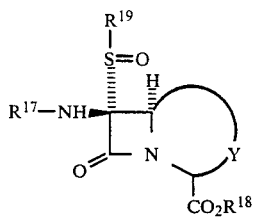
(XIV)

wherein $R^{17}$, $R^{18}$ and $R^{19}$ are as hereinbefore defined; with anhydrous ammonia, an ammonium salt or an amine of the formula (XII) as hereinbefore defined and thereafter if necessary removing any protecting group to form the compound of the formula (X).

Suitably such a reaction is performed at a non-extreme temperature for example 0° C.–60° C., normally 10° C.–40° C. and preferably ambient. The reaction is conveniently performed in an aprotic solvent such as tetrahydrofuran or dioxan.

It will be appreciated that the processes for preparation of a compound of formula (X) described hereinbefore proceed via an imine intermediate; other processes proceeding via such an intermediate are also included herein.

The compounds of the formula (XIV) may be prepared by the oxidation of a compound of the formula (XI) as hereinbefore defined. Such oxidation may conveniently performed in conventional manner, for example using a per-acid such as peracetic acid or m-chloroperbenzoic acid, suitably at an ambient or depressed temperature. Suitable solvents for such a sulphoxidation include ethylacetate, chloroform, dichloromethane, dioxan and tetrahydrofuran.

Examples of suitable protecting groups for the group $R^{20}$ include those known in the art as being cleavable to provide the —NH—. Mention may be made of silyl groups such as trimethylsilyl, tertiarybutyldimethylsilyl, and tri-isopropylsilyl. A preferred protecting group is (p-methoxymethoxy)phenyl which is removable by cerium ammonium nitrate. Other protecting groups of interest include those cleavable by methanolysis such as —C(CO$_2$R)=O (This moiety may be derived from groups of the type —C(CO$_2$R)=C(CH$_3$)$_2$). Further suitable protecting groups include 4-nitrobenzyl and 2,4-dimethoxybenzyl which is removable with potassium persulphate.

The oxidation of a compound of the formula (XI) which contains sulphur atoms in addition to that shown in the formula may oxidise the additional sulphur atoms and accordingly it may be necessary to reduce the thus formed sulphoxide or sulphone to the corresponding sulphide.

Preferably Y in the compound of formula (XIII) is —O—CH$_2$—CZ= wherein Z is as hereinbefore defined.

The starting material for the above processes i.e. compound of formula (XI) above may be prepared by acylation or protection, under conventional conditions of the compound (XV):

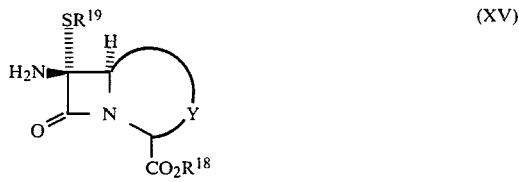
(XV)

wherein $R^{18}$, $R^{19}$ and Y are as defined hereinbefore.

Compounds of the formula (XV) may be prepared by methods known or analogous to those known for the preparation of 7α-substituted-thio cephalosporins and 6α-substituted-thio penicillins.

Compounds of formula (XV) may suitably be prepared from a Schiff's base derivative as outlined in Scheme 1.

Scheme 1

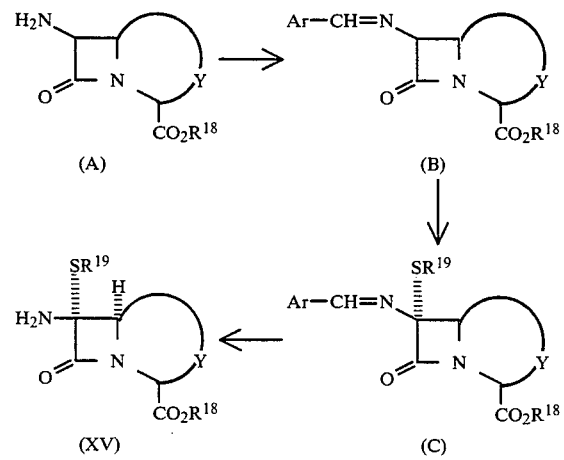

The compound of formula (XV) is prepared by reacting the amino compound (A) with an aldehyde of formula Ar—CHO wherein Ar is an aryl group to form the Schiff base (B). The Schiff base (B) is reacted with a base to form an anion which is treated with a thiosulphonate of formula:

$R^{19}S.SO_2R^{19}$ or a sulphenyl chloride of formula:

$R^{19}SCl$ wherein $R^{19}$ is as hereinbefore defined to give the compound of formula (C). Acidic hydrolysis of the Schiff base gives the β-amino compound of formula (XV).

Compounds of formula (XV) may also be prepared by reacting a thiooxime compound of formula (XVI):

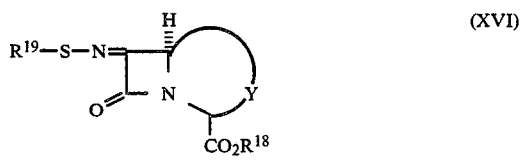
(XVI)

where $R^{18}$ and $R^{19}$ are as defined hereinbefore above with a tri(alkyl)phosphine or tri(aryl)phosphine, followed by treatment with an acid catalyst such as silica gel. The process is as described in U.S. Pat. No. 4,119,778 and in J Amer Chem Soc, 1980, 102, 1690.

Compounds within formula (XV) and (XVI) may also be prepared by the process disclosed in U.S. Pat. No. 3,962,214 or an appropriate modification thereof.

The antibacterially active compounds of formula (II) as hereinbefore defined may suitably be prepared by reacting a compound of formula (XVII):

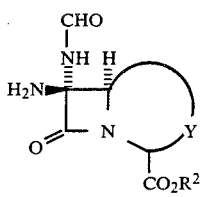 (XVII)

wherein the amino group is optionally substituted with a group which permits acylation to take place and $R^2$ is as hereinbefore defined with reference to formula (I) above, with an N-acylating derivative of an acid of formula (XVIII):

$R^3CO_2H$ (XVIII)

wherein $R^3$ is as defined with respect to formula (II) and wherein any reactive groups therein may be protected; and thereafter, in necessary, carrying out one or more of the following steps:
(i) removing any carboxyl-protecting group $R^2$;
(ii) removing any protecting groups on the side-chain group;
(iii) further derivatising the side chain group;
(iv) converting one group Z to a different group Z;
(v) converting the product into a salt or in vivo hydrolysable ester thereof.

Suitable groups which permit acylation to take place and which are optionally present on the amino group of the starting material of the formula (XVII) include N-silyl, N-stannyl and N-phosphorus groups, for example trialkylsilyl groups such as trimethylsilyl, trialkyltin groups such as tri-n-butyltin, groups of formula —P.-$R^aR^b$ wherein $R^a$ is an alkyl, haloalkyl, aryl, aralkyl, alkoxy, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being —P-$(OC_2H_5)_2$, —$P(C_2H_5)_2$,

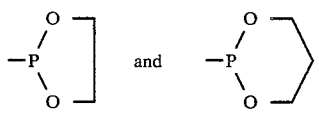

The carboxyl group may be regenerated from any of the above esters by usual methods appropriate to the particular $R^2$ group, for example, acid - and base -catalysed hydrolysis, or by enzymically - catalysed hydrolysis, or by hydrogenolysis.

Suitable carboxyl-protecting derivatives for the group —$CO_2R^2$ in formula (XVII) include salts and ester derivatives of the carboxylic acid as described hereinbefore with reference to formula (I).

A reactive N-acylating derivative of the acid (XVIII) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example, tertiary amine (such as triethylamine, pyridine or dimethylaniline), an inorganic base (such as calcium carbonate or sodium bicarbonate) or an oxirane, which binds hydrogen halide liberated in the acylation reaction. The oxirane is preferably a $(C_{1-6})$-1,2-alkylene oxide - such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (XVIII) or a salt thereof with a halogenating (e.g. chlorinating or brominating) agent such as phosphorus pentachloride, thionyl chloride or oxalyl chloride.

Alternatively, the N-acylating derivative of the acid (XVIII) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as p-toluenesulphonic acid). When a symmetrical anhydride is employed, the reaction may be carried out in the presence of 2,6-lutidine as catalyst.

Alternative N-acylating derivatives of acid (XVIII) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, or 8-hydroxyquinoline; or amides such as N-acylsaccharins, N-acylthiazolidin-2-thione or N-acylphthalimides; or an alkylidene iminoester prepared by reaction of the acid (XVIII) with an oxime.

Other reactive N-acylating derivatives of the acid (XVIII) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

Aptly the acid of formula (XVIII) is an acid of formula (XIX):

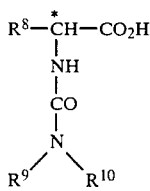 (XIX)

wherein $R^8$, $R^9$ and $R^{10}$ are as hereinbefore defined; thereby affording a compound of formula (III) as hereinbefore defined.

Aptly Y in formula (XVII) is —S—C(CH$_3$)$_2$— and the acid of formula (XVIII) is an acid of formula (XX):

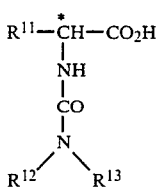 (XX)

wherein $R^{11}$, $R^{12}$ and $R^{13}$ are as hereinbefore defined: thereby affording a compound of formula (IV) as hereinbefore defined.

The compounds of formula (III) may also suitably be prepared by reacting a compound of formula (XXI):

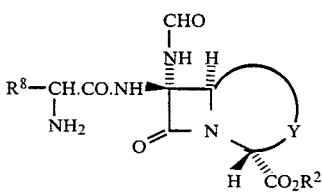 (XXI)

wherein $R^2$, $R^8$ and Y are as hereinbefore defined and the α-amino group is optionally substituted with a group which permits acylation to take place, and any reactive groups may be protected with an N-acylating derivative of an acid of formula (XXII):

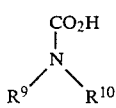 (XXII)

wherein $R^9$ and $R^{10}$ are as hereinbefore defined and wherein any reactive groups may be protected; and thereafter, if necessary, carrying out one or more of the following steps:
(i) removing any carboxyl-protecting group $R^2$;
(ii) removing any protecting groups on the side-chain group;
(iii) converting one group Z to a different group Z;
(iv) converting the product into a salt or in vivo hydrolysable ester thereof.

The compounds of formula (IV) as hereinbefore defined are aptly prepared by reacting a compound of formula (XXIII):

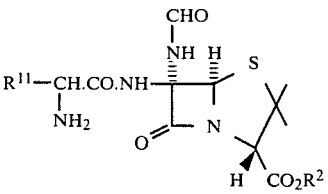 (XXIII)

wherein the α-amino group is optionally substituted with a group which permits acylation to take place and any reactive groups may be protected, and $R^2$ and $R^{11}$ are as hereinbefore defined with an N-acylating derivative of an acid of formula (XXIV):

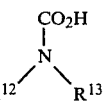 (XXIV)

wherein $R^{12}$ and $R^{13}$ are as defined with respect to formula (IV) above and any reactive groups may be protected; and thereafter, if necessary, carrying out one or more of the following steps:
(i) removing any carboxyl-protecting group $R^2$;
(ii) removing any protecting groups on the side-chain group;
(iii) converting the product into a salt or in vivo hydrolysable ester thereof.

The compounds of formula (XXI) herein which are inter alia intermediates for the compounds of formula (III) as hereinbefore defined may be prepared by reacting a compound of formula (XVII) with an N-acylating derivative of an acid of formula (XXV):

$$R^8.\overset{*}{C}H.CO_2H$$
$$|$$
$$NHR^{21}$$
(XXV)

wherein $R^{21}$ is an amino-protecting group and thereafter removing protecting group $R^{21}$.

Suitable amino protecting groups $R^{21}$ include those disclosed hereinbefore with reference to group $R^1$, with alkoxycarbonyl groups such as, for example, 4-nitrobenzyloxycarbonyl and trichloroethyloxycarbonyl being particularly preferred.

The compounds of formula (XXIII) herein which are inter alia intermediates for the compounds of formula (IV) as hereinbefore defined may be prepared by reacting a compound of formula (XXVI):

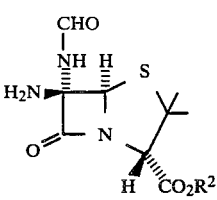 (XXVI)

wherein $R^2$ is as defined hereinbefore with an N-acylating derivative of an acid of formula (XXVII):

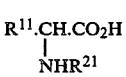 (XXVII)

wherein R[11] is as defined hereinbefore and any reactive groups therein may be protected and R[21] is an amino-protecting group as hereinbefore defined; and thereafter removing protecting group R[21].

The antibacterially active compounds of formula (II) as hereinbefore defined may also suitably be prepared by formylating a compound of formula (XXVIII):

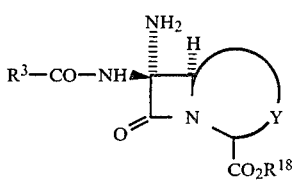
(XXVIII)

wherein $R^3$, $R^{18}$ and Y are as hereinbefore defined and wherein any reactive groups may be protected and thereafter, if necessary, carrying out one or more of the following steps:

(i) removing any carboxyl-protecting group $R^{18}$;
(ii) removing any protecting groups on the side-chain group;
(iii) converting one group Z to a different group Z;
(iv) further derivatising the side-chain group;
(v) converting the product into a salt or in vivo hydrolysable ester thereof.

When Y in formula (XXVIII) is $-S-C(CH_3)_2-$ and $R^3$ is a group of formula (XXIX):

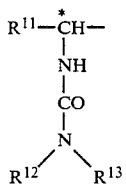
(XXIX)

wherein $R^{11}$, $R^{12}$ and $R^{13}$ are as hereinbefore defined the process affords a compound of formula (IV) as hereinbefore defined.

The intermediate compound of formula (XVII) as hereinbefore defined may suitably be prepared by formylating a compound of formula (XXX):

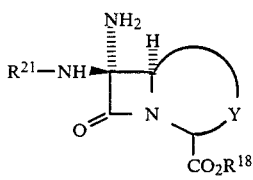
(XXX)

wherein $R^{18}$, $R^{21}$ and Y are as hereinbefore defined and thereafter removing the protecting group $R^{21}$ and if necessary, converting a group $R^{18}$ to a group $R^2$.

Suitable formylating agents and reaction conditions are as hereinbefore defined.

When Y in the compound of formula (XXX) is $-S-C(CH_3)_2-$ the process produces the compound of formula (XXVI) herein.

The sub-group of compounds within the present invention of formula (XXXI):

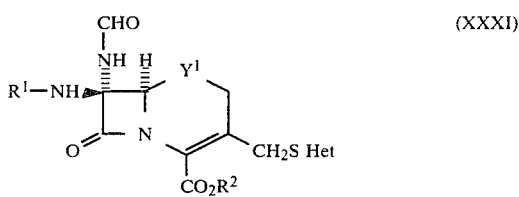
(XXXI)

wherein $Y^1$ and 'Het' are as defined hereinbefore with reference to formula (VII) and $R^1$ and $R^2$ are as defined hereinbefore with reference to formula (X) may suitably be prepared by reacting a compound of formula (XXXII):

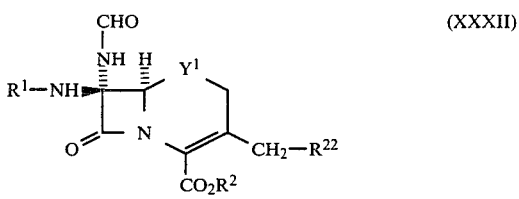
(XXXII)

wherein $Y^1$, $R^1$ and $R_2$ are as defined hereinbefore and wherein any reactive groups may be protected and $R^{22}$ is a leaving group; with a thiol of formula:

HetSH with the proviso that when $R^{22}$ is an acyloxy group $-CO_2R^2$ must be in the free acid form or a salt thereof.

Suitable leaving groups $R^{22}$ include halogen such as iodide or bromide or an acyloxy groups such as, for example the acetyloxy group.

The thiol HetSH may be reacted as the free compound or a salt with an alkali metal such as sodium or potassium. This reaction is desirably conducted in a solvent. For example, use can be made of water, or organic solvents inert to the starting compounds, such as dimethylformamide, dimethylacetamide, dioxane, acetone, alcohol, 1,2-dichloroethane, acetonitrile, dimethylsulfoxide or tetrahydrofuran, or mixtures thereof. The reaction temperature and time depend, among other factors, upon the starting compounds and solvent to be employed but generally the reaction is carried out at a selected temperature within the range of 0° to 100° C. for a selected time of a few hours to several days. The reaction is desirably conducted between pH 3 and 7.

To prevent oxidation of the thio compounds it is advantageous to carry out the reaction in an inert gaseous atmosphere, e.g. nitrogen gas.

The subgroup of compounds within the present invention of formula (XXXIII):

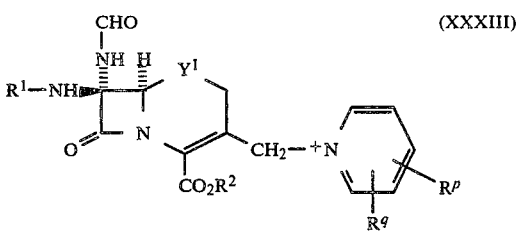
(XXXIII)

wherein $R^1$, $R^2$, $R^p$, $R^q$ and $Y^1$ are as defined hereinbefore may suitably be prepared by reacting a compound of formula (XXXII) as hereinbefore defined with the appropriately substituted pyridine.

Suitably the reaction with the pyridine is carried out in a polar solvent such as water, and in the presence of a catalyst such as an alkali metal thiocyanate or an alkali metal halide such as, for example sodium iodide.

From the foregoing it will be appreciated that the compounds of (XVII) and protected derivatives thereof are valuable intermediates and form another preferred aspect of the present invention.

Particularly preferred compounds within formula (XVII) are the zwitteronic compounds of formula (XXXIV) or a salt thereof:

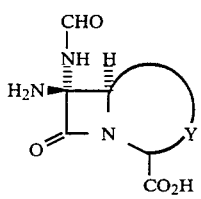
(XXXIV)

wherein Y is as defined hereinbefore.

Suitably Y in formulae (XVII) and (XXXIV) is —S—C(CH$_3$)$_2$—, —S—CH$_2$—, —S—CH$_2$—C(CH$_2$Q′)= or —O—CH$_2$—C(CH$_2$Q′)=, wherein Q′ is as hereinbefore defined.

Preferred values for Y in the compounds of formulae (XVII) and (XXXIV) are —S—C(CH$_3$)$_2$— and —S—CH$_2$—C(CH$_2$Q)=, i.e. when the compounds are derivatives of the penicillin and cephalosporin nucleus.

A particularly preferred value for Y in formulae (XVII) and (XXXIV) is —S—C(CH$_3$)$_2$—.

Specific compounds within formula (XVII) include the following or a salt thereof:

6$\beta$-amino-6$\alpha$-formamidopenicillanic acid or the benzyl ester thereof;

7$\beta$-amino-7$\alpha$-formamidocephalosporanic acid or the t-butyl ester thereof;

6$\beta$-amino-6$\alpha$-formamidopenam-3-carboxylic acid or the benzyl ester thereof;

7$\beta$-amino-7$\alpha$-formamido-3-(acetoxymethyl)-1-oxadethiaceph-3-em-4-carboxylic acid or the diphenylmethyl ester thereof;

7$\beta$-amino-7$\alpha$-formamido-3-[(1-methyl-1H-tetrazol-5-yl)thiomethyl]ceph-3-em-4-carboxylic acid or the diphenylmethyl ester thereof;

7$\beta$-amino-7$\alpha$-formamido-3-[(2-methyl-1,3,4-thiadiazol-5-yl)thiomethyl]ceph-3-em-4-carboxylic acid or the diphenylmethyl ester thereof;

7$\beta$-amino-7$\alpha$-formamido-3-methyl-1-oxadethiaceph-3-em-4-carboxylic acid or the t-butyl ester thereof;

7$\beta$-amino-7$\alpha$-formamido-3-(pyridiniummethyl)-ceph-3-em-4-carboxylic acid or the diphenylmethyl ester thereof;

7$\beta$-amino-7$\alpha$-formamido-3-[(6-hydroxy-4-methyl-5-oxo-4H-1,2,4-triazin-3-yl)thiomethyl]ceph-3-em-4-carboxylic acid or the diphenylmethyl ester thereof;

7$\beta$-amino-7$\alpha$-formamido-3-[(2-methoxy-1,3,4-thiadiazol-5-yl)thiomethyl]ceph-3-em-4-carboxylic acid or the diphenylmethyl ester thereof; and 7$\beta$-amino-7$\alpha$-formamido-3-[(1-carboxymethyl-1H-tetrazol-5-yl)thiomethyl]-ceph-3-em-4-carboxylic acid or the diphenylmethyl ester thereof.

The antibiotic compounds of the present invention are active against a wide range of gram negative and gram positive organisms including E.coli such as, for example ESS, JT4, JT425 and NCTC 10418; Pseudomonas Spp. such as Ps.aeruginosa for example 10662 and Dalgleish; Serratia marcescens US32; Klebsiella aerogenes A; Enterobacter cloacae N1; P.mirabilis such as, for example C977 and 889; P.morganii; P.rettgeri; B.subtilis; Staph aureus such as, for example Oxford and Russell; N.catarrhalis 1502; Strep faecalis I; $\beta$-Haemolytic Strep CN10. The MIC data included in the following examples is representative of the activity of the compounds of the present invention.

The following Examples illustrate the preparation and use of the compounds of the present invention.

EXAMPLE 1

6$\alpha$-Formamido-6$\beta$-phenoxyacetamido penicillanic acid sodium salt (a) Benzyl 6$\alpha$-amino-6$\beta$-phenoxyacetamido penicillanate Benzyl 6$\alpha$-methylthio-6$\beta$-phenoxyacetamido penicillanate (389 mg. 0.8 mmol) in DMF (10 ml) at $-40°$ C. under nitrogen, was treated with a solution of mercuric acetate (260 mg, 0.8 mmol) in DMF (1 ml), followed immediately by a solution of anhydrous ammonia (15 mg, 0.88 mmol) in DMF (1 ml). The reaction solution was allowed to warm to $0°$ C. over 0.75 hour before being poured into ether and washed with water and brine. The organic solution was dried over magnesium sulphate, filtered and evaporated to leave the essentially pure product as a pale yellow foam (320 mg, 88%), $\nu_{max}$(CH$_2$Cl$_2$) 3385, 3310, 1790, 1748, 1690, 1495 cm$^{-1}$; $\delta$(CDCl$_3$) 1.37 (6H, s, gem dimethyls), 2.78 (2H, br.s, amino protons), 4.51 (3H, s, PhOCH$_2$— and C-3 proton), 5.19 (2H, s, ester CH$_2$), 5.48 (1H, s, C-5 proton), 6.70–7.60 (10H, m, aromatics) and 7.90 (1H, br.s, amido proton).

(b) Benzyl 6$\alpha$-formamido-6$\beta$-phenoxyacetamido penicillanate

A solution of benzyl 6$\alpha$-amino-6$\beta$-phenoxyacetamido penicillanate (320 mg, 0.7 mmol) in anhydrous dichloromethane (20 ml) at $0°$ C., was treated sequentially with pyridine (553 mg, 565 $\mu$l, 7 mmol) and formic-acetic anhydride (310 mg, 3.5 mmol). The reaction solution was stirred at $0°$–$5°$ C. for 1.5 hour before being washed successively with 0.5 N hydrochloric acid, dilute sodium bicarbonate solution and brine. It was dried over magnesium sulphate, filtered and evaporated to leave the product as a white foam (300 mg). This was purified on silica gel to afford the title compound (240 mg, 71%), $\nu_{max}$(CH$_2$Cl$_2$) 3395, 3310, 1792, 1748, 1700, 1690 (sh.), 1495 cm$^{-1}$; $\delta$(CDCl$_3$) 1.36 (6H, s, gem dimethyls), 4.51 (3H, s, PhOCH$_2$— and C-3 proton), 5.19 (2H, s, ester CH$_2$), 5.75 (1H, s, C-5 proton), 6.70–7.50 (10H, m, aromatics), 8.19 (1H, s, formyl proton), 8.23 (1H, s, 6$\beta$-amido proton) and 8.46 (1H, s, formamido proton).

(c) 6$\alpha$-formamido-6$\beta$-phenoxyacetamido penicillanic acid, sodium salt A solution of benzyl 6$\alpha$-formamido-6$\beta$-phenoxyacetamido penicillanate (210 mg, 0.44 mmol) in THF (10 ml) was added to a suspension of 10% palladium on charcoal (250 mg) in ethanol (10 ml) and water (1 ml) which had been pre-hydrogenated for 0.5 hour. The mixture was hydrogenated for 2.5 hours and then the catalyst was filtered and washed with dilute sodium bicarbonate solution and THF. The organic solvents were evaporated and the aqueous solution washed with ethyl acetate (3×30 ml) before being acidified to pH 1.5 with dilute hydrochloric acid. The product was extracted into ethyl acetate (3×30 ml) and the combined extracts were washed with brine, dried over magnesium sulphate and evaporated to dryness. The resultant foam (130 mg) was dissolved in acetone and treated with the theoretical amount of 2N sodium ethyl hexanoate in methyl isobutyl ketone (170 µl, 0.34 mmol). Anhydrous ether was then added and the precipitated sodium salt was filtered and washed with ether. The product was dried in vacuo over phosphorous pentoxide to afford 99 mg (55%). Hplc showed one peak, $\nu_{max}$ (KBr) 1765, 1675, 1600, 1655 cm$^{-1}$. Free acid: $\delta[(CD_3)_2CO]$ 1.51 (6H, s, gem dimethyls), 4.50 (1H, s, C-3 proton), 4.68 (2H, s, PhOC$\underline{H}_2$—), 5.72 (1H, s, C-5 proton), 6.48 (br.s, —CO$_2$H and $\overline{H}_2$O), 6.80-7.60 (5H, m, aromatics) and 8.25, 8.$\overline{52}$ and 8.60 (3H, 3s, amido and formyl protons).

MIC against *P.mirabilis* 889 is >100 µg/ml.

EXAMPLE 2

6α-Formamido-6β-(2-carboxy-2-phenylacetamido)-penicillanic acid, di-sodium salt (a) benzyl 6α-methylthio-6β-[2-(p-nitrobenzyloxycarbonyl)-2-phenylacetamido]penicillanate A solution of 2-(p-nitrobenzyloxycarbonyl)-2-phenylacetyl chloride (2 mmol) in dichloromethane (10 ml) was added dropwise with stirring to an ice cooled solution of benzyl 6α-methylthio-6β-amino penicillanate (0.70 g, 2 mmol) and pyridine (0.24 g, 3 mmol) in dichloromethane (30 ml). The reaction mixture was stirred at 0°–5° C. for 1 hour, followed by 2 hours at room temperature. It was then washed sequentially with 0.5 N hydrochloric acid, dilute sodium bicarbonate solution and brine, before being dried over magnesium sulphate filtered and evaporated to dryness. The resultant pale yellow foam (1.06 g) was purified on silica gel to afford the pure product as a white foam (0.83 g, 64%), $\nu_{max}$(CH$_2$Cl$_2$) 3400, 3325, 1788, 1745, 1690, 1530, 1355, 1320 cm$^{-1}$; $\delta$(CDCl$_3$) 1.30 (6H, br.s, gem dimethyls), 2.11 and 2.20 (3H, 2s, —SCH$_3$ diastereoisomers), 4.42 (1H, s, C-3 proton), 4.85 (1$\overline{H}$, s, α-proton), 5.19 (2H, s, benzyl ester C$\underline{H}_2$), 5.29 (2H, s, PNB ester C$\underline{H}_2$), 5.56 (1H, s, C-5 proton), 7.10–7.65 (12H, m, aromatics) and 7.90–8.30 (3H, m, aromatics and amido proton).

(b) benzyl 6α-amino-6β-[2-(p-nitrobenzyloxycarbonyl)-2-phenylacetamido]penicillanate A solution of benzyl 6α-methylthio-6β-[2-(p-nitrobenzyloxycarbonyl)-2-phenylacetamido]penicillanate (390 mg, 0.6 mmol) in DMF (10 ml) at −40° C. under nitrogen, was treated with mercuric acetate (190 mg, 0.6 mmol) in dry DMF (1 ml) followed immediately by a solution of anhydrous ammonia (11 mg, 0.66 mmol) in DMF (0.5 ml). The mixture was stirred at −40° C. to −10° C. over 1 hour before being poured into ether and washed with water and brine. It was dried over magnesium sulphate, filtered and evaporated to afford the virtually pure product as a white foam (310 mg, 84%), $\nu_{max}$ (CH$_2$Cl$_2$) 3395, 3330, 1787, 1742, 1682, 1530, 1357 cm$^{-1}$; (CDCl$_3$) 1.31 (6H, br.s, gem dimethyls), 2.63 (2H, s, amino protons), 4.42 (1H, s, C-3 proton), 4.73 (1H, s, α-proton), 5.20 (2H, s, benzyl ester C$\underline{H}_2$), 5.31 (2H, s, PNB ester C$\underline{H}_2$), 5.41 (1H, s, C-5 protoin), 7.20–7.60 (12H, m, aromatics), 7.86 (1H, s, amido proton) and 8.20 (2H, part AA'BB', PNB aromatics).

(c) benzyl 6α-formamido-6β-[2-(p-nitrobenzyloxycarbonyl)-2-phenylacetamido]penicillanate A solution of benzyl 6α-amino-6β-[2-(p-nitrobenzyloxycarbonyl)-2-phenylacetamido]penicillanate (310 mg, 0.5 mmol) in dry dichloromethane (20 ml) at 0° C., was treated sequentially with pyridine (400 mg, 5 mmol) and formicacetic anhydride (220 mg, 2.5 mmol). The reaction solution was stirred at 0°–5° C. for 1 hour, before being washed with 0.5 N hydrochloric acid, dilute sodium bicarbonate solution and brine. It was dried over magnesium sulphate, filtered and evaporated to leave the crude product (250 mg). This was purified on silica gel to afford the title compound as a white foam (220 mg, 69%), $\nu_{max}$ (CH$_2$Cl$_2$) 3400, 3315, 1795, 1750, 1700, 1690 (sh), 1530, 1355 cm$^{-1}$; $\delta$(CDCl$_3$) 1.26 (6H, br.s, gem dimethyls), 4.42 and 4.46 (1H, 2s, C-3 proton diastereoisomers), 4.85 (1H, br.s, α-proton), 5.18 (2H, s, benzyl ester C$\underline{H}_2$), 5.27 (2H, s, PNB ester C$\underline{H}_2$), 5.70 (1H, s, C-5 proton), 7.10–7.60 (12H, m, aromatics) and 7.90–8.70 (5H, m, aromatics, amido and formyl protons); m/e 557, 486, 377, 270, 249, 212,136, 114, 91.

(d) 6α-formamido-6β-(2-carboxy-2-phenylacetamido) penicillanic acid, di-sodium salt A solution of benzyl 6α-formamido-6β-[2-(p-nitrobenzyloxycarbonyl)-2-phenylacetamido]penicillanate (200 mg, 0.31 mmol) in THF (10 ml) was added to a suspension of 10% palladium on charcoal (200 mg) in ethanol (10 ml) and water (1 ml) which had been pre-hydrogenated for 1 hour. The mixture was then hydrogenated for 3 hours and then the catalyst was filtered and washed with dilute sodium bicarbonate solution. The filtrate was washed with ethyl acetate (3×30 ml) before being acidified to pH 1.5 with 1 N hydrochloric acid. The product was extracted into ethyl acetate (3×30 ml) and the combined extracts were washed with brine, dried over magnesium sulphate, filtered and evaporated to dryness to leave the free acid as a colourless oil (110 mg). This was dissolved in acetone and treated with 2N sodium ethyl, hexanoate in methylisobutyl ketone (260 µl, 0.52 mmol) followed by anhydrous ether. The resultant precipitate was filtered, washed with ether and dried in vacuo to afford the product as a white solid (103 mg, 72%). Hplc showed one peak, $\nu_{max}$ (KBr) 25 1765, 1665, 1600 cm$^{-1}$. Free acid: $\delta](CD_3)_2CO]$ 1.10–1.70 (6H, 4s, gem dimethyl diastereoisomers), 4.41 and 4.48 (1H, 2s, C-3 proton diastereoisomers), 4.89 (1H, s, α-proton), 5.66 (1H, s, C-5 proton), 7.20–7.80 (m, aromatics, —CO$_2$H and water) and 8.10–9.10 (3H, m, amido and formyl $\overline{d}$iastereoisomers).

MIC against P.mirabilis 889 is 50 µg/ml.

EXAMPLE 3

6α-Formamido-6β-[2-carboxy-2-(3-thienyl)acetamido]-penicillanic acid, di-sodium salt (a) benzyl 6α-methylthio-6β-[2-(p-nitrobenzyloxycarbonyl)-2-(3-thienyl)acetamido]penicillanate A solution of benzyl 6β-amino-6α-(methylthio)-penicillanate (1.76 g) and N,N'-dicyclohexylcarbodiimide (1.13 g) in tetrahydrofuran (10 ml) was stirred and cooled to 0°–5° C. and treated dropwise with a solution of 2-(p-nitrobenzyloxycarbonyl)-2-(thien-3-yl) acetic acid in tetrahydrofuran (10 ml). The reaction mixture was stirred at 0°–5° C. for 0.5 h, then kept for 18 h at 4° C. It was diluted with ethyl acetate and the precipitated N,N'-dicyclohexylurea removed by filtration. The filtrate was evaporated to dryness in vacuo and the resulting, white foam chromatographed on silica gel 60 (230 mesh ASTM) to give the title compound (2.67 g, 81%). $\nu_{max}$(CH$_2$Cl$_2$) 3390, 3320, 1785, 1748, 1695, 1525, 1350, 1318 cm$^{-1}$; δ(CDCl$_3$) 1.31 (6H, s, gem dimethyls), 2.15 and 2.21 (3H, 2s, —SCH$_3$ diastereoisomers) 4.44 (1H, s, C-3 proton), 4.96 and 4.99 (1H, 2s, α-proton diastereoisomers), 5.20 (2H, s, benzyl ester CH$_2$), 5.32 (2H, s, PNB ester CH$_2$), 5.58 (1H, s, C-5 proton), 7.10–7.60 (10H, m, aromatics), 7.85 and 7.91 (1H, 2s, amido diastereoisomers) and 8.20 (2H, part AA'BB', PNB aromatics); m/e 655,607, 550, 456, 303, 276, 250, 136, 114, 91.

(b) benzyl 6α-amino-6β-[2-(p-nitrobenzyloxycarbonyl)-2-(3-thienyl)acetamido]penicillanate A solution of benzyl 6α-methylthio-6β-[2-(p-nitrobenzyloxycarbonyl)-2-(3-thienyl)acetamido]-penicillanate (1.33 g, 2 mmol) in DMF (30 ml) at −40° C. under nitrogen, was treated with mercuric acetate (0.64 g, 2 mmol) in dry DMF (3 ml), followed immediately by a solution of anhydrous ammonia (38 mg, 2.2 mmol) in DMF (1 ml). The mixture was stirred at −40° C. to −10° C. for 1 hour before being poured into ether and washed with water and brine. It was dried over magnesium sulphate, filtered and evaporated to afford the virtually pure product as a foam (1.18 g, 94%) $\nu_{max}$ (CH$_2$Cl$_2$) 3380, 3310, 1785, 1745, 1690, 1525, 1350 cm$^{-1}$; δ(CDCl$_3$) 1.33 (6H, s, gem dimethyls), 2.79 (2H, br.s, amino protons), 4.46 (1H, s, C-3 proton), 4.93 (1H, s, α-proton), 5.20 (2H, s, benzyl ester CH$_2$), 5.31 (2H, s, PNB ester CH$_2$), 5.43 (1H, s, C-5 proton), 7.10–7.70 (10H, m, aromatics), 7.87 (1H, s, amido proton) and 8.21 (2H, part AA'BB', PNB aromatics).

(c) benzyl 6α-formamido-6β-[2-(p-nitrobenzyloxycarbenyl)-2-(3-thienyl)acetamido]penicillanate A solution of 6α-amino-6β-[2-(p-nitrobenzyloxycarbonyl)-2-(3-thienyl)acetamido]penicillanate (1.15 g, 1.8 mmol) in dry dichloromethane (30 ml) at 0° C. was treated sequentially with pyridine (1.42 g, 18 mmol) and formic-acetic anhydride (0.79 g, 9 mmol). The reaction solution was stirred at 0°–5° C. for 2 hours before being washed with 0.5N hydrochloric acid, dilute sodium bicarbonate solution and brine. It was dried over magnesium sulphate, filtered and evaporated to leave the crude product (0.97 g). This was purified on silica gel to afford the title compound as a white foam (0.16 g, 52%) $\nu_{max}$ (CH$_2$Cl$_2$) 3390, 3310, 1790, 1745, 1695, 1525, 1350 cm$^{-1}$; δ(CDCl$_3$) 1.28 (6H, m, gem dimethyl diastereoisomers), 4.00 and 4.02 (1H, 2s, C-3 proton diastereoisomers), 4.83 and 4.86 (1H, 2s, α-proton diastereoisomers), 5.14 (2H, s, benzyl ester CH$_2$), 5.23 (2H, s, PNB ester CH$_2$), 5.60 (1H, s, C-5 protons), 700–750 (10H, m, aromatics), 7.79 and 7.82 (1H, 2s, exchangeable with D$_2$O, 6β-amido diastereoisomers) and 7.97–8.25 (4H, m, 1H exchangeable with D$_2$O, PNB aromatics, formamido and formyl proton); m/e 499, 471, 469, 456, 441, 303, 276, 250, 240, 194, 153, 136, 114, 91.

(d) 6α-formamido-6β-[2-carboxy-2-(3-thienyl)acetamido]-penicillanic acid, di-sodium salt A solution of benzyl 6α-formamido-6β-[2-(p-nitrobenzyloxycarbonyl)-2-(3-thienyl)acetamido]-penicillanate (0.55 g, 0.84 mmol) in THF (15 ml) was added to a suspension of 10% palladium on charcoal (0.6 g) in ethanol (10 ml) and water (1 ml) which had been pre-hydrogenated for 1 hour, before the addition of further catalyst (0.6 g). The hydrogenation was continued for 2 hours, and then the catalyst was filtered and washed with dilute sodium bicarbonate solution. The filtrate was washed with ether, its pH adjusted to 4, and washed with ethyl acetate. The pH was then lowered to 1 and the product extracted into ethyl acetate. The combined extracts were washed with brine, dried over magnesium sulphate and evaporated to leave the free acid as a white foam (0.25 g). This was dissolved in acetone and treated with 2N sodium ethyl hexanoate in methyl isobutyl ketone (0.59 ml, 1.18 mmol) followed by ether. The precipitate was filtered, washed with ether and dried in vacuo to afford the title penicillin 0.16 g (40%). Hplc showed one peak $\nu_{max}$ (KBr) 1765, 1665, 1600, 1550 cm$^{-1}$; δ(D$_2$O) 1.20–1.60 (6H, m, gem dimethyl diastereoisomers), 4.25 (1H, m, C-3 diastereoisomers), 5.59 (1H, s, C-5 proton), 7.05–7.50 (3H, m, aromatics) and 8.09 and 8.12 (1H, 2s, formyl diastereoisomers).

MIC against P.mirabilis 889 is 25 μg/ml.

EXAMPLE 4

6α-Formamido-6β-[D-2-[(4-ethyl-2,3-dioxopiperazin-1-yl)carbonylamino]-2-phenylacetamido]penicillanic acid, sodium salt

(a) benzyl 6α-amino-6β-[D-2-(4-ethyl-2,3-dioxopiperazin-1-yl)carbonylamino]-2-phenylacetamido]penicillanate A solution of benzyl 6α-methylthio-6β-[D-2-[(4-ethyl-2,3-dioxopiperazin-1-yl)carbonylamino]-2-phenylacetamido]penicillanate (978 mg, 1.5 mmol) in dry DMF (15 ml) at −40° C. under nitrogen, was treated with mercuric acetate (480 mg, 1.5 mmol) in DMF (2 ml) followed immediately by a solution of anhydrous ammonia (28 mg, 1.65 mmol) in DMF (1 ml). The mixture was stirred at −40° C. to −10° C. over 1 hour before being poured into ethyl acetate and washed with water and brine. It was dried over magnesium sulphate, filtered and evaporated to afford the essentially pure product as a pale yellow glass (710 mg, 76%), $\nu_{max}$(CH$_2$Cl$_2$) 3380, 3280, 1780, 1740, 1715, 1690 cm$^{-1}$; δ(CDCl$_3$) 0.80–1.50 (9H, m, gem dimethyls and —CH$_2$CH$_3$) 2.82 (2H, br.s, amino protons), 3.20–3.80 (4H, m, piperazine CH$_2$ and CH$_2$CH$_3$), 3.85–4.25 (2H, m, piperazin CH$_2$), 4.34 (1H, s, C-3 proton), 5.18 (2H, s, ester CH$_2$), 5.42 (1H, s, C-5 proton), 5.58 (1H, d, J=7 Hz, α-proton), 7.20–7.60 (11H, m, aromatics and NH) and 10.05 (1H, d, J=7 Hz, amido proton).

(b) benzyl 6α-formamido-6β-[D-2-[(4-ethyl-2,3-dioxopiperazin-1-yl)carbonylamino]-2-phenylacetamido]penicillanate A solution of benzyl 6α-amino-6β-[D-2-[(4-ethyl-2,3-dioxopiperazin-1-yl)carbonylamino]-2-phenylacetamido]penicillanate (0.50 g, 0.8 mmol) in anhydrous dichloromethane (30 ml) at 0° C., was treated sequentially with pyridine (0.63 g, 8 mmol) and formic-acetic anhydride (0.35 g, 4 mmol). The reaction solution was allowed to warm to room temperature over 3 hours, before being washed with 0.5 N hydrochloric acid, dilute sodium bicarbonate solution and brine. It was dried over magnesium sulphate, filtered and evaporated to leave the crude product (0.45 g). This was purified on silica gel to afford the title compound 0.37 g (71%), $\nu_{max}$ (KBr) 3400, 3300, 1785, 1740, 1710, 1680, 1500 cm$^{-1}$; $\delta[(CD_3)_2SO]$ 0.07–1.20 (9H, m, gem dimethyls and —CH$_2$CH$_3$), 3.20–3.65 (4H, m, piperazin CH$_2$ and CH$_2$CH$_3$), 3.75–4.00 (2H, m, piperazine CH$_2$), 4.40 (1H, s, C-3 proton), 5.14 (2H, s, ester CH$_2$), 5.45 (1H, s, C-5 proton), 5.63 (1H, d, J=7 Hz, α-proton), 7.20–7.60 (10H, m, aromatics), 8.03 (1H, s, formyl proton), 9.09 (1H, s, exchangeable in D$_2$O, 6β-amido proton) and 9.96 (2H, m, exchangeable in D$_2$O, -amido and formamido protons).

6α-formamido-6β-[D-2-[(4-ethyl-2,3-dioxopiperazin-1-yl)carbonylamino]-2-phenylacetamido]penicillanic acid, sodium salt A solution of benzyl 6α-formamido-6β-[D-2-(4-ethyl-2,3-dioxopiperazin-1-yl)carbonylamino]-2-phenylacetamido]penicillanate (200 mg, 0.31 mmol) in THF (15 ml) was added to a suspension of 10% palladium on charcoal (200 mg) in ethanol (10 ml) and water (1 ml) which had been pre-hydrogenated for 15 minutes. The mixture was then hydrogenated for 2.5 hours, and then the catalyst was filtered and washed with dilute sodium bicarbonate solution. The filtrate was then washed with ethyl acetate, saturated with sodium chloride and acidified to pH 1.5, before extraction of the product into THF/ethyl acetate (50:50). The combined extracts were washed with brine, dried over magnesium sulphate and evaporated to leave the free acid (0.12 g), $\delta[(CD_3)_2CO]$ 0.90–1.70 (9H, m, gem dimethyls and —CH$_2$CH$_3$), 3.20–4.20 (6H, m, piperazine CH$_2$'s and —CH$_2$CH$_3$), 4.40 (1H, s, C-3 proton), 5.70 (1H, s, C-5 proton), 5.82 (1H, d, J=7 Hz, α-proton), 7.30–7.90 (5H, m, aromatics), 8.30 (1H, s, formyl proton), 8.57 (1H, s, 6β-amido proton), 9.06 (1H, s, formamido proton). This was dissolved in THF and the sodium salt was formed by addition of 2N sodium ethyl hexanoate in methyl isobutyl ketone followed by ether. The product was filtered, washed with ether and dried in vacuo to afford the title penicillin (130 mg 72%). Hplc showed one peak, $\nu_{max}$ (KBr) 1765, 1710, 1675, 1600, 1515 cm$^{-1}$; (D$_2$O) 0.90–1.50 (9H, m, gem dimethyls and —CH$_2$CH$_3$), 3.10–3.95 (6H, m, piperazin CH$_2$'s and —CH$_2$CH$_3$), 4.02 (1H, s, C-3 proton), 5.37 (1H, s, C-5 proton), 5.50 (1H, s, α-proton), 7.40 (5H, s, aromatics) and 8.07 (1H, s, formyl proton).

MIC against P.mirabilis 889 is 0.2 μg/ml.

EXAMPLE 5

6αFormamido-6β-[D-2-[(4-ethyl-2,3-dioxopiperazin-1-yl)carbonylamino]-2-(4-hydroxyphenyl)acetamido]-penicillanic acid, sodium salt (a) benzyl 6α-methylthio-6β-[D-2-[(4-ethyl-2,3-dioxopiperazin-1-yl)carbonylamino]-2-(4-benzyloxycarbonyloxyphenyl)acetamido]penicillanate A solution of D-2-[(4-ethyl-2,3-dioxopiperazin-1-yl)carbonylamino]-2-(4-benzyloxycarbonyloxyphenyl)acetylchloride (12.2 mmol) in anhydrous dichloromethane (60 ml) was added dropwise to an ice-cooled solution of benzyl 6α-methylthio-6β-amino penicillanate (13.42 mmol, 1.1 equivalents) and pyridine (1.45 g, 18.3 mmol) in dichloromethane (100 ml). The reaction solution was stirred at 0° C. for 0.5 hours followed by 1 hour at room temperature. It was then evaporated to dryness, dissolved in ethyl acetate, and washed with dilute hydrochloric acid, dilute sodium bicarbonate and brine. It was then dried, evaporated and chromatographed on silica gel to afford the title compound in 19% yield, together with a 15% yield of the L-isomer.

D-isomer $\nu_{max}$ (CH$_2$Cl$_2$) 3250, 1780, 1765, 1750, 1718, 1715, 1680 (sh), 1500, 1220 cm$^{-1}$; $\delta[(CD_3)_2CO]$ 1.07 and 1.21 (6H, 2s, gem dimethyls), 1.16 (3H, t, J7 Hz, —CH$_2$CH$_3$), 2.28 (3H, s, —SCH$_3$), 3.47 (2H, q, J7 Hz, —CH$_2$CH$_3$), 3.68 (2H, m, piperazin —CH$_2$), 4.01 (2H, m, piperazin —CH$_2$), 4.37 (1H, s, C-3 proton), 5.19 (2H, s, ester —CH$_2$), 5.25 (2H, s, carbonate —CH$_2$), 5.42 (1H, s, C-5 proton), 5.71 (1H, d, J7 Hz, collapses to singlet on D$_2$O exchange, α-proton), 7.10–7.70 (14H, m, aromatics), 8.77 (1H, s, exchangeable with D$_2$O, 6β-amido proton), and 10.01 (1H, d, J7 Hz, exchangeable with D$_2$O, α-amido proton).

L-isomer $\nu_{max}$ (CH$_2$Cl$_2$) 3280, 1750, 1765, 1755, 1720, 1690, 1500, 1215 cm$^{-1}$; $\delta[(CD_3)_2CO]$ 1.16 (3H, t, J7 Hz, —CH$_2$CH$_3$), 1.35 and 1.51 (6H, 2s, gem dimethyls), 1.95 (3H, s, —SCH$_3$), 3.47 (2H, q, J7 Hz, —CH$_2$CH$_3$), 3.68 (2H, m, piperazin —CH$_2$), 4.01 (2H, m, piperazin —CH$_2$), 4.45 (1H, s, C-3 proton), 5.22 (2H, s, ester —CH$_2$), 5.27 (2H, s, carbonate —CH$_2$), 5.46 (1H, s, C-5 proton), 5.72 (1H, d, J7 Hz, collapses to singlet on D$_2$O exchange, α-proton), 7.10–7.70 (14H, m, aromatics), 8.82 (1H, s, exchangeable with D$_2$O, 6β-amido proton) and 10.02 (1H, d, J7 Hz, exchangeable with D$_2$O, amido. proton).

(b) benzyl 6α-amino-6β-[D-2-[(4-ethyl-2,3-dioxopiperazin-1-yl)carbonylamino]-2-(4-benzyloxycarbonyloxyphenyl)acetamido]penicillanate A solution of benzyl 6α-methylthio-6β-[D-2-[(4-ethyl-2,3-dioxopiperazin-1-yl)carbonylamino]-2-(4-benzyloxycarbonyloxyphenyl)acetamido]penicillanate (1.75 g, 2.18 mmol) in dry DMF (30 ml) at −50° C. under nitrogen, was treated with mercuric acetate (0.70 g, 2.18 mmol) in DMF (4 ml) followed immediately by a solution of anhydrous ammonia (41 mg, 2.4 mmol) in DMF (2 ml). The mixture was stirred at −50° C. to −30° C. for 1 hour before being poured into ethyl acetate and washed with water and brine. It was dried over magnesium sulphate, filtered and evaporated to afford the essentially pure product (1.56 g, 93%), $\nu_{max}$ (CH$_2$Cl$_2$) 3280, 1780 (sh), 1765, 1750, 1720, 1695, 1680 (sh), 1500, 1220 cm$^{-1}$; $\delta[(CD_3)_2CO]$ 0.80–1.50 (9H, m, gem dimethyls and —CH$_2$CH$_3$), 3.02 (2H, br.s, —NH$_2$), 3.25–3.80 (4H, m, piperazin —CH$_2$ and —CH$_2$CH$_3$), 3.80–4.20 (2H, m, piperazin —CH$_2$), 4.39 (1H, s, C-3 proton), 5.19 (2H, s, ester —CH$_2$), 5.28 (2H, s, carbonate —CH$_2$), 5.43 (1H, s, C-5 proton), 5.75 (1H, d, J7 Hz, α-proton), 7.10–7.90 (14H, m, aromatics), 8.87 (1H, s, 6β-amido proton) and 10.15 (1H, d, J7 Hz, α-amido proton).

(c) benzyl 6α-formamido-6β-[D-2-(4-ethyl-2,3-dioxopiperazin-1-yl)carbonylamino]-2-(4-benzyloxycarbonyloxyphenyl)acetamido]penicillanate A solution of benzyl 6α-amino-6β-[D-2-[(4-ethyl-2,3-dioxopiperazine-1-yl)carbonylamino]-2-(4-benzyloxycarbonyloxyphenyl)acetamido]penicillanate (1.56 g, 2.0 mmol) in anhydrous dichloromethane (60 ml) at 0° C., was treated with pyridine (1.55 g, 20 mmol) and formic-acetic anhydride (0.88 g, 10 mmol). The reaction solution was stirred at 0° C. for 0.25 hours followed by 1 hour at room temperature. It was then washed with 0.5 N hydrochloric acid, dilute sodium bicarbonate solution and brine, before being dried over magnesium sulphate, filtered and evaporated to dryness. The crude product (1.39 g) was purified by chromatography to afford the title compound (0.95 g, 59%), $\nu_{max}$(CH$_2$Cl$_2$) 3275, 1790, 1770, 1750, 1725, 1715, 1695, 1682 (sh), 1500, 1210 cm$^{-1}$; δ[(CD$_3$)$_2$CO] 0.97 and 1.18 (6H, 2s, gem dimethyls), 1.17 (3H, t, J7 Hz, —CH$_2$CH$_3$), 3.48 (2H, q, J7 Hz, —CH$_2$CH$_3$), 3.65 (2H, m, piperazin —CH$_2$), 4.00 (2H, m, piperazine —CH$_2$), 4.39 (1H, d, C-3 proton), 5.18 (2H, s, ester —CH$_2$), 5.26 (2H, s, carbonate —CH$_2$), 5.58 (1H, s, C-5 proton), 5.73 (1H, d, J7 Hz, collapses to singlet on D$_2$O exchange, α-proton), 7.10–7.70 (14H, m, aromatics), 8.16 (1H, s, —NHCHO), 8.23 (1H, s, exchangeable with D$_2$O, —NHCHO), 8.88 (1H, s, exchangeable with D$_2$O, 6β-amido proton), and 10.05 (1H, s, J7 Hz, exchangeable with D$_2$O, α-amido proton).

(d)
6α-formamido-6β-[D-2-[(4-ethyl-2,3-dioxopiperazin-1-yl)carbonylamino]-2-(4-hydroxyphenyl)acetamido]-penicillanic acid, sodium salt A solution of benzyl 6α-formamido-6β-[D-2-[(4-ethyl-2,3-dioxopiperazin-1-yl)carbonylamino]-2-(4-benzyloxycarbonyloxyphenyl)acetamido]penicillanate (0.50 g, 0.625 mmol in THF (15 ml) was added to a suspension of 10% palladium on charcoal (0.50 g) in ethanol (15 ml) and water (1 ml) which had been prehydrogenated for ½ hour. The mixture was then hydrogenated for 45 minutes, and the catalyst was filtered and washed with dilute sodium bicarbonate solution. The filtrate was then washed with ethyl acetate, saturated with sodium chloride and acidified to pH 1.5, before extraction of the product into THF/ethyl acetate (50:50). The combined extracts were washed with brine, dried over magnesium sulphate and evaporated to leave the free acid as a white solid (0.25 g). This was suspended in water and the pH carefully adjusted from 2.0 to 7.0 by addition of dilute sodium bicarbonate solution. The resultng solution was filtered and freeze dried to afford the title penicillin 256 mg (69%). Hplc showed one major peak, $\nu_{max}$ (KBr) 1770, 1710, 1685, 1670, 1610, 1510 cm$^{-1}$; δ(D$_2$O) 0.95 and 1.33 (6H, 2s, gem dimethyls), 1.21 (3H, t, J7 Hz, —CH$_2$CH$_3$), 3.50 (2H, q, J7 Hz, —CH$_2$CH$_3$), 3.65 (2H, m, piperazin —CH$_2$), 3.98 (2H, m, piperazin —CH$_2$), 4.16 (1H, s, C-3 proton), 5.37 (1H, s, C-5 proton), 5.59 (1H, s, α-proton), 6.86 and 7.35 (4H, AA'BB', J9 Hz, aromatics) and 8.00 (1H, s, —NHCHO).

MIC against P.mirabilis 889 is 0.1 μg/ml.

EXAMPLE 6

6α-Formamido-6β-[L-2-[(4-ethyl-2,3-dioxopiperazin-1yl)carbonylamino]-2-(4-hydroxyphenyl)acetamido]-penicillanic acid, sodium salt (a) benzyl
6α-amino-6β-[L-2-[(4-ethyl-2,3-dioxopiperazin-1-yl)carbonylamino-2-(4-benzyloxycarbonyloxyphenyl)acetamido]penicillanate This compound was prepared in 84% yield by reaction of benzyl 6α-methylthio-6β-[L-2-[(4-ethyl-2,3-dioxopiperazin-1-yl)carbonylamino]-2-(4-benzyloxycarbonyloxyphenyl)acetamido]penicillanate with ammonia in the presence of mercuric acetate as described for the D-isomer. $\nu_{max}$ (CH$_2$Cl$_2$) 3280, 1780, 1765, 1750, 1715, 1690, 1680 (sh), 1495, 1215 cm$^{-1}$; δ(CDCl$_3$) 0.95–1.40 (9H, m, gem dimethyls and —CH$_2$CH$_3$), 2.61 (2H, s, —NH$_2$) 3.10–3.70 (4H m, piperazine —CH$_2$ and —CH$_2$CH$_3$), 3.75–4.15 (2H, m, piperazine —CH$_2$), 4.31 (1H, s, C-3 proton), 5.11 (2H, s, ester —CH$_2$), 5.19 (2H, s, carbonate —CH$_2$), 5.33 (1H, s, C-5 proton), 5.45 (1H, d, J6 Hz, α-proton), 6.90–7.70 (14H, m, aromatics), 8.22 (1H, s, 6β-amido proton) and 9.81 (1H, d, J6 Hz, α-amido proton).

(b) benzyl
6α-formamido-6β-[L-2-[(4-ethyl-2,3-dioxopiperazin-1-yl)carbonylamino]-2-(4-benzyloxycarbonyloxyphenyl)acetamido]penicillanate This compound was prepared in 61% yield by reaction of benzyl 6α-amino-6β-[L-2-[(4-ethyl-2,3-dioxopiperazin-1-yl)carbonylamino]-2-(4-benzyloxycarbonyloxy-phenyl)acetamido]penicillanate with formic-acetic anhydride in the presence of pyridine, as described for the D-isomer. $\nu_{max}$ (CH$_2$Cl$_2$) 3280, 1790, 1765, 1750, 1715, 1690, 1500, 1480, 1215 cm$^{-1}$; δ [(CD$_3$)$_2$CO] 1.13 (3H, t, J7 Hz, —CH$_2$CH$_3$), 1.31 (6H, s, gem dimethyls), 3.45 (2H, q, J7 Hz, —CH$_2$CH$_3$), 3.62 (2H, m, piperazine —CH$_2$), 4.00 (2H, m, piperazine —CH$_2$), 4.46 (1H, s, C-3 proton), 5.19 (2H, s, ester —CH$_2$), 5.26 (2H, s, carbonate —CH$_2$), 5.61 (1H, s, C-5 proton), 5.75 (1H, d, J7 Hz, collapses to singlet on D$_2$O exchange, α-proton), 7.10–7.65 (14H, m, aromatics), 8.08 (1H, s, —NHCHO), 8.31 (1H, s, exchangeable with D$_2$O, —NHCHO), 8.60 (1H, s, exchangeable with D$_2$O, 6β-amido proton), and 9.99 (1H, d, J 7 Hz, exchangeable with D$_2$O, α-amido proton).

(c)
6α-formamido-6β-[L-2-[(4-ethyl-2,3-dioxopiperazin-1-yl)carbonylamino]-2-(4-hydroxyphenyl)acetamido]-penicillanic acid, sodium salt This compound was prepared in 44% yield by hydrogenolysis of benzyl 6α-formamido-6β-[L-2[(4-ethyl-2,3-dioxopiperazin-1-yl)carbonylamino]-2-(4-benzyloxycarbonyloxyphenyl)acetamido]penicillanate in the manner described for the D-isomer, $\nu_{max}$ (KBr) 1770, 1710, 1675, 1610, 1510 cm$^{-1}$; δ(D$_2$O) 1.13 (3H, s, gem dimethyl), 1.21 (3H, t, J7 Hz, —CH$_2$CH$_3$), 1.43 (3H, s, gem dimethyl), 3.52 (2H, q, J7 Hz, —CH$_2$CH$_3$), 3.69 (2H, m, piperazine —CH$_2$), 4.01 (2H, m, piperazine —CH$_2$), 4.22 (1H, s, C-3 proton), 5.49 (1H, s, C-5 proton), 5.58 (1H, s, α-proton), 6.93 and 7.36 (4H, AA'BB', J9 Hz aromatics) and 8.11 (1H, s, —NHCHO).

MIC against P.mirabilis 889 is 125 μg/ml.

EXAMPLE 7

6α-Formamido-6β-[D-2-(2-phenylamino-4-hydroxypyrimidin-5-ylureido)-2-phenylacetamido]penicillanic acid, di-sodium salt 5-Amino-2-phenylamino-4-hydroxypyrimidine (51 mg, 0.25 mmol) in anhydrous THF (10 ml) was treated with triethylamine (25 mg, 0.25 mmol) and cooled in an ice bath. A 12% w/v solution of phosgene in toluene (250 μg) was then added and the solution stirred at 0° C. for 1 hr. Excess phosgene was then removed under vacuum, and the resulting suspension was cooled and added in one portion to an ice-cooled solution of 6α-formamido ampicillin (75 mg, 0.25 mmol) and triethylamine (35 μg, 0.25 mmol) in THF (8 ml) and water (2 ml). The reaction mixture was stirred at 0° C. for 0.5 hr. followed by 1 hr. at room temperature, maintaining the pH at 7.5 throughout by the addition of triethylamine. The product was dissolved in dilute sodium bicarbonate solution and washed with ethyl acetate. The aqueous phase was saturated with sodium chloride and acidified to pH 1.5 before extraction of the product into ethyl acetate/THF (50:50). The extracts were washed with brine, dried over magnesium sulphate and evaporated to dryness to leave the free acid (20 mg). This was dissolved in methanol and treated with the theoretical amount of 2N sodium ethyl hexanoate in methyl isobutyl ketone. Addition of ether caused precipitation of the product, which was filtered and washed well with acetone/ether to afford, after drying, 20 mg (12%), $\nu_{max}$ (KBr) 1765, 1660, 1600, 1535 cm$^{-1}$; δ(D$_2$O) 0.91 and 1.28 (6H, 2s, gem dimethyls), 4.17 (1H, s, C-3 proton), 5.33 (1H, s, C-5 proton), 5.58 (1H, s, α-proton), 7.30–7.60 (10H, m, aromatics), 7.79 (1H, s, pyrimidine proton) and 8.10 (1H, s, —NHCHO).

MIC against P.mirabilis 889 is 5.0 μg/ml.

EXAMPLE 8

6α-Formamido-6β-(D-2-amino-2-phenylacetamido)-penicillanic acid (a) benzyl 6α-amino-6β-[D-2-(4-nitrobenzyloxycarbonylamino)-2-phenylacetamido]penicillanate Benzyl 6α-methylthio-6β-[D-2-(4-nitrobenzyloxycarbonylamino)-2-phenylacetamido]penicillanate (1.8 g, 3 mmol) in DMF (25 ml) at −40° C. under nitrogen was treated with a solution of mercuric acetate (0.98 g, 31 mmol) in DMF (3 ml). The reaction mixture was allowed to warm to 0° C. over 1 hr., poured into ether, washed with water and brine, dried over magnesium sulphate and evaporated to give the title compound (0.97 g, 57%), δ(CDCl$_3$), 0.96, 1.19 (6H, 2s, gem dimethyls), 2.74 (2H, m, NH$_2$), 4.38 (1H, s, C-3 proton), 5.15 (4H, s, ArCH$_2$), 5.41 (1H, s, C-5 proton), 5.53 (1H, m, α-proton), 6.89 (1H, m, NH), 7.36 (12H, m, aromatic protons), 7.90–8.40 (3H, m, NH aromatic protons); $\nu_{max}$ (CH$_2$Cl$_2$) 1610, 1680, 1715, 1745, 1780 cm$^{-1}$.

(b) benzyl 6α-formamido-6β-[D-2-(4-nitrobenzyloxycarbonylamino)-2-phenylacetamido]penicillanate Benzyl 6α-amino-6β-[D-2-(4-nitrobenzyloxycarbonylamino)-2-phenylacetamido]penicillanate (0.97 g, 1.65 mmol) in dichloromethane (40 ml) at 0° C. was treated with pyridine (1.3 ml, 16.5 mmol), then acetic formic anhydride (0.73 g, 8.2 mmol). The reaction mixture was stirred at 0°–5° C. for 1 hr., washed with 0.5N hydrochloric acid, dilute sodium bicarbonate solution and brine, dried over magnesium sulphate and evaporated to give the crude product. Purification on silica gel gave the title compound (0.60 g, 59%), δ(CDCl$_3$) 0.93, 1.17 (6H, 2s, gem dimethyls), 4.41 (1H, s, C-3 proton), 5.16 (4H, s, ArCH$_2$), 5.64 (2H, m, α- and C-5 protons), 6.89 (1H, s, NH), 7.39 (12H, m, aromatic protons), 8.14 (3H, m, aromatic protons and CHO), 8.85 (1H, m, NH); $\nu_{max}$ (CH$_2$Cl$_2$) 1605, 1690, 1740, 1785 cm$^{-1}$.

(c) 6α-formamido-6β-(D-2-amino-2-phenylacetamido)-penicillanic acid

A solution of benzyl 6α-formamido-6β-[D-2-(4-nitrobenzyloxycarbonylamino)-2-phenylacetamido]penicillanate (0.60 g, 0.9 mmol) in THF (5 ml), ethanol (10 ml), water (2 ml) was added to 10% palladium on charcoal (0.7 g) in THF (2.5 ml), ethanol (5 ml), water (1 ml) which had been prehydrogenated for 15 minutes. The mixture was hydrogenated for 2 hr., further catalyst (0.5 g) was added and hydrogenation continued for 2 hr. The catalyst was filtered and washed sequentially with THF, ethanol, water. The organic solvents were evaporated from the filtrate and the aqueous solution washed with ethyl acetate and freeze dried to give the title compound (0.33 g, 93%), δ(D$_2$O) 0.96, 1.36 (6H, 2s, gem dimethyls), 4.19 (1H, s, C-3 protons), 4.94 (1H, s, α-proton), 5.63 (1H, s, CHO); $\nu_{max}$ (KBr) 1600, 1675, 1765 cm$^{-1}$. MIC against P.mirabilis 889 is 25 μg/ml.

EXAMPLE 9

6α-Formamido-6β-[D-2-amino-2-(4-hydroxyphenyl)acetamido]penicillanic acid (a) Benzyl 6α-amino-6β-[D-2-(4-nitrobenzyloxycarbonylamino)-2-(4-benzyloxycarbonyloxyphenyl)acetamido]penicillanate Benzyl 6α-amino-6β-[D-2-(4-nitrobenzyloxycarbonylamino)-2-(4-benzyloxycarbonyloxyphenyl)acetamido]penicillanate (0.84 g, 1.03 mmol) in DMF (20 ml) was cooled to −40° C., treated with mercuric acetate (0.34 g, 1.03 mmol) in DMF (3 ml) followed by anhydrous ammonia (0.019 g, 1.1 mmol) in DMF (1.1 ml). The reaction mixture was allowed to warm to 0° C. over 1.5 hours poured into ether, washed with water, brine, dried over magnesium sulphate and evaporated to give the title compound (0.35 g, 43%), δ(CDCl$_3$) 0.96, 1.19 (6H, 2s, gem dimethyls), 2.57 (1H, m, NH$_2$), 4.34 (1H, s, C-3 proton), 5.16 (5H, m, ArCH$_2$ and -proton), 5.39 (1H, s, C-5 proton), 6.63 (1H, m, NH), 7.37, 7.42 (12H, 2s+m, aromatic protons and NH), 8.08 (2H, m, aromatic protons); $\nu_{max}$ (CH$_2$Cl$_2$) 1610, 1680, 1770 cm$^{-1}$.

(b) Benzyl 6α-formamido-6β-[D-2-(4-nitrobenzyloxycarbonylamino)-2-(4-benzyloxycarbonyloxyphenyl)acetamido]penicillanate A solution of benzyl 6α-formamido-6β-[D-2-(4-nitrobenzyloxycarbonylamino)-2-(4-benzyloxycarbonyloxyphenyl)acetamido]penicillanate (0.35 g, 0.45 mmol) in dichloromethane (10 ml) was cooled to 0° C., treated with pyridine (0.32 ml, 4.0 mmol) and acetic formic anhydride (0.19 g, 2.2 mmol). The reaction mixture was stirred at 0°–5° C. for 1 hour, washed with 0.5 N hydrochloric acid, dilute sodium bicarbonate solution, brine, dried over magnesium sulphate and evaporated. The crude product was purified on silica gel to give the title compound (0.18 g, 50%), δ(CDCl$_3$) 0.94, 1.15 (6H, 2s, gem dimethyls), 4.34 (1H, s, C-3 proton), 5.10 (2H, s, ArCH$_2$), 5.21 (2H, s, ArCH$_2$), 5.55 (2H, m, C-5 and α-protons), 7.31, 7.39 (14H, 2s+m, aromatic protons and NH), 7.99 (3H, aromatic protons and CHO), 8.86 (1H, m, NH); $\nu_{max}$ (CHCl$_2$) 1610, 1710, 1750, 1770, 1790 cm$^{-1}$.

(c)
6α-Formamido-6β-[D-2-amino-2-(4-hydroxyphenyl)acetamido]penicillanic acid

Benzyl 6α-formamido-6β-[D-2-(4-nitrobenzyloxycarbonylamino)-2-(4-benzyloxycarbonyloxyphenyl)acetamido] penicillanate (0.29 g, 0.36 mmol) in THF (2 ml), ethanol (5 ml), water (1 ml) was added to a suspension of 10% palladium on charcoal (0.3 g) in THF (2 ml), ethanol (5 ml), water (2 ml) which had been prehydrogenated for 15 minutes. The mixture was hydrogenated for 4 hr. The catalyst was filtered and washed successfully with THF, ethanol, water. The organic solvents were evaporated from the filtrate and the aqueous residue washed with ethyl acetate and freeze dried to give a quantitative recovery of the title compound. $\delta(D_2O)$ 0.97, 1.28 (6H, 2s, gem dimethyls), 6.14 (1H, s, C-3 proton), 5.25 (1H, s, α-proton), 5.55 (1H, s, C-5 proton), 6.83, 7.27 (4H, AA'BB', J10 Hz, aromatic protons), 8.18 (1H, s, CHO); $\nu_{max}$ (KBr) 1600, 1670, 1765 cm$^{-1}$. MIC against P. Mirabilis 889 is 50 μg/ml.

EXAMPLE 10

6α-Formamido-6β-[D-2-(3-cinnamoyl-3-methylureido)-2-phenylacetamido]penicillanic acid, sodium salt A solution of 6α-formamido-6β-(D-2-amino-2-phenylacetamido)penicillanic acid (0.08 g, 0.2 mmol) in water (10 ml) was adjusted to pH 7.5 with N sodium bicarbonate solution, cooled in ice and diluted with THF (2 ml). To this was added a solution of N-chlorocarbonyl-N-methylcinnamamide (0.044 g, 0.2 mmol) in THF (3 ml). The reaction mixture was stirred at ambient temperature for 2 hr., washed with ethyl acetate, acidified to pH 1.5 with N hydrochloric acid and extracted with ethyl acetate. The organic extracts were washed with brine, dried over magnesium sulphate and evaporated to give the free acid (0.08 g, 0.15 mmol). This was dissolved in acetone and treated with 2N sodium ethyl hexanoate in methylisobutyl ketone (0.08 ml), followed by ether. The precipitate was filtered and dried to give the title compound (0.085 g, 69%), $\delta(D_2O)$ 1.18 (6H, m, gem dimethyls), 2.80 (3H, s, NCH$_3$), 4.04 (1H, s, C-3 proton), 5.33 (1H, s, α-proton), 5.49 (1H, s, C-5 proton), 6.45 (1H, d, CH=), 7.17 (11H, m, aromatic protons and CH=), 8.02 (1H, s, CHO); $\nu_{max}$ (KBr) 1605, 1675, 1765 cm$^{-1}$. MIC against P. Mirabilis 889 is 1.0 μg/ml.

EXAMPLE 11

6α-Formamido-6β-[D-2-(2-oxoimidazolidin-1-ylcarbonylamino)-2-phenylacetamido]penicillanic acid sodium salt A solution of 6α-formamido-6β-(D-2-amino-2-phenylacetamido)penicillanic acid (0.2 g, 0.5 mmol) in water (10 ml) was treated with N sodium bicarbonate solution (1.25 ml), cooled in ice and diluted with acetone. To this was added a solution of 2-oxoimidazolidin-1-yl- carbonyl chloride (0.074 g, 0.5 mmol) in acetone (5 ml). The reaction mixture was stirred at room temperature for 2 hours, washed with ethyl acetate, acidified to pH 1.5 with N hydrochloric acid and extracted with ethyl acetate. The combined organic extracts were washed with brine, dried and evaporated to give the free acid. This was dissolved in water which was adjusted to pH 6.5 by careful addition of dilute sodium bicarbonate solution, and the solution filtered and freeze dried to give the sodium salt (120 mg, 45%). $\delta(D_2O)$ 0.91, 1.27 (6H, 2s, gem dimethyls). 3.3–3.6 (2H, m, imidazolidine CH$_2$), 3.7–4.0 (2H, m, imidazolidine CH$_2$), 4.13 (1H, s, C-3 proton), 5.37 (1H, s, C-5 proton), 5.54 (1H, s, α-proton), 7.40 (5H, m, aromatic protons), 8.08 (1H, s, NH<u>C</u>HO); $\nu_{max}$ (KBr) 1530, 1600, 1655, 1715, 1765 cm$^{-1}$.

MIC against P. Mirabilis 889 is 1.0 μg/ml.

EXAMPLE 12

6α-Formamido-6β-[D-2-(3-methylsulphonyl-2-oxoimidazolidin-1-ylcarbonylamino)-2-penylacetamido]penicillanic acid, sodium salt 6α-Formamido-6β-(D-2-amino-2-phenylacetamido)penicillanic acid (0.29, 0.5 mmol) in dichloromethane (10 ml) with triethylamine (0.13 ml, 0.94 mmol) and ground 4A molecular sieves was stirred for 30 minutes and filtered. The filtrate was cooled to 0° C., treated with a solution of 3-methylsulphonyl-2-oxo-imazolidin-1-ylcarbonylchloride (0.11 g, 0.5 mmol) in dichloromethane (5 ml), stirred at room temperature for 2 hours and the solvent evaporated. The residue was dissolved in ethyl acetate and water and the layers separated. The organic phase was extracted twice with N sodium bicarbonate solution. The combined aqueous extracts were washed with ethyl acetate and acidified to pH 1.5 with N hydrochloric acid. The product was extracted into ethyl acetate, washed with brine, dried and evaporated to give the free acid. This was suspended in water, which was adjusted to pH 6.5 by careful addition of dilute sodium bicarbonate solution and the resulting solution filtered and freeze dried to afford the sodium salt (81 mg, 26%), $\delta(D_2O)$ 0.88, (6H, 2s, gem dimethyls), 3.36 (3H, s, —SO$_2$CH$_3$), 3.86 (4H, m, imidazolidine methylenes), 4.14 (1H, s, C-3 proton), 5.43 (1H, s, C-5 proton), 5.56 (1H, s, α-proton), 7.3–7.6 (5H, m, aromatic protons), 8.10 (1H, s, —NH<u>C</u>HO). $\nu_{max}$ (KBr) 1520, 1600, 1670, 1725, 1765 cm$^{-1}$.

MIC against P.mirabilis 889 is 0.5 μg/ml.

EXAMPLE 13

6α-Formamido-6β-[D-2-[3-methyl-3-(2-thienylcarbonyl)ureido]-2-phenylacetamido]penicillanic acid, sodium salt A solution of 6α-formamido-6β-(D-2-amino-2-phenylacetamido)penicillanic acid (0.2 g, 0.5 mmol) in water (10 ml) with N sodium bicarbonate solution (1.25 ml) and acetone (3 ml) was cooled in ice and treated with [N-methyl-(2-thienyl)carboxamido]carbonyl chloride (0.16 g, 0.8 mmol) in acetone (5 ml). The reaction mixture was stirred at room temperature for 2 hours, diluted with water, washed with ethyl acetate and acidified to pH 1.5. The product was extracted into ethyl acetate, washed with brine, dried and evaporated to give the free acid. This was suspended in water, careful addition of dilute sodium bicarbonate to pH 6.5 to give solution, filtering and freeze drying gave the sodium salt (90 mg, 30%), $\delta(D_2O)$ 0.86, 1.22 (6H, 2s, gem dimethyls), 3.19 (3H, s, —NCH$_3$), 4.11 (3H, s, C-3 proton), 5.38 (1H, s, C-5 proton), 5.54 (1H, s, α-proton), 6.8–7.7 (8H, m, aromatic and thiophene protons), 8.09 (1H, s, NH<u>C</u>HO); $\nu_{max}$ (KBr) 1600, 1670, 1765 cm$^{-1}$. MIC against P. Mirabilis 889 is 2.5 μg/ml.

EXAMPLE 14

6α-Formamido-6β-[D-2-(7-hydroxy-1,2,4-triazolo[2,3-a]pyrimidin-6-ylcarboxamido)-2-phenylacetamido]penicillanic acid, disodium salt 6-Carboxy-7-hydroxy-1,2,4-triazolo[2,3-a]pyrimidine (0.18 g, 1.0 mmol) in dichloromethane (10 ml) with triethylamine (0.3 ml, 2.2 mmol) was cooled to −20° C. and treated with thionyl chloride (0.074 ml). The reaction mixture was stirred at −20° C. for 1.5 hours and the precipitate filtered and dried.

6α-Formamido-6β-(D-2-amino-2-phenylacetamido) penicillanic acid (0.10 g, 0.25 mmol) in dichloromethane (10 ml) with triethylamine (0.13 ml, 0.9 mmol) was stirred over ground 4A molecular sieves for 1 hour. The resulting triethylammonium salt (0.90 g, 0.18 mmol) in dichloromethane (10 ml) with triethylamine (0.07 ml, 0.5 mmol) at −20° C. was treated with the activated triazolopyrimidine derivative prepared above (0.041 g, 0.18 mmol). The reaction mixture was stirred at −10° C. for 2 hours and evaporated. The residue was taken up in sodium bicarbonate solution and washed with ethyl acetate. The solution was saturated with sodium chloride, acidified to pH 1.5 and extracted with 1:1 THF, ethyl acetate. The extracts were washed with brine, dried and evaporated. The free acid was suspended in water which was carefully adjusted to pH 6.5 with sodium bicarbonate solution. The solution was filtered and freeze dried to give the disodium salt (0.068 g, 48%); δ($D_2O$) 0.91, 1.26 (6H, 2s, gem dimethyls), 4.45 (1H, s, C3 proton), 5.84 (1H, s, α-proton) 5.57 (1H, s, C5-proton), 7.40 (5H, m, phenyl protons) 8.09 (1H, s, NCHO), 8.14 (1H, s, pyrimidine proton), 8.67 (1H, s, triazole proton); $\nu_{max}$ (KBr) 1530, 1650, 1770 cm$^{-1}$. MIC against P. Mirabilis 889 is >100 μg/ml.

EXAMPLE 15

6α-Formamido-6β-[D-2-(2-benzylamino-4-hydroxypyrimidin-5-ylcarboxamido)-2-phenylacetamido]penicillanic acid, disodium salt 2-Benzylamino-5-carboxy-4-hydroxypyrimidine (0.06 g, 0.25 mmol) in dichloromethane (10 ml) with triethylamine (0.27 ml) was cooled to −20° C. and treated with thionyl chloride (0.02 ml, 0.27 mmol). The solution was stirred at −20° C. for 1 hr. 6α-Formamido-6β-(D- 2-amino-2-phenylacetamido) penicillanic acid (0.10 g, 0.25 mmol) in dichloromethane (10 ml) with triethylamine (0.13 ml, 0.9 mmol) was stirred at room temperature for 1.5 hours. The mixture was cooled to −20° C., treated with the above solution of activated acid, stirred at −10° C. for 2 hours, filtered and evaporated. The residue was taken up in water and washed with ethyl acetate. The solution was acidified to pH 1.5 and extracted with ethyl acetate. The extracts were washed with brine, dried and evaporated. The free acid was suspended in water which was carefully adjusted to pH 6.5 using sodium bicarbonate. The resulting solution was filtered and freeze dried to give the disodium salt (80 mg, 47%); δ($D_2O$) 0.91, 1.23 (6H, 2s, gem dimethyls), 5.23 (1H, s, α-proton), 5.51 (1H, s, C-5 proton), 7.25 (10H, m, aromatic protons), 8.07 (1H, s, NCH) 8.26 (1H, s, pyrimidine proton); $\nu_{max}$(KBr) 1440, 1600, 1660, 1765 cm$^{-1}$. MIC against P. Mirabilis 889 is 50 μg/ml.

EXAMPLE 16

6α-Formamido-6β-[D-2-(2-oxoimidazolidin-1-ylcarbonylamino)-2-(4-hydroxyohenyl)acetamido]penicillanic acid, sodium salt 6α-Formamido-6β-[D-2-amino-2-(4-hydroxyphenyl)acetamido]penicillanic acid (0.10 g, 0.25 mmol) in water (10 ml) and acetone (3 ml) was adjusted to pH 7.5 with N sodium bicarbonate solution. 2-Oxoimidazolidin-1-ylcarbonylchloride (0.037 g, 0.25 mmol) in acetone (3 ml) was added and the reaction mixture maintained at pH 7.5 for 2 hours. The reaction mixture was diluted with water, washed with ethyl acetate, acidified to pH 1.5 and extracted with ethyl acetate. The extracts were washed with brine, dried and evaporated. The residue was taken up in water at pH 6.5 and freeze dried to give the sodium salt (54 mg, 41%); δ($D_2O$) 0.91, 1.25 (6H, 2s, gem dimethyls), 3.2–3.5 (2H, m, imidazolidine methylene), 3.6–3.9 (2H, m, imidazolidine methylene), 4.13 (1H, s, C-3 proton), 5.26 (1H, m, α-proton), 5.55 (1H, s, C-5 proton), 6.83 (2H, m, aromatic protons), 7.31 (2H, m, aromatic protons), 8.10 (1H, s, NCHO).
MIC against P.mirabilis 889 is 0.5 μg/ml.

EXAMPLE 17

6α-Formamido-6β-[D-2-(3-cinnamoyl-3-methyl ureido)-2-(4-hydroxyphenyl)acetamido] penicillanic acid, sodium salt 6α-Formamido-6β-[D-2-amino-2-(4-hydroxyphenyl)acetamido]penicillanic acid (0.10 g, 0.25 mmol) in water (10 ml) and THF (3 ml) was adjusted to pH 7.5 with sodium hydrogen carbonate solution. To this was added N-chlorocarbonyl-N-methyl cinnamide (0.055 g, 0.25 mmol) in THF (3 ml). The reaction mixture was stirred at pH 7.5 for 2 hours, diluted with water and washed with ethyl acetate. The reaction mixture was acidified to pH 1.5 and extracted with ethyl acetate. The extracts were washed with brine, dried and evaporated. The free acid was dissolved in water which was carefully adjusted to pH 6.5 with sodium bicarbonate solution and the resulting solution filtered and freeze dried to give the sodium salt (105 mg, 69%); δ($D_2O$) 0.92, 1.29 (6H, 2s, gem dimethyls) 2.87 (3H, s, $NCH_3$), 4.14 (1H, s, C3 proton), 5.27 (1H, s, α-proton), 5.56 (1H, s, C5 proton), 6.5–7.5 (6H, m, vinyl and aromatic protons), 8.07 (1H, s, NCHO); $\nu_{max}$ (KBr) 1515, 1610, 1675, 1770 cm$^{-1}$.
MIC against P. Mirabilis 889 is 2.5. μg/ml.

EXAMPLE 18

6α-[D-2-[(4-Ethyl-2,3-dioxopiperazin-1-yl)carbonylamino]-2-(3,4-diacetoxyphenyl)acetamido]-6α-formamidopenicillanic acid, sodium salt (a)

D-2-[(4-Ethyl-2,3-dioxopiperazin-1-yl)carbonylamino]-2-(3,4-dihydroxyphenyl)acetic acid D-3,4-Dihydroxyphenylglycine (1.00 g, 5.46 mmole) was suspended in N, N-diethyl-1,1,1-trimethylsilylamine (10 ml) and heated at 80°–90° C. under nitrogen for 3 h. There was undissolved solid at the end of this period. Excess reagent was removed by evaporation under high vacuum and the residue was suspended in dry tetrahydrofuran (10 ml). The mixture was stirred at 0° C. and 4-ethyl-2,3-dioxopiperazine-1-carbonyl chloride (1.23 g, 1.1 eq) was added in one portion. The mixture was allowed to warm to room temperature and stirring was continued for 1 h. After this time the mixture was poured into water (resulting pH 2) and extracted with 1:1 n-butanol:ethyl acetate. The aqueous phase was saturated with brine and further extracted twice with the same solvent mixture, then the combined extracts were dried over sodium sulphate. Evaporation gave an oil which on trituration with ether afforded the title acid as a light brown solid which retained solvents tenaciously (1.9 g, 99% ignoring solvent); $R_f$ 0.35 in n-butanol:acetic acid:water, 4:1:1, $[\alpha]_D^{20}$ −81.7° (c 1.0 in EtOH); $\nu_{max}$ (KBr) 1710, 1670, 1610, 1520 cm$^{-1}$; $\delta[(CD_3)_2SO]$ 1.07 (3H, t, J8 Hz, CH$_3$CH$_2$N), 3.0–3.7 (4H, m, 2 CH$_2$N), 3.7–4.0 (2H, m, CH$_2$N), 5.10 (1H, d, J 7 Hz, NCH(Ar)CO), 6.5–6.9 (3H, m, aryls), 9.0 (2H, br, D$_2$O exch, phenolic OH), 9.60 (1H, br s, J 7 Hz, NH).

(b)
D-2-[(4-Ethyl-2,3-dioxopiperazin-1-yl)carbonylamino]-2-(3,4-diacetoxyphenyl)acetic acid D-2-[(4-Ethyl-2,3-dioxopiperazin-1-yl)carbonylamino]-2-(3,4-dihydroxyphenyl)acetic acid (1.87 g, 5.33 mmole) was stirred in dry tetrahydrofuran (20 ml) under a nitrogen atmosphere at 0° C. Dry pyridine (1.36 g, 3.2 eq) and acetic anhydride (1.36 g, 2.5 eq) were added and stirring was continued. Further acetic anhydride (0.2 g) was added after about 0.5 h, then the solution was allowed to regain room temperature. It was then poured into a mixture of ethyl acetate and water and the aqueous phase acidified to pH 2. The organic phase was separated, the aqueous phase extracted twice further with ethyl acetate and the total extract dried over sodium sulphate. Evaporation gave a yellow gum which was triturated with ether and petroleum ether to give the crude product. Purification was effected by dissolving the material in chloroform and adding dropwise to a large excess of dry ether. Filtration of the resulting solid gave the desired diacetoxy acid (1.78 g, 77%) which retained ether traces tenaciously.

$R_f$ 0.25 in n-butanol:acetic acid:water, 4:1:1.
$\nu_{max}$ (KBr) 1765, 1710, 1675 and 1500 cm$^{-1}$; $\delta$(CDCl$_3$) 1.14 (3H, t, J 8 Hz, CH$_3$CH$_2$N), 2.22 (6H, s, 2 CH$_3$CO), 3.25–3.70 (4H, m, 2 CH$_2$N), 4.80–5.10 (2H, m, CH$_2$N), 5.48 (1H, d, J 7 Hz, NCHCO), 7 05–7.35 (3H, m, phenyls), 7.42 (1H, brs, D$_2$O exch, CO$_2$H), 9.88 (1H, d, J 7 Hz, NH);
(Found, after prolonged drying: C, 51.6; H, 4.9; N, 9.3 C$_{19}$H$_{21}$N$_3$O$_9$, 0.5 H$_2$O requires; C, 51.4; H, 4.95; N, 9.5%).

(c) Benzyl
6β-[D-2-[(4-Ethyl-2,3-dioxopiperazin-1-yl)carbonylamino]-2-(3,4-diacetoxyphenyl)acetamido]-6α-formamidopenicillanate Benzyl 6β-[(2,2,2-Trichloroethoxy)carbonylamino]-6α-formamidopenicillanate was subjected to deprotection using powdered zinc-phosphate buffer. The aminoester produced (0.200 g, 0.55 mmole) was dissolved in dry dichloromethane (3 ml) together with dicyclohexylcarbodi-imide (0.110 g, 1 eq). This solution was cooled to 0° C. and stirred while D-2-[(4-ethyl-2,3-dioxopiperazin-1-yl)carbonylamino]-2-(3,4-diacetoxyphenyl)acetic acid (0.220 g, 1 eq) in dry dichloromethane (3 ml) was added over 0.17 h. The solution soon began to precipitate solid and was allowed to regain room temperature. After 3 h the dicyclohexylurea precipitated, was filtered off and the filtrate evaporated to dryness. Trituration with ether gave a solid which was subjected to chromatography on silica gel (40 g) eluting with 5% methanol-chloroform. Appropriate fractions were pooled and evaporated, reprecipitation from chloroform-ether gave essentially pure penicillin ester (0.140 g, 33%).

$R_f$ 0.35 in 10% methanol-chloroform; $[\alpha]_D^{20}$ + 103° (c 0.57 in CHCl) $\nu_{max}$ (KBr) 1770, 1740, 1710, 1680 and 1500 cm$^{-1}$; $\delta$(CDCl$_3$) 0.85 and 1.18 (6H, 2s, (CH$_3$)$_2$C), 1.23 (3H, t, J 7 Hz, CH$_3$CH$_2$N), 2.22 and 2.24 (6H, 2s, 2 CH$_3$CO), 3.40–3.60 (4H, m, 2 CH$_2$N), 3.75–3.95 (2H, m, CH$_2$N), 4.36 (1H, s, 3-H), 5.12 (2H, s, PhCH$_2$O), 5.52 (1H, s, 5-H), 5.64 (1H, d, J 7 Hz, NCH(Ar)CO), 7.12 (1H, d, J 7 Hz, aryl H), 7.33 (6H, s, phenyls and one aryl H), 7.45 (1H, d, J 7 Hz, aryl H), 8.0–8.1 (2H, br s; sharp s, 1H, on D$_2$O exch, NHCHO), 8.79 (1H, brs, D$_2$O exch, 6-NH), 10.11 (1H, brd, J 7 Hz, NHCH);
(Found: C, 54.35; H, 5.0; N, 10.8. C$_{35}$H$_{38}$N$_6$O$_{12}$S.0.5-H$_2$O requires C, 54.2; H, 5.0; N, 10.8%).

(d)
6β-[D-2-[(4-Ethyl-2,3-dioxopiperazin-1-yl)carbonylamino]-2-(3,4-diacetoxyphenyl)]acetamido-6α-formamidopenicillanic acid, sodium salt Benzyl 6β-[D-2-[(4-Ethyl-2,3-dioxopiperazin-1-yl]-2-(3,4-diacetoxyphenyl)]acetamido-6α-formamidopenicillanate (0.100 g, 0.131 mmole) was dissolved in tetrahydrofuran:water (4:1, 10 ml). 10% palladium on charcoal (0.050 g) was added and the mixture was hydrogenated at ambient temperature and atmospheric pressure for 1 h. After this time no starting material was visible by t.l.c. The catalyst was filtered off and washed well with water and tetrahydrofuran. To the filtrate was added 2M sodium 2-ethylhexanoate in methyl isobutyl ketone (0.065 ml) and the solution was evaporated to dryness. Trituration of the residue with ether afforded an off-white solid which was filtered, well washed with acetone and ether, then dried to give the title penicillin sodium salt (0.060 g, 70%);

$R_f$ 0.20 in n-butanol:acetic acid:water, 4:1:1; $\nu_{max}$ (nujol) 1775, 1710 sh 1680, 1610, 1500 cm$^{-1}$; $\delta$(D$_2$O) 0.91 and 1.27 (6H, 2s, (CH$_3$)$_2$), 1.16 (3H, t, J 7 Hz, CH$_3$CH$_2$N), 2.30 (6H, s, 2 CH$_3$CO), 3.30–3.80 (4H, m, 2 CH$_2$N), 3.80–4.05 (2H, m, CH$_2$N), 4.15 (1H, s, 3-H), 5.46 (1H, s, 5-H), 5.56 (1H, s, NCHCO), 7.15–7.55 (3H, m, aryls), 8.07 (1H, s, NHCHO).

MIC against P. mirabilis 889 is 0.5 μg/ml.

The acetoxy groups of 6β-[D-2-[(4-ethyl-2,3-dioxopiperazin-1-yl)carbonylamino]-2-(3,4-diacetoxyphenyl)]acetamido-6α-formamidopenicillanic acid, are removed by treatment with Subtilisin Carlsberg to give 6β-[D-2-[(4-ethyl-2,3-dioxopiperazin-1-yl)carbonylamino]-2-(3,4-dihydroxyphenyl)]acetamido-6α-formamidopenicillanic acid, sodium salt.

EXAMPLE 19

6β-[D-2-[3-[2-(4-Aminosulphonylphenyl)amino-4-hydroxyprimidin-5-yl]ureido]-2-(4-hydroxyphenyl)acetamido]-6α-formamidopenicillanic acid, disodium salt A suspension of 4-[(5-amino-4-hydroxypyrimidin-2-yl)amino]benzene sulphonamide (281 mg) in dry tetrahydrofuran (250 ml) under nitrogen, was treated with stirring at room temperature, with triethylamine (101 mg). The mixture was refluxed for 1 h then cooled to 0° C. and treated with a solution of phosgene in toluene (1 ml of 12.5% w/v). The mixture was allowed to regain room temperature over 0.5 h, then stirred at room temperature for 0.5 h. The resulting mixture was concentrated in vacuo to a volume of about 50 ml.

6β-[D-2-Amino-2-(4-hydroxyphenyl)acetamido]-6α-formamidopenicillanic acid (462 mg) was dissolved in 50% aqueous tetrahydrofuran (30 ml) at 0° C., by addition of M aqueous sodium hydrogen carbonate solution to pH 7.5. This solution was treated at 0° C. with the above-formed solution of the acylating agent, with concomitant addition of M aqueous sodium hydrogen carbonate solution to maintain the pH of the reaction mixture between 7.0 and 7.5. After the addition, the reaction mixture was stirred at 0° C. to 5° C. for 0.5 h, then allowed to regain room temperature over 0.5 h. The organic solvents were removed in vacuo and the aqueous residue washed with ethyl acetate (2×100 ml), ether (100 ml), and acidified to pH 2 in the presence of ethyl acetate (50 ml) and ether (50 ml). The resulting precipitate was collected by filtration, washed well with ether and dried in vacuo over phosphorus pentoxide to yield the impure product (200 mg). This solid was suspended in water (20 ml), the pH adjusted to 7 with 1M aqueous sodium hydrogen carbonate, the mixture filtered and the filtrate freeze-dried to yield a light brown solid (162 mg). Chromatography on silica gel 60 (230–400 mesh ASTM), eluting with ethyl acetate/propan-2-ol/water, 5:4:2, gave, after freeze drying, 6β-[D-2-[3-[2-(4-aminosulphonylphenyl)amino-4-hydroxyprimidin-5-yl]ureido]-2-(4-hydroxyphenyl)acetamido]-6α-formamido penicillanic acid, disodium salt (52 mg, 7%); $\nu_{max}$ (KBr) 1765, 1655 1610, 1590, 1530br, 1410, 1385, 1340, 1215, 1158, and 1100 cm$^{-1}$; δ[(CD$_3$)$_2$SO+CD$_3$OD+D$_2$O] 0.95, 1.31 (6H, 2s, 2-C(CH$_3$)$_2$), 4.10 (1H, s, 3-H), 5.30 (1H, s, 5-H), 5.56 (1H, s, NCHCO), 6.88 and 7.38 (4H, 2d, J 8 Hz, C$_6$H$_4$OH) 7.70 and 7.82 (4H, 2br s, C$_6$H$_4$SO$_2$NH$_2$), 8.07 (1H, brs, pyrimidinyl), and 8.11 (1 H, s, CHO).

MIC against P. Mirabilis 889 is 0.5 μg/ml.

EXAMPLE 20

6α-Formamido-6β-[D-2-[[3-(furan-2-ylmethyleneamino)-2-oxoimidazolin-1-yl]carboxylamino]-2-(4-hydroxyphenyl)acetamido]penicillanic acid, sodium salt 6β-[D-2-Amino-2-(4-hydroxyphenyl)acetamido]-6α-formamidopenicillanic acid (0.23 g) was suspended in water (5 ml) and tetrahydrofuran (5 ml), the pH adjusted to 7.5 by addition of triethylamine and the resulting solution stirred and cooled to 0°–5° C. A suspension of [3-(furan-2-ylmethyleneamino)-2-oxoimidazolidin-1-yl]carbonyl chloride in tetrahydrofuran (10 ml) was then added dropwise, the pH of the mixture being maintained at 7.5 by addition of triethylamine. After the addition was complete the mixture was stirred at 0°–5° C. for 0.5 h, when the organic solvent was evaporated under reduced pressure. The aqueous residue was washed twice with ethyl acetate and once with diethyl ether, before being acidified to pH 2 with 5M hydrochloric acid in the presence of ethyl acetate (25 ml). The phases were separated, the aqueous phase further extracted with ethyl acetate (25 ml), the extracts combined, washed with water at pH 2, water, saturated brine, dried over anhydrous magnesium sulphate and the organic solvents evaporated to dryness under reduced pressure. The residue was suspended in water (10 ml) containing sodium hydrogen carbonate (0.018 g), the mixture filtered and the filtrate freeze-dried to the title compound (0.137 g); $\nu_{max}$ (KBr) 3320br, 1770, 1722, 1670, 1610, 1511, 1479, 1416, 1390, 1273, 1235, and 1210sh cm$^{-1}$; δ[D$_2$O/(CD$_3$)$_2$SO/CD$_3$OD; 2:1:1] 0.89 and 1.26 (6H, 2s, C(CH$_3$)$_2$), 3.81 (4H, br, s, two CH$_2$'s), 4.08 (1H, s, 3-H), 5.36(1H, d, J 8 Hz, CHCO), 5.52, (1H, s, 5H), 6.56 (1H, m, furyl-H), 6.76–6.92 (3H, m, furyl and two C$_6$H$_4$-H's), 7.21–7.43 (2H, m, furyl-H and CH=N), 7.57–7.73 (2H, m, two C$_6$H$_4$-H's), 8.08 (1H, s, CHO), 9.07 (1H, d, J 8 Hz, NHCHCO).

MIC against P. Mirabilis 889 is 0.25 μg/ml.

EXAMPLE 21

6β-[D-2-(D-2-Carbamoylamino-3-phenylpropionamido)-2-(4-hydroxyphenyl)acetamido]-6α-formamidopenicillanic acid, sodium salt A suspension of D-2-carbamoylamino-3-phenylpropionic acid (208 mg) in dry acetone (10 ml) was treated, under anhydrous conditions with triethylamine (101 mg), and the resulting mixture stirred and cooled to −10° C. to −20° C. Iso-butyl chloroformate (136 mg) was added and the mixture stirred at −10° C. to −20° C. for 20 min. The reaction mixture was cooled to −40° C. and added to an ice-cold solution of 6β-[D-2-amino-2-(4-hydroxyphenyl)acetamido]-6α-formamidopenicillanic acid (462 mg) in water (20 ml) containing acetone (5 ml), at pH 7.5. After the addition, the reaction mixture was allowed to regain room temperature over 0.5 h, then stirred for 1 h at room temperature. The organic solvents were evaporated in vacuo and the aqueous residue washed with ethyl acetate (2×50 ml), ether (50 ml), then acidified to pH 2 with 5M hydrochloric acid in the presence of ethyl acetate (25 ml) and ether (25 ml). The resulting, white precipitate was collected by filtration, washed well with ether and dried in vacuo over phosphorus pentoxide. The dried solid was suspended in water (25 ml) and the pH adjusted to 6.5 with 1M aqueous sodium hydrogen carbonate solution, the mixture filtered and the filtrate freeze-dried to yield 296 mg of impure product. Chromatography of 200 mg of this material on silica gel 60 (230–400 mesh ASTM), eluting with ethyl acetate/propan-2-ol/water, 5:3:1, gave 6β-[D-2-(D-2-carbamoylamino-3-phenylpropionamido)-2-(4 hydroxyphenyl)acetamido]-6α-formamidopenicillanic acid sodium salt (117 mg, 19%), after freeze drying;

$\nu_{max}$ (KBr) 1765, 1645 br, 1600 br, 1512, 1385, 1265, 1210 and 1178 cm$^{-1}$;

δ(D$_2$O) 0.89, 1.21 (6H, 2s, 2-C(CH$_3$)$_2$), 2.94 (2H, m, CH$_2$), 4.07 (1H, s, 3-H), 5.22 (1H, s, 5-H), 5.48 (1H, s, NCHCO), 6.75–6.90 and 7.05–7.40 (9H, m, C$_6$H$_5$ and C$_6$H$_4$) and 8.05 (1H, s, CHO).

MIC against P. Mirabilis 889 is 2.5 μg/ml.

EXAMPLE 22

6β-[2-[(Coumarin-3-yl)carbonylamino]-2-(4-hydroxyphenyl)acetamido]-6α-formamidopenicillanic acid, sodium salt (a) Coumarin-3-carbonyl chloride Coumarin-3-carboxylic acid (2.1 g, 10 m mole) was suspended in dry dichloromethane (10 ml) and heated at reflux for 2 h with thionyl chloride (5 ml). After this time a small amount of insoluble material was filtered off and petroleum ether 60°–80° C. (35 ml) was added to the filtrate. The acid chloride was filtered, washed with ether and dried (1.63 g, 71%), mp 138°–41° C.;

$\nu_{max}$ (CHCl$_3$) 1790, 1740, 1610, 1570 cm$^{-1}$;

δ(CDCl$_3$) 7.30–8.10 (4H, m, phenyls), 8.95 (1H, s, coumarin 4-H).

(b) Sodium 6β-[2-[(coumarin-3-yl)carbonylamino]-2-(4-hydroxyphenyl)acetamido]-6α-formamidopenicillanate 6β-[2-amino-2-(4-hydroxyphenyl)acetamido]-6α-formamidopenicillanic acid (0.100 g, 0.25 m mole) was suspended in water (5 ml) and cooled to 0° C. with stirring. A solution of coumarin-3-carbonyl chloride (0.060 g, 1.2 eq) in tetrahydrofuran (2 ml) was added and the pH was maintained at 8.0–8.5 by the addition of 10 M.sodium hydrogen carbonate solution. The mixture was allowed to warm to room temperature and stirring was continued for 1 h. After this time further water (5 ml) was added and the solution was washed twice with ethyl acetate, backwashing each time with a little water. The aqueous solution was saturated with sodium chloride and acidified to pH 2 with 2M.hydrochloric acid, concomitantly extracting the product into 1:1 ethyl acetate:tetrahydrofuran (2×20 ml). The total extract was washed twice with brine, dried over sodium sulphate and evaporated to give the acid form of the product (0.170 g). This was dissolved in acetone and filtered, then 1.89M sodium 2-ethylhexanoate in methyl isobutyl ketone (0.13 ml, 1 eq) was added, followed by addition of ether to complete precipitation. The title penicillin salt was filtered, washed with acetone and ether and dried (0.110 g, 73%).

$R_f$ 0.55 in n-butanol:acetic acid:water, 4:1:1;
$\nu_{max}$(Nujol) 3250, 1770, 1710, 1610, 1565, 1510 cm$^{-1}$;
δ[D$_2$O: (CD$_3$)$_2$SO:CD$_3$OD, 7:2:3] 1.13 and 1.44 (6H, 2s, (CH$_3$)$_2$C), 4.22 (1H, s, 3-H), 5.40 (1H, s, 5-H), 5.67 (1H, s, NCHCO), 6.98 (2H, d, aryl H), 7.51 (4H, m, aryl H), 7.70–8.00 (2H, m, aryl H), 8.22 (1H, s, NHC$\underline{H}$O), 8.86 (1H, s, coumarin 4-H).

MIC against P. Mirabilis 889 is 10 μg/ml.

EXAMPLE 23

Benzyl 6β-[D-2-[4-(benzyloxycarbonyloxy)phenyl]-2-[(4-ethyl-2,3-dioxopiperazin-1-yl)carbonylamino]acetamido]-6α-formamidopencillanate (a) Benzyl 6α-amino-6β-[D-2-[4-(benzyloxycarbonyloxy)phenyl]-2-(2,2,2-trichloroethoxycarbonylamino)acetamido]-penicillanate A solution of benzyl 6β-[D-2-[4-(benzyloxycarbonyloxy)phenyl]-2-(2,2,2-trichloroethoxycarbonylamino)acetamido]-6α-(methylthio)pencillanate (0.460 g) in dry N,N-dimethylformamide (7 ml) was stirred under nitrogen and cooled to −40° C. A solution of mercuric acetate (0.81 g) in N,N-dimethylformamide (1 ml) was added, followed by ammonia (0.011 g) in N,N-dimethylformamide (0.58 ml). The reaction mixture was stirred at −50° to −10° C. for 1 h and then partitioned between ethyl acetate and water. The organic phase was washed four times with water, once with brine, dried over sodium sulphate and concentrated. Chromatography of the residue on silica gel 60 (230 mesh ASTM), eluting with ethyl acetate/hexane 1:1 gave benzyl 6α-amino-6β-D-2-[4-benzyloxycarbonyloxy)phenyl]-2-(2,2,2-trichloroethoxycarbonylamino)acetamido penicillanate (0.285 g); $\nu_{max}$ (CHCl$_3$) 3400, 3310, 3020, 2950, 1765, 1745, 1685, 1605 and 1500 cm$^{-1}$; δ(CDCl$_3$) 1.00 and 1.20 (6H, 2s, 2-CH$_3$ s), 2.60(2H, s, NH$_2$), 4.30 (1H, s, 3-H), 4.64 (2H, s, CH$_2$CCl$_3$), 5.11 and 5.20 (4H, 2s, PhCH$_2$'s), 5.24 (1H, d, J 7 Hz, NCHCO), 5.36 (1H, s, 5-H), 6.41(1H, d, J 7 Hz, NH), 7.10 and 7.44 (4H, 2d, J 8 Hz, phenyl), 7.31 and 7.36 (11H, 2s, phenyl and NH).

(b) Benzyl 6β-[D-2-[4-(benzyloxycarbonyloxy)phenyl]-2-(2,2,2-trichloroethoxycarbonylamino)acetamido]-6α-formamidopencillanate A solution of benzyl 6α-amino-6β-[D-2-[4-(benzyloxycarbonyloxy)phenyl]-2-(2,2,2-trichloroethoxycarbonylamino)acetamido]pencillanate (0.256 g) in dichloromethane (10 ml) was stirred under argon and cooled to 0° C.

It was treated with pyridine (0.26 ml) and acetic formic anhydride (0.13 ml), and then allowed to warm to room temperature over a period of 3 h. The resulting solution was washed with 0.5N hydrochloric acid, dilute aqueous sodium hydrogen carbonate, brine and dried over sodium sulphate. The solution was concentrated and chromatographed on silica gel 60 (<230 mesh ASTM) eluting with ethyl acetate/hexane 1:1 to give benzyl 6β-[D-2-[4-(benzyloxycarbonyloxy)phenyl]-2-(2,2,2-trichloroethoxycarbonylamino)acetamido]-6α-formamidopencillanate (0.230 g) as a colourless foam; $\nu_{max}$ (CHCl$_3$) 3420, 3300, 3000 br, 1780 sh, 1765, 1745, 1695, 1605 and 1500 cm$^{-1}$; δ(CDCl$_3$) 1.00 and 1.20 (6H, 2s, C(CH$_3$)$_2$), 4.36 (1H, s, 3-H), 4.64 (2H, s, CH$_2$ CCl$_3$), 5.12 and 5.20 (4H, 2s, PhCH$_2$'s), 5.48 (1H, d,J 7 Hz, NCHCO), 5.56 (1H, s, 5-H), 6.56 (1H, brd, J 7 Hz, NH), 7.09 and 7.47 (4H, 2d, J 9 Hz, phenyl), 7.30 and 7.37 (11H, 2s, phenyls and NH), 8.09 (1H, s, NCHO), and 8.50 (1H, b, NH).

(c) Benzyl 6β-[D-2-amino-2-[4-(benzyloxycarbonyloxy)phenyl]-acetamido]-6α-formidopencillanate A solution of benzyl 6β-[D-2-[4-(benzyloxycarbonyloxy)phenyl]-2-(2,2,2-trichloroethoxycarbonylamino)acetamido]-6α-formamidopencillanate (0.200 g) in tetrahydrofuran (10 ml) was stirred at room temperature and treated with M. aqueous potassium dihydrogen phosphate (2 ml) followed by freshly acid washed zinc powder (0.400 g). Stirring was continued until deprotection was complete (ca 4 h) and the mixture was then filtered through celite. The filtrate was concentrated and partitioned between ethyl acetate and brine. The ethyl acetate solution was dried over sodium sulphate and concentrated to give benzyl 6β-[D-2-amino-2-[4-(benzyloxycarbonyloxy)phenyl]acetamido]-6α-formamidopencillanate.

(d) Benzyl 6β-[D-2-[4-benzyloxycarbonyloxy)phenyl]-2-[(4-ethyl-2,3-dioxopiperazin-1-yl)carbonylamino]acetamido]-6α-formamidopencillanate.

Benzyl 6β-[D-2-amino-2-[4-(benzyloxycarbonyloxy)phenyl]acetamido]-6α-formamidopencillanate was prepared from the corresponding N-trichloroethoxycarbonyl derivative (0.200 g) and then dissolved in dry tetrahydrofuran (5 ml). It was stirred at 0° C. under nitrogen and treated with 4-ethyl-2,3-dioxopiperazine-1-carbonyl chloride (0.050 g). The reaction mixture was allowed to warm to room temperature over a period of 1 h and then concentrated. The residue was taken up in ethyl acetate, washed with brine, dried over sodium sulphate and concentrated. The residue was chromatographed on silica gel 60 (<230 mesh ASTM) to give benzyl 6β-[D-2-[4-(benzyloxycarbonyloxy)phenyl]-2-[(4-ethyl-2,3-dioxopiperazin-1-yl)carbonylamino]acetamido]-6α-formamidopenicillanate (0.055 g); ν$_{max}$. (CHCl$_3$) 3280, 2980, 2875, 1780, 1765, 1745, 1710, 1685, 1610 and 1505 cm$^{-1}$; δ(CDCl$_3$) 0.85 and 1.12 (6H, 2s, 2-CH's), 1.26 (3H, t, J 7 Hz, CH$_3$ of NEt), 3.4–3.8 (6H, m, NCH$_2$CH$_2$NCH$_2$), 4.36 (1H, s, 3-H), 5.07 and 5.16,(2H, ABq, J 12 Hz, benzylic CH$_2$), 5.21 (2H, s, benzylic CH$_2$), 5.50 (1H, s, 5-H), 5.65 (1H, d, J 7 Hz, NCHCO), 7.11 and 7.53 (4H, 2d, J 9 Hz, phenyl), 7.2–7.5(10H, m, phenyls), 8.05 and 8.69 (2H, br s, NH's), 8.14 (1H, d, J 7 Hz, NH).

EXAMPLE 24

6α-Formamido-6β-[D-2-(4-hydroxyphenyl)-2-[(3-methylsulphonyl-2-oxoimidazolidin-1-yl)carbonylamino]acetamido]penicillanic acid, sodium salt (a) Benzyl 6β-[D-2-[4-(benzyloxycarbonyloxy)phenyl]-2-[(3-methylsulphonyl-2-oxoimidazolidin-1-yl)carbonylamino]acetamido]-6α-formamidopenicillanate Benzyl 6β-[D-2-amino-2-[4-(benzyloxycarbonyloxy)phenyl]acetamido]-6α-formamidopenicillanate was made from its N-trichloroethoxycarbonyl protected precursor (0.400 g). A solution of the amino compound in dry tetrahydrofuran (10 ml) was stirred at 0° C. under nitrogen and treated with 3-(methylsulphonyl)-2-oxoimidazolidine-1-carbonyl chloride (0.112 g) followed by pyridine (0.050 g). The cooling bath was removed and the reaction mixture stirred at room temperature for 2 h. It was then concentrated, dissolved in ethyl acetate, washed with brine and dried over sodium sulphate. Chromatography on silica gel 60 (<230 mesh ASTM) eluting with ethyl acetate grading to ethyl acetate/ethanol 19:1 gave benzyl 6β-[D-2-[4-(benzyloxycarbonyloxy)phenyl]-2-[3-methylsulphonyl-2-oxoimidazolidin-1-yl)carbonylamino]acetamido]-6α-formamidopenicillanate as a colourless glass (0.150 g); ν$_{max}$ (CHCl$_3$) 3330, 3020, 1780, 1760 sh, 1735, 1690, 1665, 1505, 1355, and 1170; δ(CDCl$_3$) 0.86 and 1.11 (6H,2s, 2-CH$_3$'s), 3.40(3H, s, SO$_2$CH$_3$), 3.6–4.1(4H, m, NCH$_2$CH$_2$N), 4.37 (1H, s, 3-H), 5.12 and 5.20(4H, 2s, benzylic CH$_2$'s), 5.50 (1H, d, J 7 Hz, NCHCO), 5.54(1H, s, 5-H), 7.09 and 7.49(4H, 2d, J 9 Hz,phenyl), 7.31 and 7.36(10H, 2s phenyls), 7.99,8.15 and 8.24 (3H, 3s, CHO and NH's), and 9.07 (1H, d, J 7 Hz, NH).

(b) 6α-Formamido-6β-[D-2-(4-hydroxyphenyl)-2-[(3-methylsulphonyl-2-oxoimidazolidin-1-yl)carbonylamino]acetamido]penicillanic acid, sodium salt A suspension of 10% palladium on charcoal catalyst (0.100 g) in dioxane (10 ml) and water (2.5 ml) was prehydrogenated for 15 min. To this was added a solution of benzyl 6β-[D-2-[4-(benzyloxycarbonyloxy)phenyl]-2-[(3-methylsulphonyl-2-oxoimidazolidin-1-yl)carbonylamino]acetamido]-6α-formamidopenicillanate (0.100 g) in dioxane (2.5 ml) and hydrogenation carried out at atmospheric pressure until deprotection was complete (ca 2 h). The resulting mixture was treated with a solution of sodium hydrogen carbonate (0.010 g) in water (1 ml) and then filtered. The dioxane was evaporated from the filtrate and the aqueous solution, which remained, was washed with ethyl acetate. The aqueous solution was then freeze dried to give 6α-formamido-6β-[D-2-(4-hydroxyphenyl)-2-[(3-methylsulphonyl-2-oxoimidazolidin-1-yl)carbonylamino]acetamido]penicillanic acid, sodium salt, (0.074 g); ν$_{max}$ (KBr) 3320, 3010, 2970, 2920, 1770, 1730, 1675, 1610, 1515, 1355, and 1170 cm$^{-1}$; δ(D$_2$O) 0.88 and 1.24 (6H, 2s, 2-CH$_3$'s), 3.29 (3H, s, SO$_2$CH$_3$), 3.80 (4H, br, NCH$_2$CH$_2$N), 4.09 (1H, s, 3H), 5.27 (1H, s, NCHCO), 5.49 (1H, s, 5-H), 6.79 and 7.27 (4H, 2d, J 9 Hz, phenyl), and 8.01 (1H, s, CHO).

MIC against P. Mirabilis 889 is 0.1 μg/ml.

EXAMPLE 25

6β-[D-2-[(5-Ethoxycarbonylimadazol-4-yl)carbonylamino]-2-4-hydroxyphenyl)acetamido]-6α-formamidopenicillanic acid, sodium salt (a) Benzyl 6β-[D-2-[4-(benzyloxycarbonyloxy)phenyl]-2-[(5-ethoxycarbonylimidazol-4-yl)carbonylamino]acetamido]-6α-formamidopencillanate Benzyl 6β-[D-2-amino-2-[4-(benzyloxycarbonyloxy)phenyl]acetamido]-6α-formamidopencillanate was prepared from the N-trichloroethoxycarbonyl derivative (0.400 g) and dissolved in dry dichloromethane (15 ml). To this was added diethyl 5,10-dioxo-5,10-dihydrodiimidazo [1,5-a;1'5'-d]pyrazine-1,6-dicarboxylate (0.246 g) and pyridine (0.039 g) and the mixture stirred at room temperature for 3 days. The product was centrifuged to remove solids and the supernatent solution was concentrated and chromatographed on silica gel 60 (1:1 mixture of >230 mesh and 230–400 mesh ASTM) eluting with chloroform/ethanol 1:0 grading to 4:1 to give benzyl 6β-[D-2-[4-(benzyloxycarbonyloxy)phenyl]-2-[(5-ethoxycarbonylimidazol-4-yl)carbonylamino]acetamido]-6α-formamidopencillanate as a crystalline solid (0.162 g); m.p. 216°–220° C. dec. (from chloroform/ethylacetate); ν$_{max}$ (CHCl$_3$) 3260, 2980, 1770, 1750 sh, 1695, 1640, 1580, 1520, 1510 and 1490 cm$^{-1}$; δ(CDCl$_3$) 0.95 and 1.11 (6H, 2s, 2-CH$_3$'s), 1.48 (3H, t, J 7 Hz, CH$_3$ of OEt), 4.34 (1H, s, 3-H), 4.56(2H, q, J 7Hz, OCH$_2$), 5.11 and 5.18 (4H, 2s, benzylic CH$_2$'s), 5.50 (1H, s,5-H), 6.49 (1H, d, J 8 Hz, NCHCO), 6.95 and 7.54 (4H, 2d, J 8 Hz, phenyl), 7.2–7.4 (11H, m, phenyls and NH), 7.74 (1H, s, imidizole CH), 8.08 (1H, s, CHO), 9.67 (1H, br, s, NH) and 11.79 (1H, d, J 8 Hz, NH); (Found: C,58.3; H, 4.8; N, 10.7%. C$_{39}$H$_{38}$N$_6$O$_{11}$S requires C, 58.6; H, 4.8; N, 10.5%)

(b) 6β-[D-2-[(5-Ethoxycarbonylimidazol-4-yl)carbonylamino]-2-(4-hydroxyphenyl)acetamido]-6α-formamidopencillanic acid, sodium salt A suspension of 10% palladium on charcoal catalyst (0.070 in dioxane (10 ml) and water (2.5 ml) was prehydrogenated for 15 mins. A solution of benzyl 6β-[D-2-[4-(benzyloxycarbonyloxy)phenyl]-2-[(5-ethoxycarbonylimidazol-4-yl)carbonylamino]acetamido]-6α-formamidopencillanate (0.070 g) in dioxane (5 ml) was added and the mixture hydrogenated at atmospheric pressure for 3 h, when thin layer chromatography showed complete reaction. A solution of sodium hydrogen carbonate (0.0074 g) in water (1 ml) was added and the catalyst removed by filtration. The resulting solution was evaporated to small bulk to remove the dioxane, washed with ethyl acetate, and freeze dried to give 6β-[D-2-[(5-ethoxycarbonylimidazol-4-yl)carbonylamino]-2-(4-hydroxyphenyl)acetamido]-6α-formamidopencillanic acid, sodium salt as a colourless solid (0.050 g); ν$_{max}$ (KBr) 1765, 1680, 1605, and 1510 cm$^{-1}$; δ(D$_2$O) 0.85 and 1.22 (6H, 2s, 2-CH$_3$'s), 1.25 (3H, t, J 7 Hz, CH$_3$ of OEt), 4.08 (1H, s, 3-H), 4.21 (2H, q, J 7 Hz, OCH$_2$), 5.41 and 5.49 (2H, 2s, 5-H and NCHCO), 6.80 and 7.32 (4H, 2d, J 8 Hz, phenyl), 7.72 (1H, s, imidazolyl 2-H) and 8.03 (1H, s, NCHO).

MIC against P. Mirabilis 889 is 10 μg/ml.

EXAMPLE 26

6β-[D-2-(4-Ethyl-2,3-dioxopiperazin-1-yl)carbonylamino]-2-(thien-2-yl)acetamido]-6α-formamidopenicillanic acid, sodium salt (a) Benzyl 6β-[DL-2-[(4-ethyl-2,3-dioxopiperazin-1-yl)carbonylamino]-2-(thien-2-yl)acetamido]-6α-(methylthio)-penicillanate A solution of benzyl 6β-amino-6α-(methylthio)-penicillanate (1.46 g) and N,N'-dicyclohexylcarbodiimide (0.92 g) in dichloromethane (25 ml) was stirred and cooled to 0°–5° C. and treated, dropwise, with a solution of DL-2-[(4-ethyl-2,3-dioxopiperazin-1-yl)carbonylamino]-2-(thien-2-yl)acetic acid (1.35 g) in acetone (5 ml) and dichloromethane (25 ml) over 1 hr. The reaction mixture was allowed to regain room temperature over 1 h and stirred at room temperature for 18 h. The precipitated N,N'-dicyclohexylurea was removed by filtration and washed with dichloromethane (20 ml). The organic filtrate was concentrated in vacuo and the residue chromatographed on silica gel 60 (<230 mesh ASTM) eluting with ethyl acetate to give the title compound (1.291 g); $\nu_{max}$. (KBr) 3450 br, 3280, 1778, 1740, 1710, 1680, 1510 and 1185 cm$^{-1}$; δ[(CD$_3$)$_2$CO] 1.04–1.60 (9H, m, C(CH$_3$)$_2$ and NCH$_2$CH$_3$), 2.05 and 2.28 (3H, 2s, SCH$_3$), 3.46 (2H, q, J 8 Hz, NCH$_2$CH$_3$), 3.68 and 4.02 (4H, 2m, NCH$_2$CH$_2$N), 4.39 and 4.44 (1H, 2s, 3-H), 5.19 and 5.21 (2H, 2s, PhCH$_2$'s), 5.45 (1H, s, 5-H), 5.97 (1H, d, J 7 Hz, CH), 6.88–7.03 (1H, m, thienyl-H), 7.15–7.50 (7H, m, phenyl and thienyl- H$_2$), 8.81 (1H, d, J 7 Hz NH), and 9.79–10.02 (1H, br, CONH). (b) Benzyl 6α-amino-6β-[DL-2-[(4-ethyl-2,3-dioxopiperazin-1-yl)carbonylamino]-2-(thien-2-yl)acetamido]-penicillanate A solution of benzyl 6β-[DL-2-[(4-ethyl-2,3-dioxopiperazin-1-yl)carbonylamino]-2-(thien-2-yl)acetamido]-6α-(methylthio)pencillanate (1.3 g) in N,N-dimethylformamide (13 ml) was cooled to −40° C. under nitrogen and stirred. Mercuric acetate (0.63 g), followed by a solution of ammonia in N,N-dimethylformamide (2.2 ml of 16 mg/ml), was added and the mixture stirred at −20° to −40° C. for 0.5 hr. The reaction mixture was allowed to regain room temperature over 1 h and diluted with ethyl acetate (100 ml). The mixture was filtered and the filtrate washed five times with water, saturated brine, and dried over anhydrous magnesium sulphate. The solution was concentrated in vacuo to yield the title compound (1.16 g); δ[(CD$_3$)$_2$CO] 1.00–1.50 (9H, m, C(CH$_3$)$_2$ and NCH$_2$CH$_3$), 2.67–3.10 (2H, brs, NH$_2$), 3.27–3.82 and 3.87–4.19(6H, m, piperazine CH$_2$'s), 4.36 and 4.41(1H, 2s, 3-H), 5.20 (2H, s, CH$_2$Ph), 5.37 and 5.39 (1H, 2s, 5-H), 5.91 (1H, d, J 7 Hz, CH), 6.78–7.07 and 7.10–7.45 (8H, m, phenyl and thienyl -H's), 8.50 and 8.60 (1H, 2s, CONH), 9.9C(1H, d, J 7 Hz, NHCH).

(c) Benzyl 6β-[DL-2-[(4-ethyl-2,3-dioxopiperazin-1-yl)carbonylamino]-2-(thien-2-yl)acetamido]-6α-formamidopencillanate Pyridine (1.5 ml) was added to a solution of benzyl 6α-amino-6β-[DL-2-[(4-ethyl-2,3-dioxopiperazin-1-yl)carbonylamino]-2-(thien-2-yl)acetamido]pencillanate (1.16 g) in dichloromethane (20 ml) at 0°–5° C. The solution was treated with acetic formic anhydride (0.81 g) and the mixture stirred at 0°–5° C. for 1 h, then allowed to regain room temperature over 0.5 h. It was washed with M. hydrochloric acid, dilute aqueous sodium hydrogen carbonate, water, saturated brine, and dried over anhydrous magnesium sulphate. The solution was concentrated in vacuo and chromatographed on silica gel 60 (<230 mesh ASTM), eluting with ethyl acetate, to give the separated diastereoisomers.

The first to elute was the diastereoisomer with the side-chain in the L-configuration (0.44 g); $[α]_D^{20}$+71.5° (c 1 in CHCl$_3$); $\nu_{max}$. (KBr), 3280 br, 1782, 1740, 1710, 1680 br, 1505 br, 1460, 1392, 1368, 1324 br, 1265 br, 1200 sh, and 1187 cm$^{-1}$; δ(CDCl$_3$) 1.04–1.36 (9H, m, C(CH$_3$)$_2$ and CH$_2$CH$_3$), 3.31–3.65 (4H, m, NCH$_2$CH$_2$N), 3.90 –4.15 (2H, m, CH$_2$CH$_3$), 4.39 (1H, s, 3-H), 5.13 (2H, s, CH$_2$Ph), 5.61 (1H, s, 5-H), 5.78 (1H, d, J 8 Hz, NHCH), 6.85–7.00 and 7.11–7.40 (8H, m, phenyl and thienyl–H's), 7.75 (1H, s, CONH), 8.02 (1H, s, NHCHO), 8.11 (1H, s, CHO), 9.82 (1H, d, J 8 Hz, NHCH). The diastereoisomer with the D-configuration in the side-chain eluted second (0.33 g); $[α]_D^{20}$+79.8° (C 1 in CHCl$_3$); $\nu_{max}$. (KBr) 3400 sh, 3280, 1782, 1740 sh, 1710, 1680 br, 1505, 1460, 1391, 1368, 1330, 1280, 1262, and 1185 cm$^{-1}$; δ(CDCl$_3$) 0.98 and 1.10–1.37 (9H, m, C(CH$_3$)$_2$ and CH$_2$CH$_3$), 3.25–3.98(6H, m, NCH$_2$CH$_2$NCH$_2$), 4.38 (1H, s, 3-H), 5.12 (2H, s, CH$_2$Ph), 5.54 (1H, s, 5-H), 5.82 (1H, d, J 8 Hz, NHCH), 6.80–7.00 and 7.10–7.42 (8H, m, phenyl and thienyl-H's), 8.13 (2H, brs, NHCHO), 8.58 (1H, brs, CONH), 10.00 (1H, d, J 8 Hz, NHCH).

(d) 6β-[D-2-[(4-Ethyl-2,3-dioxopiperazin-1-yl)carbonylamino]-2-(thien-2-yl)acetamido]-6α-formamidopenicillanic acid, sodium salt Benzyl 6β-[D-2-[(4-ethyl-2,3-dioxopiperazin-1-yl)carbonylamino]-2-(thien-2-yl)acetamido]-6α-formamidopenicillanate (280 mg) in tetrahydrofuran (20 ml) containing water (2 ml) was hydrogenated for 4 h over 10% palladium on carbon (280 mg). The catalyst was removed by filtration, washed with tetrahydrofuran and the filtrate and washings combined and concentrated in vacuo. The aqueous residue was covered with ethyl acetate and the pH adjusted to 8 with M. sodium hydrogen carbonate solution. The phases were separated, the aqueous phase washed with ethyl acetate and ether and acidified to pH 2 with 5M. hydrochloric acid in the presence of ethyl acetate.

The phases were separated, the aqueous phase further extracted with ethyl acetate, the extracts combined, washed with water at pH 2, saturated brine and dried over anhydrous magnesium sulphate. The solution was evaporated to dryness in vacuo to yield 6β-[D-2-[(4-ethyl-2,3-dioxopiperazin-1-yl)carbonylamino]-2-(thien-2-yl)acetamido]-6α-formidopencillanic acid (70 mg). The acid was suspended in water (30 ml), the pH adjusted to 6.1 by addition of M.aqueous sodium hydrogencarbonate and after 15 min the mixture was filtered and the filtrate freeze-dried to yield the title compound (58 mg); $\nu_{max}$. (KBr) 3740–2600, 1770, 1720, 1680 br, 1610, 1510, 1400, 1370, and 1190 cm$^{-1}$; δ(D$_2$O) 1.08 and 1.32 (6H, 2s, C(CH$_3$)$_2$), 1.18 (3H, t, J 8 Hz, NCH$_2$CH$_3$), 3.50 (2H, q, J 8 Hz, NCH$_2$CH$_3$), 3.69 (2H, brt, NCH$_2$CH$_2$N), 4.00 (2H, brt, NCH$_2$CH$_2$N), 4.20 (1H, s, 3-H), 5.59 (1H, s, 5-H), 5.78 (1H, s, CH), 7.07, 7.28, and 7.49 (3H, m, thienyl-H's), 8.10 (1H, s, CHO).

MIC against P. Mirabilis 889 is 0.1 μg/ml.

EXAMPLE 27

6β-[L-2-[(4-Ethyl-2,3-dioxopiperazin-1-yl)carbonylamino]-2-(thien-2-yl)acetamido]-6α-formamidopenicillanic acid sodium salt Benzyl 6β-[L-2-[(4-ethyl-2,3-dioxopiperazin-1-yl)carbonylamino-2-(thien-2-yl)acetamido]-6α-formamidopenicillanate (390 mg) in tetrahydrofuran (25 ml) containing water (2 ml), was hydrogenated over 10% palladium on carbon (390 mg) for 2 h. The catalyst was removed by filtration and the filtrate further hydrogenated over fresh catalyst (390 mg) for 2 h. The catalyst was removed by filtration, washed well with tetrahydrofuran and the filtrate and washings combined, concentrated in vacuo and the concentrated residue diluted with ethyl acetate. The pH of the mixture was adjusted to 7.5 with M. sodium hydrogen carbonate and the phases separated. The aqueous phase was washed with ethyl acetate and ether and acidified to pH 2 with 2M hydrochloric acid in the presence of ethyl acetate. The phases were separated, the aqueous phase further extracted with ethyl acetate, the extracts combined, washed with water at pH 2, saturated brine, dried over anhydrous magnesium sulphate and the solution evaporated to dryness in vacuo to give 6β-[L-2-[(4-ethyl-2,3-dioxopiperazin-1-yl)carbonylamino]-2-(thien-2-yl)acetamido]-6α-formamidopenicillamic acid (143 mg). This was suspended in water (30 ml) and the pH adjusted to 6.5 with M. sodium hydrogen carbonate, the mixture filtered and the filtrate freeze-dried to yield the title compound (155 mg); $\nu_{max}$ (KBr) 3800–2500, 1770, 1710, 1680br, 1610, 1505, 1465, 1395, 1370, and 1190 cm$^{-1}$; δ(D$_2$O) 1.15 (3H, t, J8 Hz, NCH$_2$C$\underline{H}_3$), 1.22 and 1.41 (6H, 2s, C(CH$_3$)$_2$), 3.45 (2H, t, J $\overline{8}$ Hz, CH$_2$), 3.50–3.77 (2H, m, CH$_2$), 3.81–4.05 (2H, m, CH$_2$), 4.19 (1H, s, 3-H), 5.54 (1H, s, 5-H), 5.83 (1H, s, CH), 6.92–7.48 (3H, m, thienyl-H's), 8.05 (1H,s,CHO).

MIC against P. Mirabilis 889 is 0.5 μg/ml.

EXAMPLE 28

6β-[D-2-Amino-2-(thien-2-yl)acetamido-6α-formamidopencillanic acid (a)
Benzyl-6α-(methylthio)-6β-[DL-2-(4-nitrobenzyloxycarbonylamino)-2-(thien-2-yl)acetamido]penicillanate A solution of benzyl 6β-amino-6α-methylthiopenicillanate 3.52 g) and N,N'-dicyclohexylcarbodiimide (2.26 g) in acetone (20 ml) was stirred and cooled to 0°–5° C. and treated dropwise, over 1 h, with a solution of DL-2-(4-nitrobenzyloxycarbonylamino)-2-(thien-2-yl)acetic acid (3.26 g) in acetone (20 ml). The mixture was allowed to regain room temperature over 1 h, then stirred at room temperature for 18 h. The precipitated N,N-dicyclohexylurea was removed by filtration, washed with acetone and dried (1.67 g). The filtrate was washings were combined and evaporated to dryness in vacuo. Chromatography on silica gel 60 (<230 mesh ASTM), eluting with 20% ethyl acetate in cyclohexane gave the title compound (5.1 g); $\nu_{max}$ (KBr) 3400sh, 3050, 1780, 1745, 1720sh, 1680, 1520, 1348, 1230, 1205, and 1183 cm$^{-1}$; δ(CDCl$_3$) 1.10, 1.25, 1.30 and 1.35 (6H, 4s, C(CH$_3$)$_2$), 2.02 and 2.19 (3H, 2s, SCH$_3$), 4.34 and 4.40 (1H, 2s, 3-H), 5.15, 5.16 and 5.22 (4H, 2s and brs, 2CH$_2$'s), 5.53(1H, s, 5-H), 5.72–5.95 (1H, m, CH), 6.31(1H, d, J 8 Hz, NH̲CH) 6.82–7.60 and 8.05–8.25(12H, m, C$_6$H$_4$; phenyl and thienyl-H's);

(found: M$^+$ 670.1194, C$_{30}$H$_{29}$N$_4$O$_8$S$_3$ requires M 670.1178).

(b) Benzyl
6α-amino-6β-[DL-2-(4-nitrobenzyloxycarbonylamino)-2-(thien-2-yl)acetamido]penicillanate Benzyl 6α-(methylthio)-6β-[DL-2-(4-nitrobenzyloxycarbonylamino)-2-(thien-2-yl)acetamido]penicillanate (5.1 g) was dissolved in N,N- dimethylformamide (40 ml), cooled to 0°–5° C. and treated with mercuric acetate (2.4 g) then ammonia (126 mg) in N,N-dimethylformamide (6 ml). It was stirred at 0°–5° C. for 15 min then diluted with ethyl acetate (150 ml), filtered and the phases separated. The ethyl acetate layer was washed five times with water, saturated brine, dried over anhydrous magnesium sulphate and evaported to dryness in vacuo. Chromatography on silica gel 60(<230 mesh ASTM), eluting with 50% ethyl acetate in cyclohexane, gave the title compound (3.3 g); $\nu_{max}$ (KBr) 3370, 3310, 1772, 1738, 1725sh, 1675br, 1520, 1350, 1264, 1240sh, 1210 and 700cm$^{-1}$.

(c) Benzyl
6α-formamido-6β-[DL-2-(4-nitrobenzyloxycarbonylamino)-2-(thien-2-yl)acetamido]penicillanate Treatment of a solution of benzyl 6α-amino-6β-[DL-2-(4-nitrobenzyloxycarbonylamino)-2-(thien-2-yl)acetamido]pencillanate (3.0 g) in dichloromethane (25 ml) at 0.5° C. with pyridine (3.7 ml), followed by acetic formic anhydride (1.72 ml), was carried out under nitrogen, After 0.5 h at 0°–5° C., the mixture was allowed to regain room temperature over 1 h, washed with M. hydrochloric acid, M. aqueous sodium hydrogen carbonate, saturated brine, dried over anhydrous magnesium sulphate, and evaporated to dryness in vacuo. Purification and separation of the diastereoisomers was accomplished using a Waters prep 500 high performance liquid chromatograph with a PrepPak-500/silica column as the stationary phase and 50% ethyl acetate in cyclohexane as the eluant. The material with the D-configuration in the side-chain eluted first (1.15 g); [α]$_D^{20}$ +168.5° (C 1 in MeOH); $\nu_{max}$(KBr) 3300br 1780, 1740, 1700, 1680, 1520, 1350, 1247, 1210, 1185 and 700 cm$^{-1}$; δ(CDCl$_3$) 1.07 and 1.26 (6H, 2s, C(CH$_3$)$_2$), 4.38 (1H, s, 3-H), 5.13 (4H, brs, 2CH$_2$'s), 5.60 (1H, s, 5-H), 5.68 (1H, d, J 8 Hz, CH), 6.81–7.49 (10H, m, phenyl, thienyl and 2 C$_6$H$_4$ protons), 7.65(1H, brs, CONH), 7.70–8.00(1H, NHCHO), 8.01–8.20 (3H, m, CHO and 2 C$_6$H$_4$ protons). The title compound with the L-configuration in the side-chain eluted second (0.92 g); [α]$_D^{20}$ +112.8° (C 1 in MeOH); $\nu_{max}$ (KBr) 3300br, 1780, 1735, 1680br, 1605, 1520, 1350, 1250br, 1210, and 700 cm$^{-1}$; δ(CDCl$_3$) 1.15 and 1.21 (6H, 2s, C(CH$_3$)$_2$), 4.39 (1H, s, 3-H), 5.12 (4H, brs, 2CH$_2$'s), 5.60 (1H, s, 5-H), 5.79 (1H, d, J 8 Hz,CH), 6.30–6.70 (1H, br, NHCH), 6.81–6.96 (2H, m, thienyl-H$_2$), 7.08–7.49 (8H, m, thienyl-H, phenyl and 2 C$_6$H$_4$ protons), 7.82 (1H, brs, CONH), 8.00–8.20 (2H, m, CHO and 2 C$_6$H$_4$ protons), 8.30–8.80 (1H, br, NH̲CHO).

(d)
6β-[D-2-Amino-2-(thien-2-yl)acetamino]-6α-formamidopenicillanic acid

Benzyl 6α-formamido-6β-[D-2-(4-nitrobenzyloycarbonylamino)-2-(thien-2-yl)acetamido]penicillanate (645 mg) was dissolved in tetrahydrofuran (10 ml) and the solution diluted with water (2 ml), before hydrogenation over 10% palladium on carbon (650 mg) for 4 h. The catalyst was removed by filtration, washed with tetrahydrofuran and water, the filtrate and washings combined, concentrated, washed well with ethyl acetate and ether and freeze dried to yield the title compound (175 mg); $\nu_{max}$(KBr) 3740–2200, 1770, 1675br, 1604, 1500, 1390, 1340 and 1250 cm$^{-1}$.

EXAMPLE 29

6β-[L-2-Amino-2-(thien-2-yl)acetamido]-6α-formamidopenicillanic acid

Benzyl 6α-formamido-6β-[L-2-(4-nitrobenzyloxycarbonylamino)-2-(thien-2-yl)acetamido[pencillanate (0.33 g) was dissolved in tetrahydrofuran (10 ml), diluted with water (5 ml) then ethanol (3 ml) and hydrogenated over 10% palladium on carbon (0.33 g) for 1 h. The catalyst was removed by filtration and fresh 10% palladium on carbon (0.33 g) added to the reaction mixture. After 1 h, the catalyst was removed by filtration, washed with tetrahydrofuran, water and ethanol, the filtrate and washings combined and concentrated. The residue was washed well with ethyl acetate and ether and freeze-dried to yield the title compound (94 mg); $\nu_{max}$(KBr) 3420b, 3230br, 1768, 1670br, 1600br, 1510br, 1380, 1340, and 1250 cm$^{-1}$.

EXAMPLE 30

6β-[(2R,3S)-3-Benzyloxy-2-[(4-ethyl-2,3-dioxopiperazin-1-yl)carbonylamino]butyramido]-6α-formamidopenicillanic acid, sodium salt (a) (2R, 3S)-3-Benzyloxy-2-[(4-ethyl-2,3-dioxopiperazin-1-yl)carbonylamino]butyric acid O-Benzyl-D-threonine (0.92 g, 4.4 mmole) (prepared by the method of T. Mizoguchi, G. Levin, D. W. Woolley, and J. M. Stewart, *J. Org. Chem.*, 1968, 33, 903, who described the L-isomer) was suspended in water (20 ml) and the pH adjusted to 9.5 , giving a virtually complete solution. This was cooled to 0° C. and stirred while 4-ethyl-2,3-dioxopiperazine-1-carbonyl chloride (1.00 g, 4.9 m mole) in AR acetone (10 ml) was added dropwise. The pH was kept at 9.5 by the addition of further base while the solution was allowed to regain room temperature. After 2 h the solution was acidified to pH 2 and the bulk of the acetone removed by evaporation. The oily product was extracted into ethyl acetate (3×50 ml), then the total organic phase was washed once with brine and dried over sodium sulphate. Evaporation gave the title acid (1.36 g, 82%) as a colourless non-crystalline foam which retained solvent traces tenaciously; $R_f$ 0.35 in chloroform:methanol:acetic acid, 17:2:1; δ(CDCl$_3$) 0.75–1.35 (5H, m, CH$_3$CH and NCH$_2$CH$_3$), 3.1–3.7 (4H, m, 2 NCH$_2$), 3.9–4.25 (2H, m, NCH$_2$), 4.50 (2H, m, CH—CH), 6.25 (1H, brs, D$_2$O exch, OH), 7.25 (5H, s, aryl), 9.50 (1H, brd), J 7 Hz, D$_2$O exch, NH), 9.70 (1H, brs, D$_2$O exch, CO$_2$H).

(b) Benzyl 6β-[(2R, 3S)-3-benzyloxy-2-[(4-ethyl-2,3-dioxopiperazin-1-yl)carbonylamino]butyramido]-6α-(methylthio)pencilanate The preceding acid benzyl ether (1.29 g, 3.42 m mole) was dissolved in dry dichloromethane (7 ml) and added dropwise with stirring at 0° C. over 0.5 hr to a solution of benzyl 6β-amino-6α-(methylthio)penicillanate (1.20 g, 3.4 m mole) and dicyclohexylcarbodi-imide (0.70 g, 3.4 mmole) in dichloromethane (5 ml). The mixture was allowed to regain room temperature and stirring was continued overnight. After 16 h the precipated dicyclohexylurea was filtered off and the filtrate evaporated to dryness. The residue was dissolved in ethyl acetate and the filtered solution washed sequentially with water, 0.5M. hydrochloric acid, water, saturated aqueous sodium hydrogen carbonate, water and brine, then dried over sodium sulphate. Evaporation gave crude product which was chromatographed on silica gel (120 g), eluting with 2% methanol in chloroform, to give the title 6α-(methylthio)penicillin ester as a colourless, crisp foam (0.59 g, 24%); $R_f$ 0.60 in 10% methanol-chloroform; δ(CDCl$_3$) 1.17 (3H, t,J 7 Hz, NCH$_2$CH$_3$), 1.26 (3H, d, J 7 Hz, CH$_3$CH), 1.32 and 1.45 (6H, 2s, (CH$_3$)$_2$C), 2.12 (3H, s, CH$_3$S), 3.50 (4H, m, 2 NCH$_2$), 3.90–4.30 (3H, m, NCH$_2$+CH(CH$_3$)), 4.42 (1H, s, 3-H), 4.45–4.65 (3H, m, Ph CH$_2$O (ether)+CHNH), 5.15 (2H, s, Ph CH$_2$O), 5.51 (1H, s, 5-H), 7.27 and 7.32 (10H, 2s,phenyls), 7.62 (1H,brs,D$_2$O exch, 6-NH), 9.50 (1H,brd, J 7 Hz, D$_2$O exch, CH—NH).

(c) Benzyl 6β-[(2R,3S)-3-benzyloxy-2-[(4-ethyl-2,3-dioxopiperazin-1-yl)carbonylamino]butyramido]-6α-aminopencillanate The preceding 6α-methylthio derivative (0.59 g, 0.83 m mole) was dissolved in dry dimethylformamide (6.4 ml) and stirred under nitrogen at −40° C. Mercuric acetate (0.26 g, 1 eq) and ammonia (0.016 g, 1 eq) in dimethylformamide (1 ml) were added sequentially, then the mixture was allowed to regain room temperature and stirred for 1.5 h. Workup was effected by partition of the reaction mixture between ethyl acetate and water; the organic phase was separated, washed further with water (4×) and brine, and dried over sodium sulphate. Evaporation gave the 6α-amino penicillin as a crisp yellow foam (0.44 g); which was sufficiently pure to be used directly; $R_f$0.4 in 10% methanol-chloroform; δ(CDCl$_3$) 1.14 (3H, t, J 7 Hz, NCH$_2$CH$_3$), 1.26 (3H, d, J 7 Hz, CH$_3$CHO), 1.30 and 1.42 (6H, 2s, (CH$_3$)$_2$C), 2.87 (2H, brs, D$_2$O exch, NH$_2$), 3.30–3.75 (4H, m, 2 NCH$_2$), 3.90–4.30 (3H, m, NCH$_2$ & CHNH), 4.41 (1H, s, 3-H), 4.50 (1H, m, CHO), 4.59 (2H, s, PhCH$_2$O of ether), 5.20 (2H, s, Ph CH$_2$O of ester), 5.33 (1H, s, 5-H), 7.2–7.5 (10H m, phenyls) 8.07 (1H, brs, D$_2$O exch, 6-NH), 9.55 (1H, brd, J 7 Hz, D$_2$O exch, CHNH).

(d) Benzyl 6β-[(2R,3S)-3-benzyloxy-2-[(4-ethyl-2,3-dioxopiperazin-1-yl)carbonylamino]butyramido]-6α-formamidopenicillanate The preceding 6α-amino derivative (0.42 g , 0.62 mmole) was dissolved in dichloromethane (5.5 ml) and stirred at 0° C. while dry pyridine (0.49 ml, 10 eq) and acetic formic anhydride (0.25 ml, 5 eq) were added. The solution was allowed to regain room temperature and stirred for 1 h. It was then partitioned between 0.5M, hydrochloric acid and sufficient ethyl acetate to make the organic layer the upper. The organic phase was separated and washed further with 0.5M hydrochloric acid, water, saturated aqueous sodium hydrogen carbonate, water and brine, then dried over sodium sulphate. Evaporation gave a yellow solid which was subjected to chromatography on silica gel (40 g), eluting with 2% methanol-chloroform. The product-rich fractions, on evaporation and trituration with ether, afforded the title 6α-formamido penicillin as a white semi-solid (0.25 g, 57%); $R_f$ 0.35 in 10% methanol-chloroform; $\delta[(CD_3)_2CO]$ 1.13(3H, t, J 7 Hz, NCH$_2$CH$_3$), 1.25 (3H, d, J 7 Hz, CHHD 3CH), 1.31 and 1.46 (6H, 2s, (CH$_3$)$_2$C), 3.30–3.75 (4H, m, 2-NCH$_2$), 3.90–4.30 (3H, m, NCH$_2$+CH NH), 4.48 (1H, s, 3-H), 4.55 (1H, m, CHO), 4.60 (2H, s, Ph CH$_2$O of ether), 5.20 (2H, s, PhCH$_2$O of ester), 5.60 (1H, s, 5-H), 7.20–7.50 (10H, m, phenyls), 8.12 (1H, s, NHCHO), 8.22 and 8.35 (2H, 2 brs, D$_2$O exch, 6-NH's), 9.55 (1H, brd, J 7 Hz, D$_2$O exch, CHNH).

(e) 6β-[(2R,3S)-3-Benzyloxy-2-[(4-ethyl 2,3-dioxopiperazin-1-yl)carbonylamino]butyramido]-6α-formamidopencillanic acid, sodium salt The preceding 6α-formamido benzyl ester (0.23 g; 0.32 m mole) was dissolved in tetrahydrofuran: water (10 ml, 4:1). Palladium on charcoal catalyst (0.15 g) was added and the mixture was hydrogenated for a total of 6 h, with one filtration and change of catalyst after 3 h. After this time the catalyst was filtered off and washed well with both solvents then the filtrate was concentrated to remove tetrahydrofuran and partitioned between ethyl acetate and M. sodium hydrogen carbonate solution (two portions). The aqueous phase was acidified to pH 2 with 2M hydrochloric acid and the product extracted into tetrahydrofuran: ethyl acetate (3 portions, 1:1). The organic extract was dried over sodium sulphate and evaporated to dryness. The residue was dissolved in acetone and converted to its sodium salt by addition of 2M sodium 2-ethylhexanoate in methyl isobutyl ketone. This procedure afforded the title penicillin (90 mg, 55%), $R_f$0.45 in n-butanol:acetic acid:water, 4:1:1, $\nu_{max}$. (KBr) 1765,1710 cm$^{-1}$; $\delta$ (D$_2$O) 1.18 (3H, t, J 7 Hz, NCH$_2$CH$_3$), 1.2–1.5 (9H, m, CH$_3$CH & (CH$_3$)$_2$C), 3.30–3.75 (4H, m, 2 NCH$_2$), 3.90–4.10 (2H, m, NCH$_2$), 5.21 (2H, s, PhCH$_2$O), 5.51 (1H, s,5-H), 7.30 (5H, s, phenyls), 8.05 (1H, s, NHCHO), 8.15 (1H, brd, J 7 Hz, exch, NH). Other signals are obscured by the water peak.

MIC against P. Mirabilis 889 is 100 μg/ml.

EXAMPLE 31

Benzyl 6β-amino-6α-formamidopenicillanate (a) Benzyl 6β-(2,2,2-trichloroethoxycarbonylamino)-6α-(methylthio)penicillanate Benzyl 6β-amino-6α-(methylthio)penicillanate (3.52 g, 10 mmole) was stirred at 0° C. with dry pyridine (1.22 ml, 1.5 eq) in dry dichloromethane (20 ml). A solution of 2,2,2-trichloroethyl chloroformate (2.20 g, 1.5 eq) in the same solvent was added dropwise over about 0.25 h. The resulting mixture was allowed to regain room temperature, then poured into a mixture of ethyl acetate (50 ml) and 0.5 M hydrochloric acid (30 ml). The organic phase was separated and washed further with 0.5 M hydrochloric acid (2×), water, saturated sodium hydrogen carbonate solution, water and brine, then dried over sodium sulphate. Evaporation gave the protected 6α-(methylthio) derivative as a crisp, near-colourless foam (5.17 g, 98%); $R_f$0.80 in 10% methanol-chloroform; $\delta$ (CDCl$_3$) 1.45 and 1.60 (6H, 2s, C(CH$_3$)$_2$), 2.40 (3H, s, CH$_3$S), 4.60(1H, s, 3-H), 4.85 (2H, narrow d, Cl$_3$CCH$_2$O), 5.30 (2H, s, PhCH$_2$O), 5.60 (1H, s, 5-H), 6.40 (1H, brs, D$_2$O exch, NH), 7.50 (5H, s, phenyls); (Found: M$^+$, 525.9943. C$_{19}$H$_{21}$Cl$_3$N$_2$O$_5$S$_2$ requires M, 525.9940).

(b) Benzyl 6β-(2,2,2-trichloroethoxycarbonylamino)-6α-aminopenicillanate

Benzyl 6β-(2,2,2-trichloroethoxycarbonylamino)-6α-(methylthio)penicillanate (5.15 g, 9.76 mmole) was dissolved in dry dimethylformamide (20 ml) and cooled to −40° C. with stirring. To this solution were added sequentially, mercuric acetate (3.15 g, 1 eq) and a solution of anhydrous ammonia (0.17 g, 1 eq) in dry dimethylformamide (6 ml). The resulting mixture was allowed to warm to room temperature over 1 h, then poured into a mixture of ethyl acetate (100 ml) and water (50 ml). The organic phase was separated and washed further with water (4×), then with brine, and dried over sodium sulphate. Evaporation gave the 6α-amino penicillin as a pale yellow foam (4.44 g, 89%) which was used without further purification; $R_f$0.65 in 10% methanol-chloroform; $\delta$ (CDCl$_3$) 1.40 and 1.55 (6H, 2s, (CH$_3$)$_2$C), 2.65 (2H, brs, D$_2$O exch, NH$_2$), 4.55 (1H, s, 3-H), 4.80 (2H, s, Cl$_3$CCH$_2$O), 5.25 (2H, s, PhCH$_2$O), 5.45 (2H, s, 5-H), 6.45 (1H, brs, D$_2$O exch, NH), 7.45 (5H, s, phenyls).

(c) Benzyl 6β-(2,2,2-trichloroethoxycarbonylamino)-6α-formamidopencillanate

Benzyl 6β-(2,2,2-trichloroethoxycarbonylamino)-6α-aminopencilliianate (4.40 g, 8.86 mmole) was stirred at 0° C. in dry dichloromethane (30 ml). To this solution were added dry pyridine (6.95 ml, 10 eq) and acetic formic anhydride (3.51 ml, 10 eq). The resulting pale yellow solution was allowed to warm to room temperature over 1 h, then washed sequentially with 0.5M hydrochloric acid (2×200 ml), water, saturated sodium hydrogen carbonate solution, water and brine and finally dried over sodium suplhate. Evaporation gave the crude product which was subjected to chromatography on silica gel (350 g), eluting with 2% methanol-chloroform, to give the desired 6α-formamido penicillin (3.03 g, 65%). This was subsequently found to crystallise on trituration with ether; m.p. 132°–4° C.; $R_f$0.45 in 10% methanol-chloroform; $\nu_{max}$. (KBr). 3340, 3160, 1790, 1745 and 1670 cm$^{-1}$; $\delta$ (CDCl$_3$) 1.37 and 1.53 (6H, 2s, (CH$_3$)$_2$C), 4.52 (1H, s, 3-H), 4.72 (2H, s, Cl$_3$CCH$_2$O), 5.17 (2H, s, PhCH$_2$O), 5.66 (1H, s, 5-H), 6.75 (1H, brs, D$_2$O exch, NH), 7.34 (5H, s, phenyls), 7.70 (1H, brs, D$_2$O exch, NH), 8.19 (1H, s, NHCHO); (Found: C, 43.6; H, 4.1; N, 7.85%. C$_{19}$H$_{20}$Cl$_3$N$_3$O$_6$S requires C, 43.5; H, 3.8; N, 8.0%).

(d) Benzyl 6β-amino-6α-formamidopenicillanate

Benzyl 6β-(2,2,2-trichloroethoxycarbonylamino)-6α-formamidopenicillanate (1.44 g, 2.75 mmole) was dissolved in tetrahydrofuran (45 ml) and M. potassium dihydrogen phosphate (9 ml). The resulting mixture was stirred at room temperature and powdered zinc (2 g), which had been freshly activated by washing with hydrochloric acid, then with water, was added. The pH of the mixture was kept at 4.5 by the addition of 2M. hydrochloric acid. The progress of the reaction was monitored by t.l.c., and after about 4 h no starting material was visible. For workup the zinc was filtered off and the filtrate partitioned between ethyl acetate and water. The organic phase was separated and further washed with water and brine, then dried over sodium sulphate. Evaporation gave the crude product as a pale yellow gum (0.66 g, 84%); $R_f$0.30 in 10% methanol-chloroform. The material was not stable in this form. It could, however, be converted into its crystalline toluene-p-sulphonate salt by mixing an ethyl acetate solution with the stoichiometric quantity of toluene-p-sulphonic acid as a slurry in ethyl acetate. In this way 0.44 g (1.26 mmole) of impure free base gave 0.44 g (67%) of the 6β-amino derivative as its toluene-p-sulphonate. The salt had to be dissolved in d⁴-methanol or d⁶-dimethyl sulphoxide for n.m.r. purposes and rather facile. decomposition ensued. However, recovery of the free base form after the salt had been standing in a desiccator for a week gave material of good purity; $R_f$ as above; δ (CDCl₃) 1.45 and 1.70 (6H, 2s, (CH₃)₂C); 2.60 (2H, brs, D₂O exch, NH₂); 4.60 (1H, s, 3-H); 5.30 (2H, s, PhCH₂O); 5.70 (1H, s, 5-H), 7.05 (1H, brs, D₂O exch, NHCHO), 7.50 (5H, s, phenyls), 8.35 (1H, s, NHCHO).

EXAMPLE 32

6α-Formamido-6β-[D-2-(4-hydroxyphenyl)-2-[3-[4-hydroxy-2-(phenylamino)pyrimidin-5-yl]ureido]acetamido]penicillanic acid, sodium salt 6β-[D-2-Amino-2-(4-hydroxyphenyl)acetamido]-6α-formamidopenicillanic acid (0.20 g) was suspended in water (20 ml) and the pH adjusted to 7.5 by the addition of triethylamine. The resulting solution was stirred and cooled to 0°–5° C. and treated portionwise with [4-hydroxy-2-(phenylamino) pyrimidin-5-yl]aminocarbonyl chloride (0.114 g) the pH being maintained between 7 and 7.5 by addition of triethylamine. The mixture was stirred at 0°–5° C. for 0.5 h, then concentrated under reduced pressure. The aqueous residue was washed twice with ethyl acetate (25 ml) and diethyl ether, before being acidified to pH 2 with 5M hydrochloric acid in the presence of ethyl acetate (25 ml). The resulting precipitate was collected by filtration, washed with water, ethyl acetate and diethylether and suspended in water (10 ml) containing sodium hydrogencarbonate (0.018 g), the mixture filtered and the filtrate freeze-dried to give the title compound (0.15 g):$\nu_{max}$(KBr) 3700–3200, 1770, 1660, 1610, 1593, 1540, 1518, 1499, 1444, 1390, 1350sh, 1265sh, and 1217cm⁻¹; δ[D₂O/(CD₃)₂SO/CD₃OD; 2:1:1:]0.95 and 1.29 (6H, 2s, C(CH₃)₂), 4.05 (1H, s, 3-H), 5.26 (1H, s, CHCO), 5.50, (1H, s, 5-H), 6.64–6.90 and 7.00–7.50 (9H, 2 m, phenyl and C₆H₄), 7.90 (1H, s, pyrimidine-H), 8.02 (1H, s, CHO).

MIC against P. Mirabilis 889 is 5.0 μg/ml.

EXAMPLE 33

6β-[2[(4-Ethyl-2,3-dioxopiperazin-1-yl)carbonylamino]-2-(3,4-dihydroxyophenyl)acetamido]-6α-formamidopenicillanic acid, sodium salt Subtilisin alcalase on Mitibishu WH-105 was washed thoroughly with water to remove all supernatant buffer traces. The damp resin-bound enzyme (2 g) was added to a stirred solution of 6β-[2-[(4-ethyl-2,3-dioxopiperazin-1-yl)carbonylamino]-2-(3,4-diacetoxyphenyl)acetamido]-6α-formamidopenicillanic acid, sodium salt (100 mg, 0.143 mmol) in water (10 ml) at room temperature. The effective pH was 7.5–8.0. After 1 h the resin was filtered off and the filtrate was saturated with sodium chloride, then acidifed to pH 2 with 2M hydrochloric acid and concomitantly edtracted into ethyl acetate; tetrahydrofuran (1:1, 3×20 ml). The total organic extract was dried over sodium sulphate and evaporated to dryness, then suspended in water (5 ml). The pH was adjusted to 6.5 by addition of sodium hydrogen carbonate, when a clear solution resulted. Evaporation followed by trituration with acetone, filtering, washing with acetone and ether and drying gave the dihydroxy penicillin sodium salt (40 mg, 45%); $R_f$0.15 in n-butanol: acetic acid: water, 4:1:1; $\nu_{max}$ (KBr) 1770, 1710, 1675, 1560 cm⁻¹; δ (D₂O) 0.93 and 1.32 (6H, 2s, (CH₃)₂C), 1.20 (3H, t, J 7 Hz, CH₃CH₂N), 3.30–3.80(4H, m, 2×CH₂N), 3.90–4.10 (2H, m, CH₂N), 4.15(1H, s, 3-H), 5.27(1H, s, 5-H), 5.57(1H, s, COCHN), 6.80–7.00(3H, m, aryl H), 8.10(1H, s, NHCHO)

MIC against P.mirabilis 889 is 0.2 μg/ml.

EXAMPLE 34

7β-amino-7α-formamidocephalosporanic acid, trifuluoroacetic acid salt (a) t-Butyl 7α-methythio-7β-(trichloroethoxycarbonyl-amino)-cephalosporanate t-Butyl 7β-amino-7α-(methylthio)cephalosporanate (6.92 g, 18.5 mmol) in dichloromethane (50 ml) with pyridine (2.2 ml, 27.2 mmol) was cooled to 0° C. and treated dropwise over 0.5 h with a solution of 2,2,2-trichloroethyl chloroformate (2.5 ml, 18.5 mmol) in dichloromethane (10 ml). Once addition was complete the reaction was stirred for 5 min., washed with N. hydrochloric acid, brine, dried over magnesium sulphate, and evaporated to give the almost pure product (9.86 g, 97%), δ (CDCl₃) 1.54 (9H, s, C(CH₃)₃), 2.06 (3H, s, OCOCH₃), 2.38 (3H, s, SCH₃), 3.35 & 3.49 (2H, ABq, J 18 Hz, 2-H₂) 4.6–5.2 (5H, m, 6-H, CH₂OAc, CH₂CCl₃), 6.08 (1H, s,NH); $\nu_{max.}$ (CH₂Cl₂) 3380, 2930, 1780, 1740, 1620 cm⁻¹; (Found: M⁺, 548.0010. C₁₈H₂₃C₂₃N₂O₇S₂ requires M, 548.0010).

(b) t-Butyl 7α-amino-7β-(trichloroethoxycarbonylamino)-cephalosporanate t-Butyl 7α-methylthio-7β-trichloroethoxycarbonylamino cephalosporanate (9.86 g, 17.9 mmol) in dimethylformamide (60 ml) at −40° C. was treated with a solution of mercuric acetate (5.72 g, 17.9 mmol) in dimethylformamide (10 ml), followed by ammonia (0.30 g, 17.9 mmol) in dimethylformamide (15 ml). The reaction mixture was allowed to warm to 0° C. over 1.5 h., then poured into ethyl acetate, washed well with water, brine, dried and evaporated to give the title compound (8.0 g, 86%); δ (CDl₃) 1.56 (9H, s, C(CH₃)₃), 2.10 (3H, s, OCOCH₃), 2.75 (2H, brs, NH₂), 3.32 & 3.52 (2H, ABq, J 18 Hz, 2-H₂), 4.4–5.2 (5H, m, 6-H, CH₂OAc, CH₂CCl₃), 6.53 (1H, s, NH). $\nu_{max.}$ (THF) 3200, 1790, 1740, 1730 cm⁻¹.

(c) t-Butyl 7α-formamido-7β-(trichloroethoxycarbonylamino)-cephalosporanate t-Butyl 7α-amino-7β-(trichloroethoxycarbonylamino)cephalosporanate (8.0 g, 0.015 mol) in dichloromethane (60 ml) was cooled to 0° C. and treated with pyridine (13 ml, 0.16 mol) and acetic formic anhydride (6.5 ml 0.082 mol). The reaction mixture was stirred at 0° C. for 1.5 h., washed with N. hydrochloric acid, saturated sodium hydrogen carbonate solution brine, dried and evaporated to give the title compound (8.13 g, 96%); δ (CDCl₃) 1.53 (9H, s, C(CH₃)₃), 2.07 (3H, s, OCOCH₃), 3.28 & 3.46 (2H, ABq, J 17 Hz, 2-H₂), 4.7–5.3 (5H, m, 6-H, CH₂OAc, CH₂CCl₃), 6.66 (1H, s, NH), 7.63 (1H, br s, NH), 8.22 (1H, s, CHO); $\nu_{max.}$ (CH$_2$Cl$_2$), 3380, 1790, 1735, 1700 cm$^{-1}$.

(d) t-Butyl 7β-amino-7α-formamidocephalosporanate t-Butyl 7α-formamido-7β-(trichloroethoxycarbonylamino)cephalosporanate (8.13 g, 14.9 mmol) in tetrahydrofuran (100 ml) and M. potassium dihydrogen phosphate solution (20 ml) was stirred with zinc powder (15 g) which had been freshly activated by washing with 5N. hydrochloric acid followed by water. After 6 h. the reaction mixture was filtered and the tetrahydrofuran evaporated. The residue was diluted with ethyl acetate, washed with water, brine, dried and evaporated. The crude material was recrystallized from ethyl acetate/hexane to give the product (2.5 g, 45%); m.p. 166°–170° C. (dec.); δ(CDCl$_3$) 1.58 (9H, s, C(CH$_3$)$_3$), 2.10 (3H, s, OCOCH$_3$), 2.43 (2H, s, NH$_2$), 3.35 & 3.55 (2H, ABq, J 18 Hz, 2-H$_2$), 4.81 & 4.99 (2H, ABq, J 13 Hz, CH$_2$OCO), 5.11 (1H, s, 6-H), 6.92 (1H, s, NH), 8.25 & 8.26 (1H, 2s, CHO); $\nu_{max.}$ (CH$_2$Cl$_2$) 3410, 1790, 1740, 1700 cm$^{-1}$; (Found: C, 48.5; H, 5.9; N, 11.4%. C$_{15}$H$_{21}$N$_3$O$_6$S requires C, 48.5; H, 5.7; N, 11.3%).

(e) 7β-Amino-7α-formamidocephalosporanic acid, trifluoroacetic acid salt t-Butyl 7β-amino-7α-formamidocephalosporanate (0.10 g, 0.23 mmol) in trifluoroacetic acid (5 ml) was stirred at room temperature for 0.5 h. The solution was evaporated to dryness and the residue triturated with ether and the solid product filtered and dried, (0.083 g, 72%); δ (CF$_3$COOH), 2.23 (3H, s, COCH$_3$), 3.74 (2H, s, 2-H$_2$), 5.27 and 5.41 (2H, ABq, J 15 Hz, CH$_2$OCO); 5.41 (1H, s, 6-H), 8.52 (1H, s, CHO); $\nu_{max.}$ (KBr) 3320, 2980, 2960, 1795, 1780, 1725 and 1665 cm$^{-1}$.

EXAMPLE 35

7β-(D-2-Amino-2-phenylacetamido)-7α-formamidocephalosporanic acid, trifluoroacetic acid salt (a) t-Butyl 7β-[D-2-(t-butoxycarbonylamino)-2-phenylacetamido]-7α-formamidocephalosporanate A solution of D-2-(t-butoxycarbonylamino)-2-phenylacetic acid (0.126 g, 0.5 mmol) in dichloromethane (10 ml) was added slowly, dropwise to a stirred solution of t-butyl 7β-amino-7α-formamidocephalosporanate (0.186 g, 0.5 mmol) and N,N'-dicyclohexylcarbodiimide (0.113 g, 0.55 mmol) in dichloromethane (15 ml). The reaction mixture was stirred at room temperature for 2 days before being filtered and evaporated to dryness. The residue was dissolved in ethyl acetate, filtered, washed with dilute hydrochloric acid, dilute aqueous sodium hydrogen carbonate, brine, and drived over magnesium sulphate. The solution was then evaporated to dryness and the crude product chromatographed on silica gel 60 (<230 mesh) eluting with ethyl acetate/hexane 1:1 to afford the title compound (0.100 g, 33%): $\lambda_{max.}$ (EtOH) 261 nm (ε 7340); $\nu_{max.}$ (CH$_2$Cl$_2$) 3380, 3265, 1788, 1740 sh, 1722, 1685 cm$^{-1}$; δ (CDCl$_3$) 1.37 (9H, s, (CH$_3$)$_3$COCONH), 1.51 (9H, s, (CH$_3$)$_3$COCO), 2.01 (3H, s, OCOCH$_3$), 2.95 and 3.21 (2H, ABq, J 17 Hz, 2-H$_2$), 4.78 and 4.95 (2H, ABq, J 13 Hz, —CH$_2$OCOCH$_3$), 5.21 (1H, s, 6-H), 5.44 (1H, d, J 8 Hz, α-proton), 7.20–7.60 (6H, m, aromatics, and α-NHCO), 7.83 (1H, brs, NHCHO), 8.07 (1H, s, NHCHO) and 8.68 (1H, s, 7β-NHCO).

(b) 7β-(D-2-Amino-2-phenylacetamido)-7α-formamidocephalosporanic acid, trifluoroacetic acid salt A soltuion of t-butyl 7β-[D-2-(t-butoxycarbonylamino)-2-phenylacetamido]-7α-formamidocephalosporanate (0.087 g, 0.144 mmol) in trifluroracetic acid (5 ml), was allowed to stand at room temperature for 0.5 h. It was then evaporated to dryness, treated with toluene, and re-evaporated. The residue was triturated with ether, and the resulting solid was filtered and washed well with ether and ethyl acetate. It was dried in vacuo to afford the product as a pale yellow solid (0.041 g, 51%); $\lambda_{max.}$ (H$_2$O) 260 nm (ε 8959); $\nu_{max.}$ (KBr) 1780, 1735, sh, 1680, 1620 sh, 1500 cm$^{-1}$; δ (CH$_3$CO$_2$D) 2.23 (3H, s, OCOCH$_3$), 3.12 and 3.40 (2H, ABq, J 17 Hz, 2-H$_2$), 5.22 and 5.42 (2H, ABq, J 14 Hz, CH$_2$OCOCH$_3$), 5.39 (1H, s, 6-H), 5.54 (1H, s, α-proton), 7.57 (5H, s, aromatics) and 8.33 (1H, s, NHCHO).

MIC against P. Mirabilis 889 is >100 μg/ml.

EXAMPLE 36

7β-[D-2-[(4-Ethyl-2,3-dioxopiperazin-1-yl)carbonylamino]-2-phenylacetamido]-7α-Formamidocephalosporanic acid, sodium salt (a) t-Butyl 7β-[D-2-[(4-ethyl-2,3-dioxopiperazin-1-yl)carbonylamino]-2-phenylacetamido]-7α-(methylthio)-cephalosporanate D-2-[(4-Ethyl-2,3-dioxopiperazin-1-yl)carbonylamino]-2-phenylacetic acid (0.48 g, 1.5 mmol) in dichloromethane (30 ml) was converted to its acid chloride by treatment with oxalyl chloride (0.38 g, 3 mmol). After stirring at room temperature for 1 h, the reaction solution was evaporated to dryness. The resulting acid chloride in dichloromethane (20 ml) was then added dropwise to a stirred mixture of t-butyl 7α-amino-7β-(methylthio) cephalosporanate (0.56 g, 1.5 mmol) and ground 4A molecular sieves (3.0 g) in dichloromethane (25 ml) at 0° C. The mixture was stirred at 0°–5° C. for 0.5 h followed by 2 h at room temperature, before being filtered and evaporated to dryness. The crude product was chromatographed on silica gel 60 (<230 mesh ASTM) eluting with ethyl acetate/hexane 2:1 through to ethyl acetate, to afford the desired product 0.61 g(60%)$\nu_{max}$(CH$_2$Cl$_2$) 3390, 3280, 1790, 1740sh, 1725, 1698 cm$^{-1}$; δ(CDCl$_3$) 1.22(3H, t, J 7 Hz, CH$_2$CH$_3$), 1.53 (9H, s, C(CH$_3$)$_3$), 2.09(3H, s, OCOCH$_3$), 2.30(3H, s, SCH$_3$), 3.20 and 3.40 (2H, ABq, J 18 Hz, 2-H$_2$), 3.54(4H, m, piperazine CH$_2$ and CH$_2$CH$_3$), 3.90–4.20 (2H, m, piperazine CH$_2$), 4.77 and 5.03 (2H, ABq, J 13 Hz, CH$_2$OCOCH$_3$), 4.91(1H, s, 6-H) 5.67 (1H, d, J 7 Hz, α proton), 7.16 (1H, s, 7β—NHCO—), 7.30–7.55 (5H, m, aromatics) and 10.01 (1H, d, J 7 Hz, α—NHCO—).

(b) t-Butyl 7α-amino-7β-[D-2-[(4-ethyl-2,3-dioxopiperazin-1-yl)carbonylamino]-2-phenylacetamido]cephalosporanate t-Butyl 7β-[D-2-ethyl-2,3-dioxopiperazin-1-yl)carbonylamino]-2-phenylacetamido]-7α-(methylthio)cephalosporanate (0.52 g, 0.77 mmol) in dimethylformamide (15 ml) was cooled to −50° C. under nitrogen. A solution of mercuic acetate (0.25 g, 0.77 mmol) in dimethylformamide (0.77 ml) was then added, followed immediately by ammonia (0.014 g, 0.85 mmol) in dimethylformamide (1 ml). The mixture was stirred from −50° C. to −20° C. over a period of 1 h, before being poured into ethyl acetate and washed with water and brine. The organic solution was dried over magnesium sulphate, filtered and evaporated to afford the crude product. Chromatography on silica gel 60(<230 mesh ASTM) eluting with ethyl acetate gave the title comound (0.20 g, 41%); $\nu_{max.}$ (CH$_2$Cl$_2$) 3490, 3290, 1790, 1740sh, 1725, 1695cm$^{-1}$; δ (CDCl$_3$) 1.23(3H, t, J 6 Hz, CH$_2$CH$_3$), 1.54(9H, s, C(CH$_3$)$_3$), 2.08 (3H, s, OCOCH$_3$), 2.95(2H, brs, NH$_2$), 3.09 and 3.37 (2H, ABq, J 18 Hz, 2-H$_2$), 3.54 (4H, m, piperazine CH$_2$ and —CH$_2$CH$_3$), 3.88–4.20(2H, m, piperazine CH$_2$), 4.72 and 4.97 (2H, ABq, J 13 Hz, CH$_2$OCOCH$_3$), 4.88 (1H, s, 6-H), 5.50 (1H, d, J 7 Hz, α-proton), 7.30–7.50(5H, m, aromatics), 7.65 (1H, brs, 7β-NH) and 10.00 (1H, d, J 7 Hz, α-NHCO).

(c) t-Butyl 7β-[D-2-[(4-ethtl-2,3-dioxopiperazin-1-yl) carbonylamino]-2-phenylacetamido]-7α-formamidocephalosporanate A solution of t-Butyl 7α-amino-7β-[D-2-[(4-ethyl-2,3-dioxopiperazin-1-yl)carbonyulamino]-2-phenylacetamido]celphalosporanate (0.182 g,0.29 mmol) in dichloromethane (20 ml) at 0° C., was treated with pyridine (0.095 g, 1.2 mmol) and acetic formic anhydride (0.053 g, 0.6 mmol). The solution was stirred at 0°–5° C. for 0.25 h, followed by 0.75 h at room temperature. It was then washed with 0.5 N. hydrochloric acid, dilute aqueous sodium hydrogen carbonate, brine, and dried over magnesium sulphate. The solution was evaporated and chromatographed on silica gel 60 (<230 mesh ASTM) eluting with ethyl acetate to afford the title compound (0.059 g,37%); $\nu_{max.}$(CH$_2$Cl$_2$) 3270, 1790, 1740sh, 1720, 1690 cm$^{-1}$; δ (CDCl$_3$) 1.25(3H, t, J 7 Hz, CH$_2$CH$_3$), 1.55(9H, s ,C(CH$_3$)$_3$), 2.08(3H, s, OCOCH$_3$), 2.96 and 3.28 (2H, ABq, J 18 Hz, 2-H$_2$) 3.52(4H,m,piperazine CH$_2$ and —CH$_2$CH$_3$), 3.80–4.20 (2H, m, piperazine CH$_2$), 4.77 and 4.99 (2H, ABq, J 13 Hz, CH$_2$OCOH$_3$), 5.17(1H, s, 6-H), 5.53 (1H, d, J 7 Hz, α-proton). 7.30–7.50 (5H, m, aromatics), 7.90(1H, s, 7β-NHCO), 8.16 (1H, s, 7α-NHCHO), 8.19 (1H, s, NHCHO) and 10.02 (1H, d, J 7 Hz, αNHCO—).

(d)
7β-[D-2-[(4-Ethyl-2,3,-dioxopiperazin-1-yl)carbonylamino]-2-phenylacetamido]-7α-formamidocephalosporanic acid, sodium salt t-Butyl 7β-[D-2-[(4-ethyl-2,3-di-dioxopiperazin-1-yl)carbonylamino]-2-phenylacetamido]-7α-formamidocephalosporanate (0.057 g, 0.085 mmol) was dissolved in ice cooled 88% formic acid (5 ml), and the resulting solution was stirred at room temperature for 5 h. The solution was then evaporated to dryness, and toluene (5 ml) was added and evaporated to ensure complete removal of the formic acid. The residue was dissolved in dilute aqueous sodium hydrogen carbonate and the resulting aqueous solution was washed with ethyl acetate. It was then saturated with sodium chloride, covered with ethyl acetate/tetrahydrofuran (1:1), and acidified to pH1.5 with N. hydrochloric acid. The organic phase was separated and the aqueous phase was extracted with further ethyl acetate/tetrahydrofuran. The combined organic extracts were washed with brine, dried over magnesium sulphate, and evaporated to dryness to afford the free acid. This was suspended in water and the pH was adjusted to 6.5 with dilute aqueous sodium hydrogen carbonate. The resulting solution was filtered and freeze dried to afford the title compound (0.017 g, 32%); $\nu_{max.}$(KBr) 1770, 1710, 1680, 1610, 1510 cm$^{-1}$; δ(D$_2$O) 1.20 (3H, t, J 7 Hz, CH$_2$CH$_3$), 2.09 (3H, s, OCOCH$_3$), 3.05 (1H, d, J 18 Hz, 2-H), 3.52 (5H, m, piperazine CH$_2$, CH$_2$CH$_3$ and 2-H), 3.80–4.10 (2H, m, piperazine CH$_2$) 4.62 and 4.84 (2H, ABq, J 13 Hz, CH$_2$OCOCH$_3$), 5.28 (1H, s, 6-H), 5.52 (1H, s, α-proton), 7.35–7.60 (5H, m, aromatics) and 8.15 (1H,s,NHCHO).

MIC agaiust P. Mirabilis 889 is 0.2 μg/ml.

EXAMPLE 37 t-Butyl 7β-[D-2-[(4-ethyl-2,3-dioxopiperazin-1-yl)carbonylamino]-2-phenylacetamido]-7α-formamidocephalosporanate (a) t-Butyl 7β-[D-2-(2,2,2-trichloroethoxycarbonylamino)-2-phenylacetamido]-7α-formamidocephalosporanate A solution of D-2-(2,2,2-trichloroethoxycarbonylamino)-2-phenylacetic acid (0.163 g, 0.5 mmol) and dimethylformamide (1 drop) in dichloromethane (10 ml), was treated with oxalyl chloride (0.127 g, 1 mmol), and the solution was stirred at room temperature for 1 h. The reaction solution was then evaporated to dryness, treated with toluene, and re-evaporated. The resulting acid chloride in dichloromethane (5 ml) was then added dropwise to a stirred solution of t-butyl 7β-amino-7α-formamidocephalosporanate (0.185 g, 0.5 mmol) and pyridine (0.059 g, 0.75 mmol) in dichloromethane (15 ml) at 0° C. The solution was stirred at 0° C. for 0.25 h, and then at room temperature for 2.5 h, before being washed with 0.5N. hydrochloric acid, dilute aqueous sodium hydrogen carbonate and brine. It was dried over magnesium sulphate, evaporated to dryness, and the residue chromatographed on silica gel 60 (<230 mesh ASTM) eluting with ethyl acetate/hexane 1:1 to afford the title compound (0.167 g, 50%); $\nu_{max.}$ (CH$_2$Cl$_2$) 3400, 3290, 1792, 1740, 1725 sh, 1698, 1490, 1212 cm$^{-1}$; δ(CDCl$_3$) 1.50 (9H, s, C(CH$_3$)$_3$), 2.02 (3H, s, OCOCH$_3$), 3.02 and 3.28 (2H, ABq, J, 17 Hz, 2-H$_2$), 4.67 (2H, s, CH$_2$CCl$_3$), 4.80 and 5.00 (2H, ABq, J 13 Hz, CH$_2$OCOCH$_3$), 5.14 (1H, s, 6-H), 5.41 (1H, d, J 7 Hz, α-proton), 6.47 (1H, d, J 7 Hz, α-NHCO) 7.20–7.50 (5H, m, aromatics), 7.66 (1H, s, 7β-NHCO), 8.01 (1H, s, NHHO) and 8.11 (1H, s, NHCHO).

(b) t-Butyl 7β-(D-2-amino-2-phenylacetamido)-7α-formamidocephalosporanate

A solution of t-butyl 7β-[D-2-(2,2,2-trichloroethoxycarbonylamino)-2-phenylacetamido]-7β-formamidocephalosporanate (0.083 g, 0.122 mmol) in tetrahydrofuran (6 ml), was treated with M. potassium dihydrogen phosphate (1 ml) and freshly acid washed zinc powder (0.050 g). The mixture was stirred at room temperature for 5.5 h, whilst maintaining the pH at 4 by the addition of the phosphate buffer. It was then filtered and, after addition of ethyl acetate to the filtrate, was washed with brine. It was dried over magnesium sulphate and evaporated to dryness to afford the crude title compound which was used without further purification.

(c) t-Butyl 7β-[D-2-[(4-ethyl-2,3-dioxopiperazin-1-yl)carbonylamino]-2-phenylacetamido]-7α-formamidocephalosporanate A solution of 4-ethyl-2,3-dioxopiperazine-1-carbonyl chloride (0.021 g, 0.1 mmol) in dichloromethane (5 ml) was added dropwise to a stirred solution of t-butyl 7β-

(D-2-amino-2-phenylacetamido)-7α-formamidocephalosporanate (0.050 g, 0.1 mmol) and pyridine (0.012 g, 0.15 mmol) in dichloromethane (5 ml) at 0° C. The reaction solution was stirred at 0°–5° C. for 0.5 h, followed by 2 h at room temperature. It was then washed with 0.5 N. hydrochloric acid, dilute aqueous sodium hydrogen carbonate and brine, and dried over magnesium sulphate. It was evaporated to dryness, and the residue chromatographed on silica gel 60 (<230 mesh ASTM) eluting with 5% ethanol/ethyl acetate to afford the title compound (0.015 g, 22%).

EXAMPLE 38

7α-Formamido-7β-[D-2-[[3-(methylsulphonyl)-2-oxoimidazolidin-1-yl]carbonylamino]-2-phenylacetamido]cephalosporanic acid, sodium salt (a) t-Butyl 7α-Formamido-7β-[D-2-[[3-(methylsulphonyl) -2-oxomidazolidin-1-yl]carbonylamino]-2-phenylacetamido]cephalosporanate A solution of 3-(methylsulphonyl)-2-oxoimidazolidine-1-carbonyl chloride (0.136 g, 0.6 mmol) in dichloromethane (10 ml) was added dropwise with stirring to a solution of t-butyl 7β-(D-2-amino-2-phenylacetamido)-7α-formamidocephalosporanate (0,302 g, 0.6 mmol) and pyridine (0.071 g, 0.9 mmol) in dichloromethane (10 ml) at 0° C. The reaction solution was stirred at 0–5° C. for 0.5 h and for 3 h at room temperature, before being washed with 0.5N. hydrochloric acid, dilute aqueous sodium hydrogen carbonate and brine. It was dried over magnesium sulphate, evaporated to dryness, and the residue was chromatographed on silica gel 60 (<230 mesh ASTM) eluting with ethyl acetate/hexane 2:1 through to neat ethyl acetate, to afford the title compound (0.081 g, 19%); $\nu_{max}$ (CH$_2$Cl$_2$) 3325, 1790, 1738, 1695, 1675, 1390, 1170 cm$^{-1}$; δ(CDCl$_3$). 1.52 (9 H, s, C(CH$_3$)$_3$), 2.06 (3H, s, OCOCH$_3$), 2.88 and 3.25(2H, ABq, J 17 Hz 2-H$_2$), 3.43(3H, s, SO$_2$CH$_3$), 3.60–4.10 (4H,m, imidazolidine-H's), 4.75 and 5.00(2H, ABq, J 13 Hz, CH$_2$COCH$_3$), 5.20(1H, s, 6-H), 5.63(1H, d, J 7 Hz, α-proton), 7.40(5H, brs, aromatics), 8.00–8.45(3H, m, NHCHO and 7β-NHCH) and 9.05(1H, d, J 7 Hz, α-NHCO)

(b) 7α-Formamido-7β-[D-2-[[3-(methysulphonyl)-2-oxoimidazolidin-1-yl]carbonylamino]-2-phenylacetamido]cephalosporanic acid, sodium salt t-Butyl 7α-Formanido-7β-[D-2-[[3-(methylsulphonyl)-2-oxoimidazolidin-1-yl]carbonylamino]-2-phenylacetamido]cephalosporanate (0.67 g, 0.097 mmol) was dissolved in ice cooled trifluroracetic acid (5 ml), and the resulting solution was stirred at room temperature for 0.5 h. It was then evaporated to dryness, treated with toluene, and re-evaporated. The residue was dissolved in dilute aqueous sodium hydrogen carbonate and the solution was washed with ethyl acetate, before being saturated with sodium chloride. The pH was then adjusted to 1.5 with N. hydrochloric acid, and the product was extracted into tetrahydrofuran/ethyl acetate (1:1). The combined extracts were washed with brine, dried over magnesium sulphate, and evaporated to dryness to yield the free acid. This was suspended in water and the pH adjusted to 6.5 with dilute aqueous sodium hydrogen carbonate. The resulting solution was filtered and freeze dried to afford the title sodium salt (0.054 g, 84%); $\nu_{max}$(KBr) 1765, 1730, 1675, 1605, 1525 cm$^{-1}$; δ(D$_2$O) 1.93 (1H, s, OCOCH$_3$), 2.85 and 3.26(2H, ABq, J 17 Hz, 2-H$_2$), 3.21 (3H, s, SO$_2$CH$_3$), 3.50–3.85(4H, m, imidazolidine-H's) 4.35–4.75(m, CH$_2$OCOCH$_3$plus HOD) 5.11 (1H, s, 6-H), 5.35 (1H, s, α-proton), 7.20–7.50 (5H, m, aromatics) and 8.00 (1H, s, NHCHO).

MIC against P. Mirabilis 889 is 1.0 μg/ml.

EXAMPLE 39

7β-[D-2-[(4-Ethyl-2,3-dioxopiperazin-1-yl)carbonylamino]2-(4-hydroxyphenyl)acetamido]-7α-formamidocehalosporanic acid, sodium salt (a) t-Butyl 7β-[D-2-[4-(benzyloxycarbonyloxy)phenyl]-2-[(4-ethyl-2,3-dioxopiperazin-1-yl)carbonylamino]acetamido]-7α-(methylthio)cephalosporanate D-2-[4-(Benzyloxycarbonyloxy)phenyl]-2-[(4-ethyl-2,3-dioxopiperazin-1-yl)carbonylamino]acetic acid (1.88 g, 4 mmol) in tetrahydrofuran (40 ml) containing dimethylformamide (1 drop), was treated with oxalyl chloride (1.02 g, 8 mmol). After stirring at room temperature for 1.5 h the solution was evaporated to dryness, treated with toluene, and re-evaporated. The resulting acid chloride in dichloromethane (50 ml) was then added dropwise with stirring to a mixture of t-butyl 78-amino7α-(methylthio)cephalosporanate (1.50 g, 4 mmol) and 4A molecular sieves (9.0 g) at 0° C. The mixture was then stirred at 0°–5° C. for 0.75 h, followed by 1.75 h at room temperature, before being filtered and the filtrate evaporated to dryness. The crude product was chromatographed on silica gel 60 (<230 mesh ASTM) to afford an inseperable mixture of the title compound and t-butyl 7β-[L-2-[4-(benzyloxycarbonyloxy)phenyl]-2-[(4-ethyl-2,3-dioxypiperazin-1-yl)carbonylamino]acetamido]-7α-(methylthio)cephalosporante (1.07 g, 32%). $\nu_{max}$ (CH$_2$Cl$_2$) 3380, 3275, 1785, 1765 sh, 1740 sh, 1720, 1695, 1500, 1220 cm$^{-1}$;

δ(CDCl$_3$) 1.21 (3H, t, J 7 Hz, CH$_2$CH$_3$), 1.54 (9H, s, C(CH$_3$)$_3$), 2.00 and 2.29 (3H, 2s, SCH$^-$), 2.08 (3H, s, OCOCH$_3$), 3.19 and 3.38, and 3.27 and 3.45 (2H, 2ABq, J 7 Hz, 2-H$_2$), 3.55 (4H, m, piperazine CH$_2$ and -CH$_2$CH$_3$), 4.05 (2H, m, piperazine CH$_2$), 4.77 and 5.05 (2H, ABq, J 13 Hz, CH$_2$OCOCH$_3$), 4.88 and 4.90 (1H, 2s, 6-H's), 5.26 (2H, s, CH$_2$Ph), 5.64 (1H, d, J 9 Hz, α-proton), 7.00–7.60 (10 H, m, aromatics and 7β-NH), and 10.02 (1H, d, J 7 Hz, α-NHCO).

(b) t-Butyl 7α-amino-7β-[D-2-[4-(benzyloxycarbonyloxy)phenyl]-2-[(4-ethyl-2,3-dioxopiperazin-1-yl)carbonylamino]acetamido]ceohalosporanate t-Butyl 7β-[DL-2-[4-(benzyloxycarbonyloxy)phenyl]-2-[(4-ethyl-2,3-dioxopiperazin-1-yl)carbonylamino]acetamido-7α-(methylthio)cephalosporanate (1.07 g, 1.3 mmol) in dry dimethylformamide (25 ml) at −50° C. under nitrogen, was treated with mercuric acetate (0.42 g, 1.3 mmol) in dimethylformamide (3 ml) followed immediately by ammonia (0.024 g, 1.43 mmol) in dimethylformamide (1 ml). The reaction mixture was stirred at −50° C. to −20° C. for 1 h, before being poured into ethyl acetate and washed well with water and brine. The organic solution was dried over magnesium sulphate, evaporated to dryness, and chromatographed on silica gel 60 (<230 mesh ASTM) to afford the title compound (0.29 g, 28%).

$\nu_{max}$ (CH$_2$Cl$_2$) 3380, 3275, 1785, 1765, 1742, 1720, 1695, 1502, 1220 cm$^{-1}$;

δ (CDCl₃) 1.21 (3H, t, J 7 Hz, —CH₂CH₃), 1.53 (9H, s, C(CH₃)₃), 2.08 (3H, s, OCOCH₃), 2.60–3.20 (2H, br s, NH₂), 3.04 and 3.33 (2H, ABq, J 18 Hz, 2-H₂), 3.65 (4H, m, piperazine CH₂ and CH₂CH₃), 4.00 (2H, m, piperazine CH₂), 4.72 and 4.98 (2H, ABq, J 13 Hz, CH₂O-COCH₃), 4.84 (1H, s, 6-H), 5.26 (2H, s, CH₂Ph), 5.57 (1H, d, J 7 Hz, α-proton), 7.10–7.57 (9H, m, aromatics), 7.83 (1H, s, 7β-NHCO) and 10.05 (1H, d, J 7 Hz, α-NHCO—).

Also isolated from the reaction mixture was t-butyl 7α-amino-7β-[L-2-[4-(benzyloxycarbonyloxy)phenyl]-2-[(4-ethyl-2,3-dioxopiperazin-1-yl)carbonylamino]acetamido]cephalosporanate (0.36 g, 35%).

ν_max (CH₂Cl₂) 3380, 3275, 1785, 1765, 1740 sh, 1720, 1692, 1500, 1220 cm⁻¹;

δ(CDCl₃) 1.22 (3H, t, J 7 Hz, CH₂CH₃), 1.54 (9H, s, C(CH₃)₃), 2.10 (3H, s, OCOCH₃), 2.50–2.80 (2H, br s, NH₂), 3.19 and 3.45 (2H, ABq, J 18 Hz, 2-H₂), 3.55 (4H, m, piperazine CH₂ and —CH₂CH₃), 4.02 (2H, m, piperazine CH₂), 4.77 and 5.00 (2H, ABq, J 13 Hz, CH₂O-COCH₃), 4.88 (1H, s, 6-H), 5.27 (2H, s, CH₂Ph), 5.53 (1H, d, J 7 Hz, α-proton), 7.15–7.50 (10 H, m, aromatics and 7β-NHCO) and 9.94 (1H, d, J 7 Hz, α-NHCO).

(c) t-Butyl 7β-[D-2-[4-(benzyloxycarbonyloxy)phenyl]-2-[(4-ethyl-2,3-dioxopiperazin-1-yl)carbonylamino]acetamido]-7α-formamidocephalosporanate A solution of t-butyl 7α-amino-7β-[D-2-[4-(benzyloxycarbonyloxy)phenyl]-2-[(4-ethyl-2,3-dioxopiperazin-1-yl)carbonylamino]acetamido]cephalosporanate (0.272 g, 0.343 mmol) and pyridine (0.171 g, 2.17 mmol) in dichloromethane (20 ml) was cooled in an ice bath and treated with acetic formic anhydride (0.096 g, 1.09 mmol). The reaction solution was stirred at 0°–5° C. for 0.5 h, and for 1 h at room temperature, before being washed with 0.5N. hydrochloric acid, dilute aqueous sodium hydrogen carbonate and brine. It was then dried over magnesium sulphate, evaporated to dryness, and the crude product chromatographed on silica gel 60 (<230 mesh ASTM) to afford the title compound (0.200 g, 71%).

ν_max (CH₂Cl₂) 3375 sh, 3270, 1790, 1765, 1740 sh, 1720, 1692, 1500, 1220 cm⁻¹;

δ(CDCl₃) 1.25 (3H, t, J 7 Hz, CH₂CH₃), 1.54 (9H, s, C(CH₃)₃), 2.07 (3H, s, OCOCH₃), 2.88 and 3.22 (2H, ABq, J 18 Hz, 2-H₂), 3.54 (3H, m, piperazine-H and —CH₂CH₃), 3.68–4.20 (3H, m, piperazine-H's), 4.74 and 5.00 (2H, ABq, J 13 Hz, CH₂OCOCH₃), 5.13 (1H, s, 6-H), 5.26 (2H, s, CH₂Ph), 5.61 (1H, d, J 7 Hz, α-proton), 7.10–7.60 (9H, m, aromatics), 7.99 and 8.35 (2H, 2 br s, 7β-NHCO and 7α-NHCHO), 8.16 (1H, s, NHCHO), and 10.07 (1H, d, J 7 Hz, α-NHCO).

(d) t-Butyl 7β-[D-2-[(4-ethyl-2,3-dioxopiperazin-1-yl)carbonylamino]-2-(4-hydroxyphenyl)acetamido]-7α-formamidocephalosporanate A mixture of t-butyl 7β-[D-2-[4-(benzyloxycarbonyloxy)phenyl]-2-[(4-ethyl-2,3-dioxopiperazin-1-yl)carbonylamino]acetamido]-7α-formamidocephalosporanate (0.096 g, 0.117 mmol) and 10% palladium on charcoal (0.100 g) in tetrahydrofuran (12 ml) and water (2 ml), was shaken under an atmosphere of hydrogen for 2 h. The catalyst was then filtered off, the filtrate evaporated to near dryness, and the residue dissolved in a mixture of ethyl acetate/tetrahydrofuran (1:1). This solution was then washed with brine, dried over magnesium sulphate, and evaporated to dryness to leave the title compound (0.068 g, 85%).

ν_max (CH₂Cl₂) 3280, 1788, 1740 sh, 1718, 1690, 1515 cm⁻¹;

δ(CDCl₃) 1.20 (3H, t, J 7 Hz, CH₂CH₃), 1.52 (9H, s, C(CH₃)₃), 2.08 (3H, s, OCOCH₃), 3.01 and 3.30 (2H, ABq, J 18 Hz, 2-H₂), 3.50 (3H, m, piperazine-H and —CH₂CH₃), 3.60–4.20 (3H, m, piperazine-H's), 4.74 and 4.98 (2H, ABq, J 13 Hz, CH₂OCOCH₃), 5.16 (1H, s, 6-H), 5.49 (1H, d, J 13 Hz, α-proton), 6.75 and 7.25 (4H, 2d, J 8 Hz, aromatics), 8.10 and 8.33 (3H, 2 br s, NHCHO and 7β-NHCO—) and 9.86 (1H, d, J 7 Hz, α-NHCO).

(e) 7β-[D-2-[(4-Ethyl-2,3-dioxopiperazin-1-yl)carbonylamino]-2-(4-hydroxyphenyl)acetamido]-7α-formamidocephalosporanic acid, sodium salt t-Butyl 7β-[D-2-[(4-ethyl-2,3-dioxopiperazin-1-yl)carbonylamino]-2-(4-hydroxyphenyl)acetamido]-7α-formamidocephalosporanate (0.047 g, 0.068 mmol) was dissolved in ice cold 98% formic acid (5 ml) and the resulting solution was stirred at room temperature for 4.5 h. The reaction solution was then evaporated to dryness, treated with toluene, and re-evaporated. The residue was dissolved in dilute aqueous sodium hydrogen carbonate and washed with ethyl acetate. The aqueous solution was saturated with sodium chloride, covered with ethyl acetate/tetrahydrofuran (1:1), and acidified to pH 1.5 with N.hydrochloric acid. The organic layer was separated and the aqueous phase extracted with further ethyl acetate/tetrahydrofuran. The combined extracts were washed with brine, dried over magnesium sulphate, and evaporated to dryness to leave the free acid. This was suspended in water and the pH adjusted to 6.5 with dilute aqueous sodium hydrogen carbonate. The resulting solution was filtered and freeze dried to afford the title compound (0.018 g, 40%).

ν_max(KBr) 1770, 1715, 1675, 1615 cm⁻¹;

δ(D₂O) 1.18 (3H, t, J 7 Hz, CH₂CH₃), 2.07 (3H, s, OCOCH₃), 3.08 (1H, d, J 18 Hz, 2-H), 3.50 (3H, m, 2-H and CH₂CH₃), 3.69 (2H, m, piperazine-H₂), 4.00 (2H, m, piperazine-H₂), 5.27 (1H, s, 6-H), 5.40 (1H, s, α-proton), 6.90 and 7.39 (4H, 2d, J 8 Hz, aromatics) and 8.12 (1H, s, NHCHO).

(f) Alternative route to t-Butyl 7β-[D-2-[(4-ethyl-2,3-dioxopiperazin-1-yl)carbonylamino]-2-(4-hydroxyphenyl)acetamido]-7α-formamidocephalosporanate D-2-[(4-Ethyl-2,3,dioxopiperazin-1-yl)carbonylamino]-2-(4-hydroxyphenyl)acetic acid (0.335 g, 1 mmol) in tetrahydrofuran (30 ml), was added dropwise over 2 h to a stirred solution of t-butyl 7β-amino-7α-formamidocephalosporanate (0.371 g, 1 mmol) and N,N'-dicyclohexylcarbodiimide (0.220 g, 1.1 mmol) in tetrahydrofuran (10 ml). The reaction mixture was stirred for 24 h at room temperature, and then evaporated to dryness. The residue was dissolved in ethyl acetate, filtered, and the filtrate evaporated to dryness. The crude product was chromatographed on silica gel 60 (<230 mesh ASTM) eluting with ethyl acetate through 5% ethanol/ethyl acetate, to afford the title compound (0.100 g, 15%).

MIC against P. Mirabilis 889 is 0.2 μg/ml.

EXAMPLE 40

7β-[L-2-[(4-Ethyl-2,3-dioxopiperazin-1-yl)carbonylamino]-2-(4-hydroxyphenyl)acetamido]-α-formamidocephalosporanic acid, sodium salt

(a) t-Butyl 7β-[L-2-[4-(benzyloxycarbonyloxy)phenyl]-2-[(4-ethyl-2,3-dioxopiperazin-1-yl)carbonylamino]acetamido]-7α-formamidocephalosporanate A solution of t-butyl 7α-amino-7β-[L-2-[4-(benzyloxycarbonyloxy)phenyl]-2-[(4-ethyl-2,3-dioxopiperazin-1-yl)carbonylamino]acetamido]cephalosporanate (0.350 g, 0.44 mmol) and Pyridine (0.350 g, 4.4 mmol) in dichloromethane (20 ml) was cooled in an ice bath and treated with acetic formic anhydride (0.194 g, 2.2 mmol). The reaction solution was stirred at 0°–5° C. for 0.5 h, followed by 1 h at room temperature. It was then washed with 0.5N. hydrochloric acid, dilute aqueous sodium hydrogen carbonate, brine, and dried over magnesium sulphate. The solution was evaporated to dryness, and the residue chromatographed on silica gel 60 (<230 mesh) to afford the title compound (0.250 g, 69%); $\nu_{max}(CH_2Cl_2)$, 3380, 3260, 1790, 1765, 1740sh, 1720, 1695, 1500, 1220 cm$^{-1}$; δ(CDCl$_3$) 1.24 (3H, t, J 7 Hz, CH$_2$CH$_3$), 1.53 (9H, s, C(CH$_3$)$_3$), 2.10(3H, s, OCOCH$_3$), 3.03(2H, s, 2-H$_2$), 3.57(3H, m, piperazine-H and -CH$_2$CH$_3$), 3.71, 3.89 and 4.36 (3H, 3M, piperazine-H's), 4.83 and 4.16(2H, ABq, J 13 Hz, CH$_2$OCOCH$_3$), 4.98(1H, s, 6-H), 5.29(2H, s, CH$_2$Ph), 5.91(1H, d, J 7 Hz, α-proton), 7.21 and 7.60 (4H, 2d, J 8 Hz, phenyl), 7.43(5H, m, phenyl), 8.01(1H, s, NHCHO), 8.08(1H, s, NHCHO), 9.22(1H, brs, 7β-NHCO), and 10.06(1H, d, J 7 Hz, α-NHCO.

(b) t-Butyl 7β-[L-2-[(4-ethyl-2,3-dioxopiperazin-1-yl)carbonylamino]-2-(4-hydroxyphenyl)acetamido]-7α-formamidocephalosporanate A mixture of t-butyl 7β-[L-2-[4-(benzyloxycarbonyloxy)phenyl]-2-[(4-ethyl-2,3-dioxopiperazin-1-yl)carbonylamino]acetamido]-7α-formamidocephalosporanate (0.113 g, 0.138 mmol) and 10% palladium on charcoal (0.120 g) in tetrahydrofuran (12 ml) and water (2 ml) was shaken under an atmosphere of hydrogen for 1.75 h. The catalyst was then filtered off, the filtrate evaporated to near dryness, and the residue dissolved in a mixture of ethyl acetate/tetrahydrofuran (1:1). This solution was then washed with brine, dried over magnesium sulphate, and evaporated to dryness to leave the title compound (0.092 g, 97%); $\nu_{max}$.(CH$_2$Cl$_2$) 3375, 3290, 1790, 1740sh, 1715, 1695, 1515 cm$^{-1}$; δ[(CD$_3$)$_2$CO] 1.18 (3H, t, J 7 Hz, CH$_2$CH$_3$), 1.52 (9H, s, C(CH$_3$)$_3$), 2.03 (3H, s, OCOCH$_3$), 3.20–3.87 (6 H, m, piperazine-H$_2$, 2-H$_2$, and —CH$_2$CH$_3$), 3.90–4.30 (2H, m, piperazine-H$_2$), 4.75 and 5.05 (2H, ABq, J 13 Hz, CH$_2$)COCH$_3$), 5.26(1H, s, 6-H), 5.75 (1H, d, J 7 Hz, α-proton), 6.89 and 7.40 (4H, 2d, J 8 Hz, aromatics). 8.20 (1H, s, NHCHO) 8.38 (1H, s, NHCHO), 8.95 (1H, brs, 7β-NHCO) and 10.00 (1H, d, J 7 Hz, α-NHCO).

(c) 7β-[L-2-[(4-Ethyl-2,3-dioxopiperazin-1-yl)carbonylamino]-2-(4-hydroxyphenyl)acetamido]-7α-formamidocephalosporanic acid, sodium salt t-Butyl 7β-[L-2-[(4-ethyl-2,3, dioxopiperazin-1-yl)carbonylamino]-2-(4-hydroxyphenyl)acetamido]-7α-formamidocephalosporanate (0.089 g, 0.129 mmol) was dissolved in ice cooled 98% formic acid (10 ml), and the resulting solution was stirred at room temperature for 5 h. The reaction solution was then evaporated to dryness, treated with toluene, and re-evaporated. The residue was dissolved in dilute aqueous sodium hydrogen carbonate and washed with ethyl acetate. The aqueous solution was saturated with sodium chloride, covered with ethyl acetate/tetrahydrofuran (1:1), and acidified to pH 1.5 with N. hydrochloric acid. The organic layer was separated and the aqueous phase extracted with further ethyl acetate/tetrahydrofuran. The combined extracts were washed with brine, dried over magnesium sulphate, and evaporated to dryness to leave the free acid. This was suspended in water and pH adjusted to 6.5 with dilute aqueous sodium hydrggen carbonate. The resulting solution was filtered and freeze dried to afford the title compound (0.020 g, 24%); $\nu_{max}$.(KBr) 1770, 1710, 1675, 1615, 1515 cm$^{-1}$; δ(D$_2$O) 1.16 (3H, t, J 7 Hz, CH$_2$CH$_3$), 2.07 (3H, s, OCOCH$_3$), 3.04 (1H, d, J 18 Hz, 2-H), 3.47 (3H, m, 2-H and CH$_2$CH$_3$), 3.66 (2H, m, piperazine-H$_2$), 3.98 (2H, m, piperazine-H$_2$), 4.64 (1H, d, J 13 Hz, CHOCOCH$_3$), 5.19 (1H, s, 6-H), 5.42 (1H, s, α-proton), 6.89 and 7.33 (4H, 2d, J 8 Hz, aromatics) and 8.06 (1H, s, NHCHO).

MIC against P. Mirabilis 889 is 100 μg/ml.

EXAMPLE 41

7β-[D-2-(4-Ethyl-2,3-dioxopiperazin-1-yl)carbonylamino]-2-(3,4-diacetoxyphenyl)acetamido]-7α-formamidocephalosporanic acid, sodium salt

(a) t-Butyl 7β-[D-2-[(4-ethyl-2,3-dioxopiperazin-1-yl) carbonylamino]-2-(3,4-diacetoxyphenyl)acetamido]-7α-formamidocehalosporanate D-2-(3,4-Diacetoxphenyl)-2-[(4-ethyl-2,3-dioxopiperazin-1-yl) carbonylamino]acetic acid (0.11 g, 0.25 mmol) was dissolved in dichloromethane (10 ml) and added dropwise to a solution of t-butyl 7β-amino-7α-formamidocephalosporanate (0.09 g, 0.24 mmol) and N, N'-dicyclohexylcarbodiimide (0.55 g, 0.24 mmol) in dichloromethane (10 ml). The mixture was stirred at room temperature for 3 days. The solvent was evaporated and the residue taken up in ethyl acetate, washed with N. hydrochloric acid, saturated sodium hydrogen carbonate solution, brine, dried over magnesium sulphate and evaporated Chromatography (silica gel; 5% ethanol in ethyl acetate) gave the title compound (0.067 g, 35%) δ (CDCl$_3$) 1.24 (3H, t, J 8 Hz, CH$_2$CH$_3$), 1.54 (9H, s, C(CH$_3$)$_3$), 2.07 (3H, s, CH$_2$OCOCH$_3$), 2.25 and 2.27 (6H, 2s, aryl-OCOCH's), 2.87, 3.20 (2H, ABq, J 16 Hz, 2-H$_2$), 3.4–4.2 (6H, m, NCH$_2$CH$_2$NCH$_2$), 4.76, 5.03 (2H, ABq, J 14 Hz, CH$_2$O), 5.11 (1H, s, 6-H), 5.65 (1H, d, J 7 Hz, CH), 7.1–7.5 (3H, m, aromatic-H's), 7.97 (1H, brs, NH), 8.11 (1H, s, CHO), 8.56 (1H, brs, NH), 10.08 (1H, d, J 8 Hz, NH); $\nu_{max}$. (CH$_2$Cl$_2$) 3270, 2930, 1715 1690, cm$^{-1}$.

(b) 7β-[D-2-[(4-Ethyl-2,3-dioxopiperazin-1-yl)carbonylamino]-2-(3,4-diacetoxyphenyl)acetamido]-7α-formamidocephalosporanic acid t-Butyl 7β-[D-2-[(4-ethyl-2,3-dioxopiperazin-1-yl)carbonylamino]-2-(3,4-diacetoxyphenyl)acetamido]-7α-formamidocephalosporanate (0.068 g, 0.086 mmol) was stirred with trifluoroacetic acid for 1 h and evaporated to dryness. The residue was triturated with ether and the resulting solid taken up in water which has been carefully adjusted to pH 6.5 with dilute sodium hydrogen carbonate solution. The solution was washed with ethyl acetate, filtered and freeze dried to give the title compound (0.048 g, 74%); δ(D₂O) 1.10 (3H, t, J 6 Hz, CH₂CH₃), 1.98 (3H, s, OCOCH₃), 2.23 (6H, s, OCOCH₃'s), 2.85, 3.25 (2H, ABq, J 18 Hz, 2-H₂), 3.25, 4.00 (6H, m, NCH₂CH₂NCH₂), 4.48 (CH₂OAC covered by HOD), 5.16 (1H, s, 6-H), 5.42 (1H, s, CH), 7.06–7.53 (3H, m, aromatic-H's), 8.05 (1H, s, CHO); ν$_{max}$ (KBr) 3440, 1765, 1710, 1675, 1610 cm⁻¹.

MIC against P. Mirabilis 889 is 0.1 μg/ml.

EXAMPLE 42

7α-Formamido-7β-(thien-2-ylacetamido)cephalosporanic acid, sodium salt

(a) t-Butyl 7β-(thien-2-ylacetamido)-7α-(methylthio)cephalosporanate

Thiophene-2-acetic acid (0.85 g, 6.0 mmol) was refluxed in thionyl chloride (5 ml) for 1 h. Excess thionyl chloride was evaporated, and the residual acid chloride in dichloromethane (10 ml) added to an ice cooled solution of t-butyl 7β-amino-7α-(methylthio)cephalosporanate (1.80 g, 4.8 mmol) in dichloromethane (25 ml) with pyridine (0.57 ml, 7.0 mmol). The reaction mixture was stirred at room temperature for 2 h. The solvent was evaporated and the residue taken up in ethylacetate, washed with N. hydrochloric acid, saturated sodium hydrogen carbonate solution, brine, dried over magnesium suplhate, and evaporated. Chromatography (silica gel, 3:1 hexane/ethyl acetate) afforded the title compound (1.75 g, 73%); δ(CDCl₃) 1.51(9H,s, C(CH₃)₃), 2.04(3H,s, OCOCH₃), 2.24(3H,s,SCH₃), 3.30, 3.42 (2H,ABq, J 18Hz, 2-H₂), 3.84 (2H, s, ArCH₂), 4.84, 5.05 (2H, ABq, J 13.5 Hz, CH₂O), 4.89(1H s, 6-H), 6.46 (1H,s, NH), 6.92–7.04 (2H, m, thiophene-H's), 7.16–7.30 (1H,m, thiophene-H); Γ$_{max}$ (CH₂Cl₂), 3280, 2970, 2920, 1775, 1735 sh, 1720, 1670, 1510 cm⁻¹; (Found: M⁺, 498.0930. C₂₁H₂₆N₂O₆S₃ requires M,498.0952).

(b) t-Butyl 7α-amino-7β-(thien-2-ylacetamido)cephalosporanate t-Butyl 7β-(thien-2-ylacetamido)-7α-(methylthio)-cephalosporanate (1.00 g, 2.0 mmol) in dimethylformamide (20 ml) at −40° C., was treated with a solution of mercuric acetate (0.64 g, 2.0 mmol) in dimethylformamide (5 ml) followed by a solution of ammonia (0.034 g, 2.0 mmol) in dimethylformamide (1.5 ml). The reaction mixture was allowed to warm over 1.5 h, poured into ethyl acetate, washed well with water, brine, dried over magnesium sulphate and evaporated to give the desired product (0.90 g, 96%); δ(CDCl₃) 1.54(9H, s, C(CH₃)₃), 2.09 (3H,s, OCOCH₃), 2.81(2H,brs, NH₂) 3.25, 3.55 (2H, ABq, J 18 Hz, 2-H₂), 3.90(2H, s, ArCH₂), 4.5–5.3 (3H, m, 6-H and CH₂O), 6.87–7.4(3H,m, aromatic); ν$_{max}$.(tetrahydrofuran) 1790, 1745, 1725 & 1680 cm¹.

(c) t-Butyl 7α-formamido-7β-(thien-2-ylacetamido)cephalosphoranate t-Butyl 7α-amino-7β-(thien-2-ylacetamido)cephalosporanate (0.90 g, 1.9 mmol) in dichloromethane (20 ml) at 0° C. was treated wtih pyridine (1.51 ml, 19 mmol) and acetic formic anhydride (0.76, 9.5 mmol). The reaction mixture was stirred at 0° C. for 1 h, washed with N. hydrochloric acid, saturated sodium hydrogen carbonate solution, brine, dried over magnesium sulphate and evaporated. The product was recrystallised from dichloromethane/hexane m.p. 160°–164° C. (0.62 g,66%); δ((CD3)₂CO) 1.54 (9H, s, C(CH₃)₃) 2.00 (3H, s, OCOCH₃), 3.33, 3.61 (2H, ABq, J 18 Hz, 2-H₂), 3.92 (2H, s, ArCH₂), 4.73, 4.99(2H, ABq, J 13 Hz, CH₂O), 5.21 (1H,s, 6-H) 6.8–7.1 (2H,m,thienyl-H's) 7.2–7.4 (1H,m, thienyl-H), 8.19(1H,sCHO); ν$_{max}$. (KBr) 3330,2980, 1770, 1740, 1720, 1695, 1660 & 1530 cm⁻¹, (Found: C,50.7; H,5.1; N,8.04%. C₂₁H₂₅N₃O₇S₂ requires C, 50.9; H,5.1; N, 8.5%).

(d) 7α-Formamido-7β-(thien-2-ylacetamido)cephalosporanic acid, sodium salt t-Butyl 7α-formamido-7β-(thien-2-ylacetamido)cephalosporanate (0.100 g, 0.2 mmol) was added to ice cold 98% formic acid (8 ml) and water (5 drops). The reaction mixture was stirred at room temperature for 4 h. Formic acid was evaporated and the residue taken up in dilute sodium hydrogen carbonate solution and washed with ethyl acetate. The aqueous phase was acidified to pH 1.5 and extracted with ethylacetate. The extracts were washed with brine, dried and evaporated. The residue was taken up in water, which was adjusted to pH 6.5 with sodium hydrogen carbonate solution. The solution was filtered and freeze dried to give the title compound (0.054 g 58%); δ(D₂O) 2.09(3H,s,OCH₃), 3.23,3.57 (2H,ABq, J 17 Hz, 2-H₂), 3.92(2H,s,ArCH₂), 5.28 (2H,s, CH₂O), 5.60(1H,s,6-H), 6.9–7.2(2H,m,thiophene-H's), 7.3–7.5(1H,m,thiophene-H), 8.14(2H,s,CHO); ν$_{max}$ (KBr) 1770, 1740, 1720, 1695 & 1660 cm⁻¹.

MIC against P. Mirabilis 889 is 10 μg/ml.

EXAMPLE 43

7β-[2-Carboxy-2-(thien-3-yl)acetamido]-7α-formamido cephalosporanic acid, disodium salt

(a) t-Butyl 7α-formamido-7β-[2-(4-nitrobenzyloxycarbonyl)-2-(thien-3-yl)acetamido]cephalosporanate 2-(4-Nitrobenzyloxycarbonyl)-2-(thien-3-yl)acetic acid (0.170 g, 0.53 mmol) in thionyl chloride (5 ml), was heated at 70° C. for 2 h. The solution was then evaporated to dryness, and the residue treated with toluene and re-evaporated. The resulting acid chloride was dissolved in dichloromethane (10 ml) and added dropwise with stirring to a solution of t-butyl 7β-amino-7α-formamidocephalosporanate (0.186 g, 0.5 mmol) and pyridine (0.059 g, 0.75 mmol) in dichloromethane (10 ml) at 0° C. The reaction solution was stirred at 0°–5° C. for 0.75 h, followed by 0.5 h at room temperature, before being evaporated to dryness. The residue was dissolved in ethyl acetate, washed with 0.5N. hydrochloric acid, dilute aqueous sodium hydrogen carbonate and brine. The solution was dried, evaporated to dryness and the residue chromatographed on silica gel 60 (<230 mesh) eluting with ethyl acetate/hexane (1:1) to afford the title compound (0.168 g, 50%); λ$_{max}$(EtOH) 245 nm (ε15147), 262 nm (ε16862); ν$_{max}$. (CH₂Cl₂) 3390, 3305, 1790, 1740, 1700, 1525, 1350, 1212, 1160 cm⁻¹; δ(CDCl₃) 1.56 (9H, s, C(CH₃)₃), 2.10 (3H, s, OCOCH₃), 3.12 and 3.39(2 H, ABq, J 18 Hz, 2-H₂), 4.85 and 5.08 (2H, ABq, J 13 Hz, CH₂OCOCH₃), 4.85 (1H, s, α-proton), 5.12 (1H, s, 6-H), 5.30 (2H, s, CH₂Ar), 7.13 (1H, m, thienyl-H) 7.33–7.50(5H, m, aromatics and 7β-NHCO), 7.78 and 7.86(1H,2s, 7α-NHCHO diastereoisomers) and 8.11–8.23(3H, m, aromatics and -NHCHO).

(b) t-Butyl 7β-[2-carboxy-2-(thien-3yl)acetamido]-7α-formamidocephalosporanate t-Butyl 7α-Formamido-7β-[2-(4-nitrobenzyloxycarbonyl)-2-(thien-3-yl)acetamido]cephalosporanate (0.163 g, 0.25 mmol) and 10% palladium on charcoal (0.20 g) in tetrahydrofuran (10 ml) and water 2 ml), were shaken under an atmosphere of hydrogen for 1 h. Further catalyst (0.20 g) was then added and the procedure repeated for 1.5 h. The catalyst was then filtered and washed well with dilute aqueous sodium hydrogen carbonate. The filtrate was washed with ethyl acetate, the pH was adjusted to 2 with N. hydrochloric acid, and the product was extracted into ethyl acetate. The extract was washed with brine, dried over magnesium sulphate, and evaporated to dryness to afford the title compound. (0.072 g, 53%); $\lambda_{max}$. (EtOH) 239 nm ($\epsilon$10267); $\nu_{max}(CH_2Cl_2)$ 3275, 1790, 1740, 1725, 1695, 1500 cm$^{-1}$; δ(CDCl$_3$) 1.52 (9H, s, C(CH$_3$)$_3$), 2.08 and 2.09 (3H, 2s, OCOCH$_3$ diastereoisomers), 3.07 and 3.34, and 3.12 and 3.37(2H, 2ABq, J 17 Hz, 2-H$_2$ diastereoisomers), 4.83 and 4.91 (1H,2s, α-proton), 4.81 and 5.02, and 4.88 and 5.07 (2H, 2ABq, J 12 Hz, CH$_2$OCOCH$_3$ diastereoisomers), 5.17 and 5.20 (1H, 2s, 6-H diastereoisomers), 7.13–7.45 (3H, m, aromatics), 8.13 (1H, s, NHCHO), 8.13 and 8.22 (1H,2s, NHCHO diastereomers), 8.36 and 8.61 (1H,2s,7β-NHCO).

(c) 7β-[2-Carboxy-2-(thien-3-yl)acetamido]-7α-formamidocephalosporanic acid, disodium salt A solution of t-butyl 7β-[2-carboxy-2-(thien-3-yl)acetamido]-7α-formamidocephalosporanate (0.62 g, 0.115 mmol) in 98% formic acid (5 ml), was stirred at room temperature for 6 h. The formic acid was then removed under vacuum, the residue was treated with toluene, and the solution was evaporated. The resulting gum was dissolved in dilute aqueous sodium hydrogen carbonate, and washed with ethyl acetate; before being acidified to pH 4 and washed with ethyl acetate. The pH was then adjusted to 1.5 and the product extracted into ethyl acetate/tetrahydrofuran (1:1). The combined extracts were washed with brine, dried over magnesium sulphate, and evaporated to dryness to afford the free acid. This was suspended in water, the pH was adjusted to 6.5 with dilute aqueous sodium hydrogen carbonate, and the resulting solution was filtered and freeze dried to afford the title compound (0.026 g, 43% ); $\lambda_{max}$ (H$_2$O) 234 nm ($\epsilon$9589); $\nu_{max}$ (KBr) 1765, 1670, 1600, 1505 cm$^{-1}$; δ(D$_2$O) 2.08 and 2.09 (3H, 2s, OCOCH$_3$ diastereoisomers), 3.17 and 3.56, and 3.25 and 3.58 (2H, 2ABq, J 18 Hz 2-H$_2$ diastereoisomers), 4.60–4.90 (2ABq, HOD, CH$_2$OCOCH$_3$ diastereoisomers), 5.28 and 5.32 (1H,2s, 6-H), 7.00–7.50 (3H, m, aromatics) and 8.13 and 8.17 (1H, 2s, NHCHO diastereoisomers).

MIC against P. Mirabilis 889 is 100 μg/ml.

EXAMPLE 44

7β-[D-2-[(4-Ethyl-2,3-dioxopiperazin-1-yl)carbonylamino]-2-(thien-2-yl)acetamido]-7α-formamidocephalosporanic acid, sodium salt (a) t-Butyl 7β-[DL-2-[(4-ethyl-2,3-dioxopiperazin-1-yl)carbonylamino]-2-(thien-2-yl)acetamido]-7α-formamidocephalosporanate α-[(4-Ethyl-2,3-dioxopiperazin-1-yl)carbonylamino]-thiophene-2-acetic acid (0.49 g, 1.5 mmol) in dichloromethane (5 ml) was treated with oxalyl chloride (0.20 ml, 2.5 mmol) and dimethylformamide (2 drops) and stirred at room temperature for 1 h. The solvent was evaporated and the residue in dichloromethane (5 ml) was added to an ice cooled solution of t-butyl 7β-amino-7α-formamidocephalosporanate (0.45 g, 1.2 mmol) and pyridine (0.18 ml, 2.2 mmol) in dichloromethane (10 ml). The reaction mixture was stirred at room temperature for 3 h and the solvent evaporated. The residue was dissolved in ethyl acetate, washed with N. hydrochloric acid, saturated sodium hydrogen carbonate solution, brine, dried over magnesium sulphate and evaporated. Chromatography (silica gel, ethyl acetate) gave the separated diastereoisomers. The D-isomer (0.14 g, 17%) showed δ(CDCl$_3$) 1.25 (3H, t, J 7 Hz, NCH$_2$CH$_3$), 1.50 (9H, s, C(CH$_3$)$_3$), 3.0–4.3 (8H,m,2-H$_2$ and NCH$_2$CH$_2$NCH$_2$), 4.71, 4.97 (2H, ABq, J 13 Hz, CH$_2$O) 5.18 (1H, s, 6-H), 6.00 (1H, d, ArCH), 6.7–7.4 (3H, m, thiophene-H's), 8.0–8.4 (2H, m, CHO & NH), 8.4–8.8 (1H,m, NH), 9.2–10–2 (1H, m, NH); $\nu_{max}$. (CH$_2$Cl$_2$) 3260, 1790, 1710, 1690 & 1500 cm$^{-1}$. The L-isomer (0.079 g 10%) exhibited δ(CDCl$_3$) 1.20 (3H, t, NHCH$_2$CH$_3$), 1.51 (9H, s, C(CH$_3$)$_3$), 2.05 (3H, s, OCOCH$_3$), 3.16 (2H, s, 2-H$_2$) 3.3–4.5 (6H, m, NCH$_2$CH$_2$NCH$_2$), 4.84 5.10 (2H, ABq, J 13 Hz, CH$_2$O), 4.96 (1H, s, 6-H), 6.10 (1H, d, ArCH), 6.7–7.4 (3H, m, thiophene-H's), 8.04(2H, m, CHO & NH), 9.30 (1H, s, NH), 9.87 (1H, d, NH); $\nu_{max}$(CH$_2$Cl$_2$) 3260 br, 1770, 1740 sh, 1690 & 1520 cm$^{-1}$.

(b) 7β-[D-2-[(4-ethyl-2,3-dioxopiperazine-1-yl)carbonylamino-2-(thien-2-yl)acetamido]-7α-formamidocephalosporanic acid, sodium salt t-Butyl 7β-[D-2-[(4-ethyl-2,3-dioxopiperazine-1-yl)carbonylamino]-2-(thien-2-yl)acetamido]-7α-formamidocephalosporanate (0.14 g 0.21 mmol) was stirred with trifluoroacetic acid (2.5 ml) at room temperature for 0.5 h. The trifluoroacetic acid was evaporated and the residue was dissolved in dilute sodium hydrogen carbonate solution washed, with ethyl acetate, acidified with N. hydrochloric acid to pH 1.5 and extracted with ethyl acetate. The extracts were washed with brine, dried over magnesium sulphate and evaporated. The residue was suspended in water and adjusted to pH 6.5 with dilute sodium hydrogen carbonate solution. The resultant solution was filtered and freeze dried to give the title compound (0.054 g, 41%); δ(D$_2$O) 1.15 (3H, t, J 6 Hz, NCH$_2$CH$_3$), 2.05 (3H, s, OCOCH$_3$), 3.05–4.10 (10H, m, 2-H$_2$, CH$_2$O and N$_2$CH$_2$CH$_2$NCH$_2$), 5.24 (1H, s, ArCH), 5.78 (1H, s, 6-H), 6.9–7.5 (3H, m, thiophene-H's), 8.10 (1H, s, CHO); $\nu_{max}$(KBr) 3440, 2980, 1770, 1680 & 1610 cm$^{-1}$.

MIC against P. Mirabilis 889 is 0.1 μg/ml.

EXAMPLE 45

7β-[L-2-[(4-Ethyl-2,3-dioxopiperazin-1-yl)carbonylamino]-2-(thien-2-yl)acetamido]-7α-formamido cephalosporanic acid, sodium salt t-Butyl 7α-[L-2-[(4-Ethyl-2,3-dioxopiperazin-1-yl)carbonylamino]-2-(thien-2-yl)acetamido]-7α-formamidocephalosporanate (0.079 g, 0.12 mmol) in trifluoroacetic acid (2 ml) was stirred at room temperature for 0.5 h. The trifluoroacetic acid was evaporated and the residue dissolved in dilute sodium hydrogen carbonate solution. The solution was washed with ethyl acetate, acidified to pH 1.5 with N. hydrochloric acid and extracted with ethyl acetate. The extracts were washed with brine, dried, and evaporated. The residue was suspended in water and adjusted to pH 6.5 with dilute sodium hydrogen carbonate solution. The resultant solution was filtered and freeze dried to give the title compound 0.024 g, 32%); δ(D$_2$O) 1.20 (3H, t, NCH$_2$CHHD 3), 2.09 (3H, s, OCOCH$_3$) 3.00–4.15 (10H, m, 2-H$_2$, CH$_2$O and NCH$_2$CH$_2$NCH$_2$), 5.22 (1H, s, ArCH), 5.84 (1H,s, 6-H), 6.97–7.52 (3H,m thiophene -H's) and 8.08 (1H, s, CHO); ν$_{max}$ (KBr) 3400, 2970, 2920, 1730, 1710, 1650 & 1610 cm$^{-1}$.

MIC against P. Mirabilis 889 is 0.25 μg/ml.

EXAMPLE 46

7β-[2-(2-Aminothiazol-4-yl)acetamido]-7α-formamidocephalosporanic acid, trifluoroacetic acid salt (a) t-Butyl 7α-formamido-7β-[2-[2-(triphenylmethylamino)thiazol-4-yl]acetamido]cephalosporanate A solution of 2-[2-(triphenylmethylaminothiazol-4-yl]acetic acid (0.200 g, 0.5 mmol) in tetrahydrofuran (10 ml) was slowly added dropwise to a solution of N,N'-dicyclohexylcarbodiimide (0.227 g, 1.1 mmol) in tetrahydrofuran (5 ml) at 0° C. After the addition, a solution of t-butyl 7β-amino-7α-formamidocephalosporanate (0.185 g, 0.5 mmol) in tetrahydrofuran (5 ml) was added dropwise, and the reaction mixture was stirred at room temperature for 16 h. The solution was then filtered, evaporated to dryness, and the residue dissolved in ethyl acetate and washed with 0.5N hydrochloric acid, dilute aqueous sodium hydrogen carbonate and brine. It was dried over magnesium sulphate, evaporated to dryness, and the crude product was chromatographed on silica gel 60 (<230 mesh) eluting with ethyl acetate/hexane (4:1) to afford the title compound (0.23 g, 61%)λ$_{max}$(EtOH) 262 nm (ε13928); ν$_{max}$(CH$_2$Cl$_2$) 3400, 3200, 1792, 1740, 1725, 1700, 1680, 1520, 1225 cm$^{-1}$; δ(CDCl$_3$) 1.52 (9H, s, C(CH$_3$)$_3$), 2.01 (3H, s, OCOCH$_3$), 3.28 (2H, brs, 2-H$_2$), 3.51 (2H, brs, ArCH$_2$CO), 4.83 and 5.06 (2H, ABq, J 14 Hz, CH$_2$OCOCH$_3$), 5.18 (1H, s, 6-H) 6.07 (1H, s, thiazolyl-H), 7.05 (1H, brs, exchangeable with D$_2$O, NHCPh$_3$), 7.28 (15H, s, CPh$_3$), 8.15 (1H, s, NHCHO), 8.28 (1H,brs, exchangeable with D$_2$O, NHCHO) and 9.23 (1H,brs, exchangeable with D$_2$O, 7β-NHCO).

(b) 7β-[2-(2-Aminothiazol-4-yl)acetamido]-7α-formamidocephalosporanic acid, trifluoroacetate salt A solution of t-butyl 7α-formamido-7β-[2-[2-(triphenylmethylamino) thiazol-4-yl]acetamido]cephalosporanate (0.150 g, 0.20 mmol) in trifluoroacetic acid (5 ml) was stirred at room temperature for 2 h. The solution was then evaporated to dryness, and the residue treated with toluene and re-evaporated. The resulting gum was treated with ethyl acetate, and the solid was filtered and washed well with ethyl acetate and ether. It was dried in vacuo to afford the title compound (0.078 g, 69%); ν$_{max}$(KBr) 1775, 1725, 1670, 1630sh, 1525 cm$^{-1}$; δ(CF$_3$CO$_2$D) 2.25 (3H, s, OCOCH$_3$), 3.48 and 3.65 (2H, ABq, J 17 Hz, 2-H$_2$), 3.98 (2H, s, ArCH$_2$CO), 5.26 and 5.42 (2H, ABq, J 14 Hz, CH$_2$OCOCH$_3$), 5.42 (1H, s, 6-H), 6.69 (1H, s, thiazolyl-H) and 8.40 (1H, s, NHCHO).

MIC against P. Mirabilis 889 is 100 μg/ml.

EXAMPLE 47

6β-[D-2-[3-Coumarin-3-yl)ureido]-2-(4-hydroxyphenyl)acetamido]-6α-formamidopenicillanic acid, sodium salt 6β-[D-2-Amino-2-(4-hydroxyphenyl)acetamido]-6α-formamidopenicillanic acid (0.231 g) in water (25 ml) was treated with triethylamine to give pH 6.5 and the solution diluted with tetrahydrofuran (25 ml). Coumarin-3-ylisocyanate (0.094 g) in tetrahydrofuran (15 ml) was added and the pH maintained between 6.5 and 7.5 by addition of triethylamine. The mixture was stirred at room temperature for 0.5 h then concentrated in vacuo. The aqueous residue was washed with ethyl acetate (2×35 ml), ether (35 ml), and then covered with a layer of ethyl acetate (35 ml) and acidified to pH 2 with 5M hydrochloric acid. The phases were separated and the aqueous phase further extracted with ethyl acetate (35 ml), the organic extracts combined, washed with water at pH 2 (35 ml), water (35 ml) saturated brine (25 ml) and dried over anhydrous magnesium sulphate. Evaporation to dryness in vacuo gave a pale pink foam (0.266 g), which was redissolved in dry acetone (10 ml) and treated with a solution of 2M sodium 2-ethylhexanoate in 4-methylpentan-2-one (0.22 ml), followed by ether. The resulting precipitate was collected by filtration, washed with ether and dried in vacuo (yield 0.292 g), ν$_{max}$(KBr) 3300 br, 1763, 1675, 1675 br, 1600, 1530 br, 1460, 1362, 1230, 1205 sh, and 1175 cm$^{-1}$; δ(D$_2$O) 0.96 and 1.31 (6H, 2s, C(CH$_3$)$_2$), 4.15 (1H, s, 3-H), 5.20 (1H, s, 5-H), 5.45 (1H, s, CH), 6.30–6.60 (1H, m, coumarin-H), 6.75–7.13 (5H, m, phenyl-H$_2$ and coumarin-H$_3$), 7.38 (2H, d, J 8 Hz, phenyl), 7.60 (1H, s, coumarin-H), 8.14 (1H, s, CHO).

MIC against P. Mirabilis 889 is 100 μg/ml.

EXAMPLE 48

6β-[D-2-[3-(4-Oxo-4H-1-benzopyran-3-yl)ureido]-2-(4-hydroxyphenyl)acetamido]-6α-formamidopenicillanic acid, sodium salt (a) 4-Oxo-4H-1-benzopyran-3-ylisocyanate Chromone-3-carboxylic acid (0.19 g) in dry dichloromethane (10 ml) was treated at room temperature with oxalyl chloride(0.1 ml) followed by dry N,N-dimethylformamide (2 drops). It was stirred for one hour at room temperature, evaporated to dryness in vacuo, redissolved in 1,2-dichloroethane (10 ml) and treated with trimethylsilylazide (0.13 ml). It was stirred for one hour at room temperature and then heated at 90° C. for one hour. Evaporation to dryness in vacuo yielded an off-white solid (0.186 g), ν$_{max}$(1,2-dichloroethane) 2230, 1680, 1645, 1615, 1462, 1376, 1250, 850, and 760 cm$^{-1}$.

(b) 6β-[D-2-[3-(4-Oxo-4H-1-benzopyran-3-yl)ureido]-2-(4-hydroxyphenyl)acetamido]-6α-formamidopenicillanic acid, sodium salt 6β-[D-2-Amino-2-(4-hydroxyphenyl)acetamido]-6α-formamidopenicillanic acid (0.231 g) was suspended in 50% aqueous tetrahydrofuran (20 ml), triethylamine added to pH 6.5, and this mixture treated with a solution of 4-oxo-4H-1-benzopyran-3-ylisocyanate (0.093 g) in tetrahydrofuran (10 ml). The pH was maintained at 6.5–7.0 throughout by addition of triethylamine. After 0.5 h at room temperature, the mixture was concentrated in vacuo, the residue washed with ethyl acetate (2×25 ml), ether (25 ml), and covered with a layer of ethyl acetate (25 ml), acidified to pH 2 with 5M hydrochloric acid and the phases separated. The aqueous phase was further extracted with ethyl acetate (25 ml), the organic extracts combined, washed with water at pH 2 (25 ml), water (25 ml) and saturated brine (25 ml) before being dried over anhydrous magnesium sulphate. Evaporation in vacuo gave an off-white powder(0.227 g), which was redissolved in dry acetone (10 ml) and treated with 2M sodium 2-ethylhexanoate in 4-methylpentan-2-one (0.19 ml) followed by ether. The precipitate was collected by filtration, washed with ether and dried in vacuo to yield the title compound (0.217 g), $\nu_{max}$(KBr) 3320 br, 1765, 1665 br, 1607, 1540, 1510, 1468, 1382, 1265 sh, and 1215 cm$^{-1}$; $\delta$(D$_2$O) 0.99 and 1.33(6H, 2s, C(CH$_3$)$_2$), 4.18 (1H, s, 3-H), 5.28 (1H, s, CH), 5.56 (1H, s, 5-H), 6.60–7.55 (8H, m, aromatic and chromone protons), 8.09 (1H, s, CHO), and 8.38 (1H, s, chromone 2-H).

MIC against P. Mirabilis 889 is 50 $\mu$g/ml.

EXAMPLE 49

6$\alpha$-Formamido-6$\beta$-[D-2-[(4-hydroxy-7-methyl-1,8-naphthyridin-3-yl)carbonylamino]-2-(4-hydroxyphenyl)acetamido]penicillanic acid, sodium salt (a) Benzyl 6$\beta$-[D-2-[4-(benzyloxycarbonyloxy)phenyl]-2-[(4-hydroxy-7-methyl-1,8-naphthyridin-3-yl)carbonylamino]acetamido]-6$\alpha$-formamidopenicillanate 4-Hydroxy-7-methyl-1,8-naphthyridine-3-carboxylic acid (0.204 g) was suspended in dry dichloromethane (20 ml) and treated with triethylamine (0.42 ml). The resulting solution was cooled to $-20°$ to $-25°$ C. and treated with phosgene in toluene (0.8 ml; 12.5% w/w) and the mixture stirred at $-20°$ to $-25°$ C. for 0.5 h. Then a solution of benzyl 6$\beta$-[D-2-amino-2-[4-(benzyloxycarbonyloxy)phenyl]acetamido]-6$\alpha$-formamidopenicillanate (0.632 g) in dry dichloromethane (20 ml) was added. It was allowed to regain 0° C. and then stirred for one hour at 0°–5° C. It was evaporated to dryness in vacuo and the residue treated with ethyl acetate (100 ml) and water (50 ml), the phases separated and the aqueous phase further extracted with ethyl acetate (50 ml). The organic extracts were combined, washed with water (50 ml), brine (25 ml), dried over anhydrous magnesium sulphate and evaporated to dryness in vacuo to yield a brown foam, which was purified by chromatography on silica gel 60 (<230 mesh ASTM), eluting with ethyl acetate grading to 5% ethanol in ethyl acetate. Concentration of the appropriate fractions and dilution with ether followed by trituration and filtration gave the title compound as an off-white powder (0.232 g), $\nu_{max}$(KBr) 3240 br, 1780, 1760, 1680 sh, 1650, 1612, 1525, 1508, 1450, 1240, 1216, and 1182 cm$^{-1}$; $\delta$[CDCl$_3$+D$_2$O] 0.9 and 1.18 (6H, 2s, C(CH$_3$)$_2$), 2.71 (3H, s, naphthyridine CH$_3$), 4.45 (1H, s, 3-H), 5.14 and 5.26 (4H, 2s, 2CH$_2$'s), 5.41 (1H, m, CH), 5.81 (1H, s, 5-H), 6.99–8.15 (17H, m, aromatics, CHO and 2 naphthyridine - H's), 8.42 (1H, s, naphthyridine 2-H).

(b) 6$\alpha$-Formamido-6$\beta$-[D-2-[(4-hydroxy-7-methyl-1,8-naphthyridin-3-yl)carbonylamino]-2-(4-hydroxyphenyl)acetamido]penicillanic acid, sodium salt Benzyl 6$\beta$-[D-2-[4-(benzyloxycarbonyloxy)phenyl]-2-[(4-hydroxy-7-methyl-1,8-naphthyridin-3-yl)carbonylamino]acetamido]-6$\alpha$-formamidopenicillanate (0.202 g) was hydrogenated over prehydrogenated 10% palladium on carbon in a mixture of 1,4-dioxane (15 ml) and water (2.5 ml) for 3.5 h. The reaction mixture was treated with a solution of sodium hydrogen carbonate (0.02 g) in water (10 ml), filtered, and the filtrate washed with ethyl acetate (2$\times$50 ml), ether (25 ml) and the aqueous phase freezedried to give the product as a white powder (0.116 g), $\nu_{max}$ (KBr) 3420 br, 3230 br, 1765, 1650, 1610, 1525 sh, 1511, 1450, 1358, and 1250 cm$^{-1}$; $\delta$(D$_2$O) 0.91 and 1.27 (6H, 2s, C(CH$_3$)$_2$), 2.15 (3H, s, naphthyridine CH$_3$), 4.12 (1H, s, 3-H), 5.44 (1H, s, CH), 5.55 (1H, s, 5-H), 6.60 (1H, d, J 9 Hz, naphthyridine - H), 6.88 and 7.37 (4H, 2d, J 8 Hz, aromatics), 7.79 (1H, d, J 9 Hz, naphthyridine-H), 8.06 (1H, s, CHO), 8.20 (1H, s, naphthyridine 2-H)

MIC against P. Mirabilis 889 is 5.0 $\mu$g/ml.

EXAMPLE 50

6$\beta$-[D-2-[D-2-amino-3-(N-methylcarbamoyl)propionamido]-2-(4-hydroxyphenyl)acetamido]-6$\alpha$-formamidopenicillanic acid, sodium salt (a) Methyl $\beta$-D-aspartate, hydrochloride This was prepared on a 50 m molar scale according to the procedure of K Hofmann et al, J Amer Chem Soc 1957, 79, 5701, in the L-series. After recrystallisation from methanol-ether there was obtained 6.19 g (67%) of compound; mp. 183°–185° C. A second recrystallisation gave material of mp 185.5°–187° C.; $[\alpha]_D^{20}$ $-14.8°$ (cl, ethanol:water, 1:3); R$_f$0.1 in n-butanol:acetic acid:water, 4:1:1.

(b) D-2-Amino-3-(N-methylcarbamoyl)propionic acid

The preceding methyl ester hydrochloride (1.83 g, 10 m mole) was dissolved in methanol (8 ml) and a solution of methylamine in ethanol (33% w/v, 4.7 ml) was added. The flask was tightly stoppered and left at room temperature for 65 h, after which a considerable amount of solid had separated. This was filtered, washed with methanol and ether and dried. The filtrate and washings were evaporated to dryness and dissolved in water (20 ml), then the pH was adjusted to 5.5 by addition of hydrochloric acid. The solution was again evaporated to dryness, then triturated with methanol to obtain further product, which was isolated as above; total yield, 1.28 g (88%); mp. 230°–235° C. (dec); $[\alpha]_D^{20}$ $-30.8°$ (cl, M hydrochloric acid); $\delta$(D$_2$O) 2.73 (3H, s, CH$_3$N), 2.90 (2H, d, J 6 Hz, CH$_2$—CH), 4.16 (1H, t, J 6 Hz, CHCH$_2$); R$_f$0.05 in n-butanol:acetic acid: water, 4:1:1; (Found: C, 41.1; H, 6,85; N, 19.2. C$_5$H$_{10}$N$_2$O$_3$ requires C, 41.1; H, 6.85; N, 19.2%).

(c) D-2-(4-Nitrobenzyloxycarbonylamino)-3-(N-methylcarbamoyl)propionic acid

The preceding amino acid N-methylamide (0.73 g, 5 m mole) was dissolved in M sodium hydrogen carbonate solution (10 ml). A solution of 4-nitrobenzyloxycarbonyl chloride (1.35 g, 1.25 eq) in tetrahydrofuran (2 ml) was added and the mixture was vigorously stirred at room temperature for 16 h. After this time water was added and the solution was twice washed with ethyl acetate, backwashing with water each time. The total aqueous phase was acidified to pH 2 by the addition of 2M hydrochloric acid, precipitating the product as a white solid, which was filtered, washed with water and dried; yield 1.23 g (76%). Recrystallisation from tetrahydrofuran-petroleum ether (60°–80°) afforded pure material, mp. 135°–136° C.; $[\alpha]_D^{20}$ $-0.23°$ (cl, dimethylformamide); δ[(CD₃)₂SO]2.40–2.65 (5H, m, CH₃N+CHCH₂), 4.35 (1H, m; t, J 7 Hz on D₂O exch, CH—CH₂), 5.17 (2H, s, ArCH₂O), 7.50–7.90 (4H, m, 2H, d, on D₂O exch, aryl-H and 2-NH), 8.23 (2H, d, aryl-H), 12.60 (1H, br s, D₂O exch, CO₂H); R$_f$0.50 in n-butanol:acetic acid:water, 4:1:1; (Found: C, 47.8; H, 4.75; N, 12.5. C₁₃H₁₅N₃O₇ requires C, 48.0; H, 4.6; N, 12.9%).

(d)
D-2-(4-Nitrobenzyloxycarbonylamino)-3-(N-methylcarbamoyl)propionic acid, N-hydroxysuccinimide ester The preceding protected acid (0.65 g, 2 m mole) was dissolved with N- hydroxy succinimide (0.23 g, 1 eq) in dry dimethylformamide (10 ml). The solution was cooled to 0° C. and stirred, then dicyclohexylcarbodiimide (0.41 g, 1 eq) was added. After addition was complete, stirring was continued for one hour, during which time the mixture regained room temperature, then the well-stoppered flask was stored at 5° C. for 16 h. The precipitated solid was filtered off and washed with tetrahydrofuran, then the combined filtrate and washings were evaporated to dryness. Trituration of the residue with propan-2-ol afforded the active ester as a white solid which was filtered, washed with a little cold propan-2-ol, ether and dried; yield, 0.59 g (70%), mp.128°–129° C.; [α]$_D^{20}$+19.7° (cl, dimethyformamide); δ[(CD₃)₂SO]2.45–2.75 (5H, m, CH₃N+CHCH₂), 2.80 (4H, s, COCH₂CH₂CO), 4.90 (1H, m, CHCH₂), 5.21 (2H, s, ArCH₂O), 7.61 (2H, d, aryl-H), 7.90 (2H, br m, D₂O exch, 2NH), 8.23 (2H, d, aryl-H). (Found: C, 48.2; H, 4.3; N, 13.1. C₁₇H₁₈N₄O₉ requires C, 48.3; H, 4.3; N, 13.3%).

(e) Sodium
6β-[D-2-[D-2-(4-nitrobenzyloxycarbonylamino)-3-(N-methylcarbamoyl)propionamido]-2-(4-hydroxyphenyl)acetamido]-6α-formamidopenicillanate 6β-[D-2-Amino-2-(4-hydroxyphenyl)acetamido]-6α-formamidopenicillanic acid (0.150 g, 0.325 m mole) was suspended in a mixture of dry dichloromethane (2 ml) and dry dimethylformamide (1 ml). The suspension was cooled to 0° C. and stirred; then were added sequentially triethylamine (0.06 ml) and the preceding active ester (0.137 g, 1 eq). Stirring was continued at 0°–5° C., a clear yellow solution being obtained, but it was necessary to add further dimethylformamide (1 ml) to prevent its becoming highly viscous. After 2.5 h, most of the dimethylformamide was removed by evaporation at <1 mm Hg at ambient temperature and the residue partitioned between ethyl acetate and water containing sufficient sodium hydrogen carbonate to give a pH of about 8. The aqueous phase was washed once more with ethyl acetate, backwashing with a little water each time, then the total was acidified to pH 2 with hydrochloric acid and extracted twice with ethyl acetate:tetrahydrofuran, 1:1. The organic extracts were washed once with brine, dried over sodium sulphate and evaporated to a semi-solid yellow gum. This was taken up in acetone, filtering a little insoluble material, and a 2M solution of sodium 2-ethylhexanoate in 4-methylpentan-2-one (0.17 ml, 1 eq) was added. The resultant suspension was concentrated and dry ether was added to give the penicillin sodium salt as an off-white solid which was filtered, washed with acetone and ether, and dried; yield, 0.15 g (63%); ν$_{max}$(KBr) 1770, 1665, 1610, and 1515 cm⁻¹; δ(D₂O) 0.90 and 1.27 (6H, 2s, (CH₃)₂C), 2.67 (5H, m, CH₃N +CH₂CH), 4.11 (1H, s, 3-H), 5.11 (2H, s, ArCH₂O), 5.29 (1H, s, 5-H), 5.53 (1H, s, ArCHNH), 6.60–6.80 (2H, m, aryl-H), 7.00–7.50 (4H, m, aryl-H) 7.90–8.10 (2H, m, aryl-H), 8.04 (1H, s, NHCHO); R$_f$0.35 n-butanol:acetic acid: water, 4:1:1.

(f) Sodium
6β-[D-2-[D-2-amino-3-(N-methylcarbamoyl)propionamido]-2-(4-hydroxphenyl)acetamido]-6α-formamidopenicillanate Sodium 6β-[D-2-[D-2-(4-nitobenzyloxycarbonylamino)-3-(N-methylcarbamoyl)propionamido]-2-(4-hydroxyphenyl)acetamido]-6α-formamidopenicillanate (0.13 g, 0.18 m mole) was dissolved in water (5 ml) and 10% palladium on charcoal (0.06 g) was added. The mixture was hydrogenated at atmospheric pressure and room temperature for one hour, then the catalyst was filtered and washed well with water. The filtrate was washed twice with ethyl acetate, backwashing with a little water each time, then the aqueous phase was evaporated to dryness. Trituration with ether afforded the deprotected penicillin sodium salt (0.08 g, 81%) as a pale yellow powder; ν$_{max}$ (KBr) 1770, 1650 br, 1605, 1510 cm⁻¹; δ(D₂O) 0.93 and 1.28 (6H, 2s, (CH₃)₂C), 2.50–2.75 (5H, m, CH₃N+CH₂CH), 3.80 (1H, m, CH(NH₂)CO), 4.12 (1H, s, 3-H), 5.31 (1H, s, 5-H), 5.54 (1H, s, ArCH(NH)CO), 6.87 (2H, d, aryl-H), 7.35 (2H, d, aryl-H), 8.09 (1H, s, NHCHO); R$_f$0.05 in n-butanol: acetic acid:water, 4:1:1.

MIC against P. Mirabilis 889 is 1.0 μg/ml.

EXAMPLE 51
7β-[2-(Cyanomethylthio)acetamido]-7α-formamidocephalosporanic acid, sodium salt (a) t-Butyl
7β-[2-(cyanomethylthio)acetamido]-7α-formamidocephalosporanate 2-(Cyanomethylthio)acetic acid (0.144 g, 1.1 mmol) in dichloromethane (10 ml) containing dimethylformamide (1 drop), was converted to its acid chloride by treatment with oxalyl chloride (0.279 g, 2.2 mmol). After stirring at room temperature for 0.75 h the solution was evaporated to dryness, treated with toluene, and re-evaporated. The residue was dissolved in dichloromethane (5 ml) and added dropwise to a solution of t-butyl 7β-amino-7α-formamidocephalosporanate (0.371 g, 1.0 mmol) and pyridine (0.119 g, 1.5 mmol) in dichloromethane (25 ml) at 0° C. The reaction solution was stirred at 0°–5° C. for 0.5 h, followed by 2 h at room temperature, before being washed with 0.5N hydrochloric acid, dilute aqueous sodium hydrogen carbonate and brine. It was dried over magnesium sulphate, filtered and evaporated. The crude product was chromatographed on silica gel 60 (<230 mesh ASTM) eluting with ethyl acetate/hexane 2:1 to afford the title compound (0.207 g, 43%); ν$_{max}$ (CH₂Cl₂) 3285, 2240, 1790, 1742, 1730, 1695, 1495, 1215 cm⁻¹; δ(CDCl₃) 1.54 (9H, s, C(CH₃)₃), 2.08 (3H, s, OCOCH₃), 3.27 and 3.51 (2H, ABq, J 17 Hz, 2-H₂), 3.50 (4H, s, CH₂SCH₂), 4.82 and 5.06 (2H, ABq, J 13 Hz, CH₂OCOCH₃), 5.21 (1H, s, 6-H), 8.00 and 8.33 (2H, 2s after exch D₂O, NHCO's) and 8.20 (1H, s, CHO).

(b)
7β-[2-(Cyanomethylthio)acetamido]-7α-formamidocephalosporanic acid, sodium salt t-Butyl 7β-[2-(cyanomethylthio)acetamido]-7α-formamidocephalosporanate (0.157 g, 0.32 mmol) was dissolved in ice cooled trifluoroacetic acid (5 ml) and the resulting solution was stirred at room temperature for 0.5 h. It was then evaporated to dryness, the residue treated with toluene and then re-evaporated. The residue was dissolved in dilute aqueous sodium hydrogen carbonate solution and washed with ethyl acetate. The aqueous solution was saturated with sodium chloride, adjusted to pH 1.5 with N-hydrochloric acid, and the product was extracted into tetrahydrofuran/ethyl acetate (1:1). The extracts were washed with brine, dried over magnesium sulphate, and evaporated to dryness to leave the free acid. This was suspended in water and the pH adjusted to 6.5 with dilute aqueous sodium hydrogen carbonate. The resulting solution was filtered and freeze dried to afford the title compound (0.091 g, 62%); $\nu_{max}$(KBr), 2240, 1765, 1675, 1610 cm$^{-1}$; δ(D$_2$O) 2.04 (3H, s, OCOCH$_3$), 3.15–3.75 (6H, m, CH$_2$SCH$_2$ and 2-H$_2$), 4.50–4.95 (m, HOD and CH$_2$OCOCH$_3$), 5.29 (1H, s, 6-H), and 8.10 (1H, s, CHO).

MIC against P. Mirabilis 889 is 25 μg/ml.

EXAMPLE 52

7β-[2-[(Aminocarbonyl)amino]-2-(thien-2-yl)acetamido]-7α-formamidocephalosporanic acid, sodium salt (a) t-Butyl 7α-[2-[(aminocarbonyl)amino]-2-(thien-2-yl)acetamido]-7α-formamidocephalosporanate Thionyl chloride (0.87 g, 7.3 mmol) was added to a suspension of 2-[(aminocarbonyl)amino]-2-(thien-2-yl) acetic acid (0.60 g, 3 mmol) in dry acetonitrile (17 ml) at 0°–5° C. under a nitrogen atmosphere. After 5 minutes dry ether (29 ml) was added and the resulting slurry was stirred for 10 minutes. The precipitate was then filtered under nitrogen, and washed well with ether. The product was dried in vacuo to afford 2-amino-4-(thien2-yl)-4H-oxazol-5-one hydrochloride (0.60 g, 92%) as a salmon pink powder; $\nu_{max}$(Nujol) 1878, 1745, 1725 cm$^{-1}$.

t-Butyl 7β-amino-7α-formamidocephalosporanate (0.557 g, 1.5 mmol) in dry dichloromethane (10 ml) under nitrogen, was cooled to −60° C. Dry dimethylformamide (10 ml) and propylene oxide (1.3 ml, 1.08 g, 18.6 mmol) were then added and the mixture re-cooled to −60° C. The above oxazolone hydrochloride (0.60 g) was then added in one portion and the resulting solution was stirred at −60° C. to −20° C. over 3 h. The volatile components were then removed under vacuum, and the remaining solution was diluted with ethyl acetate and washed with water, dilute aqueous sodium hydrogen carbonate, 0.5N hydrochloric acid, and brine. The organic solution was dried over magnesium sulphate and evaporated to dryness to leave the crude product. Chromatography on silica gel 60 (<230 mesh ASTM) eluting with ethyl acetate/hexane 4:1 through to 5% ethanol/ethyl acetate afforded two isomers. Isomer 1 was the less polar of the two isomers.

Isomer 1: $\nu_{max}$(tetrahydrofuran 3460, 3350, 3200, 1790, 1745, 1695 br, 1670 sh cm$^{-1}$; δ[(CD$_3$)$_2$CO]1.51 (9H, s, C(CH$_3$)$_3$), 2.01 (3H, s, OCOCH$_3$), 3.28 and 3.56 (2H, ABq, J 17 Hz, 2-H$_2$), 4.71 and 5.03 (2H, ABq, J 13 Hz, CH$_2$OCOCH$_3$), 5.21 (1H, s, 6-H), 5.50 (2H,br,s CON$\underline{H_2}$), 6.14 (1H, d, J 8 Hz, α-proton), 6.69 (1H, d, J 8 Hz, α-NHCO), 6.85–7.40 (3H, m, aromatics), 8.16 (1H, s, CHO) and 8.40 and 9.12 (2H, 2s, 7β-NHCO and NHCHO).

Isomer 2: mp 194° C. (dec) (from acetone); $\nu_{max}$(tetrahydrofuran) 3460, 3350, 3190, 1785, 1740, 1695 br, 1660 cm$^{-1}$; δ[(CD$_3$)$_2$NCDO]1.52 (9H, s, C(CH$_3$)$_3$), 2.05 (3H, s, OCOCH$_3$), 3.31 and 3.62 (2H, ABq, J 18 Hz, 2-H$_2$), 4.68 and 4.95 (2H, ABq, J 12 Hz, CH$_2$OCOCH$_3$), 5.29 (1H, s, 6-H), 5.92 (3H, m, α-proton and NHCON$\underline{H_2}$), 6.85 (1H, d, J 8 Hz, NCON$\underline{H_2}$), 6.95 (1H, dd, J 5 and 3 Hz, thienyl 4-H), 7.21 (1H, d, J 3 Hz, thienyl 3-H), 7.43 (1H, d, J 5 Hz, thienyl 5-H), 8.22 (1H, s, CHO), 9.29 and 9.61 (2H, 2s, N$\underline{H}$CHO and 7β-NH). (Found: C, 47.9; H, 4.8; N, 12.7. C$_{22}$H$_{27}$N$_5$O$_8$S$_2$ requires C, 47.7; H, 4.9; N, 12.65). (b) 7β-[2-[(Aminocarbonyl)amino]-2-(thien-2-yl)acetamido]-7α-formamidocephalosporanic acid, sodium salt (Isomer 1)

t-Butyl 7β-[2-[(aminocarbonyl)amino]-2-(thien-2-yl)acetamido]-7α-formamidocephalosporanate (Isomer 1) (0.216 g, 0.39 mmol) was dissolved in ice-cooled trifluoroacetic acid (5 ml) and stirred at room temperature for 0.75 h. The solution was evaporated to dryness, toluene was added and evaporated. The residue was dissolved in dilute aqueous sodium hydrogen carbonate and the resulting solution was washed with ethyl acetate. It was then saturated with sodium chloride, the pH adjusted to 1.5 with N hydrochloric acid, and the product was extracted into tetrahydrofuran/ethyl acetate. The extracts were washed with brine, dried over magnesium sulphate, and then evaporated to dryness to afford the free acid. This was suspended in water, the pH adjusted to 6.5 with dilute aqueous sodium bicarbonate, and the resulting solution was filtered and freeze dried to afford the title sodium salt (0.181 g, 89%); $\nu_{max}$(KBr) 1760, 1680, 1615, 1530, 1380 cm$^{-1}$; δ(D$_2$O) 2.01 (3H, s, OCOCH$_3$) 3.11 and 3.49 (2H, ABq, J 17 Hz, 2-H$_2$), 4.40–4.80 (m, HOD and CH$_2$OCOCH$_3$), 5.18 (1H, s, 6-H), 5.58 (1H, s, α-proton), 6.90–7.50 (3H, m, aromatics) and 8.03 (1H, s, CHO).

MIC against P. Mirabilis 889 is 125 μg/ml.

(c)

7β-[2-[(Aminocarbonyl)amino]-2-(thien-2-yl)acetamido]-7α-formamidocephalosporanic acid, sodium salt (Isomer 2)

t-Butyl 7β-[2-[(aminocarbonyl)amino]-2-(thien-2-yl) acetamido]-7α-formamidocephalosporanate (Isomer 2) (0.080 g, 0.14 mmol) was dissolved in ice-cooled trifluoroacetic acid (5 ml), and stirred at room temperature for 0.5 h. The solution was evaporated to dryness, toluene was added and evaporated. The residue was dried under vacuum to afford the free acid as a white solid. This was suspended in water and the pH adjusted to 6.5 by the addition of dilute aqueous sodium hydrogen carbonate. The resulting solution was washed with ethyl acetate and then freeze dried to afford the title compound; $\xi_{max}$ (KBr) 1760, 1675, 1620, 1530 cm$^{-1}$; δ(D$_2$O) 2.01 (3H, s, OCOCH$_3$), 3.06 and 3.46 (2H, ABq, J 17 Hz, 2-H$_2$), 4.50–4.85 (m, HOD and CH$_2$OCOCH$_3$), 5.22 (1H, s, 6-H), 5.55 (1H, s, α-proton), 6.90–7.50 (3H, m, aromatics) and 8.10 and 8.41 (1H, 2s, CHO rotamers).

MIC against P. Mirabilis 889 is 25 μg/ml.

EXAMPLE 53

7α-Formamido-7β-[2-(thien-2-yl)acetamido]-3-[(1-methyl-1H-tetrazol-5-yl)thiomethyl]ceph-3-em-4-carboxylic acid, sodium salt (a) Benzhydryl 7α-formamido-7β-[2-(thien-2-yl)acetamido]-3-[(1-methyl-1H-tetrazol-5-yl)thiomethyl]ceph-3-em-4-carboxylate 7α-Formamido-7β-[2 - (thien-2-yl)acetamido]cephalosporanic acid (0.35 g, 0.8 mmol) in 1,2-dichloroethane (15 ml) with 1-methyl-1H-tetrazole-5-thiol (0.10 g, 0.86 mmol) was heated at 80° C. for 6 h, allowed to cool and stood at room temperature overnight. A solution of diphenyl diazomethane (0.27 g, 1.4 mmol) in dichlcromethane (10 ml) was added and the reaction mixture stirred at room temperature for 3 h. The reaction mixture was quenched with glacial acetic acid (1 ml) and evaporated. The residue was chromatographed (silica gel 60; 1:1 hexane/ethyl acetate) to give the title compound (0.072 g, 14%); $\delta$(CDCl$_3$) 3.22, 3.48 (2H, ABq, J 16 Hz, 2H$_2$), 3.85 (2H, s, ArCH$_2$), 3.87 (3H, s, NCH$_3$), 4.36, 4.52 (2H, ABq, J 13 Hz, CH$_2$S), 5.17 (1H, s, 6-H), 6.86–7.04 (3H, m, thiophene-H's and Ph2CH), 7.2–7.6 (11H, m, thiophene-H and aromatic-H's), 8.16 (1H, s, CHO); $\nu_{max}$(CH$_2$Cl$_2$) 1790, 1698, 1630 cm$^{-1}$.

(b) 7α-Formamido-7β-[2-(thien-2-yl)acetamido]-3-[(1-methyl-1H-tetrazol-5-yl)thiomethyl]ceph-3-em-4-carboxylic acid, sodium salt Benzhydryl 7α-formamido-7β-[2-(thien-2-yl)acetamido]-3-[(1-methyl-1H-tetrazol-5-yl)thiomethyl]cephz-3-em-4-carboxylate (0.07 g, 0.11 mmol) in trifluoroacetic acid (5 ml) was stirred at room temperature for 0.5 h and evaporated to dryness. The residue was triturated with ether and suspended in water which was adjusted to pH 6.5 with saturated sodium hydrogen carbonate solution. The resulting solution was washed with ethyl acetate, filtered and freeze dried to give the title compound (0.03 g, 55%); $\delta$(D$_2$O) 3.34, 3.68 (2H, ABq, J 17 Hz, 2-H$_2$) 3.96 (2H, s, ArCH$_2$), 4.04 (3H, s, NCH$_3$)(3.96, 4.04 signals hiding 1H of CH$_2$S), 4.2–4.3 (1H, d, J 13 Hz, CH$_2$S), 5.28 (1H, s, 6-H) 6.95–7.15 (2H, m, thiophene-H's), 7.3–7.45 (1H, m, thiophene-H), 8.16 (1H, s, CHO); $\nu_{max}$ (KBr) 1610, 1677, 1764 cm$^{-1}$.

MIC against P. Mirabilis 889 is 10 μg/ml.

EXAMPLE 54

Diphenylmethyl 7β-amino-7α-formamido-3-[(1-methyl-1H-tetrazol-5-yl)thiomethyl]ceph-3-em-4-carboxylate (a) t-Butyl 7α-formamido-7β-[(4-nitrobenzyl)oxycarbonylamino]-cephalosporanate A solution of 4-nitrobenzylchloroformate (3.24 g, 15 mmol) in tetrahydrofuran (20 ml) was added dropwise to a stirred solution of t-butyl 7β-amino-7α-formamidocephalosporanate (1.11 g, 3 mmol) and pyridine (1.19 g, 15 mmol) in tetrahydrofuran (30 ml) at 0° C. The reaction solution was stirred at 0°–5° C. for 0.5 h, followed by 6 h at room temperature. It was then evaporated to dryness, the residue was dissolved in ethyl acetate and the resulting solution was washed with dilute aqueous sodium hydrogen carbonate, 0.5N hydrochloric acid and brine. It was then dried over magnesium sulphate, and the crude product was chromatographed on silica gel 60 (<230 mesh ASTM) eluting with ethyl acetate/hexane 1:2 through to 3:2, to afford the title compound (1.06 g, 64%); $\nu_{max}$(CH$_2$Cl$_2$) 3395, 3300, 1795, 1740, 1725, 1700, 1525, 1495, 1350, 1230 cm$^{-1}$; $\delta$(CDCl$_3$) 1.51 (9H, s, C(CH$_3$)$_3$), 2.06 (3H, s, OCOCH$_3$), 3.21 and 3.45 (2H, ABq, J 17 Hz, 2-H$_2$), 4.82 and 5.07 (2H, ABq, J 13 Hz, CH$_2$OCOCH$_3$), 5.15 (1H, s, 6-H), 5.21 (2H, s, CH$_2$Ar), 6.60 (1H, s, NHCOO), 7.49 and 8.18 (4H, 2d, J 8 Hz, aromatics), 7.61 (1H, br s, NHCHO) and 8.20 (1H, s, CHO)

(b) 7α-Formamido-7β-[(4-nitrobenzyl)oxycarbonylamino]-cephalosporanic acid t-Butyl 7α-formamido-7β-[(4-nitrobenzyl)oxycarbonylamino]cephalosporanate (0.94 g, 1.7 mmol) was dissolved in ice cooled trifluoroacetic acid (10 ml) and stirred at room temperature for 0.75 h. The solution was evaporated to dryness and the residue was dissolved in ethyl acetate (30 ml). After concentrating the solution to 5 ml, ether was added and the precipitated product was filtered, washed well with ether and dried in vacuo to afford the title compound (0.66 g, 78%); $\nu_{max}$(KBr) 3420 br, 1780, 1720 br, 1680 sh, 1520, 1350 cm$^{-1}$; $\delta$(CF$_3$CO$_2$H) 2.26 (3H, s, OCOCH$_3$), 3.39 and 3.62 (2H, ABq, J 17 Hz, 2-H$_2$), 5.20–5.60 (5H, m, CH$_2$OCOCH$_3$, CH$_2$Ar and 6-H), 7.64 (2H, d, J 8 Hz, aromatics), 8.33 (2H, d, J 8 Hz, aromatics) and 8.42 (1H, s, CHO).

(c) Diphenylmethyl 7α-formamido-7β-[(4-nitrobenzyl)oxycarbonylamino]-3-[(1-methyl-1H-tetrazol-5-yl)thiomethyl]ceph-3-em-4-carboxylate 7α-Formamido-7β-[(4-nitrobenzyl)oxycarbonylamino]cephalosporanic acid (0.60 g, 1.21 mmol) and 1-methyl-1H-tetrazole-5-thiol (0.16 g, 1.34 mmol) in 1,2-dichloroethane (50 ml) was heated under reflux for 6.5 h. The resulting solution was decanted from insoluble material and, after cooling to room temperature, it was treated with a solution of diphenyldiazomethane in dichloromethane (14 ml). The reaction solution was stirred at room temperature for 0.5 h and then glacial acetic acid (1 drop) was added and stirring continued for 10 minutes. It was then evaporated to dryness and the crude product chromatographed on silica gel 60 (<230 mesh ASTM) eluting with ethyl acetate/hexane 1:1 through to 2:1 to afford the title compound (0.198 g, 23%); $\nu_{max}$(CH$_2$Cl$_2$) 3395, 1795, 1725, 1700, 1525, 1495, 1350, 1230 cm$^{-1}$; $\delta$(CDCl$_3$) 3.47 (2H, br s, 2-H$_2$), 3.79 (3H, s, NCH$_3$), 4.27 and 4.51 (2H, ABq, J 13 Hz, CH$_2$S), 5.14 (2H, s, CH$_2$Ar), 5.24 (1H, s, 6-H), 6.61 (1H, s, NHCOO), 6.88 (1H, s, CHPh$_2$) 7.10–7.60 (13H, m, aromatics and NHCHO), 8.05–8.25 (3H, m, aromatics and CHO).

(d) Diphenylmethyl 7β-amino-7α-formamido-3-[(1-methyl-1H-tetrazol-5-yl)thiomethyl]ceph-3-em-4-carboxylate A suspension of 10% palladium on charcoal (0.100 g) in tetrahydrofuran (10 ml) and water (1 ml) was prehydrogenated for 0.5 h. Diphenylmethyl 7α-formamido-7β-[(4nitrobenzyl)oxycarbonylamino]-3-[(1-methyl-1H-tetrazol-5-yl)thiomethyl]ceph-3-em-4-carboxylate (0.100 g, 0.14 mmol) in tetrahydrofuran (5 ml) was then added and hydrogenation was continued for 0.5 h. The catalyst was filtered and washed well with tetrahydrofuran and ethyl acetate. The filtrate was evaporated to dryness, the residue was dissolved in tetrahydrofuran (10 ml) and water (1 ml), 10% palladium on charcoal (0.100 g) was added, and hydrogenation was resumed for a further 0.75 h. The catalyst was then filtered, washed with ethyl acetate, and the filtrate was washed with brine. After drying over magnesium sulphate, the solution was evaporated to dryness and the residue chromatographed on silica gel 60 (<230 mesh ASTM) to afford the title compound (0.006 g, 8%); $\nu_{max}$(CH$_2$Cl$_2$) 3395, 1782, 1720 sh, 1695, 1380 cm$^{-1}$; δ(CDCl$_3$) 2.43 (2H, br s, NH$_2$), 3.60 and 3.67 (2H, ABq, J 16 Hz, 2-H$_2$), 3.86 (3H, s, NCH$_3$), 4.31 and 4.45 (2H, ABq, J 13 Hz, CH$_2$S), 5.17 (1H, s, 6-H), 6.48 (1H, s, NHCHO), 6.97 (1H, s, CHPh$_2$), 7.20–7.55 (10H, m, aromatics) and 8.23 (1H, s, CHO).

(e) Diphenylmethyl 7β-amino-7α-formamido-3-[(1-methyl-1H-tetrazol-5-yl)thiomethyl]ceph-3-em-4-carboxylate 7β-Amino-7α-formamido cephalosporanic acid trifluoroacetate salt (1.2 g, 2.8 mmol) in water (25 ml) and acetone (10 ml) was adjusted to pH 6.5 with sodium hydrogen carbonate solution. To this was added 1-methyl-1H-tetrazole-5-thiol (0.4 g, 3.4 mmol) and the reaction mixture stirred at 60° C. for 6 h. The reaction mixture was allowed to cool, acidified to pH 2.0 and evaporated to dryness. The residue was taken up in dimethylformamide (60 ml) and treated with diphenyldiazomethane in dichloromethane (30 ml). The reaction mixture was stirred at room temperature for 2.5 h, quenched with glacial acetic acid (0.5 ml), diluted with ethyl acetate, washed well with water, brine, dried over magnesium sulphate and evaporated. The residue was chromatographed (silica gel 60, 1:3 hexane/ethyl acetate) to give the title compound (0.47 g, 26%).

EXAMPLE 55

Diphenylmethyl 7α-formamido-7β-[(trichloroethoxy)carbonylamino]-3-[(1-methyl-1H-tetrazol-5-yl)thiomethyl]ceph-3-em-4-carboxylate (a) 7α-Formamido-7β-[(trichloroethoxy)carbonylamino]-cephalosporanic acid t-Butyl 7α-formamido-7β-[(trichloroethoxy)carbonylamino]cephalosporanate (1.44 g, 2.6 mmol) was dissolved in cold trifluoroacetic acid (15 ml) and stirred at room temperature for 0.75 h. The solution was then evaporated to dryness, treated with toluene, and re-evaporated. The residue was dissolved in dilute sodium hydrogen carbonate and the aqueous solution was washed with ethyl acetate before being acidified to pH 1.5 with N hydrochloric acid. The product was extracted into tetrahydrofuran/ethyl acetate, and the combined extracts were washed with brine, dried over magnesium sulphate, and evaporated to dryness to afford the title compound (0.96 g, 74%); δ[(CD$_3$)$_2$CO] 2.08 (3H, s, OCOCH$_3$), 3.60 (2H, br s, 2-H$_2$), 4.88 (2H, br s, CH$_2$CCl$_3$), 4.87 and 4.19 (2H, ABq, J 13 Hz, CH$_2$OCOCH$_3$), 5.39 (1H, s, 6-H), 8.10–8.80 (3H, 3s, NHCO and NHCHO) and 10.53 (1H, s, CO$_2$H).

(b) Diphenylmethyl 7α-formamido-7β-[(trichloroethoxy)carbonylamino]-3-[(1-methyl-1H-tetrazol-5-yl)thiomethyl]ceph-3-em-4-carboxylate 7α-Formamido-7β-[(trichloroethoxy)carbonylamino]cephalosporanic acid (0.49 g, 1 mmol) and 1-methyl-1H-tetrazole-5-thiol (0.13 g, 1.1 mmol) in 1,2-dichloroethane (30 ml) were heated under reflux for 7h. The reaction solution was evaporated to dryness and the crude 7α-formamido-7β-[(trichloroethoxy)carbonylamino]-3-[(1-methyl-1H-tetrazol-5-yl)thiomethyl]ceph-3-em-4-carboxylic acid was used without purification.

A solution of the above acid (1 mmol) in dichloromethane (25 ml) was treated with a solution of diphenyldiazomethane in dichloromethane (12 ml) (i.e. sufficient for completion of reaction as judged by tlc). After stirring at room temperature for 0.5 h glacial acetic acid (3 drops) was added and the stirring was continued for a further 0.25 h. The solution was then evaporated to dryness and the crude product chromatographed on silica gel 60 (<230 mesh ASTM) eluting with ethyl acetate/hexane 1:2 through to 1:1, to afford the title compound (0.121 g, 17%); $\nu_{max}$(CH$_2$Cl$_2$) 3390, 1798, 1735, 1705, 1490 br, 1382, 1230 cm$^{-1}$; δ(CDCl$_3$) 3.48 and 3.62 (2H, ABq, J 17 Hz, 2-H$_2$),3.87 (3H, s, NCH$_3$), 4.37 and 4.60 (2H, ABq, J 13 Hz, CH$_2$S), 4.72 and 4.81 (2H, ABq, J 12 Hz, CH$_2$CCl$_3$), 5.20 (1H, s, 6-H), 6.61 (1H, s, NHCOO), 6.93 (1H, s, CHPh$_2$), 7.20–7.60 (11H, m, aromatics and NHCHO) and 8.21 (1H, s, NHCHO).

EXAMPLE 56

7α-Formamido 7β-[2-(thien-2-yl)acetamido]-3-[(2-methyl-1,3,4-thiadiazol-5-yl)thiomethyl]ceph-3-em-4-carboxylic acid, sodium salt (a) Diphenylmethyl 7α-formamido7β-[2-(thien-2-yl)acetamido]-3-[(2-methyl-1,3,4-thiadiazol-5-yl)thiomethyl]ceph-3-em-4-carboxylate 7α-Formamido7β-[2-(thien-2-yl)acetamido ]cephalosporanic acid (0.50 g, 1.14 mmol) in 1,2-dichloroethane (20 ml) with 2-methyl-1,3,4-thiadiazole-5-thiol (0.18 g, 1.36 mmol) was heated at 80° C. for 6 h and stood at room temperature 16 h. A solution of diphenyl diazomethane in dichloromethane (10 ml) (i.e. sufficient for complete reaction based on tlc) was added to the reaction mixture, which was stirred for 3 h, quenched with glacial acetic acid (0.5 ml) and evaporated to dryness. The residue was chromatographed (silica gel, 1:1 hexane/ethyl acetate) to give the title compound (0.042 g, 6%); δ(CDCl$_3$) 2.64 (3H, s, CH$_3$), 3.21, 3.38 (2H, ABq, J 16 Hz, 2-H), 3.78 (2H, s, CH$_2$CO), 4.28, 4.58 (2H, ABq, J 13.5 Hz, CH$_2$S), 5.15 (1H, s, 6-H), 6.83–7.02 (3H, m, Ph$_2$CH, thiophene-H's), 7.10–7.75 (12H, m, aromatic H's and NH), 7.86 (1H, s, NH), 8.06 (1H, s, CHO); $\nu_{max}$ (CH$_2$Cl$_2$) 1789, 1728, 1695 cm$^{-1}$.

(b) 7α-Formamido7β-[2-(thien-2-yl)acetamido]-3-[(2-methyl-1,3,4-thiadiazol-5-yl)thiomethyl]ceph-3-em-4-carboxylic acid, sodium salt Diphenylmethyl 7α-formamido7β-[2-(thien-2-yl)acetamido]-3-[(2-methyl-1,3,4-thiadiazol-5-yl)thiomethyl]-ceph-3-em-4-carboxylate (0.038 g, 0.06 mmol) in trifluoroacetic acid (4 ml) was stirred at room temperature for 0.5 h and evaporated to dryness. The residue was triturated with ether and filtered. The solid obtained was suspended in water which was then adjusted to pH 6.5 with sodium hydrogen carbonate solution. The solution obtained was washed with ethyl acetate, filtered and freeze dried to give the title compound (0.018 g, 63%); δ(D$_2$O) 2.72 (3H, s, CH$_3$), 3.24, 3.62 (2H, ABq, J 17.5 Hz, 2-H), 3.82–3.98 (3H, m, CH$_2$CO and 1H of CH₂S), 4.34–4.44 (1H, d, J 18 Hz, CH₂S), 5.23 (1H, s, 6-H), 6.9–7.4 (3H, m, thiophene - H's), 8.13 (1H, s, CHO); $\nu_{max}$(KBr) 1767, 1678, 1574 cm$^{-1}$.

MIC against P. Mirabilis 889 is 25 μg/ml.

EXAMPLE 57

7β-[2-(3,4-Diacetoxyphenyl)-2-[(4-ethyl-2,3-dioxopiperazin-l-yl)carbonylamino]acetamido]-7α-formamido-3-[(1-methyl-1H-tetrazol-5-yl)thiomethyl]ceph-3-em-4-carboxylic acid, sodium salt

(a) Diphenylmethyl 7β-[D,L-2-(3,4-diacetoxyphenyl)-2-[(4-ethyl-2,3-dioxopiperazin-1-yl)carbonylamino]acetamido]-7α-formamido3-[(1-methyl-1H-tetrazol-5-yl)thiomethyl]ceph-3-em-4-carboxylate A solution of D,L-2-(3,4-diacetoxyphenyl)-2-[(4-ethyl-2,3-dioxopiperazin-l-yl)carbonynlamino]acetic acid (0.31 g, 0.71 mmol) in dichloromethane (15 ml) was added slowly dropwise to a solution of diphenylmethyl 7β-amino-7α-formamido3-[(1-methyl-1H-tetrazol-5-yl)thiomethyl]ceph-3-em-4-carboxylate (0.47 g, 0.88 mmol) and N,N'-dicyclohexylcarbodiimide (0.16 g, 0.78 mmol) in dichloromethane (25 ml). The reaction mixture was stirred at room temperature for three days and evaporated. The residue was taken up in ethyl acetate, washed with N hydrochloric acid, saturated sodium hydrogen carbonate solution, brine, dried over magnesium sulphate and evaporated. Chromatography (silica gel; ethyl acetate) gave only partial separation of the two isomers. Isomer 1 (contaminated with 20% isomer 2) (0.06 g, 10%) possessed δ(CDCl₃) 1.19 (3H, t, J 7 Hz, CH₂CH₃), 2.22, 2.23 (6H, 2s, CH₃CO's), 2.78, 3.04 (2H, ABq, J 17.5 Hz, 2-H), 3.4–3.7 (4H, m, piperazine CH₂ and CH₂CH₃), 3.84 (3H, s, NCH₃), 3.8–4.1 (2H, m, piperazine CH₂), 4.26, 4.56 (2H, ABq, J 12.5 Hz, CH₂S), 5.18 (1H, s, 6-H), 5.65 (1H, d, J 7 Hz, ArCH), 6.88 (1H, s, Ar₂CH), 7.05-7.60 (13H, m, aromatic–H's), 8.02 (1H, s, NH), 8.10 (1H, s, CHO), 8.51 (1H, m, NH), 10.10 (1H, d, J 7 Hz, NH); $\nu_{max}$(CH₂Cl₂) 1779, 1718, 1692 cm$^{-1}$. Isomer 2 (contaminated with ca. 30% isomer 1) (0.12 g, 20%) possessed δ(CDCl₃) 1.21 (3H, t, J 7 Hz, CH₂CH₃), 2.26, 2.28 (6H, 2s, CH₃CO), 2.74, 3.14 (2H,ABq, J 17.5 Hz, 2-H), 3.4–3.7 (4H, m, piperazine CH₂ and CH₂CH₃), 3.86 (3H, s, NCH₃), 3.8–4.2 (3H, m, piperazine CH₂+1H of CH₂S), 4.77 (1H, d, J 12.5 Hz, CH₂S), 5.07 (1H, s, 6-H), 5.76 (1H, d, J 7 Hz, ArCH), 6.84 (1H, s, Ar₂CH), 7.1–7.6 (13H, m, aromatic protons), 7.94 (1H, s, NH), 8.02 (1H, s, CHO), 8.48 (1H, m, NH), 9.91 (1H, d, J 7 Hz, NH); $\nu_{max}$(CH₂Cl₂) 1779, 1718, 1692 cm$^{-1}$.

(b) 7β-[2-(3,4-Diacetoxyohenyl)-2-[(4-ethyl-2,3-dioxopiperazin-l-yl)carbonylamino]acetamido]-7α-formamido-3- [(1-methyl-1H-tetrazol-5-yl)thiomethyl]ceph -3-em-4-carboxylic acid, sodium salt, isomer 1

Diphenylmethyl 7β-[2-(3,4-diacetoxyphenyl)-2-[(4-ethyl-2,3-dioxopiperazin-1-yl)carbonylamino]acetamido]-7α-formamido3-[(1-methyl-1H-tetrazol-5-yl)thiomethyl]ceph-3-em-4-carboxylate, Isomer 1 (containing ca. 20% Isomer 2) (0.06 g, 0.07 mmol) in trifluoroacetic acid (5 ml) was stirred at room temperature for 0.5 h and evaporated to dryness. The residue was triturated with ether, taken up in water, which was adjusted to pH 6.5 with dilute sodium hydrogen carbonate solution, washed with ethyl acetate and freeze dried to give the title compound, isomer 1 (containing ca. 20% isomer 2) (0.04 g, 63%) δ(D₂O) 1.21 (3H, t, J 7 Hz, CH₂CH₃), 2.34, 2.36 (6H, 2s, CH₃CO), 3.00, 3.39 (2H, ABq, J 17.5 Hz, 2-H), 3.53 (2H, q, J 7 Hz, CH₂CH₃), 3.6–3.8 (2H, m, piperazine CH₂), 3.8–4.2 (3H, m, piperazine CH₂ +1H of CH₂S), 3.98 (3H, s, NCH₃), 4.24 (1H, d, J 13 Hz, 1H of CH₂S), 5.26 (1H, s, 6-H), 5.56 (1H, s, ArCH), 7.3–7.6 (3H, m, aromatic protons), 8.15 (1H, s, CHO); $\nu_{max}$(KBr) 3430, 1770, 1676, 1620 cm$^{-1}$.

(c) 7β-[2-(3,4-Diacetoxyphenyl)-2-[(4-ethyl-2,3-dioxopiperazin-1-yl)carbonylamino]acetamido]-7α-formamido3-[(1-methyl-1H-tetrazol-5-yl)thiomethyl]-ceph-3-em-4-carboxylic acid, sodium salt, isomer 2

Diphenylmethyl 7β-[2-(3,4-diacetoxyphenyl)-2-[(4-ethyl-2,3-dioxopiperazin-1-yl)carbonylamino]acetamido]-7α-formamido3-[(1-methyl-1H-tetrazol-5-yl)thiometh yl]-ceph-3-em-4-carboxylate, Isomer 2 (containing ca. 30% isomer 1) (0.12 g, 0.14 mmol) in trifluoroacetic acid (5 ml) was stirred at room temperature for 0.5 h and evaporated to dryness. The residue was triturated with ether and taken up in water which was adjusted to pH 6.5 with dilute sodium hydrogen carbonate solution. The solution was washed with ethyl acetate and freeze dried to give the title compound, isomer 2 (containing ca. 30% isomer 1); δ(D₂O) 1.21 (3H, t, J 7 Hz, CH₂CH₃), 2.47 (6H, m, CH₃CO), 3.12 (1H, d, J 17 Hz, 1H of 2-H), 3.45–3.64 (3H, m, 1H of 2-H and CH₂CH₃), 3.65–3.83 (2H, m, piperazine CH₂), 3.9–4.2 (6H, m, NCH₃, piperazine CH₂ and 1H of CH₂S), 4.36 (1H, d, J 3 Hz, 1H of CH₂S), 5.17 (1H, s, 6-H), 5.60 (1H, s, ArCH), 7.3–7.6 (3H, m, aromatic - H's), 8.13 (1H, m, CHO); $\nu_{max}$(KBr), 3440, 1770, 1680, 1630 cm$^{-1}$.

MIC against P. mirabilis 889 is 0.1 μg/ml.

EXAMPLE 58

6β-[L-2-[(4-ethyl-2,3-dioxopiperazin-1-yl)carbonylamino]2-(3,4 diacetoxisphenyl) acetamido]-6α-formamido penicillani acid, sodium salt

(a) DL-2-[(4-Ethyl-2,3-dioxopiperazin-1-yl)carbonylamino]-2-(3, 4-dihydroxyphenyl)acetic acid This was prepared on a 27.3 m molar scale in two steps from DL-3,4-dihydroxyphenylglycine in a manner identical to that described for the D-enantiomer (Example 18). The overall yield was 70% and the material exhibited identical spectroscopic and chromatographic properties to those shown by the D - enantiomer, except for its lack of optical rotation. (b) Benzyl 6β-[L-2-[(4-ethyl-2,3-dioxopiperazin-1-yl) carbonylamino]₋2-(3,4-diacetoxyphenyl) acetamido]-6α-formamido-penicillanate Benzyl 6β-amino6α-formamidopenicillanate was obtained by zinc-mediated reduction of its N-2,2,2trichloroethoxycarbonyl derivative on a 4m molar scale as previously described (Example 31). The material was not isolated as a solid, but its ethyl acetate solution was dried and concentrated to 10 ml, then dicyclohexylcarbodiimide (0.80 g, 3.91m mole) was added. The resulting yellow solution was cooled to 0° C. and stirred while a solution of DL-2- [(4-ethyl-2,3-dioxopiperazin-1-yl)carbonylamino]-2-(3, 4-diacetoxyphenyl acetic acid (1.70g, 3.91 m mole) in dry dichloromethane (15 ml) was added dropwise over about 0.5 h. The mixture was allowed to regain room temperature and stirring was continued for 2.5 h. After this time t.l.c. analysis showed negligible acid component, so the precipitated dicyclohexylurea was filtered off and the residue evaporated to dryness. The crude product was dissolved in a small volume of 5% methanol-chloroform and applied to a column of silica gel (350 g) equilibrated in the same solvent. Elution afforded firstly some coloured, low-polarity impurities, then the desired benzyl ester (0.91 g, 30%). Further elution afforded the D-benzyl ester previously described (0.97 g, 32%). The L-enantiomer showed $\nu_{max}$ (KBr)1780, 1745, 1710, and 1685 cm$^{-1}$, $\delta$(CDCl$_3$) 1.02 and 1.27(6H,2s, (CH$_3$)$_2$C), 1.20 (3H, t, J 7 Hz, CH$_3$ CH$_2$N), 2.26 and 2.28 (6H, 2s, 2×CH$_3$ CO), 3.35–3.65 (4H, m, 2 x CH$_2$N), 3.95–4.15 (2H, m, CH$_2$N), 4.38 (1H, s, 3-H), 5.16 (2H, Ph CH$_2$O), 5.55 (1H, s, 5-H), 5.64 (1H, d, J 7 Hz, Ar CH CO), 7.15–7.45 (8H, m, aryl-H), 7.59 (1H, s, D$_2$O exch, NH), 7.96 (2H, brs, 1H, s on D$_2$O exch, NHCHO), 9.99 (1H, d, D$_2$O exch, CHNH), R$_F$0.41 in 10% methanol-chloroform,[α]$_D$20+57.3 (c 0.4,CHCl$_3$).

(Found:C, 53.35, H, 5.1, N, 10.75. C$_{35}$H$_{38}$N$_6$O$_{12}$S, H$_2$O requires C, 53.6, H, 5.1, N, 10.7%).

(c) 6β[L-2-[(4-ethyl-2,3-dioxopiperazin-1-yl) carbonylamino]-2-(3, 4-dihydroxyphenyl) acetamido]-6α-formamidopenicillanic acid, sodium salt Benzyl 6β[L-2- [(4-ethyl-2, 3-dioxopiperazin-1-yl) carbonylamino]2-(3, 4-diacetoxyphenyl) acetamido]-6α-formamidopenicillanate (0.3 g, 0.39 m mole) was dissolved in tetrahydrofuran : water, 4 :1 (15 ml). 10% Palladium on charcoal (250 mg) was added and the mixture hydrogenated at room temperature and atmospheric pressure for 1h. After this time t.l.c. showed negligible starting material remaining, so the catalyst was filtered and well washed with water and tetrahydrofuran. The solution was concentrated to remove most organic solvent, then the residual aqueous solution (10 ml) was stirred for 1.5 h with thoroughly washed resin-bound subtilisin (6 g). After this time the enzyme was filtered off and washed, then the filtrate was twice washed with ethyl acetate. The aqueous phase was saturated with sodium chloride, acidified with 2M hydrochloric acid and extracted into 1:1 ethylacetate:tetrahydrofuran (2×20 ml). To the organic extracts, after drying over sodium sulphate, was added 1.89M sodium 2-ethylhexanoate (1 eq. based on the benzyl ester taken) followed by excess dry ether. The precipitated sodium salt was collected by filtration, washed with acetone, ether and dried to afford the sodium salt (0.15 g, 63%). T.l.c. and n.m.r. analysis showed that only partial deacetylation had occurred. Hence the intermediate product (0.060 g, 0.085 m mole) was dissolved in saturated sodium hydrogen carbonate solution (3 ml), the pH was adjusted to 9 and the solution left at ambient temperature for 0.5 h. After this time the solution was diluted with water and twice washed with ethylacetate, followed by saturation with sodium chloride, acidification to pH2 with 2M hydrochloric acid and extraction of the acid into tetrahydrofuran:ethylacetate 1:1 (2×25 ml). The combined organic extract was dried over sodium sulphate, evaporated to dryness and suspended in water. This aqueous suspension was basified to pH 6.5 with saturated sodium hydrogen carbonate solution, then evaporated to dryness. Trituration with ether followed by collection of the resulting solid gave the dihydroxypenicillin sodium salt (0.040 g, 75%) $\nu_{max}$(K Br) 1770, 1715, 1680, 1610 cm$^{-1}$, $\delta$(D$_2$O) 1.03 and 1.38 (6H, 2s, (CH$_3$)$_2$C), 1.16 (3H, t, J 7Hz, CH$_3$—CH$_2$N), 3.30–3.80 (4H, m, 2×CH$_2$N), 3.80–4.10 (2H, m, CH$_2$N), 4.19 (1H, s, 3-H), 5.30 (1H, s, 5-H), 5.40 (1H, s, ArCH-CO ), 6.93 (3H, br s, aryl-H), 8.16 (1H, s, NH CHO), R$_F$ 0.14 (n-butanol:acetic acid;water, 4:1 1).

MIC against P. Mirabilis 889 is 100 μg/ml.

EXAMPLE 59

6β-phenoxyacetamido6α-formamidopenam-3-carboxylic acid (a) Benzyl 6β-(4-nitrobenzylideneamino)penam-3-caboxylate Benzyl 6β-aminopenam-3-carboxylate (1.11 g, 4 m mol) in dry dichloromethane (4ml) with trimethylorthoformate (0.42 g, 0.44 ml, 4 m mol) was treated with 4-nitrobenzaldehyde (0.61 g, 0.4 m mol) in dry methanol (10 ml) at room temperature for 1.5 h. The mixture was then evaporated to dryness, triturated with ethanol and the solid material collected by filtration. Renystallisation from ethanol/ethylacetate gave almost colourless needles (1.2 g 74%); m.p. 95–96 C; $\nu_{max}$ (CH$_2$Cl$_2$) 1795, 1750, 1530, 1360 cm$^{-1}$; $\delta$(CDCl$_3$) 8.68 (1H, d, J 2Hz, CH=N), 8.27 and 7.94 (4H, 2d, J 9Hz, nitrophenyl), 7.38 (5H, s, phenyl), 5.51 (1H, d, J 4Hz, 5-H), 5.45 (1H, dd, J 2Hz and 4 Hz, 6-H), 5.23 (2H, s, CH$_2$Ph), 4.93 (1H, t, J 5.5Hz, 3-H) and 3.45 (2H, d, J 5.5H±, 2-H)

(b) Benzyl 6β-amino6α-(methylthio)penam-3-carboxylate

Benzyl 6β-(4-nitrobenzylideneamino) penam-3-carboxylate (1.05 g, 2.55 m mol) in dry ethylacetate (30 ml) was cooled to −10° C. and methyl methanethiolsulphonate (0.32 g, 0.26 ml, 2.55 m mol) followed by potassium hydroxide (0.16 g, 2.55 m mol) in ethanol (5 ml) were added. After the addition the mixture was stirred for 0.5 h, poured into water (25 ml) and the organic phase separated, washed with water (2×25 ml) brine (2×25 ml) then dried (Mg SO$_4$) and finally concentrated to ca 10 ml. This solution was treated with toluene-sulphonic acid monohydrate (0.48 g, 2.55 m mol) and stirred at room temperature for 3 h. The solution was then washed with dilute sodium hydrogen carbonate solution, brine, dried and evaporated to give an orange gum which was chromatographed on silica gel 60 ( 230 mesh ASTM) to give the title compound as a yellow gum (0.41 g, 49%); $\nu_{max}$ (CH$_2$Cl$_2$) 1795, 1750 cm$^{-1}$; $\delta$(CDCl$_3$) 7.45 (5H, s, phenyl), 5.27 (3H, s, 5-H and CH$_2$Ph), 5.15 (1H, m, 3-H), 3.45–3.25 (2H, m, 2-H$_2$), 2.31 (3H, s, SCH$_3$) and 2.18 (2H, rs, NH$_2$)

(c) Benzyl 6β-phenoxyacetamido-6α-(methylthio)penam-3-carboxylate

Benzyl 6β-amino6α- (methylthio) penam-3-carboxylate (0.11 g, 0.34 m mol) in dry dichloromethane (5 ml) at 0° C. was treated with pyridine (0.035 g, 0.036 ml, 1.3 eq.) and then with phenoxyacetyl chloride (0.058 g, 0.038 ml, 0.34 m mol). The mixture was allowed to warm to room temperature and stirred for 2 h, when it was washed with dilute hydrochloric acid (10 ml), dilute sodium hydrogen carbonate solution (10 m water (10 ml), brine (10 ml), dried (MgSO$_4$), and evaporated to give an orange gum. This crude material was chromatographed on silica gel 60 (<230 mesh ASTM) to give the title compound as a pale yellow foam (0.062 g, 54%); $\nu_{max}$ (CH$_2$Cl$_2$) 1800, 1755, 1700, 1500 cm$^{-1}$; $\delta$(CDCl$_3$) 7.41–6.92 (11H, m, aryl -H's and NH), 5.32 (1H, s, 5-H), 5.20 (2H, ABq, CH$_2$Ph), 5.08 (1H, dd, J 6 and 2 Hz, 3-H), 4.57 (2H, s, PhOCH$_2$), 3.42 (2H, m, 2-H$_2$) and 2.32 (3H, s, SCH$_3$).

(d) Benzyl 6β-phenoxyacetamido-6α-aminopenam-3-carboxylate

Benzyl 6β-phenoxyacetamido-6αmethylthio) penam-3-carboxylate (0.048g, 0.105 m mol) in dry dimethylformamide (1 ml) at −50° C. under nitrogen was treated with mercuric acetate (0.033 g, 0.105 m mol) in dimethylformamide (1 ml) followed by a saturated solution of ammonia in dimethylformamide (0.002 g in 0.1 ml). The mixture was stirred for 1h during which time the temperature was allowed to rise to −10° C. The mixture was then diluted with ethyl acetate (30 ml), washed with water (3×10 ml), brine (20 ml), dried (Mg SO$_4$), and evaporated to give the title compound as a semi-solid material (0.044 g, 98%); $\nu_{max}$. (CH$_2$Cl$_2$) 1795, 1750 1690 cm$^{-1}$;δ[CDCl$_3$+(CD$_3$)$_2$CO] 7.42–6.85 (11H, m, aryl–H's and NH), 5.18 (4H, m, 3-H, 5-H and CH$_2$Ph), 4.58 (2H, s, OCH$_2$), 3.33 (2H, m, 2-H$_2$) and 2.60 (2H, brs, NH$_2$).

(e) Benzyl 6β-phenoxyacetamido-6α-formamidopenam-3-carboxylate

Benzyl 6β-phenoxyacetamido-6α-aminopenam-3carboxylate (0.042 g, 0.103 m mol) in dry dichloromethane (5 ml) at 0° C. under nitrogen was treated with pyridine (0.08 g, 0.084ml 1.03 m mol) and then acetic formic anhychide (0.045 g, 0.52 m mol). The mixture gas allowed to warm to room temperature and stirred for 3 h. When it was washed with dilute hydrochloric acid, dilute sodium hydrogen carbonate, brine, dried (MgSO$_4$) and evaporated. The crude product was chromatographed on silica gel 60 (<230 mesh ASTM) to give the title compound as a colourless gum (0.01 g, 20%); $\nu_{max}$. (CH$_2$Cl$_2$) 1795, 1745, 1690 and 1260 cm$^{-1}$; δ(CDCl$_3$) 8.21 (1H, d, J 2Hz, NH CHO), 7.89 (1H, d, J 1Hz NH CHO), 7.45–6.86 (11H, M, aryl -H's and NH), 5.48 (1H, s, 5-H), 5.17 (2H, m, CH$_2$Ph), 5.04 (1H, d, J 7Hz, 3-H), 4.52 (2H, m, PhOCH$_2$), 3.27 (1H, d, J 11Hz, 2-H), and 2.84 (1H, dd, J 11 and 7Hz, 2-H).

The benzyl group is removed by hydrogenolysis under conventional conditions to give 6β-phenoxyacetamido6α-formamidopenam-3-carboxylic acid.

EXAMPLE 60
7αFormamido-3-(pyridiniummethyl)-7β-(thien-2-ylacetamido)-ceph-3-em-4-carboxylate Sodium 3-(acetoxymethyl)-7α-formamido7β-(thien-2yl acetamido)-ceph-3-em-4-carboxylate (0.300 g) was dissolved in water (approx. 2 ml), containing sodium iodide (0.975 g) and pyridine (approx. 0.5 ml). The pH of the mixture was adjusted to 6.5 with phosphoric acid. The mixture was heated at 65° C. for 3 h, then cooled and diluted with water (approx. 5 ml). The solution was chromatographed on Diaion HP20SS (approx. 25 ml), eluting initially with water, then acetone/water. The product containing fractions were lyophilized to give the product (0.045 g);λ$_{max}$ 236 nm (ε13,800); $\nu_{max}$. (KBr) 3390, 3240, 1775, 1675 and 1615 cm$^{-1}$; δ(D$_2$O) 3.05 3.56 (2H, ABq, J 17Hz, 2-H) , 3.91 (2H, s, CH$_2$CO), 5.29 and 5.45 (2H, ABq, J 12Hz, NCH$_2$), 5.36 (1H s, 6-H), 6.97–7.10 (2H, m, thienyl-H's), 7.30–7.42 (1H, m, thienyl -H), 8.00–8.16 (2H, m, pyridyl-H's), 8.17 (1H, s, CHO), 8.51–8.64 (1H, m, pyridyl-H) and 8.80–8.99, (2H, m, pyridyl-H's).

MIC against P. Mirabilis 889 is 50 μg/ml.

EXAMPLE 61
7β-[D-2- [(4-Ethyl-2,3-dioxopiperazin -1-yl) carbonylamino]-2-phenyl-acetamido]-7α-formamido3-methyl-1-oxadethia-ceph-3-em-4-carboxylic acid.

(a) t-Butyl 7β-(4-nitrobenzylideneamino)-3-methyl-1-oxa dethia-ceph-3-em-4-carboxylate A solution of t-butyl 7β-amino3-methyl-1-oxa-dethia-ceph-3-em-4-carboxylate (C. L. Branch and M. J. Pearson; *J. Chem. Soc. Perkin Trans* 1. 1979; 2268) (186 mg; 0.73 m mol) and 4-nitrobenzaldehyde (110 mg; 0.73 m mol) in an anhydrous mixture of toluene (25 ml) and ethyl acetate (5 ml) was stirred for 6 h at room temperature over 4A molecular sieves. The reaction mixture was then filtered and the filtrate evaporated to dryness. The residue was redissolved in dry toluene and the solution evaporated; this was repeated. Trituration of the residue with ether gave the title compound as a white solid (227 mg; 80%); $\nu_{max}$. (CHCl$_3$) 1780, 1715, 1640, 1525, 1350 cm$^{-1}$; δ(CDCl$_3$) 1.56 (9H, s), 2.01 (3H, s), 4.36 (1H, s), 5.31 (2H, s), 7.98 (2H, d, J 8Hz), 8.29 (2H, d, J 8Hz), 8.78 (1H, s).

(b) t-butyl 7β-(4-nitrobenzylid eneamino) -7α-methylthio 3-methyl-1-oxadethia-ceph-3-em-4-carboxylate t-Butyl 7β-(4-nitrobenzylideneamino)-3-methyl-1-oxadethia-ceph-3-em-4-carboxylate (257 mg; 0.66 m mol) was dissolved in anhydrous methylene dichloride (5 ml) containing methyl methanethiol sulphonate (92 mg; 0.73 m mol) and cooled to 0° C. under argon. To the vigorously stirred solution was added dropwise 1,8-diazabicyclo [5.4.0]undec7-ene (100 mg; 0.66 m mol) in methylene dichloride (2 ml). After 1 h at 0°–5° C., the solution was diluted with methylene dichloride and washed successively with saturated aqueous ammonium chloride (×2), brine, dried (MgSO$_4$), and evaporated. Chromatography of the residue on silica gel afforded the title compound as a pale yellow solid (242 mg; 84%); $\nu_{max}$. (Nujol) 1740, 1620 cm$^{-1}$; δ(CDCl$_3$) 1.57 (9H, s), 1.99 (3H, s), 2.30 (3H, s), 4.33 (2H, s), 5.14 (1H, s), 8.02 (2H, d, J 8Hz), 8.29 (2H, d, J 8Hz), 8.87 (1H, s).

(c) t-Butyl 7β-amino7α-methylthio3-methyl-1-oxadethia-ceph-3-em-4-carboxylate, toluene-β-sulphonic acid salt t-Butyl 7β-(4-nitrobenzylideneamino)-7α-methylthio-3-methyl-1-oxadethia-ceph-3-em-4-carboxylate (238 mg; 0.54 m mol) was dissolved in a mixture of ethyl acetate (8 ml) and methylene dichloride (4 ml) and a solution of toluene-p-sulphonic acid monohydrate (105 mg; 0.55 m mol) in a little ethyl acetate added. Precipitation occurred almost immediately and after stirring at room temperature for 2 h, the product was filtered off, washed well with ethyl acetate, ether, and dried in vacuo to afford the title product as a white solid (193 mg; 75%);$\nu_{max}$. (Nujol) 3150, 1780, 1715, 1705, 1640 cm$^{-1}$; δ[(CD$_3$)$_2$SO]1.47 (9H, s), 1.94 (3H, s), 2.30 (3H, s), 2.39 (3H, s), 4.49 (2H, AA'), 5.35 (1H, s), 7.10 (2H, d, J 9Hz), 7.47 (2H, d, J 9Hz), 8.0–9.7 (3H, br, exch.).

(d) t-Butyl 7β-[D-2- [(4-ethyl-2, 3-dioxopiperazin-1-yl) carbonylamino-2-phenylacetamido 7α-methylthio-3-methyl-1-oxadethia-ceph-3-em-4-carboxylate D-2- [(4-Ethyl-2-, 3-dioxopiperazin-1-yl) carbonylamino]-2-phenylacetic acid (200 mg; 0.63 m mol) in anhydrous methylene chloride (5 ml) containing a catalytic amount of dimethylformamide, was treated with oxalyl chloride (174mg; 1.34 m mol). After stirring at room temperature for 1.5 h the solution was evaporated to dryness, treated with toluene and re-evaporated. The resulting acid chloride was taken up in dry methylene chloride (5 ml) and added dropwise with stirring to a mixture of t-butyl 7β-amino7α-methylthio3-methyl-1-oxadethia-ceph-3-em-4-carboxylate, toluene-p-sulphonic acid salt (193 mg; 0.41 m mol), and pyridine (84 mg; 0.94 m mol) in methylene dichloride (5 ml) at 0° C. After stirring at 0°-5° C. for 0.5 h and 1h at 5° C.-room temperature, the reaction mixture was washed with dilute hydrochloric acid, saturated aqueous sodium hydrogencarbonate, brine, dried (MgSO4), and evaporated. Chromatography of the residue on silica gel gave the title compound as an amorphous solid (169 mg; 67%); $\nu_{max}$. (CHCl3) 3400, 3275, 1785, 1720 sh, 1710, 1690, 1640 sh cm$^{-1}$; δ(CDCl3) 1.20 (3H, t, J 8Hz), 1.51 (9H, s), 1.93 (3H, s), 2.28 (3H,s), 3.4–3.7 (4H, m), 3.9–4.3 (2H, m) overlapping 4.03 and 4.19 (2H, ABq, J 17Hz), 4.93 (1H, s), 5.55 (1H, d, J 6Hz), 6.52 (1H, s), 7.3–7.5 (5H, m), 9.89 (1H, d, J 6Hz).

(e) t-Butyl 7α-Amino7β-[D-2- [(4-ethyl-2-, 3-dioxooiperazin-1-yl carbonylamino]-2-phenylacetamido]3-methyl-1-oxadethia-ceph-3-em-4-carboxylate To a vigorously stirred solution of t-Butyl 7β-[D-2-[(4-ethyl-2, 3-dioxopiperazin-1-yl) carbonylamino]-2-phenylaoetamido]-7α-methylthio3-methyl-1-oxadethia-ceph-3-em-4-car boxylate (30 mg; 0.05 m mol) in dioxan (2 ml) at room temperature was added peracetic acid (75 ml of 5.07% solution in acetic acid; 0.05 m mol). After 15 min. the solution was evaporated to dryness. The residue was taken up in dry toluene and the solution evaporated; this was repeated twice. Chromatography of the residue on silica gel gave t-Butyl 7β-[D-2-[(4-ethyl-2, 3-dioxopiperazin-1-yl) carbonylamino]-2-phenylacetamido]-7α-methylsulphinyl-3-methyl-1-oxadethia-ceph-3-em-4-carboxylate as a white solid (29 mg; 94%), which was dissolved in anhydrous tetrahydrofura (2 ml) and ammonia (2.3 ml; 0.10 m mol) added. The reaction mixture was left overnight at room temperature, evaporated and the residue chromatographed on silica gel to afford an inseparable mixture of the title compound; $\nu_{max}$ (CHCl3) 3400, 3275, 1780, 1715, 1690, 1640 sh cm$^{-1}$; δ(CDCl3) inter alia 1.22 (3H, t, J 6Hz), 1.52 (9H, s), 1.94 (3H, s), 2.5–2.9 (2H, br s, exch.) 3.4–3.7 (4H, m), 3.9–4.2 (2H, m), 4.02 and 4.22 (2H, ABq, J 18Hz), 4.87 (1H, s), 5.42 (1H, d, J 6.5 Hz), 6.57 (1H, s exch.), 7.3–7.5 (5H, s), 9.92 (1H, d, J 6.5Hz); and t-butyl 7β-amino7α-[D-2-[(4-ethyl -2, 3-dioxopiperazin-1-yl) carbonylamino]-2-phenylacetamido]3-methyl-1-oxadethia-ceph-3-em-4-carboxylate (20 mg; 75%); δ(CDCl3) inter alia 1.22 (3H, t, J 6Hz), 1.52 (9H, s), 1.95 (3H, s), 2.5–2.9 (2H, br s, exch.); 3.4–3.7 (4H, m), 3.9–4.2 (2H, m), 4.40 (2H, s), 5.03 (1H, s), 5.42 (1H, d, J 6.5 Hz), 6.59 (1H, s, exch.), 7.3–7.5 (5H, s), 9.92 (1H, d, 6.5 Hz).

(f) Alternative route to t-Butyl 7α-amino -7β-[D-2-[(4-ethyl-2, 3-dioxopiperazin-1-yl) carbonylamino]-2-phenylacetamido]-3-methyl-1-oxadethia-ceph-3-em-4-carboxylate t-Butyl 7β-[D-2- [(4-ethyl-2, 3-dioxopiperazin-1-yl) carbonylamino]-2-phenylacetamido]-7-α-methylthio3-methyl-1-oxadethia-ceph-3-em-4-carboxylate (30 mg; 0.05 m mol) in dry dimethylformamide (0.5 ml) at −50° C. under argon, was treated with mercuric acetate (16 mg; 0.05 m mol) in dimethylformamide (0.1 ml) followed immediately by ammonia (17 mg; 0.08 m mol) in dimethylformamide (0.1 ml). The reaction mixture was stirred at −50° to −20° C. for 1h, before being poured into ethyl acetate and washed well with water and brine. The organic solution was dried over magnesium sulphate, evaporated, and the residue chromatographed on silica gel to afford the title product and t-butyl 7β-amino7α-[D-2-[(4-ethyl-2, 3-dioxopiperazin-1-yl) carbonylamino]-2-phenylacetamido]-3-methyl-1-oxadethiaceph-3-em-4-carboxylate as an inseparable mixture (18 mg; 63%).

(g) t-Butyl 7β- [-D-2- [(4-ethyl-2, 3-dioxopiperazin-1-yl) carbonylamino]-2-phenylacetamido]-7α-formamido-3-methyl-1-oxadethia-ceph-3-em-4-carboxylate A solution of the mixed C-7 isomers of t-Butyl 7-amino7-[D-2- [(4-ethyl-2, 3-dioxopiperazin-1-yl) carbonylamino]-2-phenylacetamido]-3-methyl-1-oxadethia-ceph-3-em-4-carboxy late (80 mg; 0.14 m mol) and pyridine (109 mg; 1.4 m mol) in methylene dichloride (3 ml) was cooled to 0° C. and treated with acetic formic anhydride (62 mg; 0.7 m mol). The reaction was stirred at 0°-5° C. for 0.5h and for 1h at room temperature before being diluted with dry toluene and evaporated. The residue was redissolved in dry toluene and the solution evaporated; this was repeated twice. Chromatography of the residue on silica gel gave the title product as an amorphous solid (45 mg; 54%); $\lambda_{max}$.(EtOH) 257 n m (ε12211),$\nu_{max}$. (CHCl3) 3400, 3275, 1790, 1715, 1690, 1640 sh cm$^{-1}$; δ(CDCl3) 1.20 (3H, t, J 7Hz), 1.50 (9H, s), 1.92 (3H, s), 3.4–3.7 (4H, m), 3.9–4.3 (2H, m) overlaps 4.08 and 4.23 (2H, ABq, J 17Hz), 5.14 (1H, s), 5.49 (1H, d, J 6Hz), 7.2–7.5 (6H, m), 7.57 (1H, s, exch.), 8.15 and 8.49 (s and d, J 13 Hz, together 1H, collapses to 2 s at 8.15 and 8.49 on exch.), 9.90 (1H, d, J 6Hz). Also isolated the reaction mixture was t-butyl 7α-[D-2-[(4-ethyl-2, 3-dioxopiperazin-1-yl) carbonylamino]-2-phenylacetamido]-7β-formamido3-methyl-1-oxadethia-ceph-3-em-4-carboxylate (6 mg; 7%); $\nu_{max}$. (CHCl3) 3400, 3275, 1790, 1715, 1690, 1640 sh cm$^{-1}$; δ(CDCl3) inter alia 1.20 (3H, t, J 7Hz), 1.50 (9H, s), 1.94 (3H, s), 3.4–3.8 (4H, m), 3.9–4.2 (2H, m), 4.31 (2H, s), 5.08 (1H, s), 5.5 (1H, d, J 6Hz), 7.2–7.5 (6H, m), 7.88 (1H, exch.), 8.05 and 8.27 (s and d, J 13Hz, together 1H; collapses to 2s, at 8.05 and 8.27 on exch.), 9.92 (1H, d, J 6Hz).

(h) 7β[-D-2-[(4-Ethyl-2, 3-dioxopiperazin-1-yl)carbonylamino]-2-phenylacetamido]-7α-formamido3-methyl-1-oxadethia-ceph-3-em-4-carboxylic acid t-Butyl 7β-[D-2-[(4-Ethyl-2, 3-dioxopiperazin-1-yl) carbonylamino]-2-phenylacetamido]-7α-formamido3-methyl-1-oxadethia-ceph-3-em-4-carboxylate was briefly treated with trifluoroacetic acid to afford the title compound as an off-white solid;

$\nu_{max}$. (KBr) 3400–3300 br, 1785, 1710, 1680 cm$^{-1}$.

EXAMPLE 62

7α-Formamido7β-[DL-2-phenoxycarbonyl-2-(thien-3-yl)acetamido]-3-methyl-1-oxadethia-ceph-3-em-4-carboxylic acid

(a) t-Butyl 7αmethylthio7β-trichloroethoxycarbonylamino-3-methyl-1-oxadethia-ceph-3-em-4-carboxylate Trichloroethylchloroformate (64mg; 0.3 mmol) in anhydrous methylene dichloride (1 ml) was added dropwise to a well stirred mixture of t-butyl 7β-amino7αmethylthio-3-methyl-1-oxadethia-ceph-3-em-4-carboxylate, toluene-p-sulphonic acid salt (129 mg; 0.27 mmol) and pyridine (56 mg; 0.7 mmol) in anhydrous methylene dichloride (5 ml) at 0° C. After 0.25 h the reaction mixture was washed with dilute hydrochloric acid, dilute aqueous sodium hydrogen carbonate, brine, dried (MgSO$_4$), and evaporated. Chromatography of the residue on silica gel afforded the title product (112 mg; 93%); $v_{max}$ 3400, 1790, 1745, 1730, 1640 cm$^{-1}$; δ (CDCl$_3$) 1.55 (9H,s), 1.99 (3H,s), 2.40 (3H,s), 4.29 (2H,s), 4.73 and 4.80 (2H, ABq, J 11Hz), 4.93 (1H,s), 5.7 (1H, br s, exch.).

(b) t-Butyl 7αamino7β-trichloroethoxycarbonylamino-3-methyl-1-oxadethia-ceph-3-em-4-carboxylate t-Butyl 7α-methylthio7β-trichloroethoxycarbonylamino-3-methyl-1-oxadethia-ceph-3-em-4-carboxylate (100 mg; 0.225 mmol) in dry dimethylformamide (2 ml) at −50° C. under argon was treated with mercuric acetate (72 mg; 0.225 mmol) in dimethylformamide (0.4 ml) followed immediately by ammonia (6.5 mg; 0.38 mmol) in dry dimethylformamide (0.3 ml). After stirring at −50° C. for 0.75 h, the reaction mixture was poured into ethyl acetate and washed well with water and brine. The organic solution was dried over magnesium sulphate, evaporated and the residue chromatographed on silica gel to afford the title product (74 mg; 79%); $v_{max}$ (CHCl$_3$) 3400, 1790, 1735, 1715, 1640 cm$^{-1}$; δ(CDCl$_3$) 1.55 (9H,s), 1.99 (3H,s), 2.2–2.9 (2H, br s, exch.), 4.33 (2H,s), 4.77 (2H, s), 4.89 (1H,s), 6.01 (1H, br s, exch.).

Also isolated from the reaction mixture was t-butyl 7β-amino-7α-trichloroethoxycarbonylamino-3-methyl-1-oxadethia-ceph-3-em-4-carboxylate (6 mg; 6%); $v_{max}$ (CHCl$_3$) 3400, 1790, 1740, 1718, 1640 cm$^{-1}$; δ (CDCl$_3$) inter alia 1.52 (9H,s), 1.96 (3H,s), 1.9–2.6(2H,s, exch.), 4.37 (2H,s), 4.77 (2H,s), 5.13 (1H,s), 5.94 (1H,s, exch.).

(c) t-Butyl 7α-formamido7β-trichloroethoxycarbonylamino-3-methyl-1-oxadethia-ceph-3-em-4-carboxylate t-Butyl 7α-amino7β-trichloroethoxycarbonylamino3-methyl-1-oxadethia-ceph-3-em-4-carboxylate (60 mg; 0.145 mmol) was dissolved in dry methylene dichloride (2 ml) containing pyridine (115 mg; 1.45 mmol), cooled to 0° C. under argon and treated with acetic formic anhydride (64 mg; 0.725 mmol). The reaction was stirred at 0° to 10° C. for 1 h., diluted with dry toluene and evaporated to dryness. The residue was redissolved in dry toluene and the solution evaporated; this was repeated twice. Chromatography of the residue on silica gel afforded the title product (63 mg; 100%); $v_{max}$(CHCl$_3$) 3400, 1795, 1740, 1700, 1690 sh cm$^{-1}$; δ(CDCl$_3$) 1.54 (9H,s), 2.01 and 2.03 (together 3H), 4.36 and 4.41 (together 2H), 4.74 and 4.78 (together 2H), 5.06 and 5.28 (together 1H), 6.21 and 6.45 (1H, exch.), 8.29 (d, J 1Hz) and 8.61 (d, J 11.6Hz) (together 1H).

(d) t-Butyl 7β-amino-7α-formamido-3-methyl-1-oxadethia-ceph-3-em-4-carboxylate t-Butyl 7α-formamido-7β-trichloroethoxycarbonylamino-3-methyl-1-oxadethia-ceph-3-em-4-carboxylate (33 mg; 0.075 mmol) was dissolved in tetrahydrofuran (2 ml) and potassium dihydrogen phosphate (1M; 0.4 ml) and vigorously stirred with activated zinc (60 mg; 0.92 mmol) at room temperature for 3 h. The mixture was diluted with ethyl acetate, filtered through Kielselguhr, and the organic phase separated, washed with brine, dried (MgSO$_4$), and evaporated. Chromatography of the residue on silica gel gave the title compound (14 mg; 70%), which showed a 3:1 ratio of the two preferred conformations of the formamido group; $\lambda_{max}$(EtOH) 272 nm ($\epsilon$6916); $v_{max}$(CHCl$_3$) 3400, 3275, 1780, 1700, 1640 sh cm$^{-1}$; δ(CDCl$_3$) trans 1.56 (9H,s), 1.98 (3H,s), 1.9–2.5 (2H,s, exch.) 4.35 (2H,s), 5.14 (1H,s), 6.29 (1H, broad s, exch.), 8.24 (1H,d,J 1.1Hz); cis 1.54 (9H,s), 1.9–2.5 (2H,s,exch.), 2.02(3H,s) 4.35 (2H,s), 4.87 (1H,s), 6.05 (1H,d,J 11.6 Hz exch.), 8.42 (1H,d,J 11.6 Hz).

(e) t-Butyl 7α-formamido-7β-[DL-2-phenoxycarbonyl-2-(thien-3-yl)acetamido]-3-methyl-1-oxadethia-ceph-3-em-4-carboxylate DL-2-Phenoxycarbonyl-2-(thien-3-yl)acetic acid (27 mg; 0.11 mmol) in anhydrous methylene dichloride (1 ml) containing a catalytic amount of dimethylformamide, was treated with oxalyl chloride (21 mg; 0.16 mmol). After stirring at room temperature for 1.5 h., the solution was evaporated to dryness, treated with methylene dichloride and re-evaporated. The process was repeated twice. The resulting acid chloride was taken up in dry methylene dichloride (0.5 ml) and added dropwise with stirring to a mixture of t-butyl 7β-amino7α-formamido-3-methyl-1-oxadethia-ceph-3-em-4-carboxylate (20 mg; 0.075 mmol) and pyridine (9 mg; 0.11 mmol) in methylene dichloride (2 ml) at −10° C. After 15 min. the reaction mixture was diluted with ethyl acetate, washed successively with dilute hydrochloric acid, dilute aqueous sodium hydrogencarbonate, brine, dried (MgSO$_4$), and evaporated. Chromatography of the residue on silica gel gave the title compound (23 mg, 57%); $\lambda_{max}$(EtOH) 263 nm ($\epsilon$13545), 314 nm ($\epsilon$5545); $v_{max}$(CHCl$_3$) 3400, 1790, 1740, 1720 sh., 1690 cm$^{-1}$; δ (CDCl$_3$) 1.52 (9H,s), 1.97 and 2.00 (together 3H,s), 4.15–4.40 (2H,m), 4.91 and 4.95 (together 1H,s), 5.21 and 5.23 (together 1H,s), 7.0–7.5 (10H,m), 7.80(∼0.5H,s), 8.16, 8.19 and 8.52 (together 1H), 8.22 (∼0.5H,s).

The t-butyl protecting group is removed under conventional conditions to afford 7α-formamido-7β-[DL-2-phenoxycarbonyl-2-(thien-3-yl)acetamido]-3-methyl-1-oxadethia-ceph-3-em-4carboxylic acid.

EXAMPLE 63

6α-Formamido6β-(R-2-phenyl-2-sulphoacetamido) penicillanate, disodium salt

(i) Benzyl 6α-amino-6β-(R-2-phenyl-2-sulphoacetamido) penicillanate, triethylammonium salt Benzyl 6α-methylthio-6α-(R-2-phenyl-2-sulphoacetamido) penicillanate, triethylammonium salt (3.25 g) in dimethylformamide (1.60 g) followed after 1 minute by a solution of ammonium acetate (0.77 g) and triethylamine (1.05 ml) in DMF (10 ml). After 10 minutes chloroform (250 ml) and 0.5M aqueous triethylammonium sulphide (15 ml, pH7.3) were added, the mixture filtered, the aqueous layer discarded and the chloroform solution dried over anhydrous magnesium sulphate then evaporated to an oil in vacuo. The oil was triturated with ether (2×100 ml) then acetone (20 ml) added and set aside to crystallise. The crystals (1.67 g) were collected, washed with acetone, then ether and dried in vacuo; $\nu_{max}$(KBr) 1780, 1740, 1670, 1535, 1325, 1245, 1205, 1175 and 1040 cm$^{-1}$; δ[(CD$_3$)$_2$SO]1.15 (9H,t,J 7Hz, HN(CH$_2$CH$_3$)$_3$) 1.27, 1.40 (6H, 2s, 2-(CH$_3$)$_2$), 3.06 (6H,q,J 7Hz, HN(CH$_2$CH$_3$)$_3$), 3.23 (2H, brs, NH$_2$), 4.45(1H,s,3-H), 4.51(1H,s,CHCONH), 5.18 (2H,s,OCH$_2$Ph), 5.21(1H,s,5-H), 7.1–7.5 (10H,m,phenyls), 9.27 (1H,s,CONH).

(ii) Benzyl 6α-formamido-6β-(R-2-phenyl-2-sulphoacetamido) penicillanate, triethylammonium salt Benzyl 6α-amino6β-(R-2-phenyl-2-sulphoacetamido) penicillanate, triethylammonium salt (0.62 g) in dichloromethane (5 ml) was treated with acetic formic anhydride (0.2 ml) followed by pyridine (1 ml). After 5 minutes at room temperature the solution was poured into ether (100 ml) and the precipitated solid collected, washed with ether and dried in vacuo to give the title compound (0.49 g, 75.6%); $\nu_{max}$(KBr)1785, 1742, 1675, 1320, 1245, 1205, 1180, and 1040 cm$^{-1}$; δ[(CD$_3$)$_2$CO]1.20 (9H,t,J 7Hz, N$^+$H(CH$_2$ CH$_3$)$_3$), 1.30, 1.48 (6H, 2s, 2-(CH$_3$)$_2$), 3.08 (6H, q, J 7Hz, N$^+$H(CH$_2$CH$_3$)$_3$), 4.49 (1H,s,3-H), 4.98 (1H,s,CHCONH), 5.21 (2H,s,OCH$_2$Ph), 5.68 (1H,s,5-H), 7.2–7.8(10H,m,phenyls), 8.04 (1H,s,CONH), 8.17(1H,s,NHCHO), 8.4–9.2 (1H,brs,N$^+$H), 9.38 (1H,s,CONH).

(iii) 6α-Formamido-6β-(R-2-phenyl-2-sulphoacetamido) penicillanate, disodium salt Benzyl 6α-formamido-6β-(R-2-phenyl-2-sulphoacetamido) penicillanate triethylammonium salt (0.30 g) in water (10 ml) containing N sodium hydrogen carbonate (0.93 ml) was hydrogenated in the presence of 10% palladium on carbon catalyst (0.3 g) for 0.5 h. The catalyst was filtered off and the filtrate passed through an Amberlite IR120 (Na) column, then freeze dried (0.22 g, 94%); $\nu_{max}$(KBr) 1772, 1675, 1610, 1210 and 1042 cm$^{-1}$; δ (D$_2$O) 1.09, 1.28 (6H,2s,2-(CH$_3$)$_3$), 4.15 (1H,s,3-H), 5.05 (1H,s,CHCONH), 5.56 (1H,s,5-H), 7.3–7.7 (5H,m,Ph), 8.10(1H,s,NHCHO).

EXAMPLE 64

6β-[D-2-Amino-2-(3,4-diacetoxyphenyl) acetamido]-6α-formamido penicillanic acid

(i) DL-2-(4-Nitrobenzyloxycarbonylamino)-2-(3,4-dihydroxy phenyl) acetic acid DL-3,4-Dihydroxyphenylglycine (2.0 g, 10.9 m mole) was heated to 60° C. under nitrogen in N, N-diethyl-1,1,1-trimethylsilylamine (8 ml). A complete solution was obtained in 0.5 h. Excess reagent was removed by evaporation (oil pump, <1 mm Hg) and the residue dissolved in dry tetrahydrofuran (20 ml). The solution was cooled to 0° C. and stirred while a solution of 4-nitrobenzyl chloroformate (2.58 g, 1.1 equivalents) in tetrahydrofuran (5 ml) was added. The resulting mixture was allowed to warm to room temperature while stirring was continued for 1 h. It was then poured into water and stirred for 0.5 h, followed by saturation with sodium chloride and extraction with ethyl acetate:tetrahydrofuran, 1:1 (2×50 ml). The combihed extracts were dried over sodium sulphate and evaporated to give crude product. For purification this was partitioned between sodium hydrogen carbonate solution and ethyl acetate (3×30 ml), discarding the organic washings. The aqueous phase was acidified to pH2 with 2M hydrochloric acid and extracted with ethyl acetate (2×50 ml). The combined organic extract was washed with a small volume of water, then brine, and dried over sodium sulphate. Evaporation followed by standing the residue under petroleum ether (60°–80°) containing a little diethyl ether afforded the title protected acid as a gum which gradually solidified: it was filtered, washed with petroleum ether (60°–80°) and dried to give the product (2.12 g, 54%); m.p. 154°–7° C; δ[(C$_3$)$_2$CO] 5.17 (1H,d,J 7Hz,s on D$_2$O exchange, NCHCO), 5.22 (2H,s,ArCH$_2$O), 6.75–7.05 (4H,m,3H on D$_2$O exch., aryl-H$_3$ +NH), 7.60 and 8.20 (4H, 2d, aryl H), 7.0–9.0 (3H, brs, D$_2$O exchanged, 3×OH); Rf 0.80 in n-butanol: acetic acid: water, 4:1:1.

(ii) DL-2-(4-Nitrobenzyloxycarbonylamino)-2-(3,4-diacetoxyphenyl)acetic acid DL-2-(4-Nitrobenzyloxycarbonylamino)-2-(3,4-dihydroxyphenyl) acetic acid (1.81 g, 5 m mole) was dissolved in dry tetrahydrofuran (19 ml). The solution was cooled to 0° C. and stirred while dry pyridine (1.30 ml, 3 equivalents) and acetic anhydride (1.18 ml, 2.5 equivalents) were added. The solution was allowed to regain room temperature and stirred for 3 h, further acetic anhydride (0.5 ml) being added after 1 h. The tetrahydrofuran was then removed by evaporation, the residue was partitioned between ethyl acetate and water and the pH raised to 7.5. The aqueous phase was separated and again washed with ethyl acetate, the organic phases being discarded, then acidified to pH2 with 2M hydrochloric acid and extracted with ethyl acetate (2×). The total organic extract was washed with water and brine, then dried over sodium sulphate and evaporated to give crude product. Reprecipitation was effected by adding dropwise a solution of the crude material in dichloromethane to an excess of petrol, with vigorous stirring, to give the title acid as an amorphous powder which was filtered, washed with petrol and dried; it retained solvents tenaciously (1.46 g, 65%); δ (CDCl$_3$) 8.24 and 8.26 (6H,2s,2×CH$_3$CO), 5.15(2H,s,ArCH$_2$O), 5.22

(1H,d,J 7 Hz, NCHCO) 7.0–7.6 (7H,m,5H on D$_2$O exch, aryl-H+NH+OH), 8.13(2H,d,J 9 Hz, aryl-H); R$_F$0.50 in chloroform:methanol:acetic acid, 17:2:1.

(iii) Benzyl 6β-[DL-2-(4-nitrobenzyloxycarbonylamino)-2-(3,4-diacetoxyphenyl)acetamido]-6α-formamidopenicillanate Benzyl 6β-(2,2,2-trichloroethoxycarbonylamino)-6α-formamidopenicillanate (1.51 g, 3 m mole) was subjected to zinc-mediated reduction as described previously (Example 31). The final ethyl acetate extract of benzyl 6β-amino6α-formamidopenicillanate was concentrated to 10 ml and stirred at 0° C. with dicyclohexylcarbodi-imide (0.62 g, 1 equivalent). To this solution was added dropwise over 0.4 h a solution of DL-2-(4-nitrobenzyloxycarbonylamino)-2-(3,4-diacetoxyphenyl) acetic acid (1.34 g, 1 equivalent) in dry dichloromethane (10 ml) The mixture was allowed to regain room temperature and stirring was continued for 3 h. After this time the precipitated dicyclohexylurea was filtered off and washed with ethyl acetate. The filtrate was washed sequentially with water, 0.5M hydrochloric acid (2×), water, saturated sodium hydrogen carbonate (2×), water and brine. Drying over sodium sulphate and evaporation gave the crude product (2.27 g) as a mixture of diastereoisomers. Chromatography on silica gel (230 g), eluting with 2.5% methanol in chloroform, afforded firstly some impurities of low polarity, then the L-isomer (0.62 g, R$_F$ 0.46 in 10% methanol-chloroform), then the desired title ester (0.58 g); $v_{max}$(CHCl$_3$) 1780, 1750, 1690 and 1610 cm$^{-1}$; δ (CDCl$_3$) (D-isomer) 0.95 and 1.20(6H,2s,(CH$_3$)$_2$C), 2.15 and 2.22 (6H,2s, OCOCH$_3$'s), 4.35 (1H,s,3-H), 5.10 (4H,brs, 2 x ArCH$_2$O), 5.30–5.65 (2H,m, NCHCO and 5-H), 6.50 (1H, brs, D$_2$O exch, NH), 6.95–7.50 (11H,m, 10 aryl-H+NH), 8.10 (3H m, aryl-H$_2$ and CHO), 8.75 (1H, brs,D$_2$O exch, NH); R$_F$0.53 in 10% MeOH—CHCl$_3$;

(iv) 6β-[D-2-Amino2-(3,4-diacetoxyphenyl)acetamido]-6α-formamidopenicillanic acid Benzyl 6β-[D-2-(4-nitrobenzyloxycarbonylamino)-2-(3,4-diacetoxyphenyl)acetamido]-6α-formamidopenicillanate (0.55 g, 0.7 m mole) was dissolved in tetrahydrofuran:water, 4:1(20 ml). 10% Palladium on charcoal (0.55 g) was added and the mixture was hydrogenated at S T P for 3 h. After this time t.l.c. showed no significant starting material and clean conversion to a single more polar product. The catalyst was filtered off and washed well with tetrahydrofuran and water, then the filtrate was washed twice with ethyl acetate, backwashing each time with a little water. The total aqueous phase was again filtered, then evaporated in the cold to give the title zwitterionic penicillin as a pale yellow flaky solid (0.33 g, 92%); $v_{max}$(KBr) 1770 br, 1685, 1600 and 1505cm$^{-1}$; δ [D$_2$O: (CD$_3$)$_2$SO,1:1]0.73 and 1.14 (6H,2s,(CH$_3$)$_2$C), 2.17 (6H,s,OCOCH$_3$'s), 3.88 (1H,s,3-H), 4.93 (1H,s,NCHCO), 5.39 (1H,s,5-H), 7.15–7.50 (3H,m,aryl-H$_3$), 7.96 (1H,s,CHO); R$_F$0.15 in n-butanol:acetic acid: water, 4:1:1.

MIC against P.mirabilis 889 is 100 μg/ml.

EXAMPLE 65

Diphenylmethyl 7β-amino7α-formamido-3-[(2-methyl-1,3,4-thiadiazol-5-yl)thiomethyl]ceph-3-em-4-carboxylate 7β-amino7α-formamido-cephalosporanic acid (2.0 g, 4.7 mmol) in water (30 ml) and acetone (10 ml) was adjusted to pH6.5 with saturated sodium hydrogen carbonate solution. 2-Methyl-1,3,4-thiadiazol-5-thiol (0.8 g, 6.0 mmol) was added and the reaction mixture stirred at 60° for 6 h. After acidification with N hydrochloric acid the reaction mixture was evaporated to dryness. The residue was taken up in dimethylformamide (15 ml), treated with an excess of diphenyldiazomethane in dichloromethane and stirred at room temperature for 2 h. The reaction mixture was diluted with ethyl acetate, washed well with water, brine, dried over magnesium sulphate and evaporated. Chromatography (Silica gel, 1:3 hexane/ethyl acetate) gave the title compound (0.78 g, 50%); δ (CDCl$_3$) 2.2–2.5 (2H, brs, NH$_2$) 2.69 (3H,s,CH$_3$), 3.54, 3.65 (2H, ABq, J 17Hz, 2-H), 4.27, 4.55 (2H, ABq, J 13Hz, CH$_2$S), 5.16(1H,s,6-H), 6.60 (1H,s,NH), 6.98 (1H,s,Ar$_2$CH), 7.2–7.6 (10H,m, aromatic -H's), 8.10 (0.85H, d,J 1 Hz, CH0 trans), 8.41 (0.15H, d, J 11 Hz, CHO cis); $v_{max}$(CH$_2$Cl$_2$) 1781, 1720, 1692 cm$^{-1}$.

EXAMPLE 66

6α-formamido-6β-(phenylacetamido) penicillanic acid (a) Benzyl 6α-methylsulphinyl-6β-(phenylacetamido)penicillanate A solution of benzyl 6α-methylthio-6β-(phenylacetamido) penicillanate in dichloromethane at 0° C. was treated with a solution of m-chloroperbenzoic acid (1.1 eq) in dichloromethane. After stirring at that temperature for 75 mins, the reaction mixture was washed with saturated aqueous sodium hydrogen carbonate, dried (MgSO$_4$), and evaporated. Silica-gel column chromatography of the residue gave, among other products, the title compound; $v_{max}$(CH$_2$Cl$_2$) 3400, 1785, 1745, and 1690cm$^{-1}$; δ (CDCl$_3$) 1.32 and 1.39 (6H, 2s, 2-(CH$_3$)$_2$), 2.68(3H,s,SMe), 3.63 (2H,s,Ph CH$_2$CO), 4.49 (1H,s,3-H), 5.13 (2H,s,PhCH$_2$O), 6.01 (1H,s,5-H), 7.35 and 7.37 (10H, 2s, aromatics), and 7.51 (1H,s,NH).

(b) Benzyl 6α-amino-6β-(phenylacetamido)penicillanate

A solution of benzyl 6α-methylsulphinyl-6β(phenylacetamido)penicillanate (0.183 g, 0.377 mmol) in tetrahydrofuran (5 ml), in a flask fitted with a septum cap, was cooled to 0° C. and ammonia gas (17 ml, 0.759 mmol) injected. The resulting mixture was stirred at room temperature for 16 h, the solvent was evaporated in vacuo, and the residue chromatographed on silica gel to give the title compound (0.078 g, 47%); $v_{max}$(CHCl$_3$) 3520, 3390, 3300, 1780, 1745, 1670 and 1490 cm$^{-1}$; δ (CDCl$_3$) 1.25 and 1.30 (6H, 2s, 2-(CH$_3$)$_2$), 2.50 (2H, br, D$_2$O exch, 6α-NH$_2$), 3.56 (2H,s,PhCH$_2$CO), 4.36(1H,s,3-H), 5.13 (2H, ABq, J 12Hz, PhCH$_2$O), 5.34 (1H,s,5-H), 6.75 br (1H,D$_2$O exch., 6β-NH), and 7.26 and 7.33 (10H, 2s, aromatics).

(c) Benzyl 6α-formamido-6β-(phenylacetamido)penicillanate

A solution of benzyl 6α-amino-6β-(phenylacetamido) penicillanate in dichloromethane was reacted with acetic formic anhydride and pyridine as in Example 1b to afford formamidopenicillin; δ(CDCl₃) 1.25 and 1.29 (6H, 2s, 2—(CH₃)₂), 3.54 (2H,s, PhCH₂CO), 4.42 (1H,s,3-H), 5.15 (2H,s,PhCH₂O), 5.60 (1H, s,5-H), 7.1–7.5 (11H, m, phenyls and NH), 7.84 (1H, brs, NH), and 8.05 (1H,s,CHO).

The benzyl ester is removed as described in Example 1c to afford 6α-formamido-6β-(phenylacetamido)-penicillanic acid.

EXAMPLE 67

7β-[(Z)-2-(2-Aminothiazol-4-yl)-2-(1-carboxy-1-methylethoxyimino)acetamido]-7α-formamidocephalosporanic acid disodium salt (i) t-Butyl 7β-[(Z)-2-(1-t-butoxycarbonyl-1-methylethoxyimino)-2-[2-(triphenylmethylamino)thiazol-4-yl]acetamido]-7α-formamidoceohalosporanate A solution of (Z)-2-(1-t-butoxycarbonyl-1-methylethoxyimino)-2-[2-(triphenylmethylamino)thiazol-4-yl]acetic acid (2.53 g, 5.0 mmol) in dichloromethane (15 ml) was added slowly to a solution of t-butyl 7β-amino-7α-formamidocephalosporanate (1.9 g, 5.0 mmol) and N,N'-dicyclohexylcarbodiimide (1.1 g 5.5 mmol) in dichloromethane. The reaction mixture was stirred at room temperature for 4 days and evaporated. The residue in ethyl acetate was washed with N. hydrochloric acid, saturated sodium hydrogen carbonate solution, brine, dried and evaporated. The residue was chromatographed (silica gel, 2:1 hexane/ethyl acetate) and evaporated to give the title compound (0.50 g, 11%); δ(CDCl₃) 1.45 (9H, s, C(CH₃)₃), 1.57 (9H, s, C(CH₃)₃), 1.55 (3H, s, OCCH₃), 1.64 (3H, s, OCCH₃), 2.08 (3H, s, OCOCH₃), 3.23, 3.53 (2H, ABq, J 18.5 Hz, 2-H₂), 4.79, 4.98 (2H, ABq, J 13 Hz, CH₂O), 5.39 (1H, s, 6-H), 6.92 (2H, m, thiazole-H and NH), 7.28 (15H, s, trityl), 7.57 (1H, s, NH), 8.13 (1H, s, NH), 8.27 (1H, s, CHO).

(ii) 7β-[(Z)-2-(1-Carboxy-1-methylethoxyimino)-2-[2-(triphenylmethylamino)thiazol-4-yl]acetamido]-7β-formamidocephalosporanic acid t-Butyl 7β-[(Z)-2-(1-t-butoxycarbonyl-1-methylethoxyimino)-2-[2-(triphenylmethylamino)thiazol-4-yl]acetamido]-7α-formamidocephalosporanate (0.05 g, 0.055 mmol) in trifluoroacetic acid (5 ml) was stirred at room temperature for 0.5 h, evaporated to dryness, triturated with ether, and dried to give the title compound; δ(CF₃CO₂H) 1.83 (6H, s, C(CH₃)₂), 2.24 (3H, s, OCH₃), 3.49, 3.58 (2H, ABq, J 16 Hz, 2-H₂), 5.32, 5.48 (2H, ABq, J 14 Hz, CH₂O), 5.47 (1H, s, 6-H), 7.49 (1H, s, thiazole-H), 7.64–8.50 (15H, m, trityl).

(iii) 7β-[(Z)-2-(2-Aminothiazol-4-yl)-2-(1-carboxy-1-methylethoxyimino)acetamido]-7α-formamidocephalosporanic acid, disodium salt 7β-[(Z)-2-(1-Carboxy-1-methylethoxyimino)-2-[2-(triphenylmethylamino)thiazol-4-yl]acetamido]-7β-formamidocephalosporanic acid was stirred with 70% aqueous formic acid (4 ml) at room temperature for 1.5 h and evaporated. The residue was triturated with ether, taken up in water at pH 6.5, filtered and freeze dried to give the title compound (0.011 g, 33%); δ(D₂O) 1.48 (3H, s, CH₃), 1.50 (3H, s, CH₃), 2.11 (3H, s, OCOCH₃), 3.38, 3.69 (2H, ABq, J 17 Hz, 2-H₂), 4.69, 4.87 (2H, ABq, J 13.5 Hz, CH₂O), 5.37 (1H, s, 6-H), 7.08 (1H, s, thiazole-H), 8.45 (1H, s, CHO); ν$_{max}$(KBr) 3400, 2980, 1765, 1720 sh 1670, 1590 cm⁻¹.

MIC against P.mirabilis 889 is 30 μg/ml.

EXAMPLE 68

7β-[2-(3,4-Diacetoxyohenyl)-2-[(4-ethyl-2,3-dioxopiperazin-1-yl)carbonylamino]acetamido]-7α-formamido-3-[(2-methyl-1,3,4-thiadiazol-5-yl)thiomethyl]ceph-3-em-4-carboxylic acid, sodium salt (i) Diphenylmethyl 7β-[2-(3,4-diacetoxyphenyl)-2-[(4-ethyl-2,3-dioxopiperazin-1-yl)carbonylamino]acetamido]-7α-formamido-3-[(2-methyl-1,3,4-thiadiazol-5-yl)thiomethyl]ceph-3-em-4-carboxylate Diphenylmethyl 7β-amino-7α-formamido-3-[(2-methyl-1,3,4-thiadiazol-5-yl)thiomethyl]ceph-3-em-4-carboxylate (0.3 g 0.63 mmol) in dichloromethane (10 ml) with N,N'-dicyclohexylcarbondiimide (0.11 g, 0.53 mmol) was treated slowly with a solution of 2-(3,4-diacetoxyphenyl)-2-[(4-ethyl-2,3-dioxopiperazin-1-yl)carbonylamino]-acetic acid (0.22 g, 0.51 mmol) in dichloromethane (10 ml). The reaction mixture was stirred for 24 h and evaporated. The residue was chromatographed (silica gel, ethyl acetate) to give the cephalosporin ester (0.23 g 42%) which consisted of two diastereoisomers. Isomer 1 showed δ(CDCl₃) 1.19 (3H, t, CH₂CH₃), 2.22, 2.25 (6H, 2s, OCOCH₃'s), 2.58 (3H, s, CH₃), 2.77, 3.12 (2H, ABq, J 17 Hz, 2-H₂), 3.4–3.6 (4H, m, NCH₂ and piperazine CH₂), 3.9–4.1 (2H, m, piperazine CH₂), 4.21, 4.58 (2H, ABq, J 13 Hz, CH₂S), 5.23 (1H, s, 6-H), 5.64 (1H, d, J 7 Hz, CH), 6.87 (1H, s, Ar₂CH), 7.1–7.6 (13H, m, aromatic - H's), 8.09 (1H, s, NH), 8.16 (1H, s, CHO), 8.81 (1H, s, NH), 10.0–10.2 (1H, m, NH). Isomer 2 showed δ(CDCl₃), 1.18 (3H, t, CH₂CH₃), 2.25, 2.26 (6H, 2s, OCOCH₃'s), 2.77, 3.22 (2H, ABq, J 17 Hz, 2-H₂), 3.4–3.6 (4H, m, NCH₂ and piperazine CH₂), 3.9–4.1 (2H, m, piperazine CH₂), 4.16, 4.76 (2H, ABq, J 13 Hz, CH₂S), 5.11 (1H, s, 6-H), 5.77 (1H, d, J 7 Hz, CH), 6.86 (1H, s, Ar₂CH), 7.1–7.6 (13H, m, aromatic - H's), 7.87 (1H, s, NH), 8.11 (1H, s, CHO), 8.51 (1H, s, NH), 10.0–10.2 (1H, m, NH); ν$_{max}$(CH₂Cl₂) 1775, 1730, 1690 cm⁻¹.

(ii) 7β-[2-(3,4-Diacetoxyphenyl)-2-[(4-ethyl-2,3-dioxopiperazin-1-yl)carbonylamino]acetamido]-7α-formamido-3-[(2-methyl-1,3,4-thiadiazol-5-yl)thiomethyl]ceph-3-em-4-carboxylic acid, sodium salt Diphenylmethyl 7β-[2-(3,4-Diacetoxyphenyl)-2-[(4-ethyl-2,3-dioxopiperazin-1-yl)carbonylamino]acetamido]-7α-formamido-3-[(2-methyl-1,3,4-thiadiazol-5-yl)thiomethyl]ceph-3-em-4-carboxylate (0.23 g, 0.42 mmol) was stirred in trifluoroacetic acid (5 ml) at room termperature for 0.5 h and evaporated to dryness. The residue was triturated with ether, taken up in water which had been adjusted to pH 6.5 using dilute sodium hydrogen carbonate solution, washed with ethyl acetate filtered and freeze dried to give the title compound (0.15 g, 69%) as a mixture of two diastereoisomers. Isomer 1 exhibited δ(D₂O), 1.19 (3H, t, J 7.5 Hz, NCH₂CH₃), 2.31, 2.34 (6H, 2s, OCOCH₃'s), 2.93, 3.36 (2H, ABq, J 17 Hz, 2-H₂), 3.50 (2H, ABq, J 7.5 Hz, NCH₂), 3.6–3.8 (2H, m, piperazine CH₂), 3.9–4.1 (2H, m, piperazine CH₂), 4.21, 4.32 (2H, ABq, J 12 Hz, CH₂S), 5.25 (1H, s, 6-H), 5.54 (1H, s, CH), 7.1–7.6 (3H, m, aromatic - H's), 8.13 (1H, s, CHO). Isomer 2 showed δ(D₂O) 1.19 (3H, t, J 7.5 Hz, $CH_2CH_3$), 2.32, 2.35 (6H, 2s, $OCOCH_3$'s), 3.07 (1H, d, J 17 Hz, 2-H), 3.4–3.6 (3H, m, $NCH_2$ and 2-H), 3.6–3.8 (2H, m, piperazine $CH_2$), 3.85–4.15 (3H, m, piperazine $CH_2$ and 1H of $CH_2S$), 4.41 (1H, d, 1H of $CH_2S$), 5.14 (1H, s, 6-H), 5.58 (1H, s, CH), 7.1–7.6 (3H, m, aromatic - H's), 8.11 (1H, s, CHO); $\nu_{max}$ (KBr) 3400, 1770, 1680 cm$^{-1}$.

MIC against P.mirabilis 889 is 0.1 µg/ml.

EXAMPLE 69

7β-[D-2-[(4-Ethyl-2,3-dioxopiperazin-1-yl)carbonylamino]-2-(3,4-dihydroxyphenyl)acetamido]-7α-formamidocephalosporanic acid, sodium salt 7β-[D-2-(3,4-Diacetoxyphenyl)-2-[(4-ethyl-2,3-dioxopiperazin-1-yl)carbonylamino]-7α-formamidocephalosporanic acid, sodium salt (0.03 g, 0.04 mmol) in water (5 ml) was adjusted to pH 8.5 with dilute sodium hydrogen carbonate solution. The reaction mixture was stirred at room temperature for 0.5 h, acidified to pH 1.5 with N hydrochloric acid and saturated with sodium chloride. The aqueous phase was extracted with tetrahydrofuran/ethyl acetate (1:1) and the extracts washed with brine, dried and evaporated. The residue was taken up in water at pH 6.5, filtered and freeze dried to give the title compound (0.01 g, 38%); δ($D_2O$) 1.17 (3H, t, J 7 Hz, $NCH_2CH_3$), 2.06 (3H, s, $OCOCH_3$), 3.15 (1H, d, J 18 Hz, 2-H), 3.3–3.6 (3H, m, N—$CH_2CH_3$ and 2-H), 3.6–3.8 (2H, m, piperazine $CH_2$), 3.9–4.1 (2H, m, piperazine $CH_2$), 5.2–5.4 (2H, m, CH and 6-H), 6.8–7.1 (3H, m, aromatic-H's), 8.12 (1H, s, CHO); $\nu_{max}$(KBr) 3420, 2670, 1765, 1710, 1675 cm$^{-1}$.

MIC against P.mirabilis 889 is 0.1 µg/ml.

EXAMPLE 70

6β[D-2-(3,4-diacetoxyphenyl)-2-[3-[2-(4-aminosulphonylphenyl)amino-4-hydroxypyrimidin-5-yl]ureido]acetamido-6α-formamidopenicillanic acid sodium salt 4-[(5-Amino-4-hydroxypyrimidin-2-yl)amino]benzenesulphonamide (56 mg, 0.20 mmole) was heated at reflux in dry tetrahydrofuran (50 ml) containing triethylamine (0.03 ml) for 1 h. The suspension was then cooled to 0° C. and stirred with a 12.5% w/w solution of phosgene in toluene (0.20 ml) after which it was allowed to warm to room temperature over 0.75 h. The resulting pale yellow suspension was concentrated to low volume, diluted to 10 ml with tetrahydrofuran and added to a stirred solution of 6β-[D-2-amino-2-(3,4-diacetoxyphenyl)acetamido[-6α-formamidopenicillanic acid (110 mg, 0.22 mmole) in water: tetrahydrofuran (10 ml, 2:1 v/v) at 0° C. The pH was maintained at about 7.5 by the addition of sodium hydrogen carbonate solution and the solution allowed to regain room temperature over 0.5 h. After this period a small quantitiy of insoluble material was filtered off and the filtrate was concentrated, diluted with water and washed with ethyl acetate. The organic phase was backwashed with a little water, then the total aqueous phase was saturated with sodium chloride, acidified with 2M hydrochloric acid to pH 2 and extracted with tetrahydrofuran:ethyl acetate (1:1,3×15 ml). The combined organic extracts were dried over sodium sulphate and evaporated to a gum, which was suspended in water and basified to pH 6.5. A further small quantiity of insoluble material was filtered off, then the filtrate was evaporated to afford the penicillin sodium salt (80 mg, 48%); $R_f$ 0.35 in n-butanol:acetic acid:water, 4:1:1, $\nu_{max}$ (KBr) 1770, 1660, 1595, 1540, 1500 cm$^{-1}$; δ[$D_2O$: ($CD_3$)$_2$SO:$CD_3$OD, 2:1:1] 1.05 and 1.38 [6H, 2s, ($CH_3$)$_2$ C], 2.37 (6H, s, 2x$CH_3CO$), 4.14 (1H, s, 3-H), 5.51 (1H, s, NCHCO), 5.63 (1H, s, 5-H), 7.20–7.70 (5H, m, aryl-H's), 7.70–8.00 (3H, m, aryl-$H_2$ and pyrimidinyl 6-H), 8.18 (1H, s, NHCHO).

EXAMPLE 71

Preparation of oral dosage units in the form of a tablet

6β-[D-2-(4-ethyl-2,3-dioxopiperazin-1-yl)carbonylamino]-2-(4-hydroxyphenyl)acetamido-]-6α-formamidopenicillanic acid sodium salt Ingredients:

1. 6β-[D-2-[(4-ethyl-2,3-dioxopiperazin-1-yl)carbonylamino]-2-(4-hydroxyphenyl)acetamido]-6α-formamidopenicillanic acid sodium salt—500 mg (free acid)
2. Carboxymethyl sodium starch glycollate—15 mg
3. Magnesium stearate—12 mg
4. Microcrystalline cellulose—to 850 mg Items 1, 2 and 4 are blended with two thirds of item 3, and compressed on a rotary tablet machine. The slugs produced are milled, and the milled material blended with the remainder of item 3. The mixture is then compressed on a rotary tablet machine to form the final tablets.

The tablets may be uncoated or a conventional film coating may be applied.

Preparation of parenteral dosaoe units 25 g of 6β-[D-2-[(4-ethyl-2,3-dioxopiperazin-1-yl)carbonylamino]-2-(4-hydroxyphenyl)acetamido-]-6α-formamidopenicillanic acid sodium salt is dissolved under aseptic conditions in 2,00 ml of distilled water suitable for injection, and the solution is filtered through a millipore-filter (pore size 0.22 mm). 2.0 ml portions of the filtrate are filled into 10 ml glass vials, the contents are freeze-dried, and the vials are then closed with a rubber stopper and an aluminium cap. Each vial contains 246 mg of active ingredient.

The contents of a vial are poured into and thoroughly admixed with 2 ml of water for injection to provide an injectable dosage unit composition for intravenous adminstration.

20 ml of distilled water suitable for injection are added to the contents of a vial, and the resulting solution is dissolved in 250 ml of an aqueous 0.9% sodium chloride suitable for injection. A solution suitable for continuous intravenous infusion is obtained.

In vivo Biological Data

The compound of Example 5 was tested in vivo in mice against experimental infections. The results of these tests are shown in the following table:

| Organism | Total* s.c. $CD_{50}$ (Mg/Kg) |
| --- | --- |
| E. coli 96 R+ | 5.2 |
| E. coli 96 R− | <<3.1 |
| K. aerogenes T767 | 3.7 |

*dosed at 1 and 5 hours after infection
(5 mice/group)
(s.c. = subcutaneous)

The compound of Example 5 was administered to mice (5) by the subcutaneous route at a dosage of 50 mg/kg and the blood concentration determined. The results are shown in the following table:

| Compound of Example No. | Concentration (μg/ml) at ... mins | | | | | | A.U.C. (μg-min/ml) |
| --- | --- | --- | --- | --- | --- | --- | --- |
| | 5 | 10 | 20 | 30 | 60 | 120 | |
| 5 | 24.4 | 23.2 | 14.5 | 11.0 | <0.9 | <0.9 | 660.3 |

EXAMPLE 72

Pivaloyloxymethyl 6β-{D-2-{(2,3-dioxo-4-ethylpiperazin-1yl)carbonylamino}-2-(4-hydroxyohenyl)acetamido}-6α-formamidopenicillanate Sodium 6β-{2,3-dioxo-4-ethylpiperazin-1-yl)carbonylamino}-2-(4-hydroxyphenyl)acetamido}-6α-formamidopenicillanate (238 mg) was suspended in dry acetone (20 ml) and the mixture treated with dry N,N-dimethylformamide (5 ml), which resulted in an almost clear solution. This mixture was treated with bromomethyl pivalate (73 mg) and then stirred at room temperature for 24 h. Concentration in vacuo gave a residue, which was diluted with ethyl acetate (100 ml) and washed six times with water then saturated brine, dired over anhydrous magnesium sulphate and concentration to low volume in vacuo. Addition of diethyl ether (100 ml) gave a white precipitate, which was collected by filtration, washed with ether and dried in vacuo to give the title compound (137 mg, 50%); $\nu_{max}$ (KBr) 3300 br, 1788, 1763, 1715, 1680 br, 1613, 1515, 1270 br, 1183 br, 1110 and 937 cm$^{-1}$; δ{(CD$_3$)$_2$CO} 0.92–1.37 (18H, m, CH$_3$'s), 3.48 (2H, q, J8 Hz, NCH$_2$CH$_3$), 3.60–4.13 (4H, m, N(CH$_2$)$_2$N), 4.38 (1H, s, 3-H), 5.53 (1H, s, 5-H), 5.57 (1H, d, J 7 Hz, CH), 5.77 and 5.83 (2H, ABq, J6 Hz, CO$_2$CH$_2$O), 6.80 (2H, d, J9 Hz, phenyl), 7.38 (2H, d, J9 Hz, phenyl), 8.11–8.69 (4H, m, NHCHO, CONH and OH), 9.90 (1H, d, J7 Hz, NHCH).

EXAMPLE 73

7β-[2-[(4-Ethyl-2,3-dioxopiperazin-1-yl) carbonylamino]-2-(3,4-dihydroxyphenyl) acetamido]-7α-formamido-3-[(1-methyl-1H-tetrazol-5-yl) thiomethyl]ceph-3-em-4-carbocylic acid, sodium salt 7β-[2-(3,4-Diacetoxy phenyl)-2-[(4-ethyl-2,3-dioxopiperazin-1-yl) carbonylamino]acetamido]-7α-formamido-3-[(1-methyl-1H-tetrazol-5-yl) thiomethyl]-ceph-3-em-4-carboxylic acid, sodium salt (0.048 g 0.06 mmol) in water (5 ml) was adjusted to pH 9.0 with a mixture of saturated sodium hydrogen carbonate solution and dilute sodium carbonate solution. The reaction mixture was stirred at nom temperature for 0.5 h, acidified to pH 1.5 with N. hydrochloric acid, saturated with sodium chloride and extracted with a mixture of tetrahydrofuran and ethyl acetate (1:1). The organic extracts were washed with brine dried and evaporated. The residue was taken up in water which was adjusted to pH 6.5 with dilute sodium hydrogen carbonate solution, washed with ethyl acetate, and freeze dried to give the title compound (0.022 g, 58%). δ(D$_2$O) 1.20 (3H, t, J 8 Hz, NCH$_2$CH$_3$), 3.11 (1H, d, J 17.5 Hz 1H of 2-H), 3.3–3.6 (3H, m, 1H of 2-H and NCH$_2$CH$_3$), 3.71 (2H, m, piperazine-CH$_2$), 3.8–4.4 (7H,m,NCH$_3$, piperazine CH$_2$ and CH$_2$S), 5.00 (1H,S, 6-H), 5.41 (1H,S, CH), 6.9–7.6 3H, M, phenyl - H'S) 8.12 (1H,S,CHO); $\nu_{max}$ (KBr) 3430, 1780, 1722 sh, 1678, 1613 cm$^{-1}$.

EXAMPLE 74

Diphenylmethyl 7β-amino-7α-formamido-3-[(6-hydroxy-4-methyl-5-oxo-4H-1,2,4-triazin-3-yl)thiomethyl]ceph-3-em-4-carboxylate 3-Acetoxymethyl-7β-amino-7α-formamidoceph-3-em-4-carboxylic acid, trifluoroacetic acid salt (0.54 g) and 6-hydroxy-3-mercapto-4-methyl-5-oxo-4H-1,2,4-triazine (0.20 g) were suspended in water (15 ml) and sodium hydrogen carbonate (0.28 g) added to give pH8. 5M Hydrochloric acid was added to give a pH of 6.5. The mixture was heated under argon at 60° C. for 3 h then cooled to 0°–5° C. and acidified to pH2 with 5M hydrochloric acid. The resulting mixture was evaporated to dryness in vacuo and the residue treated with NN-dimethylformamide (25 ml) followed by a solution of diphenyldiazomethane in dichloromethane until the red colour persisted. It was stirred overnight at room temperature and then glacial acetic acid added to destroy excess diphenyldiazomethane. The volatile solvents were removed under reduced pressure and the residue treated with ethyl acetate (100 ml) and water (100 ml). The phases were separated, the organic phase washed five times with water, once with saturated brine, dried over anhydrous magnesium sulphate and evaporated to dryness in vacuo. Chromatography on silica gel 60 (<230 mesh ASTM), eluting with ethyl acetate, gave the title compound as a white solid (0.105 g, 19%) after tritration under diethyl ether, m.p. 135°–140° C., $\nu_{max}$. (CHCl$_3$) 1780 and 1710 cm$^{-1}$; δCDCl$_3$ 2.68 (2H,br s,NH$_2$), 3.33 (3H,s,CH$_3$), 3.35 and 3.53 (2H,ABq, J 17 Hz, 2-H$_2$) 3,88 and 4.30 (2H ABq, J 13.7 Hz, 3-CH$_2$), 5.18 (1H, s, 6-H), 7.02 (1H, s, CH Ph$_2$) 7.20–7.61 (IOH, m, 2 phenyls), 8.18 (1H, s, CHO), 10.18–11.09 (1H, brs, CH).

EXAMPLE 75

6β-[D-2-amino-3-(N-methylcarbamoyl)propionamido]-2-(3,4-diacetoxyphenyl)acetamido]-6α-formamidopenicillanic acid, sodium salt (a)

6β-[D-2-[D-2-(4-nitrobenzyloxycarbonylamino)-3-(N-methylcarbamoyl)propionamido]-2-(3,4-diacetoxyphenyl)acetamido]-6α-formamidopenicillanic acid, sodium salt 6β-[D-2-amino-2-(3,4-diacetoxyphenyl)acetamido]-6α-formamidopenicillanic acid (150 mg, 0.30 mmole) was suspended in a mixture of dry dichloromethane (2 ml) and dimethylformamide (1 ml) at 0° C. Triethylamine (0.055 ml) was added and the mixture stirred; a clear yellow solution resulting in a few minutes. The temperature was maintained at 0° C. while D-2-(4-nitrobenzyloxycarbonylamino)-3-(N-methoxycarbamoyl)propionic acid, succinimido ester (125 mg, 0.30 mmole) was added in one portion. The solution was stored at 5° C. for 2 hours, then evaporated to near dryness. The residue was partitioned between water and ethyl acetate, raising the pH of the aqueous phase to 7.0. The aqueous phase was separated and washed once more with ethyl acetate, backwashing each time with a little water. The total aqueous phase was acidified to pH 2.0 and extracted twice with ethyl acetate:tetrahydrofuran, 1:1. The total organic extract was washed with brine and dried over sodium sulphate, followed by evaporation to dryness. The residue was taken up in dry acetone and sodium 2-ethylhexanoate (1.89 M in 4-methylpentan-2-one) (0.13 ml) was added. Concentration of the milky colloid solution to low volume followed by addition of dry ether afforded the penicillin sodium salt, which was filtered, washed with acetone:ether (1:1), ether, and dried; (180 mg, 75%); R$_f$0.50 in n-butanol:acetic acid:water, 4:1:1, $\nu_{max}$ (KBr) 1170, 1665, 1605 and 1520 cm$^{-1}$; $\delta$(D$_2$O) 0.87 and 1.23 (6H, 2s, (CH$_3$)$_2$C), 2.22 (6H, s, 2=CH$_3$CO), 2.45–2.75 (5H, m, CH$_3$N+CHCH$_2$CO), 4.09 (1H, s, 3-H), 4.93 (1H, s, CH$_2$CH(NH)CO), 5.22 (1H, s, 5-H), 5.52 (1H, s, ArCH(NH)CO), 6.95–7.50 (5H, m, aryl 1-H), 7.90–8.15 (2H, m, aryl-H), 8.04 (1H, s, NHCHO).

(b)
6β-[D-2-[D-2-amino-3-(N-methylcarbamoyl)propionamido]-2-(3,4-diacetoxyphenyl)acetamido]-6α-formamidopenicillanic acid, sodium salt Sodium 6β-[D-2-[D-2-(4-nitrobenzyloxycarbonylamino)-3-(N-methylcarbamoyl]propionamido]-2-(3,4-diacetoxyphenyl)acetamido]-6α-formamidopenicillanate (140 mg, 0.17 mmole) was dissolved in water (10 ml). 10% Palladium on charcoal (70 mg) was added and the mixture was hydrogenated for 1 hour. After this time t.l.c. analysis showed no starting material remaining. The catalyst was filtered off and washed with water; the total filtrate was evaporated to dryness and triturated with ether to afford an off-white solid (110 mg), $\nu_{max}$ (KBr) 1770, 1665, 1610 and 1550 br cm$^{-1}$.

EXAMPLE 76

7β-[2-[(4-Ethyl-2,3-dioxopiperazin-1-yl)carbonylamino]-2-(4-hydroxyphenyl)acetamido]-7α-formamido-3-[(1-methyl-1H-tetrazol-5-yl)thiomethyl]-ceph-3-em-4-carboxylic acid, sodium salt (a) Diphenylmethyl 7β-[2-[(4-ethyl-2,3-dioxooiperazin-1-yl)carbonylamino]-2-(4-hydroxyphenyl)acetamido]-7α-formamido-3-[(1-methyl-1H-tetrazol-5-yl)thiomethyl]-ceph-3-em-4-carboxylate A solution of D-2-[(4-ethyl-2,3-dioxopiperazin-1-yl)carbonylamino]-2-(4-hydroxyphenyl)acetic acid (0.168 g, 0.5 mmol) in tetrahydrofuran (15 ml) was added slowly to a stirred solution of diphenylmethyl 7β-amino-7α-formamido-3-[(1-methyl-1H-tetrazol-5-yl)thiomethyl]ceph-3-em-4-carboxylate (0.269 g, 0.5 mmol) and N,N'-dicyclohexylcarbodiimide (0.113 g 0.55 mmol) in tetrahydrofuran (10 ml). The reaction mixture was stirred for three days at room temperature before being evaporated to dryness. The residue was chromatographed on silica gel 60 (<230 mesh ASTM) eluting with ethyl acetate/hexane 3:1 through to 2% ethanol in ethyl acetate to afford the title compound as a mixture of diastereoisomers (ca 2:1 ratio) (0.065 g, 15%); $\nu_{max}$ (THF) 1790, 1715, 1695, 1510, 1380 cm$^{-1}$; $\delta$[(CD$_3$)$_2$CO] 1.16 (3H, t, J 7 Hz, CH$_2$CH$_3$), 3.30–3.75 (6H, m, piperazine CH$_2$ and CH$_2$CH$_3$), 3.92 and 3.95 (3H, 2s, 2-H$_2$ NCH$_3$ diastereoisomers), 4.29 and 4.31, and 4.50 and 4.52 (2H, 2ABq, J 13 Hz, CH$_2$S diastereoisomers), 5.25 and 5.26 (iH, 2s, 6-H), 5.61 and 5.65 (1H, 2d, J 7 Hz, ArCH), 6.90 (1H, s, CHAr$_2$), 6.80 and 6.82 (2H, dd, J 8 Hz, aromatic diastereoisomers), 7.20–7.70 (13H, m, aromatics and 7β-NH), 8.22 and 8.27 (1H, 2s CHO diastereoisomers) 8.49 and 8.60 (1H, 2s, NHCHO diastereoisomers) and 9.90 (1H, m, α-NH diastereomers).

(b)
7β-[2-[4-Ethyl-2,3-dioxopiperazin-1-yl)carbonylamino]-2-(4-hydroxyphenyl)acetamido]-7α-formamido-3-[(1-methyl-1H-tetrazol-5-yl)thiomethyl]-ceph-3-em-4-carboxylic acid, sodium salt Diphenylmethyl 7β-[2-[(4-ethyl-2,3-dioxopiperazin-1-yl)carbonylamino]-2-(4-hydroxyphenyl)acetamido]-7α-formamido-3-[(1-methyl-1H-tetrazol-5-yl)thiomethyl]ceph-3-em-4-carboxylate (0.065 g, 0.076 mmol) was dissolved in trifluoroacetic acid (5 ml) and the resulting solution was stirred at room temperature for 0.75 h. It was then evaporated to dryness, and the residue was suspended in water and the pH adjusted to 6.5 with dilute aqueous sodium hydrogen carbonate solution. The resulting solution was washed with ethyl acetate filtered and freeze dried to afford the title sodium salt in quantitative yield; $\nu_{max}$(KBr) 1770, 1680 br, 1615, 1515 cm$^{-1}$; $\delta$(D$_2$O) 1.17 (3H, t, J 7 Hz, CH$_2$CH$_3$), 3.08 and 3.12 (1H, 2ABq, J 17 Hz, 2-H diastereoisomers), 3.39–3.58 (3H, m, CH$_2$CH$_3$ and 2-H diastereoisomers), 3.66 (2H, m, piperazine CH$_2$), 3.87–4.33 (7H, m, NCH$_3$, piperazine CH$_2$ and CH$_2$S diastereoisomers), 5.15 and 5.23 (1H, 2s, 6-H diastereoisomers), 5.38 and 5.44 (1H, 2s, ArCH diastereoisomers), 6.88 (2H, d, J 7.5 Hz, aromatics), 7.33 and 7.38 (2H, 2d, J 7.5 Hz, aromatic dioistereoisomers) and 8.06 and 8.12 (1H, 2s, CHO diastereoisomers).

EXAMPLE 77

Diphenylmethyl 7β-amino-7α-formamido-3-((2-methoxy-1,3,4-thiadiazol-5-yl)thiomethyl)ceph-3-em-4-carboxylate 7β-Amino-7α-formamidecephalosporanic acid, trifluoroacetic acid salt (1.04 g, 2.4 mmol) in water (25 ml) and acetone (10 ml) was adjusted to pH6.5 with with sodium hydrogen carbonate solution. 2-methoxy-1,3,4-thiadiazole-5-thiol (0.39 g, 2.6 mmol)was added and the reaction mixture stirred at 60° C. for 6 h. After acidification to pH2 with N hydrochloric acid, the reaction residue was dissolved in dimethylformamide (40 ml), treated with an excess of diphenyldiazomethane in dichloromethane, and stirred at room temperature for 2 h. The reaction mixture was diluted with ethyl acetate, washed well with water, brine, dried over magnesium sulphate and evaporated. The crude product was chromatographed on silica gel 60 (<230 mesh ASTM) eluting with ethyl acetate/hexane 1:1 through to 4:1 to afford the title compound (0.43 g, 32%); $\nu_{max}$(CH$_2$Cl$_2$) 3495, 1785, 1720, 1692, 1520, 1380 cm$^{-1}$; $\delta$(CDCl$_3$) 2.54(2H, brs, NH$_2$), 3.56(2H,brs,2-H$_2$), 4.11 and 4.45 (2H, ABq, J 13 Hz, CH$_2$S), 4.13(3H, s, OCH$_3$), 5.20(1H, s,6-H), 7.08(1H,s,CHAr$_2$), 7.20–7.80(11H, m, aromatics and NHCHO) and 8.18(1H,2, NHCHO)

EXAMPLE 78

Diphenylmethyl 7β-amino-7α-formamido-3-((1-diphenylmethyloxycarbonylmethyl-1H-tetrazol-5-yl) thiomethyl)ceph-3-em-4-carboxylate 7β-Amino-7α-Formamidocephalosporanic acid, trifluoracetic acid salt (1.20 g, 2.8 mmol) in water (30 ml) and acetone (12 ml) was adjusted to pH6.5 with sodium hydrogen carbonate solution. 1-Carboxymethyl-(H-tetrazole-5-thiol (0.49, 3.1 mmol) was added and the pH re-adjusted to 6.5. The reaction mixture was then stirred at 60° C. for 6 h. After acidification to pH2 with N- hydrochloric acid, the reaction mixture was evaporated to dryness. The residue was dissolved in dimethylformamide (50 ml), treated with an excess of diphenyldiazomethyane in dichlormethane, and stirred at room temperature overnight. The reaction mixture was diluted with ethyl acetate, washed well with water, brine, dried over magnesium sulphate and evaporated. The crude product was chromagraphed on silica gel 60 (<230 mesh ASTM) eluting with ehtyl acetate/hexane 3:2 to afford the title product, contaminated slightly with the D2 isomer (0.08 g, 4%); $\nu_{max}$(CH$_2$Cl$_2$) 3390, 1785, 1760, 1730 sh, 1690 cm$^{-1}$; $\delta$(CDCl$_3$)2.28(2H,brs, NH$_2$), 3.49(2H,brs, 2-H$_2$), 4.20 (2H,m,CH$_2$S), 5.12(3H,m,CH$_2$CO$_2$R and 6-H), 6.95(1H,s,CHAr$_2$), 7.10–7.60 (21H,m, aromatics and NHCHO) and 8.11(1H,s, NHCHO).

EXAMPLE 79
7$\beta$-[2-[(4-Ethyl-2,3-dioxopiperazin-1-yl)carbonylamino]-2-(3,4-diacetoxyphenyl)acetamido]-7$\alpha$-formamido-3-[(2-methoxy-1,3,4-thiadiazol-5-yl)thiomethyl]ceph-3-em-4-carboxylic acid, sodium salt (a) Diphenylmethyl 7$\beta$-[2-[(4-ethyl-2,3-dioxopiperazin-1-yl)carbonylamino]-2-(3,4-diacetoxyphenyl)acetamido]-7$\alpha$-formamido-3-[(2-methoxy-1,3,4-thiadiazol-5-yl)thiomethyl]ceph-3-em-4-carboxylate A solution of DL-2-(3,4-diacetoxyphenyl)-2-[(4-ethyl-2,3-dioxopiperazin-1-y-)carbonylamino]acetic acid (0.161 g, 0.37 mmol) in dichloromethane (10 ml) was added slowly dropwise to a solution of diphenylmethyl 7$\beta$-amino-7$\alpha$-formamido-3-[(2-methoxy-1,3,4-thiadiazol-5-yl)thiomethyl]ceph-3-em-4-carboxylate (0.210 g, 0.37 mmol) and N,N'-dicyclohexylcarbodiimide (0.084 g, 0.41 mmol) in dichloromethane (10 ml). The reaction mixture was stirred for three days at room temperature, and then evaporated to dryness. The residue was chromatographed on silica gel 60 (<230 mesh ASTM) eluting with ethyl acetate through to 5% ethanol in ethyl acetate to afford the title compound (0.130 g, 36%) as a mixture of diastereoisomers. $\nu_{max}$ (CH$_2$Cl$_2$), 3380, 1780, 1720, 1690, 1500, 1370, 1210, 1185 cm$^{-1}$; $\delta$[(CD$_3$)$_2$CO]1.15 (3H, 2t, J 7 Hz, CH$_2$CH$_3$diastereoisomers), 2.25 (6H, m, OCOCH$_3$ diastereoisomers), 2.79 and 2.84 and 3.23 and 3.29 (2H, 2ABq, J 16 Hz, 2-H$_2$ diastereoisomers), 3.49 (2H, m, CH$_2$CH$_3$ diastereoisomers) 3.67 (2H, m, piperazine CH$_2$), 3.95–4.21 (6H, m, piperazine CH$_2$, CHS and OCH$_3$ diastereoisomers), 4.62 and 4.63 (1H, ABq, CHS diastereoisomers), 5.32 (1H, s, 6-H), 5.78 and 5.85 (1H, 2d, J 7 Hz, CHAr diastereoisomers), 6.85 and 6.87 (1H, 2s, CHAr$_2$ diastereoisomers), 7.20–7.70 (13H, m, aromatics), 8.22 and 8.30 (1H, 2s, CHO diastereoisomers), 8.49, 8.60, 8.65 and 8.86 (2H, 4s, NHCHO and 7$\beta$-NHCO diastereoisomers), 10.07 and 10.12 (1H, 2d, J 7 Hz, $\alpha$-NHCO).

(b) 7$\beta$-[2-[(4-ethyl-2,3-dioxopiperazin-1-yl)carbonylamino]-2-(3,4-diacetoxyphenyl)acetamido]-7$\alpha$-formamido-3-[(2-methoxy-1,3,4-thiadiazol-5-yl)thiomethyl]ceph-3-em-4-carboxylic acid, sodium salt Diphenylmethyl 7$\beta$-[2-[(4-ethyl-2,3-dioxopiperazin-1-yl)carbonylamino]-2-(3,4-diacetoxyphenyl)acetamido]-7$\alpha$-formamido-3-[(2-methoxy-1,3,4-thiadiazol-5-y-)thiomethyl]ceph-3-em-4-carboxylate was treated briefly with trifluoroacetic acid, and the resulting solution was evaporated to dryness. The residue was suspended in water, adjusted to pH 6.5 with dilute sodium hydrogen carbonate solution, washed with ethyl acetate, and freeze dried to afford the title sodium salt.

I claim:

1. A method of treating bacterial infections in humans and animals which comprises administering to a human or animal in need thereof an antibacterially effective amount of a compound of the formula (II) or a pharmaceutically acceptable salt or in-vivo hydrolyzable ester thereof:

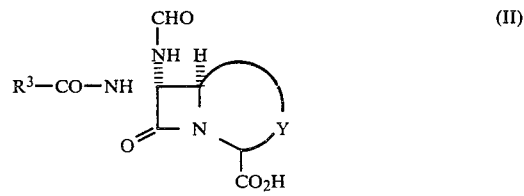

wherein Y is:

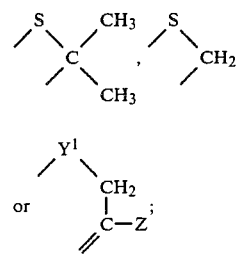

wherein Y$^1$ is oxygen, sulphur or —CH$_2$— and Z is hydrogen, halogen, alkoxy of 1 to 4 carbon atoms, —CH$_2$Q or —CH=CH—Q wherein Q is hydrogen, halogen, hydroxy, mercapto, cyano, carboxy, carboxylic ester, alkoxy of 1 to 4 carbon atoms, acyloxy, aryl, a heterocyclyl group bonded via a carbon atom, a heterocyclylthio group or a nitrogen containing heterocyclic group bonded via a nitrogen atom; and R$^3$ is a group such that R$^3$—CO—NH is an acylamino group, in combination with a pharmaceutically acceptable carrier.

2. A method according to claim 1 wherein the compound is at least 50% pure on a w/w basis.

3. A method according to claim 1 wherein the compound is at least 75% pure on a w/w basis.

4. A method according to claim 1 wherein the compound is at least 90% pure on a w/w basis.

5. A method according to claim 1 wherein the compound has antibacterial activity against gram negative organisms.

6. A method according to claim 1 wherein the compound is in zwitterionic form.

7. A method according to claim 1 wherein the compound is in the form of a salt.

8. A method according to claim 1 wherein the compound is in the form of an acid.

9. A method according to claim 1 wherein the hydrogen atoms of the —NH—CHO formamido group are cis.

10. A method according to claim 1 wherein the hydrogen atoms of the —NH—CHO formamido group are trans.

11. A method according to claim 1 wherein Y is —S—C(CH$_3$)$_2$— and —S—CH$_2$—C(CH$_2$Q)=.

12. A method according to claim 1 wherein Y is —S—C(CH₃)₂—.

13. A method according to claim 1 wherein Y is —S—CH₂—CZ=.

14. A method according to claim 1 wherein R³CO— is a group selected from the sub-formula (a)–(e):

$$A_1-(CH_2)_n-\underset{X}{CH}-(CH_2)_m-CO- \quad (a)$$

$$A_2-CO- \quad (b)$$

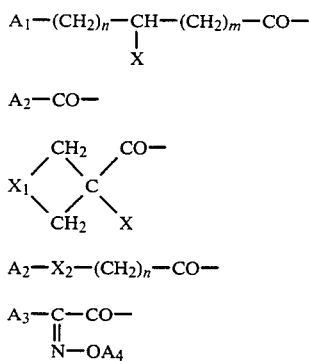 (c)

$$A_2-X_2-(CH_2)_n-CO- \quad (d)$$

$$A_3-\underset{\underset{N-OA_4}{\|}}{C}-CO- \quad (e)$$

wherein n is 0, 1 or 2; m is 0, 1 or 2; A₁ is alkyl of 1 to 6 carbon atoms, cycloalkyl of 3 to 6 carbon atoms, cyclohexenyl, cyclohexadienyl, phenyl unsubstituted or substituted with up to 5 halo, alkyl of 1 to 6 carbon atoms, alkoxy of 1 to 6 carbon atoms, haloalkyl of 1 to 6 carbon atoms in the alkyl moiety, hydroxyl, amino, carboxy, alkoxycarbonyl of 1 to 6 carbon atoms in the alkoxy moiety or alkoxycarbonylalkyl of 1 to 6 carbon atoms in the alkyl and alkoxy moieties, thienyl, pyridyl, thiazolyl, alkylthio of 1 to 6 carbon atoms or alkyloxy of 1 to 6 carbon atoms; X is hydrogen, halogen, a carboxylic acid, carboxylic ester, sulphonic acid, azido, tetrazolyl, hydroxy, acyloxy, amino, ureido, acylamino, heterocyclylamino, guanidino or acylureido grup; A₂ is an aromatic group; X₁ is CH₂OCH₂, CH₂SCH₂ or (CH₂)ₙ; X₂ is oxygen or sulphur; A₃ is aryl or heteroaryl; and A₄ is hydrogen, alkyl of 1 to 6 carbon atoms, cycloalkyl of 3 to 6 carbon atoms, arylaminocarbonyl, alkylaminocarbonyl of 1 to 6 carbon atoms, alkanoyl of 1 to 6 carbon atoms, alkoxycarbonyl of 1 to 6 carbon atoms, alkenyl of 2 to 6 carbon atoms, carboxy alkyl of 1 to 6 carbon atoms, alkylsulphonyl of 1 to 6 carbon atoms or di-alkylphosphatomethyl of 1 to 6 carbon atoms in each alkyl moiety.

15. A method according to claim 1 wherein R³ is a group of sub-formula (f) or (g):

$$R^4-\underset{R^5}{CH}- \quad (f)$$

$$R^6-\underset{R^7}{CH}- \quad (g)$$

wherein R⁴ is phenyl, thienyl or phenoxy; R⁵ is hydrogen or methyl; R⁶ is phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy, of 1 to 6 carbon in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety, thienyl or cyclohexadienyl; and R⁷ is hydroxyl, carboxylic acid or a lower alkyl, phenyl, tolyl or indanyl ester thereof, amino, ureido, acylamino or acylureido.

16. A method according to claim 15 wherein R⁶ is Phenyl substituted with up to three groups selected from the group consisting of alkyl of 1 to 6 carbon atoms, phenyl, halogen, alkoxy of 1 to 6 carbon atoms, amino, nitro, hydroxy, alkylamido of 1 to 6 carbon atoms, alkylcarbonyloxy of 1 to 6 carbon atoms, carboxy, alkoxycarbonyl of 1 to 6 carbon atoms, haloalkyl of 1 to 6 carbon atoms, oxyalkyl of 1 to 6 carbon atoms, alkylcarbonyl of 1 to 6 carbon atoms, aryloxy, aralkyloxy, arylcarbonyl, alkylamino of 1 to 6 carbon atoms or dialkylamino of 1 to 6 carbon atoms in each alkyl moiety.

17. A method according to claim 15 wherein R⁷ is ureido, acylamino or acylureido.

18. A method according to claim 1 wherein the compound is of the formula (III) or a pharmaceutically acceptable salt or in-vivo hydrolyzable ester thereof:

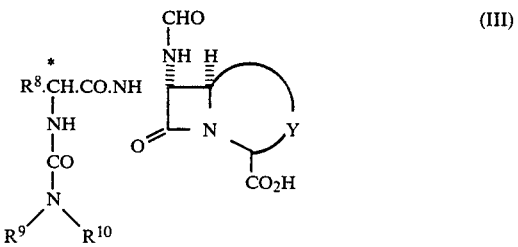 (III)

wehrein Y is:

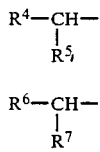

or 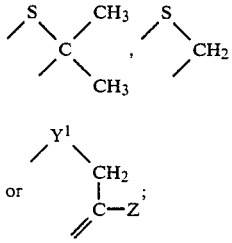 ;

wherein Y¹ is oxygen, sulphur or —CH₂— and Z represents hydrogen, halogen, alkoxy of 1 to 4 carbon atoms, —CH₂Q or —CH=CH—Q wherein Q is hydrogen, halogen, hydroxy, mercapto, cyano, carboxy, carboxylic ester, alkoxy of 1 to 4 carbon atoms, acyloxy, aryl, a heterocyclyl group bonded via a carbon atom, a heterocyclylthio group or a nitrogen containing heterocyclic group bonded via a nitrogen atom; and R⁸ is phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety, cyclohexenyl, cyclohexadienyl, or a 5- or 6-membered heterocyclic ring containing up to three heteroatoms selected from oxygen, sulphur or nitrogen, optionally substituted with hydroxy, amino, halogen, ureido, acylamino, acylureido or alkoxy of 1 to 6 carbon atoms; $R^9$ is hydrogen or alkyl of 1 to 6 carbon atoms; and $R^{10}$ is an optionally substituted 5- or 6-membered heterocyclic group containing one or two nitrogen heteroatoms; or $R^9$ and $R^{10}$ together with the nitrogen atom to which they are attached form an optionally substituted 5- or 6-membered heterocyclic group containing one or two nitrogen heteroatoms wherein the substituents are alkyl, alkenyl or alkynyl of up to 6 carbon atoms; cyclohexyl; cyclohexenyl; phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di- alkylcarbonyl of 1 to 6 carbon atoms in each alkyl moiety; oxo; hydroxyl optionally substituted by alkyl or alkenyl of up to 6 carbon atoms or by cyclohexyl, phenyl, pyridyl, pyrimidyl or benzyl; mercapto, alkylsuphonylamino unsubstituted or substituted by alkyl or alkenyl of up to 6 carbon atoms by cyclohexyl, phenyl substituted by up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety or by benzyl.

19. A method according to claim 18 wherein $R^8$ is phenyl substituted with up to three groups selected from the group consisting of alkyl of 1 to 6 carbon atoms, phenyl, halogen, alkoxy of 1 to 6 carbon atoms, amino, nitro, hydroxy, alkylamido of 1 to 6 carbon atoms, alkylcarbonyloxy of 1 to 6 carbon atoms, carboxy, alkoxycarbonyl of 1 to 6 carbon atoms, haloalkyl of 1 to 6 carbon atoms, oxoalkyl of 1 to 6 carbon atoms, alkylcarbonyl of 1 to 6 carbon atoms, aryloxy, arylcarbonyl, alkylamino of 1 to 6 carbon atoms or dialkylamino of 1 to 6 carbon atoms.

20. A method according to claim 18 wehrein $R^8$ is phenyl, 4-hydroxyphenyl, 3,4-di($C_{1-6}$alkylcarbonyloxy)phenyl, 3,4-dihydroxyphenyl, 2-thienyl, 3-thienyl or 2-amino-4-thiazolyl.

21. A method according to claim 18 wehrein $R^8$ is 3,4-dihydroxyphenyl or 3,4-diacetoxyphenyl.

22. A method according to claim 18 wherein the compound is of the formula (IV) or a pharmaceutically acceptable salt or in-vivo hydrolyzable ester thereof:

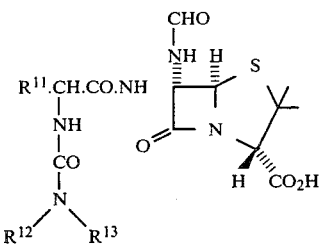

wherein $R^{11}$ is phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety, cyclohexenyl, cyclohexadienyl, or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; $R^{12}$ is hydrogen or alkyl of 1 to 6 carbon atoms and $R^{13}$ is an optionally substituted 5- or 6-membered heterocyclic group containing one or two nitrogen heteroatoms; or $R^{12}$ and $R^{13}$ together with the nitrogen atom to which they are attached form an optionally substituted 5- or 6-membered heterocyclic group containing one or two nitrogen heteroatoms wherein the substituents are alkyl, alkenyl or alkynyl of up to 6 carbon atoms; cyclohexyl; cyclohexenyl; phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety; oxo; hydroxyl optionally substituted by alkyl or alkenyl of up to 6 carbon atoms or by cyclohexyl, phenyl, pyridyl, pyrimidyl or benzyl; mercapto, alkylsulphonylamino unsubstituted or substituted by alkyl or alkenyl of up to 6 carbon atoms by cyclohexyl, phenyl substituted by up to 3 alkyl of 1 to 6 carbon atoms, phenyl, halo, alkoxy of 1 to 6 carbon atoms amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety or by benzyl.

23. A method according to claim 22 wherein R¹¹ is phenyl, 4-hydroxyphenyl, 2-thienyl, 3-thienyl, 2-amino-4-thiazolyl, 3,4-dihydroxyphenyl or 3,4-diacetoxyphenyl.

24. A method according to claim 22 wherein R¹¹ is 3,4-dihydroxyphenyl or 3,4-diacetoxyphenyl.

25. A method according to claim 18 wherein the compound is of the formula (V) or a pharmaceutically acceptable salt or in-vivo hydrolysable ester thereof:

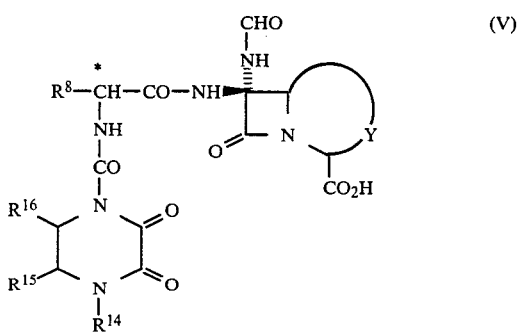

(V)

wherein R⁸ is phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety, cyclohexenyl, cyclohexadienyl, or a 5- or 6-membered heterocyclic ring containing up to three heteroatoms selected from the group consisting of oxygen, sulphur and nitrogen, optionally substituted with hydroxy, amino, halogen, ureido, acylamino, acylureido or alkoxy of 1 to 6 carbon atoms; Y is

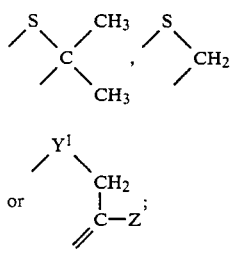

wherein Y¹ is oxygen, sulphur or —CH₂— and Z represents hydrogen, halogen, alkoxy of 1 to 4 carbon atoms, —CH₂Q or —CH═CH—Q wherein Q is hydrogen, halogen, hydroxy, mercapto, cyano, carboxy, carboxylic ester, alkoxy of 1 to 4 carbon atoms, acyloxy, aryl, a heterocyclyl group bonded via a carbon atom, a heterocyclylthio group or a nitrogen containing heterocyclic group bonded via a nitrogen atom; R¹⁴ is hydrogen, alkyl of 1 to 6 carbon atoms, aryl, or aralkyl; and R¹⁵ and R¹⁶ are the same or different and each is hydrogen, alkyl of 1 to 6 carbon atoms, halogen, amino, hydroxy or alkoxy or R¹⁵ and R¹⁶ form the residue of a 5- or 6-membered carboxylic or heterocyclic ring.

26. A method according to claim 25 wherein Y is —S—C(CH₃)₂— or —S—CH₂—C)CH₂Q)═ wherein Q is hydrogen, halogen, hydroxy, mercapto, cyano, carboxy, carboxylic ester, alkoxy of 1 to 4 carbon atoms, acyloxy, aryl, a heterocyclyl group bonded via a carbon atom, aheterocyclylthio group or a nitrogen containing heterocyclic group bonded via a nitrogen atom.

27. A method according to claim 26 wherein the compound is of the formula (VI) or a pharmaceutically acceptable salt or in-vivo hydrolysable ester thereof:

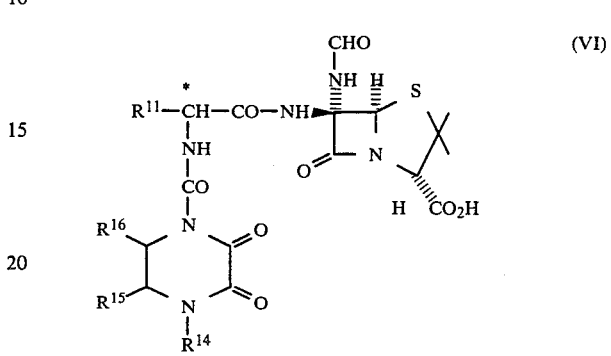

(VI)

wherein R¹¹ is phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety, cyclohexenyl, cyclohexadienyl, or a 5- or 6-membered heterocyclic ring containing up to three heteroatoms selected from the group consisting or oxygen, sulphur or nitrogen, optionally substituted with hydroxy, amino, halogen or alkoxy of 1 to 6 carbon atoms, R¹⁴ is hydrogen, alkyl of 1 to 6 carbon atoms, aryl, or aralkyl, R¹⁵ and R¹⁶ are the same or different and each is hydrogen, alkyl of 1 to 6 carbon atoms, halogen, amino, hydroxy or alkoxy of 1 to 6 carbon atoms or R¹⁵ and R¹⁶ form the residue of a 5- or 6-membered carbocyclic or heterocyclic ring.

28. A method according to claim 1 wherein the compound is of the formula (VII) or a pharmaceutically acceptable salt or in-vivo hydrolysable ester thereof:

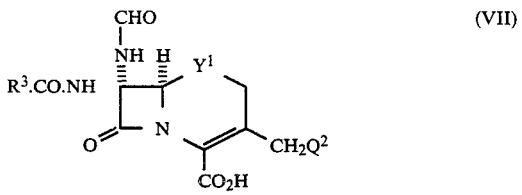

(VII)

wherein R³ is a group such that R³—CO—NH— is an acylamino group; Y¹ is oxygen or sulphur; Q² is acetyloxy, a group —SHet wherein Het is a 5- or 6-membered heterocyclic ring containing from 1 to 4 atoms selected from the group consisting of nitrgoen, oxygen and sulphur unsubstituted or substituted by one or two substituents selected from the group consisting of alkyl of 1 to 6 carbon atoms, alkoxy of 1 to 6 carbon atoms, hydroxyalkyl of 1 to 6 carbon atoms, alkenyl of 2 to 6 carbon atoms, alkoxyalkyl of 1 to 6 carbon atoms in the alkyl moiety and 1 to 6 carbon atoms in the alkoxy moiety, carboxyalkyl of 1 to 6 carbon atoms in the alkyl moiety, sulphonylalkyl of 1 to 6 carbon atoms in the alkyl moiety, carbamoylalkyl of 1 to 6 carbon atoms in the alkyl moiety, trifluoromethyl, hydroxy, halo, oxo and aminoalkyl of 1 to 6 carbon atoms in the alkyl moiety, or two of such substituents may be linked to form the residue of the heterocyclic or carbocyclic ring, or $Q^2$ is a subgroup of the formula (h):

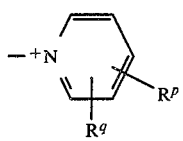

wherein $R^q$ and $R^p$ are the same or different and each is hydrogen, alkyl of 1 to 6 carbon atoms, alkoxy of 1 to 6 carbon atoms, hydroxyalkyl, alkenyl of 1 to 6 carbon atoms, alkoxyalkyl, carboxyalkyl, sulphonylalkyl, carbamoylalkyl, carbamoyl, triflurormethyl, hydroxy, halogen and aminoalkyl.

29. A method according to claim 28 wherein the 'Het' is 1,2,3-triazolyl; 1,2,4-triazolyl; tetrazolyl; oxazolyl; thiazolyl; 1,3,4-oxadiazolyl; 1,2,4-triazinyl; 1,3,4-thiadiazolyl or 1,2,4-thiadiazolyl unsubstituted or substituted with one or two groups selected fro alkyl of 1 to 6 carbon atoms, alkoxy of 1 to 6 carbon atoms, hydroxyalkyl of 1 to 6 carbon atoms in the alkyl moiety, alkenyl of 2 to 6 carbon atoms, alkoxyalkyl of 1 to 6 carbon atoms in each of the alkoxy and alkyl moieties, carboxyalkyl of 1 to 6 carbon atoms in the alkyl moiety, sulphonylalkyl of 1 to 6 carbon atoms in the alkyl moiety, carbamoylalkyl of 1 to 6 carbon atoms in the alkyl moiety, trifluoromethyl, hydroxy, halo, oxo, or aminoalkyl of 1 to 6 carbon atoms in the alkyl moiety.

30. A method according to claim 29 wherein $Y^1$ is sulphur.

31. A method according to claim 28 wherein $R^3$ is a subgroup of formula (j):

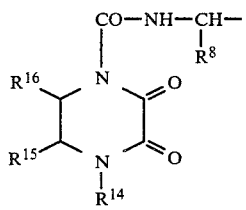

wherein $R^8$ is phenyl unsubstituted or substituted with up to 3 alkyl of 1 to 6 carbon atoms, phenyl, halo, alkoxy of 1 to 6 carbon atoms, amino, nitro, hydroxy, alkylamido of 1 to 6 carbon atoms in the alkyl moiety, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms in the alkyl moiety, oxo-alkyl of 1 to 6 carbon atoms in the alkyl moiety, alkoxycarbonyl of 1 to 6 carbon atoms in the alkyl moiety, aryloxy, aralkyloxy, arylcarbonyl, alkylamino of 1 to 6 carbon atoms in the alkyl moiety or di-alkylcarbonyl of 1 to 6 carbon atoms in each alkyl moiety, cyclohexenyl, cyclohexadienyl, or a 5- or 6-membered heterocyclic ring containing up to three heteroatoms selected from the group consisting of oxygen, sulphur or nitrogen, optionally substituted with hydroxy, amino, halogen, substituted amino or alkoxy of 1 to 6 carbon atoms, $R^{14}$ is hydrogen, alkyl of 1 to 6 carbon atoms, aryl, or aralkyl, $R^{15}$ and $R^{16}$ are the same or different and each is hydrogen, alkyl of 1 to 6 carbon atoms, halogen, amino, hydroxy or alkoxy of 1 to 6 carbon atoms, or $R^{15}$ and $R^{16}$ form the residue of a 5- or 6-membered carbocyclic or heterocyclic ring.

32. A method according to claim 1 wherein the compound is selected from the following or a pharmaceutically acceptable salt or in-vivo hydrolysable ester thereof:

(a)

6α-formamido-6β-[D-2[(4-ethyl-2,3-dioxopiperazin-1-yl)carbonylamino]-2phenylacentamido]penicillanic acid;

6α-formamido-6β-phenoxyacetamidopenicillanic acid;

6α-formamido-6β-[2-carboxy-2-(3-thienyl)acetamido]-penicillanic acid;

6α-formamido-6β-(2-carboxy-2-phenylacetamido)-penicillanic acid; and

6β-[D-2-[(4-ethyl-2,3-dioxopiperazin-1-yl)carbonyl amino]-2-(4-hydroxyphenyl)acetamido]-6α-formamidopenicillanic acid;

6β-[L-2-[(4-ethyl-2,3-dioxopiperazine-1-yl)carbonyl amino]-2-(4-hydroxyphenyl)acetamido]-6α-formamidopenicillanic acid;

6α-Formamido-6β-[D-2-[(4-hydroxy-2-phenylaminopyrimidin-5-yl)ureido]-2phenylactamido]penicillanic acid;

6β-[D-2-Amino-2-(4-hydroxyphenyl)acetamido]-6α-formamidopenicillanic acid;

6β-[D-2-(3-cinnamoyl-3-methylureido)-2-phenylacetamido]6α-formamidopenicillanic acid;

6α-Formamido-6β-[D-2-[(2-oxoimidazolidin-1-yl) carbonylamino]-2-phenylacetamido]penicillanic acid;

6α-Formamido-6β-[D-2-[(3-methylsulphonyl-2-oxoimidazolidin-1-yl)carbonylamino]-2-phenylacetamido]penicillanic acid;

6α-Formamido-6β-[D-2[3-methyl-3-(thien-2-yl-carbonyl)ureido]-2-phenylacetamido]penicillanic acid;

6α-Formamido-6β-[D-2[(7-hydroxy-1,2,4-triazolo [2,3-a]pyrimidin-6-yl)carbonylamino]-2-phenylacetamido]penicillanic acid;

6β-[D-2-[( 2-Benzylamino-4-hydroxypyrimidin-5-yl) carbonylamino]-2-phenylacetamido]-6α-formamidopenicillanic acid;

6α-Formamido-6β-[D-2-(4-hydroxyphenyl)-2-[(2-oxoimidazolidin-1-yl) carbonylamino]acetamido]-penicillanic acid;

6β-[D-2-(3-cinnamoyl-3-methylureido)-2-(4-hydroxyphenyl)acetamido]-6α-formamidopenicillanic acid; and (c)

6α-Formamido-6β-[D-2-[(4-ethyl-2,3-dioxopiperazin-1-yl) carbonylamino]-2-(3,4-diacetoxyphenyl)acetamido]penicillanic acid;

6α-Formamido-6β-[D-2-[(4-ethyl-2,3-dioxopiperazin-1-yl)carbonylamino]-2-(3,4-dihydroxyphenyl)acetamido]penicillanic acid; and (d)

6β-[D-2-[3-[2-(4-Aminosulphonylphenyl)amino-4-hydroxypyrimidin-5-yl]ureido]-2-(4-hydroxyphenyl)acetamido]-6α-formamidopenicillanic acid;

6α-Formamido-6β-[D-2-[[3-(furan-2-ylmethyleneamino)-2-oxoimidazolidin-1-yl]carbonylamino]-2(4-hydroxyphenyl)acetamido]penicillanic acid;

6β-[-D-2-Carbamoylamino-3-phenylpropionamido)-2-(4-hydroxyphenyl)acetamido]-6α-formamidopenicillanic acid;

6β-[2-[(Coumarin-3-yl)carbonylamino]-2-(4-hydroxyphenyl)acetamido]-6α-formamidopenicillanic acid;

6α-Formamido-6β-[D-2-(4-hydroxyphenyl)-2-[(3-methylsulphonyl-2-oxoimidazolidin-1-yl)carbonylamino]acetamido]penicillanic acid;

6β-[D-2-[(5-Ethoxycarbonylimadazol-4-yl)carbonylamino]-2-(4-hydroxyphenyl)acetamido]-6α-formamidopenicillanic acid;

6β-[D-2-[(4-Ethyl-2,3-dioxopiperazin-1-yl)carbonylamino]-2-(thien-2-yl)acetamido]-6α-formamido penicillanic acid;

6β-[L-2-[(4-Ethyl-2,3-dioxopiperazin-1-yl)carbonylamino]-2-(thien-2-yl)acetamido]-6α-formamidopenicillanic acid;

6β-[D-2-Amino-2-(thien-2-yl)acetamido]-6α-formamidopenicillanic acid;

6β-[L-2-Amino-2-(thien-2-yl)acetamido]-6α-formamidopenicillanic acid;

6β-[(2R,3S)-3-Benzyloxy-2-[(4-ethyl-2,3-dioxopiperazin-1-yl)carbonylamino]butyramido]-6α-formamidopenicillanic acid;

6α-Formamido-6β-[D-2-(hydroxyphenyl)-2-[3-[4-hydroxy-2-(phenylamino)pyrimidin-5-yl]ureido]acetamido]penicillanic acid;

7β-(D-2-Amino-2phenylacetamido)-7α-formamidocephalosporanic acid;

7β-[D-2-[(4-Ethyl-2,3-dioxopiperazin-1-yl)carbonylamino]2-phenylacetamido]-7α-formamidocephalosporanic acid;

7α-Formamido-7β-[D-2-[[3-(methylsulphonyl)-2-oxoimidazolidin-1-yl]carbonylamino]-2-phenylacetamido]cephalosporanic acid;

7β-[D-2-[(4-Ethyl-2,3-dioxopiperazin-1-yl)carbonyl amino]-2-(4-hydroxyphenyl)acetamido]-7α-formamidocephalosporanic acid;

7β-[L-2-[(4-Ethyl-2,3-dioxopiperazin-1-yl)carbonyl amino]-2-(4-hydroxyphenyl)acetamido]-7α-formamidocephalosporanic acid;

7β-[D-2-[(4-Ethyl-2,3-dioxopiperazin-1-yl)carbonyl amino]-2-(3,4-diacetoxyphenyl)acetamido]-7α-formamidocephalosporanic acid;

7α-Formamido-7β-(thien-2-ylacetamido)cephalosporanic acid;

7β-[2—Carboxy-2-(thien-3-yl)acetamido]-7α-formamidocephalosporanic acid;

7β-[D-2-[(4-Ethyl-2,3-dioxopiperazin-1-yl)carbonyl amino]-2-(thien-2-yl)acetamido]-7α-formamidocephalosporanic acid;

7β-[L-2-(4-Ethyl-2,3-dioxopiperazin-1-yl)carbonyl amino]-2-(thien-2-yl)acetamido]-7α-formamidocephalosporanic acid;

7β-[2-(2-Aminothiazol-4-yl)acetamido]-7α-formamido cephalosporanic acid; and (e)

6β-[D-2-[(Coumarin-3-yl)ureido]-2-(4-hydroxyphenyl)acetamido]-6α-formamidopenicillanic acid;

6β-[D-2-[3-(4-oxo-4H-1-benzopyran-3-yl)ureido]-2-(4-hydroxyphenyl)acetamido]-6α-formamidopenicillanic acid;

6α-Formamido-6β-[D-2-[(4-hydroxy-7-methyl-1,8-naphthyridin-3-yl)carbonylamino]-2-(4-hydroxyphenyl)acetamido]penicillanic acid;

6β-[D-2-[D-2-amino-3-(N-methylcarbamoyl)propionamido]-2-(4-hydroxyphenyl)acetamido]-6α-formamidopenicillanic acid;

7β-[2-(Cyanomethylthio)acetamido]-7α-formamido cephalosporanic acid;

7β-[2-[(Aminocarbonyl)amino]-2-(thien-2-yl)acetamido]-7α-formamidocephalosporanic acid;

(f)

7α-Formamido-7β-[2-(thien-2-yl)acetamido]-3-[(1-methyl-1H-tetrazol-5-yl)thiomethyl]ceph-3-em-4-carboxylic acid;

7α-Formamido-7β-[2-(thien-2-yl)acetamido]-3-[(2-methyl-1,3,4-thiadiazol-5-yl)thiomethyl]ceph-3-em--carboxylic acid; and 7β-[2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]ceph-3-em-4-carboxylic acid;

7β-[2-(3,4-dihydroxyphenyl)-2-[(4-ethyl-2,3-dioxopiperazin-1-yl)carbonylamino]-7α-formamido-3-](1-methyl-1H-tetrazol-5-yl)thiomethyl]ceph-3-em-4carboxylic acid;

6β-[L-2-[(4-ethyl-2,3-dioxopiperazin-1-yl)carbonylamino]-2-(3,4-dihydroxyphenyl)acetamido]-6α-formamidopenicillanic acid; 7α-formamido-3-(pyridiniummethyl)-7β-(thien-2-yl-acetamido)-ceph-3-em-4-carboxylic acid;

6β-phenoxyacetamido-6α-formamidopenam-3-carboxylic acid;

7β-[D-2-[(4-ethyl-2,3-dioxopiperazin-1-yl)carbonylamino]-2-phenylacetamido]-7α-formamido-3-methyl-1-oxadethia-ceph-3-em-4-carboxylic acid;

6α-formamido-6β-(R-2-phenyl-2-sulphoacetamido)-penicillanic acid;

6β-[D-2-amino-2-(3,4-diacetoxyphenyl)acetamido]-6α-formamidopenicillanic acid;

7α-formamido-7β-[DL-2-phenoxycarbonyl-2-(thien-3yl)acetamido]-3-methyl-1-oxadethia-ceph-3-em-4-carboxylic acid;

6β-[D-2-[D-2-amino-3-(N-methylcarbamoyl)propionamido]-2-(3,4-diacetoxyphenyl)acetamido]-6α-formamidopenicillanic acid;

7β-[2-[(4-ethyl-2,3-dioxopiperazin-1-yl)carbonylamino]-2-(4-hydroxyphenyl)acetamido]-7α-formamido-3-[(1-methyl-1H-tetrazol-5-yl)thiomethyl]-ceph-3-em-4-carboxylic acid;

7β-[2-[(4-ethyl-2,3-dioxopiperazin-1-yl carbonylamino[-2-(3,4-diacetoxyphenyl)acetamido[-7α-formamido-3-[(2-methoxy-1,3,4-thiadiazol-5-yl)thiomethyl]ceph-3-em-4-carboxylic acid;

6α-formamido-6β-(phenylacetamido)penicillanic acid;

7β-[(Z)-2-(2-aminothiazol-4-yl)-2-(1-carboxy-11-methylethoxyimino)acetamido]-7α-formamidocephalosporanic acid;

7β-[2-(3,4-diacetoxyphenyl)-2-[(4-ethyl-2,3-dioxopiperazin-1-yl)carbonylamino]acetamido]-7α-formamido-3-[(2-methyl-1,3,4-thiadiazol-5-yl)thiomethyl]ceph-3-em-4-carboxylic acid;

7β-[D-2-[(4-ethyl-2,3-dioxopiperazin-1-yl)carbonyl amino]-2-(3,4-dihydroxyphenyl)acetamido]-7α-formamidocephalosporanic acid;

6β-[D-2-(3,4-diacetoxyphenyl)-2-[3-[2-(4-aminosulphonylphenyl)amino-4-hydroxypyrimidin-5-yl]ureido]acetamido-6α-formamidopenpicillanic acid.

* * * * *